US009994575B2

(12) United States Patent
Hodous et al.

(10) Patent No.: US 9,994,575 B2
(45) Date of Patent: *Jun. 12, 2018

(54) COMPOSITIONS USEFUL FOR TREATING DISORDERS RELATED TO KIT

(71) Applicant: BLUEPRINT MEDICINES CORPORATION, Cambridge, MA (US)

(72) Inventors: Brian L. Hodous, Cambridge, MA (US); Joseph L. Kim, Wayland, MA (US); Kevin J. Wilson, Boston, MA (US); Douglas Wilson, Ayer, MA (US); Yulian Zhang, Acton, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/887,614

(22) Filed: Oct. 20, 2015

(65) Prior Publication Data

US 2016/0102097 A1    Apr. 14, 2016

Related U.S. Application Data

(63) Continuation of application No. 14/515,327, filed on Oct. 15, 2014, now Pat. No. 9,200,002.

(60) Provisional application No. 61/975,229, filed on Apr. 4, 2014, provisional application No. 61/931,204, filed on Jan. 24, 2014, provisional application No. 61/892,086, filed on Oct. 17, 2013.

(51) Int. Cl.
| | |
|---|---|
| *C07D 487/04* | (2006.01) |
| *C07D 403/14* | (2006.01) |
| *C07D 401/14* | (2006.01) |
| *C07D 413/14* | (2006.01) |
| *C07D 417/14* | (2006.01) |
| *A61K 31/53* | (2006.01) |
| *A61K 31/5377* | (2006.01) |
| *A61K 31/496* | (2006.01) |
| *A61P 35/00* | (2006.01) |
| *A61K 45/06* | (2006.01) |

(52) U.S. Cl.
CPC .......... *C07D 487/04* (2013.01); *A61K 31/496* (2013.01); *A61K 31/53* (2013.01); *A61K 31/5377* (2013.01); *A61K 45/06* (2013.01); *C07D 401/14* (2013.01); *C07D 403/14* (2013.01); *C07D 413/14* (2013.01); *C07D 417/14* (2013.01)

(58) Field of Classification Search
CPC .. C07D 487/04; C07D 401/14; C07D 403/14; C07D 413/14; C07D 417/14; A61K 31/53; A61K 31/5377; A61K 31/495; A61K 31/496

USPC .......................................... 544/183; 514/243
See application file for complete search history.

(56) References Cited

U.S. PATENT DOCUMENTS

| | | | |
|---|---|---|---|
| 6,982,265 B1 | 1/2006 | Hunt et al. | |
| 8,609,672 B2 | 12/2013 | Russu et al. | |
| 8,802,697 B2 | 8/2014 | Bifulco, Jr. et al. | |
| 9,126,951 B2 | 9/2015 | Bifulco, Jr. et al. | |
| 9,200,002 B2 * | 12/2015 | Hodous .................. | A61K 31/53 |
| 9,334,263 B2 | 5/2016 | Hodous et al. | |
| 9,340,514 B2 | 5/2016 | Bifulco, Jr. et al. | |
| 9,434,700 B2 | 9/2016 | Bifulco, Jr. et al. | |
| 9,499,522 B2 | 11/2016 | DiPietro et al. | |
| 9,688,680 B2 | 6/2017 | Hodous | |
| 9,695,165 B2 | 7/2017 | Bifulco, Jr. et al. | |
| 2014/0187559 A1 | 7/2014 | Miduturu | |
| 2017/0022206 A1 | 1/2017 | Hodous et al. | |
| 2017/0029409 A1 | 2/2017 | DiPietro et al. | |
| 2017/0057953 A1 | 3/2017 | Hodous et al. | |
| 2017/0066773 A1 | 3/2017 | Wenglowsky et al. | |
| 2017/0066812 A1 | 3/2017 | Bifulco, Jr. et al. | |
| 2017/0121312 A1 | 5/2017 | Brubaker et al. | |
| 2017/0145018 A1 | 5/2017 | Wenglowsky et al. | |
| 2017/0174652 A1 | 6/2017 | Bifulco, Jr. et al. | |
| 2017/0204104 A1 | 7/2017 | Hodous et al. | |
| 2017/0253593 A1 | 9/2017 | Bifulco, Jr. et al. | |
| 2017/0267661 A1 | 9/2017 | Kim et al. | |
| 2017/0298069 A1 | 10/2017 | Brooijmans et al. | |

FOREIGN PATENT DOCUMENTS

| | | | |
|---|---|---|---|
| WO | 0071129 A1 | 11/2000 | |
| WO | 01/25220 A1 | 4/2001 | |
| WO | 2005117909 A2 | 12/2005 | |
| WO | 2007085188 A1 | 8/2007 | |
| WO | 2008005956 A2 | 1/2008 | |
| WO | 2009015254 A1 | 1/2009 | |
| WO | 2009117157 A1 | 9/2009 | |
| WO | 2010022055 A2 | 2/2010 | |
| WO | 2010144345 A1 | 12/2010 | |
| WO | 2011005119 A1 | 1/2011 | |
| WO | 2011103196 A1 | 8/2011 | |
| WO | 2012027495 A1 | 3/2012 | |
| WO | WO 2014/039714 A2 | 3/2014 | |
| WO | WO 2014/100620 A2 | 6/2014 | |
| WO | 2014160521 A1 | 10/2014 | |
| WO | 2015057873 A1 | 4/2015 | |
| WO | 2015058129 A1 | 4/2015 | |
| WO | 2016022569 A1 | 2/2016 | |
| WO | WO 2017/019442 A1 | 2/2017 | |

OTHER PUBLICATIONS

Antonescu, "What lessons can be learned from the GIST paradigm that can be applied to other kinase-driven cancers" J. Pathol. (2011) vol. 223, No. 2, pp. 251-261.

Cairoli et al. "Prognostic impact of c-KIT mutations in core binding factor leukemias: an Italian retrospective study" Blood (2006) vol. 107, pp. 3463-3468.

(Continued)

*Primary Examiner* — Venkataraman Balasubramanian
(74) *Attorney, Agent, or Firm* — Finnegan, Henderson, Farabow, Garrett & Dunner, LLP

(57) ABSTRACT

Compounds and compositions useful for treating disorders related to mutant KIT are described herein.

20 Claims, 2 Drawing Sheets

(56) References Cited

OTHER PUBLICATIONS

Cecil Textbook of Medicine, Edited by Bennet and Plum (1996) 20th edition, vol. 1, pp. 1004-1010.
Cohen et al., "The development and therapeutic potential of protein kinase inhibitors" Current Opinion in Chemical Biology (1999) vol. 3, pp. 459-465.
Dermer "Another Anniversary for the War on Cancer" Bio/Technology (1994) vol. 12, pp. 320.
Fresheny et al., "Culture of Animal Cells, A Manual of Basic Technique" Alan R. Liss, Inc. (1983) pp. 1-6.
International Search Report and Written Opinion for International Application No. PCT/US2014/027008 dated Jul. 17, 2014.
International Search Report and Written Opinion for International Application No. PCT/US2014/060746 dated Dec. 17, 2014.
International Search Report and Written Opinion for International Application No. PCT/US2014/061211 dated Oct. 12, 2014.
International Search Report for International Application No. PCT/US2015/043624 dated Oct. 6, 2015.
Lee et al. "Correlation of Imatinib Resistance with the Mutational Status of KIT and ODGFRA Genes in Gastrointestinal Stromal Tumors: a Meta-analysis" J. Gastrointestin Liver Dis. (2013) vol. 22, No. 4, pp. 413-418.
Paschka et al. "Adverse Prognostic Significance of KIT Mutations in Adult Acute Myeloid Leukemia with inv(16) and t(8;21):A Cancer and Leukemia Group Study" Journal of Clinical Oncology (2006) vol. 24, No. 24, pp. 3904-3911.
Quintela et al, "A Ready One-pot Preparation for Pyrrolo[2,1-f]-[1,2,4]triazine and Pyrazolo[5,1-c]pyrimido[4,5-e]-[1,2,4]triazine Derivatives" Tetrahedron (1996) vol. 52, No. 8, pp. 3037-3048.
Schnittger et al. "KIT-D816 mutations in AML1-ETO-positive AML are associated with impaired event-free and overal survival" Blood (2006) vol. 107, pp. 1791-1799.
International Search Report anti Written Opinion for International Application No. PCT/US2016/043301, dated Oct. 17, 2016.
Notice of Allowance dated Sep. 26, 2017, in U.S. Appl. No. 15/093,354, filed Apr. 7, 2016, by Blueprint Medicines Corp.
Notice of Allowance dated Sep. 5, 2017, in U.S. Appl. No. 15/217,503, filed Jul. 22, 2016, by Blueprint Medicines Corp.
Notice of Allowance dated Oct. 25, 2017, in U.S. Appl. No. 15/340,428, filed Nov. 1, 2016, by Blueprint Medicines Corp.
Notice of Allowance dated Aug. 3, 2017, in U.S. Appl. No. 15/479,145, filed Apr. 4, 2017, by Blueprint Medicines Corp.
U.S. Appl. No. 15/548,925, filed Aug. 4, 2017, by Brooijmans et al.
U.S. Appl. No. 15/657,057, filed Jul. 21, 2017, by Brubaker et al.
U.S. Appl. No. 15/660,640, filed Jul. 26, 2017, by Brubaker et al.

* cited by examiner

COMPOSITIONS USEFUL FOR TREATING DISORDERS RELATED TO KIT

CLAIM OF PRIORITY

This application is a continuation of U.S. Ser. No. 14/515,327, filed Oct. 15, 2014, which claims priority to U.S. Ser. No. 61/892,086 filed Oct. 17, 2013, U.S. Ser. No. 61/931,204 filed Jan. 24, 2014, and U.S. Ser. No. 61/975,229 filed Apr. 4, 2014, the content of each of which is incorporated by reference in its entirety.

BACKGROUND

The invention relates to compounds and compositions useful for treating disorders related to KIT and PDGFR.

The enzyme KIT (also called CD117) is a receptor tyrosine kinase expressed on a wide variety of cell types. The KIT molecule contains a long extracellular domain, a transmembrane segment, and an intracellular portion. The ligand for KIT is stem cell factor (SCF), whose binding to the extracellular domain of KIT induces receptor dimerization and activation of downstream signaling pathways. KIT mutations generally occur in the DNA encoding the juxtumembrane domain (exon 11). They also occur, with less frequency, in exons 7, 8, 9, 13, 14, 17, and 18. Mutations make KIT function independent of activation by SCF, leading to a high cell division rate and possibly genomic instability. Mutant KIT has been implicated in the pathogenesis of several disorders and conditions including systemic mastocytosis, GIST (gastrointestinal stromal tumors), AML (acute myeloid leukemia), melanoma, and seminoma. As such, there is a need for therapeutic agents that inhibit KIT, and especially agents that inhibit mutant KIT.

Platelet-derived growth factor receptors (PDGF-R) are cell surface tyrosine kinase receptors for members of the platelet-derived growth factor (PDGF) family. PDGF subunits-A and -B are important factors regulating cell proliferation, cellular differentiation, cell growth, development and many diseases including cancer. A PDGFRA D842V mutation has been found in a distinct subset of GIST, typically from the stomach. The D842V mutation is known to be associated with tyrosine kinase inhibitor resistance. As such, there is a need for agents that target this mutation.

SUMMARY OF THE INVENTION

The present invention features compounds and compositions for treating or preventing conditions such as mastocytosis and mast cell diseases by modulating the activity of KIT, such compounds having the structural Formula I:

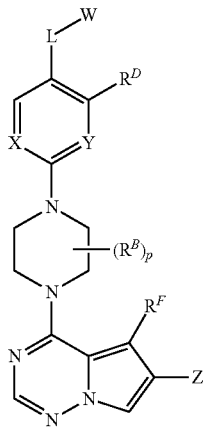

or a pharmaceutically acceptable salt thereof, wherein:
W is selected from hydrogen or

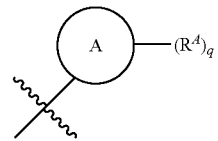

wherein Ring A is selected from monocyclic or bicyclic aryl, monocyclic or bicyclic heteroaryl, cycloalkyl or heterocyclyl;

each X and Y is independently selected from $CR^1$ or N;

Z is $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from a bond, —$(C(R^2)(R^2))_m$—, —$(C_2$-$C_6$ alkynylene)-, —$(C_2$-$C_6$ alkenylene)-, —$(C_1$-$C_6$ haloalkylene)-, —$(C_1$-$C_6$ heteroalkylene)-, —$(C_1$-$C_6$ hydroxyalkylene)-, —C(O)—, —O—, —S—, —S(O), —$SO_2$—, —$N(R^2)$—, —O—$(C_1$-$C_6$ alkylene)-, —$(C_1$-$C_6$ alkylene)-O—, —$N(R^2)$—CO—, —CO—$N(R^2)$—, —$(C_1$-$C_6$ alkylene)-$N(R^2)$—, —$N(R^2)$—$(C_1$-$C_6$ alkylene)-, —$N(R^2)$—CO—$(C_1$-$C_6$ alkylene)-, —CO—$N(R^2)$—$(C_1$-$C_6$ alkylene)-, —$N(R^2)$—$SO_2$—, —$SO_2$—$N(R^2)$—, —$N(R^2)$—$SO_2$—$(C_1$-$C_6$ alkylene)-, or —$SO_2$—$N(R^2)$—$(C_1$-$C_6$ alkylene)-;

each $R^A$ and $R^B$ is independently selected from $C_1$-$C_6$ alkyl, $C_1$-$C_6$ cycloalkyl, $C_1$-$C_6$ heterocyclyl, halo, $C_1$-$C_6$ haloalkyl, $C_1$-$C_6$ hydroxyalkyl, $C_1$-$C_6$ heteroalkyl, monocyclic or bicyclic aralkyl, —$N(R^2)(R^2)$, cyano, —$OR^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —$C(O)R^2$—, —$OC(O)R^2$, —$C(O)OR^2$, —$SR^2$, —$S(O)_2R^2$, —$S(O)_2$—$N(R^2)(R^2)$, —$(C_1$-$C_6$ alkylene)-$S(O)_2$—$N(R^2)(R^2)$, —$N(R^2)(R^2)$, —$C(O)$—$N(R^2)(R^2)$, —$N(R^2)(R^2)$—$C(O)R^2$, —$(C_1$-$C_6$ alkylene)-$N(R^2)$—$C(O)R^2$, —$NR^2S(O)_2R^2$, —$P(O)(R^2)(R^2)$, and —$OR^2$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^D$ and $R^F$ is, independently, hydrogen, $C_1$-$C_6$ alkyl, $C_1$-$C_6$ cycloalkyl, hydroxyl, halo, $C_1$-$C_6$ alkoxy, $C_1$-$C_6$ haloalkyl, —$N(R^2)(R^2)$, or cyano;

each $R^1$ is independently selected from hydrogen, $C_1$-$C_6$ alkyl, monocyclic aralkyl, $C_1$-$C_6$ hydroxyalkyl, halo, $C_1$-$C_6$ haloalkyl, —$N(R^2)(R^2)$, —$OR^2$;

each $R^2$ is independently selected from hydrogen, hydroxyl, halo, thiol, $C_1$-$C_6$ thioalkyl, —NR"R", $C_1$-$C_6$ alkyl, $C_1$-$C_6$ alkoxy, $C_1$-$C_6$ haloalkyl, $C_1$-$C_6$ hydroxyalkyl, cycloalkyl, cycloalkylalkyl, heterocyclyl, heterocyclylalkyl, wherein each of $C_1$-$C_6$ alkyl, cycloalkyl and heterocyclyl is independently substituted with 0-5 occurrences of $R^b$, or 2

$R^2$ together with the carbon or nitrogen atom to which they are attached form a cycloalkyl or heterocyclyl ring;

each $R^a$ and $R^b$ is independently hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', or cycloalkyl, wherein cycloalkyl is substituted with 0-5 occurrences of R';

each R' is hydrogen, hydroxyl, or $C_1$-$C_6$ alkyl;

each R" is hydrogen, $C_1$-$C_6$ alkyl, —C(O)—$C_1$-$C_6$ alkyl, —C(O)—NR'R'; —C(S)—NR'R'; and m, p, and q are each independently 0, 1, 2, 3, or 4.

Any of the compounds disclosed herein may be used to treat any of the diseases disclosed herein.

DETAILED DESCRIPTION OF THE INVENTION

Figure 1:
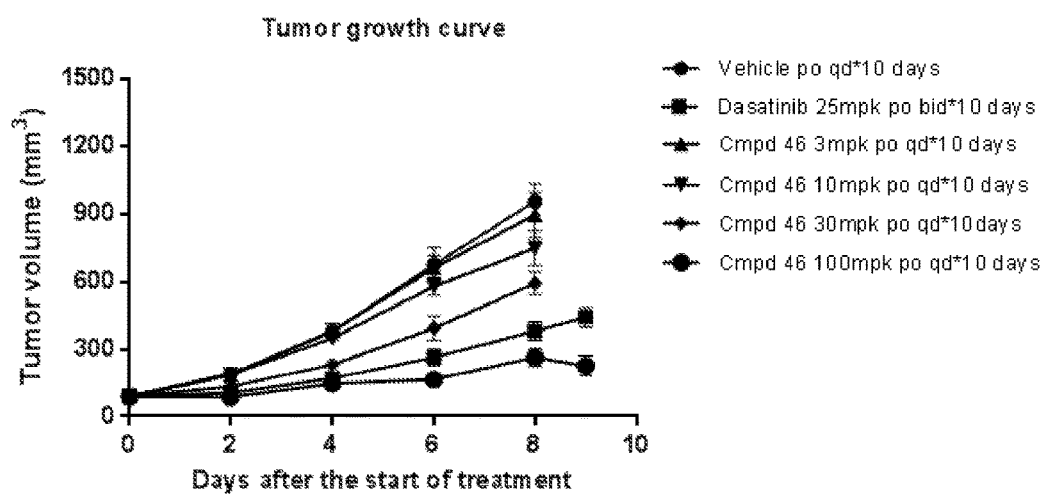
FIG. 1 is a line graph depicting tumor growth curves of different treatment groups: vehicle (●), Dasatinib at 25 mpk po bid*10 days (■), Compound 46 at 3 mpk po qd*10 days (▲), Compound 46 at 10 mpk po qd*10 days (▼), Compound 46 at 30 mpk po qd*10 days (♦), and Compound 46 at 100 mpk po qd*10 days (●).

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —$CH_2$—, —$CH_2CH_2$—, and $CH_2CH_2CH_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxy in which one or more hydrogen atoms are replaced by halo, and includes alkoxy moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as $C_1$-$C_2$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH=CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine. "Haloalkylene" refers to a divalent alkyl, e.g., —$CH_2$—, —$CH_2CH_2$—, and —$CH_2CH_2CH_2$—, in which one or more hydrogen atoms are replaced by halo, and includes alkyl moieties in which all hydrogens have been replaced by halo.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a-(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c] pyridine, and 1,2,3,4-tetrahydro-2,6-naphthyridine. In some embodiments, heterocyclyl can include:

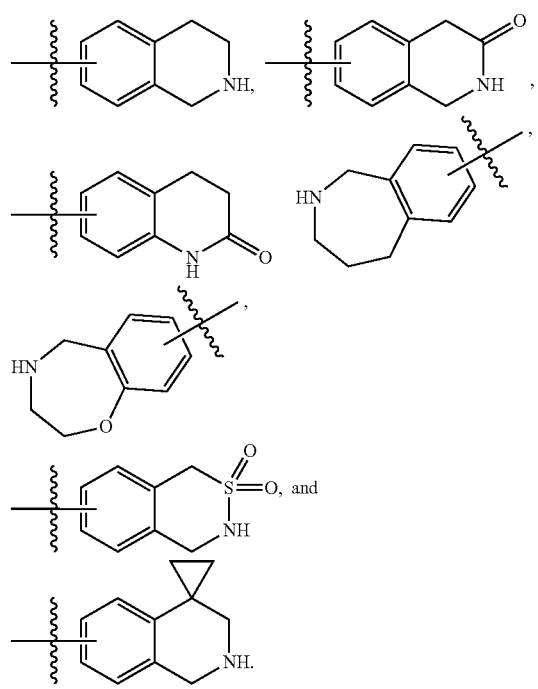

"Heterocyclylalkyl" refers to an alkyl group substituted with a heterocyclyl group.

"Cyano" refers to a —CN radical.

"Nitro" refers to —NO$_2$.

"Hydroxy" or "hydroxyl" refers to —OH.

"Hydroxyalkylene" refers to a divalent alkyl, e.g., —CH$_2$—, —CH$_2$CH$_2$—, and —CH$_2$CH$_2$CH$_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. The term "hydrate" or "hydrated" as used herein, refers to a compound formed by the union of water with the parent compound.

In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

Compounds

In one embodiment, the invention provides a compound having structural Formula I or a pharmaceutically acceptable salt thereof, wherein:

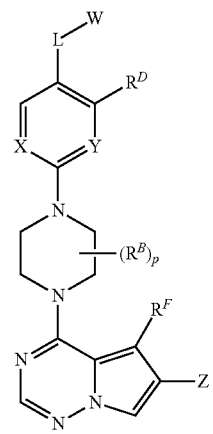

W is selected from hydrogen and

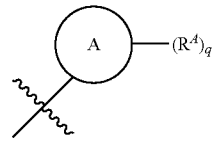

wherein Ring A is selected from monocyclic or bicyclic aryl, monocyclic or bicyclic heteroaryl, cycloalkyl and heterocyclyl;

each X and Y is independently selected from $CR^1$ and N;

Z is $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from a bond, $-(C(R^2)(R^2))_m-$, $-(C_2$-$C_6$ alkynylene)-, $-(C_2$-$C_6$ alkenylene)-, $-(C_1$-$C_6$ haloalkylene)-, —($C_1$-$C_6$ heteroalkylene)-, —($C_1$-$C_6$ hydroxyalkylene)-, —C(O)—, —O—, —S—, —S(O), —$SO_2$—, —N($R^2$)—, —O—($C_1$-$C_6$ alkylene)-, —($C_1$-$C_6$ alkylene)-O—, —N($R^2$)—CO—, —CO—N($R^2$)—, —($C_1$-$C_6$ alkylene)-N($R^2$)—, —N($R^2$)—($C_1$-$C_6$ alkylene)-, —N($R^2$)—CO—($C_1$-$C_6$ alkylene)-, —CO—N($R^2$)—($C_1$-$C_6$ alkylene)-, —N($R^2$)—$SO_2$—, —$SO_2$—N($R^2$)—, —N($R^2$)—$SO_2$—($C_1$-$C_6$ alkylene)-, and —$SO_2$—N($R^2$)—($C_1$-$C_6$ alkylene)-;

each $R^A$ and $R^B$ is independently selected from $C_1$-$C_6$ alkyl, $C_1$-$C_6$ cycloalkyl, $C_1$-$C_6$ heterocyclyl, halo, $C_1$-$C_6$ haloalkyl, $C_1$-$C_6$ hydroxyalkyl, $C_1$-$C_6$ heteroalkyl, monocyclic or bicyclic aralkyl, —N($R^2$)($R^2$), cyano, and —$OR^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^2$, —OC(O)$R^2$, —C(O)O$R^2$, —S$R^2$, —S(O)$_2$$R^2$, —S(O)$_2$—N($R^2$)($R^2$), —($C_1$-$C_6$ alkylene)-S(O)$_2$—N($R^2$)($R^2$), —N($R^2$)($R^2$), —C(O)—N($R^2$)($R^2$), —N($R^2$)($R^2$)—C(O)$R^2$, —($C_1$-$C_6$ alkylene)-N($R^2$)—C(O)$R^2$, —N$R^2$S(O)$_2$$R^2$, —P(O)($R^2$)($R^2$), and —$OR^2$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^D$ and $R^F$ is independently selected from hydrogen, $C_1$-$C_6$ alkyl, $C_1$-$C_6$ cycloalkyl, hydroxyl, halo, $C_1$-$C_6$ alkoxy, $C_1$-$C_6$ haloalkyl, —N($R^2$)($R^2$), and cyano;

each $R^1$ is independently selected from hydrogen, $C_1$-$C_6$ alkyl, monocyclic aralkyl, $C_1$-$C_6$ hydroxyalkyl, halo, $C_1$-$C_6$ haloalkyl, —N($R^2$)($R^2$), and —$OR^2$;

each $R^2$ is independently selected from hydrogen, hydroxyl, halo, thiol, $C_1$-$C_6$ thioalkyl, —NR"R", $C_1$-$C_6$ alkyl, $C_1$-$C_6$ alkoxy, $C_1$-$C_6$ haloalkyl, $C_1$-$C_6$ hydroxyalkyl, cycloalkyl, cycloalkylalkyl, heterocyclyl, and heterocyclylalkyl, wherein each of $C_1$-$C_6$ alkyl, cycloalkyl and heterocyclyl is independently substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is hydrogen, hydroxyl, or $C_1$-$C_6$ alkyl;

each R" is hydrogen, $C_1$-$C_6$ alkyl, —C(O)—$C_1$-$C_6$ alkyl, —C(O)—NR'R'; or —C(S)—NR'R'; and m, p, and q are each independently 0, 1, 2, 3, or 4.

In some embodiments, W is H. In some embodiments, W is

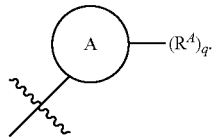

In some embodiments, Ring A is monocyclic or bicyclic aryl substituted with 0, 1, 2 or 3 $R^A$. In some embodiments, Ring A is phenyl. In some embodiments, Ring A is phenyl substituted with halo. In some embodiments, Ring A is phenyl substituted with fluoro or chloro. In some embodiments, Ring A is 4-fluorophenyl. In some embodiments, Ring A is 2,4-difluorophenyl. In some embodiments, Ring A is 2, 4, 6-trifluorophenyl. In some embodiments, Ring A is 4-chlorophenyl.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —$OR^2$. In some embodiments, $R^A$ is independently selected from $C_1$-$C_6$ alkyl and halo. In some embodiments, $R^A$ is independently selected from fluoro, chloro and methyl. In some embodiments, $R^A$ is independently selected from fluoro and chloro. In some embodiments, $R^A$ is methyl. In some embodiments, $R^A$ is fluoro and q is 1, 2, or 3. In some embodiments, $R^A$ is chloro and fluoro and q is 2. In some embodiments, $R^A$ is methyl and fluoro and q is 2.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —$OR^2$. In some embodiments, $R^B$ is $C_1$-$C_6$ alkyl or $C_1$-$C_6$ hydroxyalkyl. In some embodiments, $R^B$ is methyl, ethyl, or hydroxymethyl. In some embodiments, p is 0 or 1. In some embodiments, p is 0. In some embodiments, p is 1.

In some embodiments, at least one of X and Y is N. In some embodiments, X and Y are both N. In some embodiments, X and Y are both $CR^1$. In some embodiments, X and Y are both CH.

In some embodiments, Z is monocyclic or bicyclic aryl. In some embodiments, Z is monocyclic or bicyclic heteroaryl. In some embodiments, Z is monocyclic or bicyclic heterocyclyl. In some embodiments, Z is monocyclic heteroaryl. In some embodiments, Z is selected from pyrazolyl, isoxazolyl, thiophenyl, thiazolyl, and pyridyl. In some embodiments, Z is substituted with 0, 1 or 2 occurrences of $R^C$. In some embodiments, Z is substituted with 0 or 1 occurrences of $R^C$.

In some embodiments, $R^C$ is independently selected from cyano, $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic heterocyclyl, monocyclic or bicyclic heterocyclylalkyl, —C(O)$R^2$, —OC(O)$R^2$, —C(O)O$R^2$, —N($R^2$)($R^2$), —C(O)—N($R^2$)($R^2$), and —$OR^2$. In some embodiments, $R^C$ is independently selected from cyano, $C_1$-$C_6$ alkyl, halo, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —N($R^2$)($R^2$), —C(O)—N($R^2$)($R^2$), and —$OR^2$. In some embodiments, each $R^C$ is independently selected from $C_1$-$C_6$ alkyl, halo, monocyclic and bicyclic heterocyclyl.

In some embodiments, $R^D$ is hydrogen, $C_1$-$C_6$ alkyl, $C_1$-$C_6$ alkoxy, $C_1$-$C_6$ haloalkyl, —N($R^2$)($R^2$), or cyano. In some embodiments, $R^D$ is hydrogen or —N($R^2$)($R^2$). In some embodiments, $R^D$ is hydrogen or —$NH^2$.

In some embodiments, $R^F$ is hydrogen or halo, e.g., chloro or fluoro. In some embodiments, $R^F$ is hydrogen. In some embodiments, $R^F$ is chloro or fluoro.

In some embodiments, L is selected from a bond, —(C($R^2$)($R^2$))$_m$—, —($C_2$-$C_6$ alkenylene)-, —($C_1$-$C_6$ haloalkylene)-, —($C_1$-$C_6$ hydroxyalkylene)-, —S—, —S(O), —$SO_2$—, and —N($R^2$)—. In some embodiments, L is selected from a bond, —(C($R^2$)($R^2$))$_m$—, —S—, and —$SO_2$—. In some embodiments, L is —(C($R^2$)($R^2$))$_m$—. In some embodiments, L is a bond or $CH_2$. In some embodiments, L is —(C($R^2$)($R^2$))$_m$—, wherein each $R^2$ is independently selected from hydrogen, hydroxyl, —NR"R", $C_1$-$C_6$ alkyl, $C_1$-$C_6$ haloalkyl, $C_1$-$C_6$ hydroxyalkyl, and cycloalkyl; and m is 1.

In some embodiments, each $R^2$ is independently selected from hydrogen, hydroxyl, halo, —NR"R", $C_1$-$C_6$ alkyl, $C_1$-$C_6$ haloalkyl, $C_1$-$C_6$ hydroxyalkyl, and cycloalkyl, wherein each of $C_1$-$C_6$ alkyl and cycloalkyl is independently substituted with 0-5 occurrences of $R^b$, or 2 $R^2$ together with the carbon or nitrogen atom to which they are attached form a cycloalkyl or heterocyclyl ring. In some embodiments, each $R^2$ is independently selected from halo, hydrogen, hydroxyl, —NR"R", and $C_1$-$C_6$ alkyl wherein $C_1$-$C_6$ alkyl is independently substituted with 0-5 occurrences of $R^b$. In some embodiments, $R^b$ is independently hydrogen, halo or hydroxyl. In some embodiments, L is —NR"R". In some embodiments, R" is hydrogen or $C_1$-$C_6$ alkyl. In some embodiments, R" is hydrogen. In some embodiments, L is —S—. In some embodiments, L is —CH$_2$—.

In some embodiments, m is 0, 1 or 2. In some embodiments, m is 1. In some embodiments, m is 2.

In some embodiments, p is 0 or 1.

In some embodiments, q is 0, 1, 2 or 3. In some embodiments, q is 0. In some embodiments, q is 1. In some embodiments, q is 2. In some embodiments, q is 3.

In another embodiment, the invention features a compound of Formula II, or a pharmaceutically acceptable salt thereof, wherein:

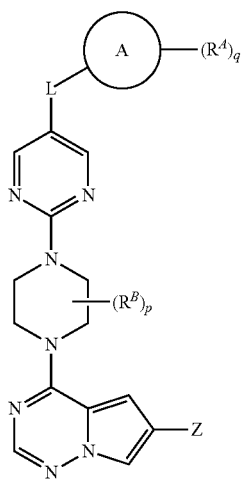

II

Ring A is selected from monocyclic or bicyclic aryl, monocyclic or bicyclic heteroaryl, cycloalkyl and heterocyclyl;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from a bond, —(C($R^2$)($R^2$))$_m$—, —($C_2$-$C_6$ alkynylene)-, —($C_2$-$C_6$ alkenylene)-, —($C_1$-$C_6$ haloalkylene)-, —($C_1$-$C_6$ heteroalkylene)-, —($C_1$-$C_6$ hydroxyalkylene)-, —C(O)—, —O—, —S—, —S(O)—, —SO$_2$—, —N($R^2$)—, —O—($C_1$-$C_6$ alkylene)-, —($C_1$-$C_6$ alkylene)-O—, —N($R^2$)—CO—, —CO—N($R^2$)—, —($C_1$-$C_6$ alkylene)-N($R^2$)—, —N($R^2$)—($C_1$-$C_6$ alkylene)-, —N($R^2$)—CO—($C_1$-$C_6$ alkylene)-, —CO—N($R^2$)—($C_1$-$C_6$ alkylene)-, —N($R^2$)—SO$_2$—, —SO$_2$—N($R^2$)—, —N($R^2$)—SO$_2$—($C_1$-$C_6$ alkylene)-, and —SO$_2$—N($R^2$)—($C_1$-$C_6$ alkylene)-;

each $R^A$ and $R^B$ is independently selected from $C_1$-$C_6$ alkyl, $C_1$-$C_6$ cycloalkyl, $C_1$-$C_6$ heterocyclyl, halo, $C_1$-$C_6$ haloalkyl, $C_1$-$C_6$ hydroxyalkyl, $C_1$-$C_6$ heteroalkyl, monocyclic or bicyclic aralkyl, —N($R^2$)($R^2$), cyano, and —OR$^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^2$—, —OC(O)$R^2$, —C(O)O$R^2$, —S$R^2$, —S(O)$_2R^2$, —S(O)$_2$—N($R^2$)($R^2$), —($C_1$-$C_6$ alkylene)-S(O)$_2$—N($R^2$)($R^2$), —N($R^2$)($R^2$), —C(O)—N($R^2$)($R^2$), —N($R^2$)($R^2$)—C(O)$R^2$, —($C_1$-$C_6$ alkylene)-N($R^2$)—C(O)$R^2$, —NR$^2$S(O)$_2R^2$, —P(O)($R^2$)($R^2$), and —O$R^2$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^2$ is independently selected from hydrogen, hydroxyl, halo, thiol, $C_1$-$C_6$ thioalkyl, —NR"R", $C_1$-$C_6$ alkyl, $C_1$-$C_6$ alkoxy, $C_1$-$C_6$ haloalkyl; $C_1$-$C_6$ hydroxyalkyl, cycloalkyl, cycloalkylalkyl, heterocyclyl, and heterocyclylalkyl, wherein each of $C_1$-$C_6$ alkyl, cycloalkyl and heterocyclyl is independently substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is hydrogen, hydroxyl, or $C_1$-$C_6$ alkyl;

each R" is hydrogen, $C_1$-$C_6$ alkyl, —C(O)—$C_1$-$C_6$ alkyl, —C(O)—NR'R'; —C(S)—NR'R'; and m, p, and q are each independently 0, 1, 2, 3, or 4.

In some embodiments, A is monocyclic or bicyclic aryl. In some embodiments, Ring A is monocyclic or bicyclic aryl substituted with 0, 1, 2 or 3 $R^A$. In some embodiments, Ring A is phenyl. In some embodiments, Ring A is phenyl substituted with halo. In some embodiments, Ring A is phenyl substituted with fluoro or chloro. In some embodiments, Ring A is 4-fluorophenyl. In some embodiments, Ring A is 2,4-difluorophenyl. In some embodiments, Ring A is 2, 4, 6-trifluorophenyl. In some embodiments, Ring A is 4-chlorophenyl.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —OR$^2$. In some embodiments, $R^A$ is independently selected from $C_1$-$C_6$ alkyl and halo. In some embodiments, $R^A$ is independently selected from fluoro, chloro and methyl. In some embodiments, $R^A$ is independently selected from fluoro and chloro. In some embodiments, $R^A$ is methyl. In some embodiments, $R^A$ is fluoro and q is 1, 2, or 3. In some embodiments, $R^A$ is chloro and fluoro and q is 2. In some embodiments, $R^A$ is methyl and fluoro and q is 2.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —OR$^2$. In some embodiments, $R^B$ is $C_1$-$C_6$ alkyl or $C_1$-$C_6$ hydroxyalkyl. In some embodiments, $R^B$ is methyl, ethyl, or hydroxymethyl. In some embodiments, p is 0 or 1. In some embodiments, p is 0. In some embodiments, p is 1.

In some embodiments, Z is monocyclic or bicyclic aryl. In some embodiments, Z is monocyclic or bicyclic heteroaryl. In some embodiments, Z is monocyclic or bicyclic heterocyclyl. In some embodiments, Z is monocyclic heteroaryl. In some embodiments, Z is selected from pyrazolyl, isoxazolyl, thiophenyl, thiazolyl, and pyridyl. In some embodiments, Z is substituted with 0, 1 or 2 occurrences of $R^C$. In some embodiments, Z is substituted with 0 or 1 occurrences of $R^C$.

In some embodiments, $R^C$ is independently selected from cyano, $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic heterocyclyl, monocyclic or bicyclic heterocyclylalkyl, —C(O)$R^2$, —OC(O)$R^2$, —C(O)O$R^2$, —N($R^2$)($R^2$), —C(O)—N($R^2$)($R^2$), and —O$R^2$. In some embodiments, $R^C$ is independently selected from cyano, $C_1$-$C_6$ alkyl, halo, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —N($R^2$)($R^2$), —C(O)—N($R^2$)($R^2$), and —O$R^2$. In some embodiments, each $R^C$ is independently selected from $C_1$-$C_6$ alkyl, halo, monocyclic or bicyclic heterocyclyl.

In some embodiments, $R^D$ is hydrogen, $C_1$-$C_6$ alkyl, $C_1$-$C_6$ alkoxy, $C_1$-$C_6$ haloalkyl, —N($R^2$)($R^2$), or cyano. In some embodiments, $R^D$ is hydrogen or —N($R^2$)($R^2$). In some embodiments, $R^D$ is hydrogen or —NH$_2$.

In some embodiments, $R^F$ is hydrogen or halo, e.g., chloro or fluoro. In some embodiments, $R^F$ is hydrogen. In some embodiments, $R^F$ is chloro or fluoro.

In some embodiments, L is selected from a bond, —C($R^2$)($R^2$))$_m$—, —($C_2$-$C_6$ alkenylene)-, —($C_1$-$C_6$ haloalkylene)-, —($C_1$-$C_6$ hydroxyalkylene)-, —S—, —S(O), —SO$_2$—, and —N($R^2$)—. In some embodiments, L is selected from a bond, —(C($R^2$)($R^2$))$_m$—, —S—, and —SO$_2$—. In some embodiments, L is —(C($R^2$)($R^2$))$_m$—. In some embodiments, L is a bond or CH$_2$. In some embodiments, L is —(C($R^2$)($R^2$))$_m$—, wherein each $R^2$ is independently selected from hydrogen, hydroxyl, —NR"R", $C_1$-$C_6$ alkyl, $C_1$-$C_6$ haloalkyl, $C_1$-$C_6$ hydroxyalkyl, and cycloalkyl; and m is 1.

In some embodiments, each $R^2$ is independently selected from hydrogen, hydroxyl, halo, —NR"R", $C_1$-$C_6$ alkyl, $C_1$-$C_6$ haloalkyl, $C_1$-$C_6$ hydroxyalkyl, cycloalkyl, wherein each of $C_1$-$C_6$ alkyl and cycloalkyl is independently substituted with 0-5 occurrences of $R^b$, or 2 $R^2$ together with the carbon or nitrogen atom to which they are attached form a cycloalkyl or heterocyclyl ring. In some embodiments, each $R^2$ is independently selected from halo, hydrogen, hydroxyl, —NR"R", $C_1$-$C_6$ alkyl wherein $C_1$-$C_6$ alkyl is independently substituted with 0-5 occurrences of $R^b$. In some embodiments, $R^b$ is independently hydrogen, halo or hydroxyl. In some embodiments, L is —NR"R". In some embodiments, R" is hydrogen or $C_1$-$C_6$ alkyl. In some embodiments, R" is hydrogen. In some embodiments, L is —S—. In some embodiments, L is —CH$_2$—.

In some embodiments, m is 0, 1 or 2. In some embodiments, m is 1. In some embodiments, m is 2.

In some embodiments, p is 0 or 1.

In some embodiments, q is 0, 1, 2 or 3. In some embodiments, q is 0. In some embodiments, q is 1. In some embodiments, q is 2. In some embodiments, q is 3.

In another embodiment, the invention features a compound of Formula III, or a pharmaceutically acceptable salt thereof, wherein:

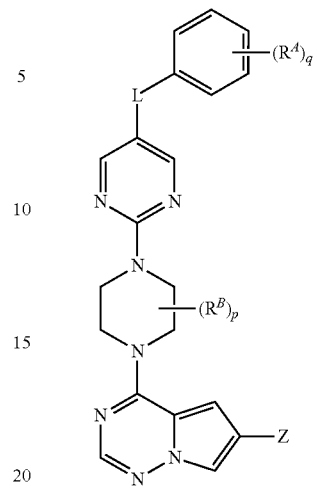

III

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from a bond, —(C($R^2$)($R^2$))$_m$—, —($C_2$-$C_6$ alkynylene)-, —($C_2$-$C_6$ alkenylene)-, —($C_1$-$C_6$ haloalkylene)-, —($C_1$-$C_6$ heteroalkylene)-, —($C_1$-$C_6$ hydroxyalkylene)-, —C(O)—, —O—, —S—, —S(O), —SO$_2$—, —N($R^2$)—, —O—($C_1$-$C_6$ alkylene)-, —($C_1$-$C_6$ alkylene)-O—, —N($R^2$)—CO—, —CO—N($R^2$)—, —($C_1$-$C_6$ alkylene)-N($R^2$)—, —N($R^2$)—($C_1$-$C_6$ alkylene)-, —N($R^2$)—CO—($C_1$-$C_6$ alkylene)-, —CO—N($R^2$)—($C_1$-$C_6$ alkylene)-, —N($R^2$)—SO$_2$—, —SO$_2$—N($R^2$)—, —N($R^2$)—SO$_2$—($C_1$-$C_6$ alkylene)-, and —SO$_2$—N($R^2$)—($C_1$-$C_6$ alkylene)-;

each $R^A$ and $R^B$ is independently selected from $C_1$-$C_6$ alkyl, $C_1$-$C_6$ cycloalkyl, $C_1$-$C_6$ heterocyclyl, halo, $C_1$-$C_6$ haloalkyl, $C_1$-$C_6$ hydroxyalkyl, $C_1$-$C_6$ heteroalkyl, monocyclic or bicyclic aralkyl, —N($R^2$)($R^2$), cyano, and —O$R^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^2$, —OC(O)$R^2$, —C(O)O$R^2$, —S$R^2$, —S(O)$_2$$R^2$, —S(O)$_2$—N($R^2$)($R^2$), —($C_1$-$C_6$ alkylene)-S(O)$_2$—N($R^2$)($R^2$), —N($R^2$)($R^2$), —C(O)—N($R^2$)($R^2$), —N($R^2$)($R^2$)—C(O)$R^2$, —($C_1$-$C_6$ alkylene)-N($R^2$)—C(O)$R^2$, —N$R^2$S(O)$_2$$R^2$, —P(O)($R^2$)($R^2$), and —O$R^2$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^2$ is independently selected from hydrogen, hydroxyl, halo, thiol, $C_1$-$C_6$ thioalkyl, —NR"R", $C_1$-$C_6$ alkyl, $C_1$-$C_6$ alkoxy, $C_1$-$C_6$ haloalkyl, $C_1$-$C_6$ hydroxyalkyl, cycloalkyl, cycloalkylalkyl, heterocyclyl, and heterocyclylalkyl, wherein each of $C_1$-$C_6$ alkyl, cycloalkyl and heterocyclyl is independently substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is hydrogen, hydroxyl, or $C_1$-$C_6$ alkyl;

each R" is hydrogen, $C_1$-$C_6$ alkyl, —C(O)—$C_1$-$C_6$ alkyl, —C(O)—NR'R'; —C(S)—NR'R'; and m, p, and q are each independently 0, 1, 2, 3, or 4.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —$OR^2$. In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, —$OR^2$. In some embodiments, $R^A$ is independently selected from $C_1$-$C_6$ alkyl and halo. In some embodiments, $R^A$ is independently selected from fluoro, chloro and methyl. In some embodiments, $R^A$ is halo. In some embodiments, $R^A$ is independently selected from fluoro and chloro. In some embodiments, $R^A$ is methyl. In some embodiments, $R^A$ is fluoro and q is 1, 2, or 3. In some embodiments, $R^A$ is chloro and fluoro and q is 2. In some embodiments, $R^A$ is methyl and fluoro and q is 2.

In some embodiments, Z is monocyclic or bicyclic aryl. In some embodiments, Z is monocyclic or bicyclic heteroaryl. In some embodiments, Z is monocyclic or bicyclic heterocyclyl. In some embodiments, Z is monocyclic heteroaryl. In some embodiments, Z is selected from pyrazolyl, isoxazolyl, thiophenyl, thiazolyl, and pyridyl. In some embodiments, Z is substituted with 0, 1 or 2 occurrences of $R^C$. In some embodiments, Z is substituted with 0 or 1 occurrences of $R^C$.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —$OR^2$. In some embodiments, $R^B$ is $C_1$-$C_6$ alkyl or $C_1$-$C_6$ hydroxyalkyl. In some embodiments, $R^B$ is methyl, ethyl, or hydroxymethyl. In some embodiments, p is 0 or 1. In some embodiments, p is 0. In some embodiments, p is 1.

In some embodiments, $R^C$ is independently selected from cyano, $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic heterocyclyl, monocyclic or bicyclic heterocyclylalkyl, —C(O)$R^2$, —OC(O)$R^2$, —C(O)O$R^2$, —N($R^2$)($R^2$), —C(O)—N($R^2$)($R^2$), and —$OR^2$. In some embodiments, $R^C$ is independently selected from cyano, $C_1$-$C_6$ alkyl, halo, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —N($R^2$)($R^2$), —C(O)—N($R^2$)($R^2$), and —$OR^2$. In some embodiments, each $R^C$ is independently selected from $C_1$-$C_6$ alkyl, halo, monocyclic or bicyclic heterocyclyl.

In some embodiments, L is selected from a bond, —(C($R^2$)($R^2$))$_m$—, —($C_2$-$C_6$ alkenylene)-, —($C_1$-$C_6$ haloalkylene)-, —($C_1$-$C_6$ hydroxyalkylene)-, —S—, —S(O), —$SO_2$—, and —N($R^2$)—. In some embodiments, L is selected from a bond, —(C($R^2$)($R^2$))$_m$—, —S—, and —$SO_2$—. In some embodiments, L is —(C($R^2$)($R^2$))$_m$—. In some embodiments, L is a bond or $CH_2$. In some embodiments, L is —(C($R^2$)($R^2$))$_m$—, wherein each $R^2$ is independently selected from hydrogen, hydroxyl, —NR"R", $C_1$-$C_6$ alkyl, $C_1$-$C_6$ haloalkyl, $C_1$-$C_6$ hydroxyalkyl, and cycloalkyl; and m is 1.

In some embodiments, q is 0, 1, 2 or 3. In some embodiments, q is 1, 2 or 3.

The invention also features pharmaceutical compositions comprising a pharmaceutically acceptable carrier and any compound of Formulas I-III.

The table below shows the structures of compounds described herein.

| Compound Number | Structure |
|---|---|
| 1 | 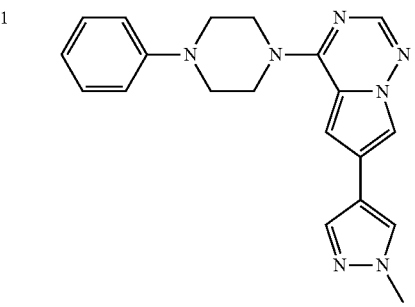 |
| 2 | 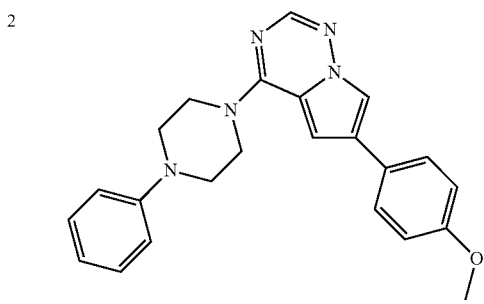 |

-continued
| Compound Number | Structure |
|---|---|
| 4 | 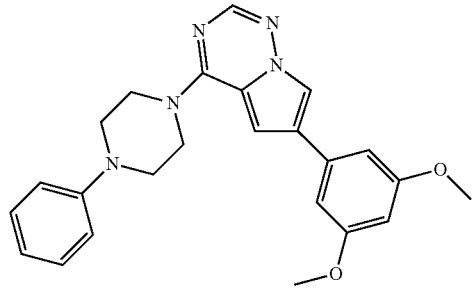 [SMILES: COc1cc(OC)cc(-c2cc3c(N4CCN(c5ccccc5)CC4)ncnn3c2)c1] |
| 6 | 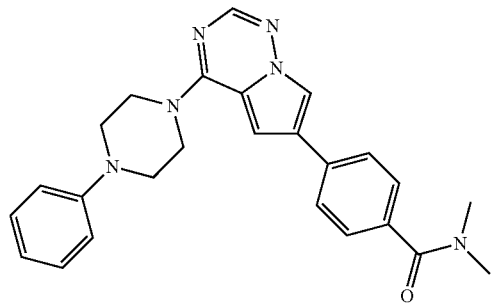 [SMILES: CN(C)C(=O)c1ccc(-c2cc3c(N4CCN(c5ccccc5)CC4)ncnn3c2)cc1] |
| 7 | 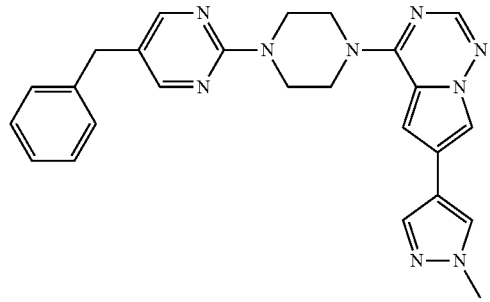 [SMILES: Cn1cc(-c2cc3c(N4CCN(c5ncc(Cc6ccccc6)cn5)CC4)ncnn3c2)cn1] |
| 8 | 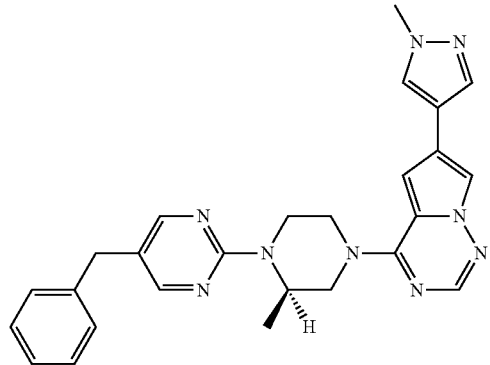 [SMILES: C[C@@H]1CN(c2ncnn3cc(-c4cnn(C)c4)cc23)CCN1c1ncc(Cc2ccccc2)cn1] |

-continued
| Compound Number | Structure |
|---|---|
| 9 | 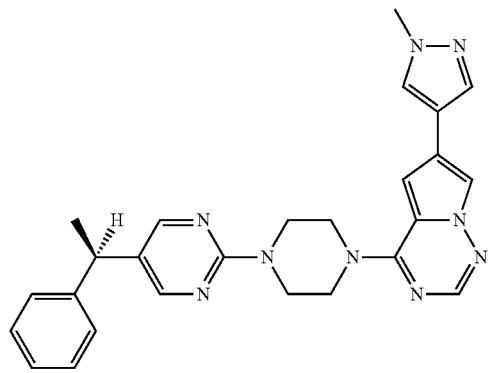 [SMILES: C[C@H](c1ccccc1)c1cnc(N2CCN(c3ncnn4cc(-c5cnn(C)c5)cc34)CC2)nc1] |
| 10 | 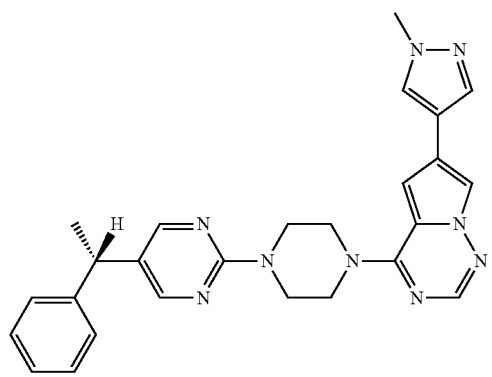 [SMILES: C[C@@H](c1ccccc1)c1cnc(N2CCN(c3ncnn4cc(-c5cnn(C)c5)cc34)CC2)nc1] |
| 11 | 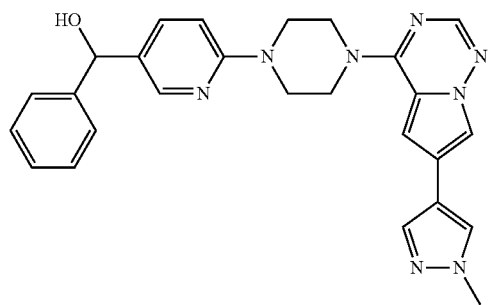 [SMILES: Cn1cc(-c2cc3c(N4CCN(c5ccc(C(O)c6ccccc6)cn5)CC4)ncnn3c2)cn1] |
| 12 | 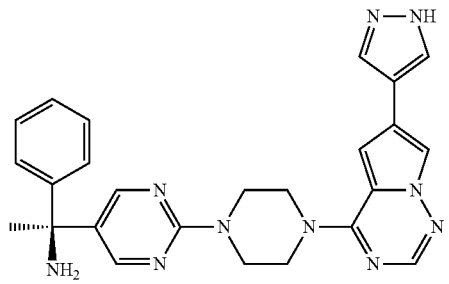 [SMILES: C[C@](N)(c1ccccc1)c1cnc(N2CCN(c3ncnn4cc(-c5cn[nH]c5)cc34)CC2)nc1] |

-continued
| Compound Number | Structure |
|---|---|
| 13 | 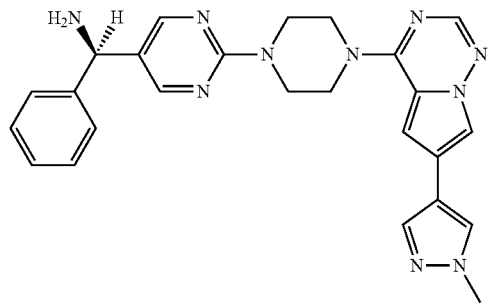 [SMILES: Cn1cc(-c2cc3c(N4CCN(c5ncc([C@H](N)c6ccccc6)cn5)CC4)ncnn3c2)cn1] |
| 14 | 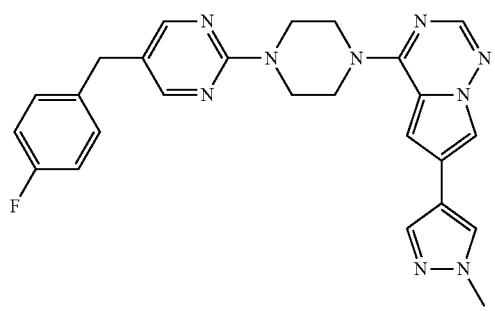 |
| 15 | 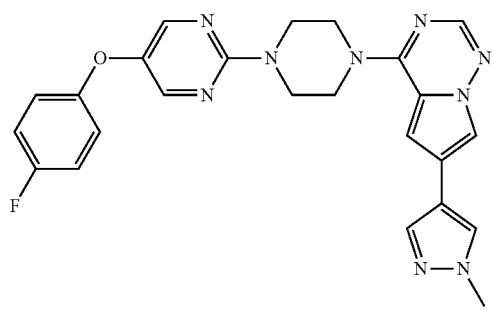 [SMILES: Cn1cc(-c2cc3c(N4CCN(c5ncc(Cc6ccc(F)cc6)cn5)CC4)ncnn3c2)cn1] |
| 16 | 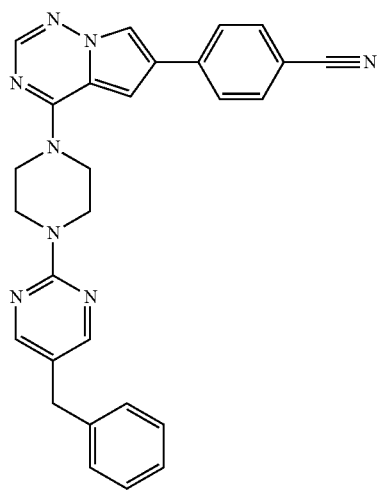 [SMILES: N#Cc1ccc(-c2cc3c(N4CCN(c5ncc(Cc6ccccc6)cn5)CC4)ncnn3c2)cc1] |

-continued
| Compound Number | Structure |
|---|---|
| 17 | 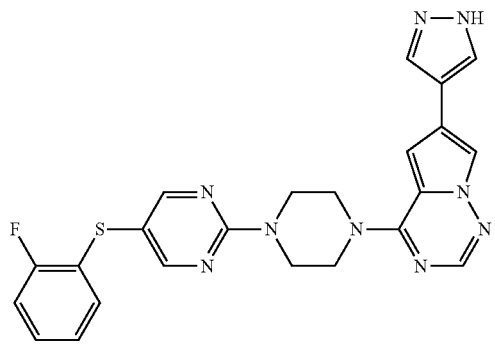 [SMILES: Fc1ccccc1Sc1cnc(N2CCN(c3ncnn4cc(-c5cn[nH]c5)cc34)CC2)nc1] |
| 18 | 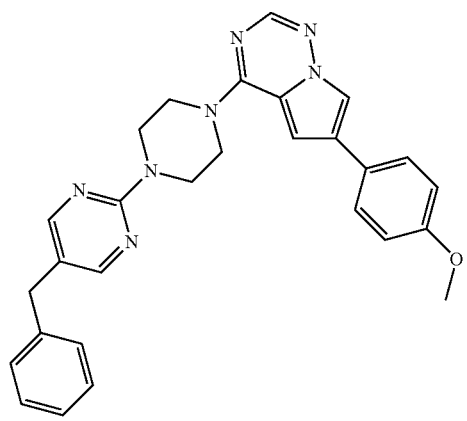 [SMILES: COc1ccc(-c2cc3c(N4CCN(c5ncc(Cc6ccccc6)cn5)CC4)ncnn3c2)cc1] |
| 19 | 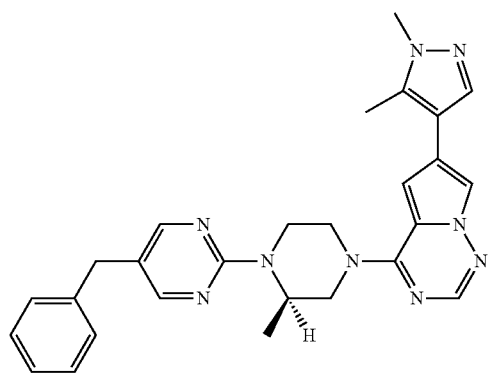 [SMILES: Cc1c(-c2cc3c(N4CCN(c5ncc(Cc6ccccc6)cn5)[C@H](C)C4)ncnn3c2)cnn1C] |
| 20 | 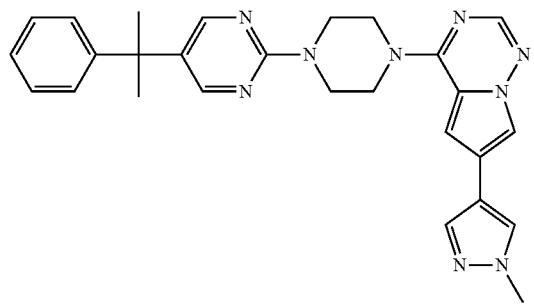 [SMILES: Cn1cc(-c2cc3c(N4CCN(c5ncc(C(C)(C)c6ccccc6)cn5)CC4)ncnn3c2)cn1] |

-continued
| Compound Number | Structure |
|---|---|
| 21 | 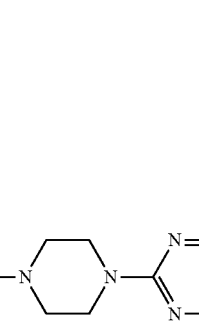 |
| 22 | 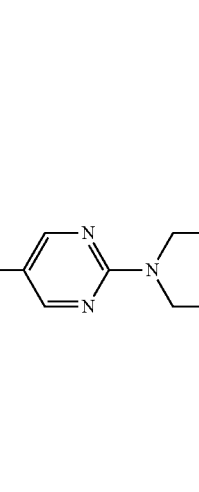 |
| 23 | 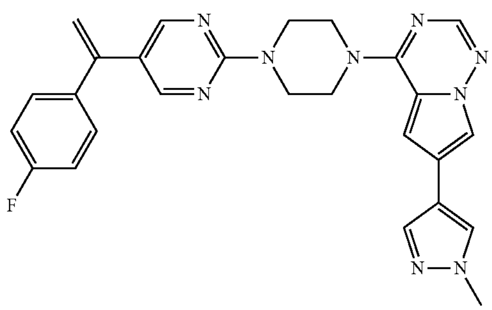 [SMILES: C=C(c1ccc(F)cc1)c1cnc(N2CCN(c3ncnn4cc(-c5cnn(C)c5)cc34)CC2)nc1] |
| 24 | 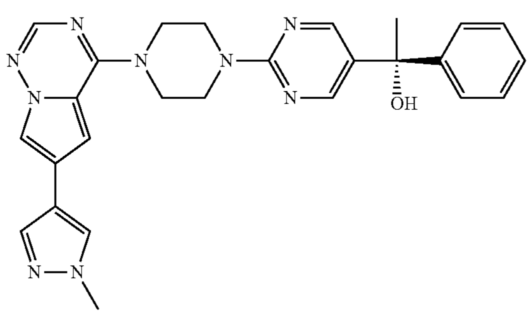 [SMILES: Cn1cc(-c2cc3c(N4CCN(c5ncc([C@](C)(O)c6ccccc6)cn5)CC4)ncnn3c2)cn1] |
| 25 | 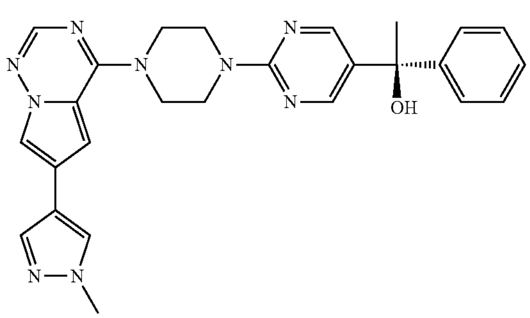 |

-continued
| Compound Number | Structure |
|---|---|
| 26 | 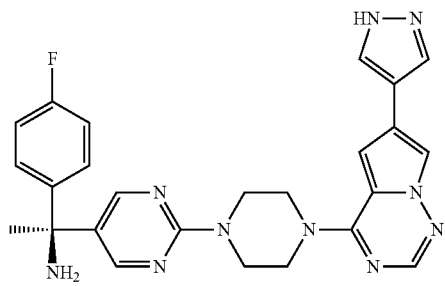 [SMILES: C[C@](N)(c1ccc(F)cc1)c1cnc(N2CCN(c3ncnn4cc(-c5cn[nH]c5)cc34)CC2)nc1] |
| 27 | 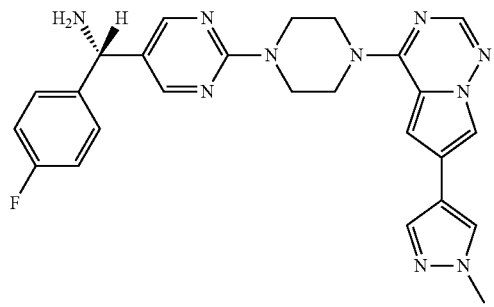 |
| 28 | 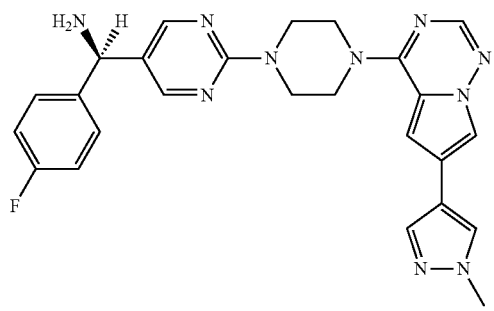 [SMILES: Cn1cc(-c2cc3c(N4CCN(c5ncc([C@H](N)c6ccc(F)cc6)cn5)CC4)ncnn3c2)cn1] |
| 29 | 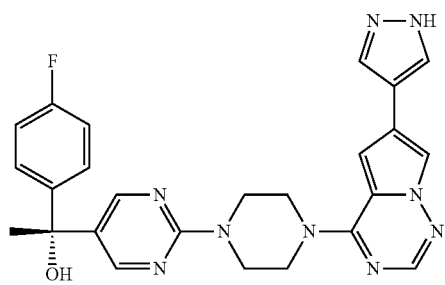 [SMILES: C[C@@](O)(c1ccc(F)cc1)c1cnc(N2CCN(c3ncnn4cc(-c5cn[nH]c5)cc34)CC2)nc1] |
| 30 | 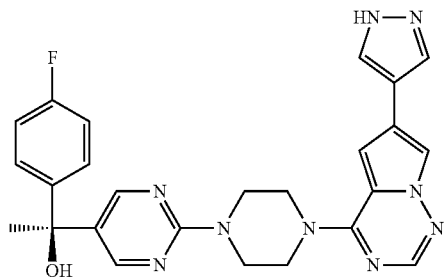 [SMILES: C[C@](O)(c1ccc(F)cc1)c1cnc(N2CCN(c3ncnn4cc(-c5cn[nH]c5)cc34)CC2)nc1] |

-continued
| Compound Number | Structure |
|---|---|
| 31 | 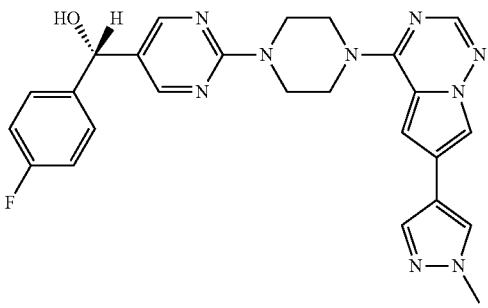 [SMILES: Cn1cc(-c2cc3c(N4CCN(c5ncc([C@@H](O)c6ccc(F)cc6)cn5)CC4)ncnn3c2)cn1] |
| 32 | 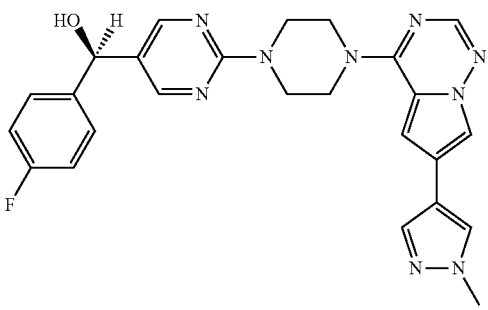 [SMILES: Cn1cc(-c2cc3c(N4CCN(c5ncc([C@H](O)c6ccc(F)cc6)cn5)CC4)ncnn3c2)cn1] |
| 33 | 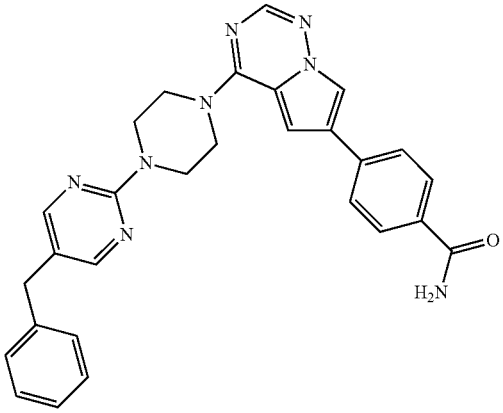 [SMILES: NC(=O)c1ccc(-c2cc3c(N4CCN(c5ncc(Cc6ccccc6)cn5)CC4)ncnn3c2)cc1] |
| 34 | 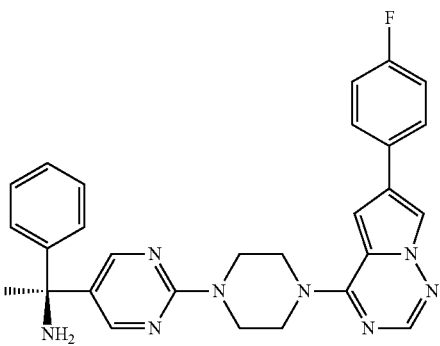 [SMILES: C[C@](N)(c1ccccc1)c1cnc(N2CCN(c3ncnn4cc(-c5ccc(F)cc5)cc34)CC2)nc1] |

-continued
| Compound Number | Structure |
|---|---|
| 35 | 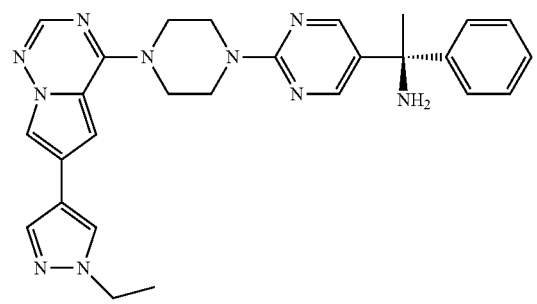 [SMILES: CCn1cc(-c2cc3c(N4CCN(c5ncc([C@@](C)(N)c6ccccc6)cn5)CC4)ncnn3c2)cn1] |
| 36 | 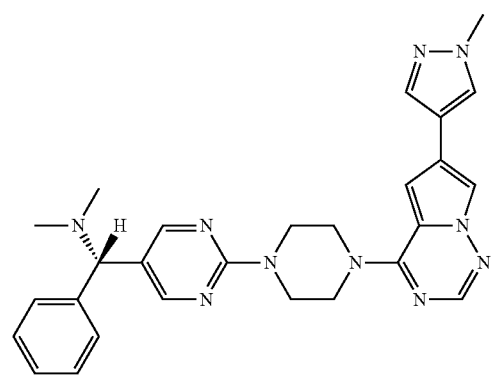 [SMILES: CN(C)[C@@H](c1ccccc1)c1cnc(N2CCN(c3ncnn4cc(-c5cnn(C)c5)cc34)CC2)nc1] |
| 37 | 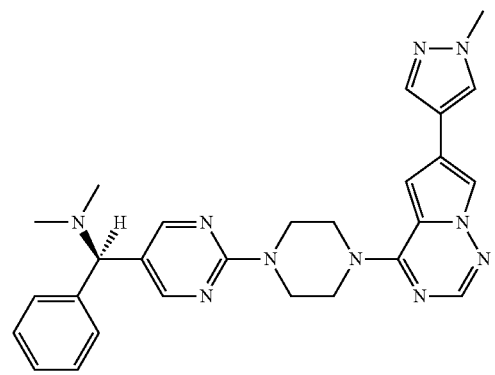 [SMILES: CN(C)[C@H](c1ccccc1)c1cnc(N2CCN(c3ncnn4cc(-c5cnn(C)c5)cc34)CC2)nc1] |
| 38 | 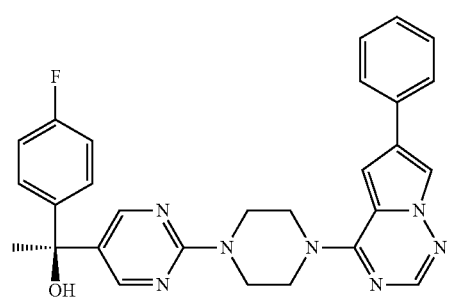 [SMILES: C[C@](O)(c1ccc(F)cc1)c1cnc(N2CCN(c3ncnn4cc(-c5ccccc5)cc34)CC2)nc1] |

-continued
| Compound Number | Structure |
|---|---|
| 39 | 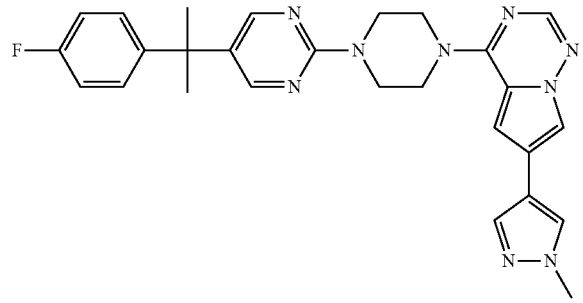 [SMILES: Cn1cc(-c2cc3c(N4CCN(c5ncc(C(C)(C)c6ccc(F)cc6)cn5)CC4)ncnn3c2)cn1] |
| 40 | 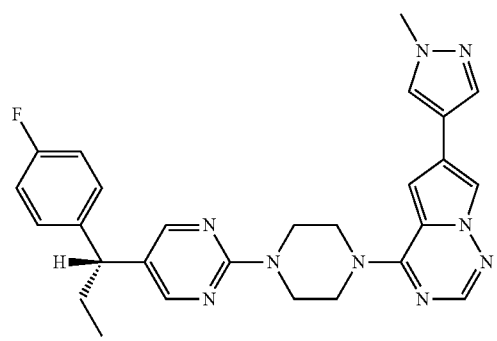 [SMILES: CC[C@H](c1ccc(F)cc1)c1cnc(N2CCN(c3ncnn4cc(-c5cnn(C)c5)cc34)CC2)nc1] |
| 41 | 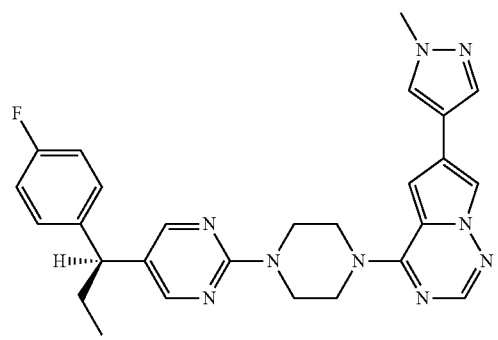 [SMILES: CC[C@@H](c1ccc(F)cc1)c1cnc(N2CCN(c3ncnn4cc(-c5cnn(C)c5)cc34)CC2)nc1] |
| 42 | 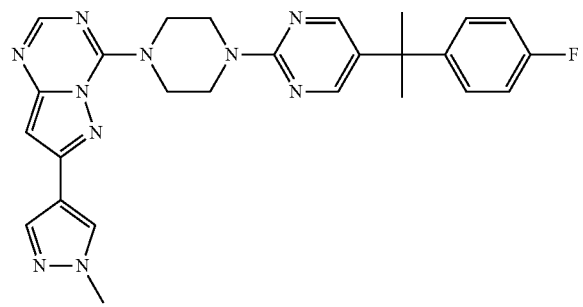 [SMILES: Cn1cc(-c2cc3ncnc(N4CCN(c5ncc(C(C)(C)c6ccc(F)cc6)cn5)CC4)n3n2)cn1] |

| Compound Number | Structure |
|---|---|
| 43 | *(structure)* |
| 44 | *(structure)* |
| 45 | *(structure)* |
| 46 | *(structure)* |
| 47 | *(structure)* |

| Compound Number | Structure |
|---|---|
| 48 | 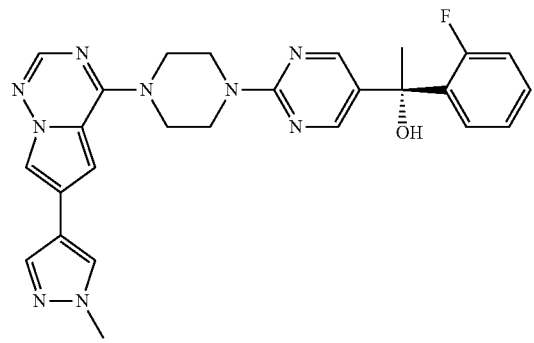 [SMILES: Cn1cc(-c2cc3c(N4CCN(c5ncc([C@](C)(O)c6ccccc6F)cn5)CC4)ncnn3c2)cn1] |
| 49 | 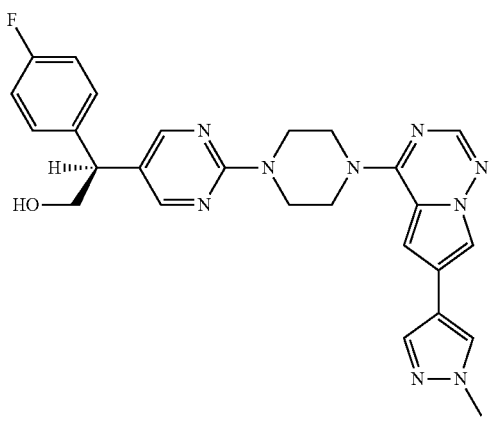 [SMILES: Cn1cc(-c2cc3c(N4CCN(c5ncc([C@@H](CO)c6ccc(F)cc6)cn5)CC4)ncnn3c2)cn1] |
| 50 | 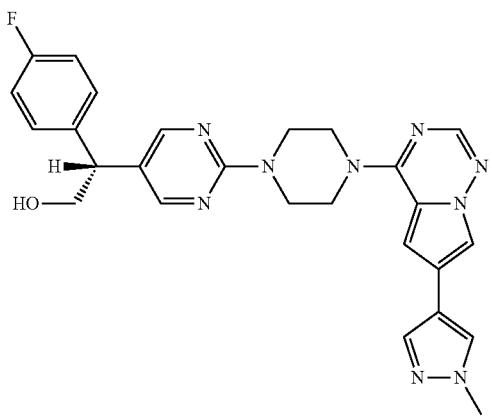 [SMILES: Cn1cc(-c2cc3c(N4CCN(c5ncc([C@H](CO)c6ccc(F)cc6)cn5)CC4)ncnn3c2)cn1] |
| 51 | 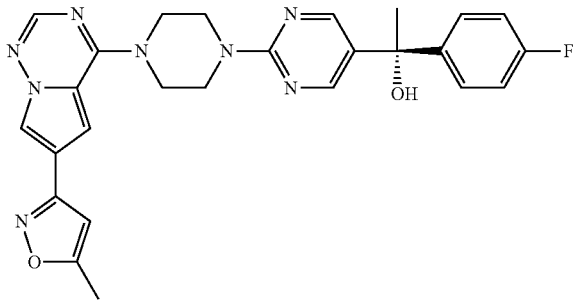 [SMILES: Cc1cc(-c2cc3c(N4CCN(c5ncc([C@](C)(O)c6ccc(F)cc6)cn5)CC4)ncnn3c2)no1] |

| Compound Number | Structure |
|---|---|
| 52 | 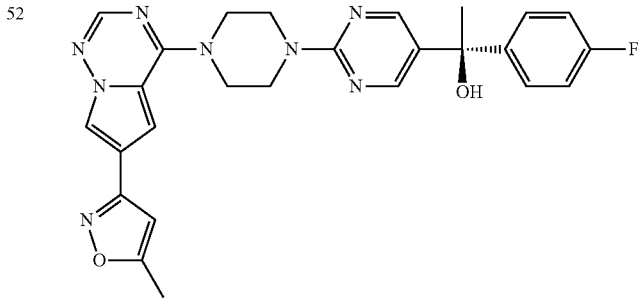 |
| 53 | 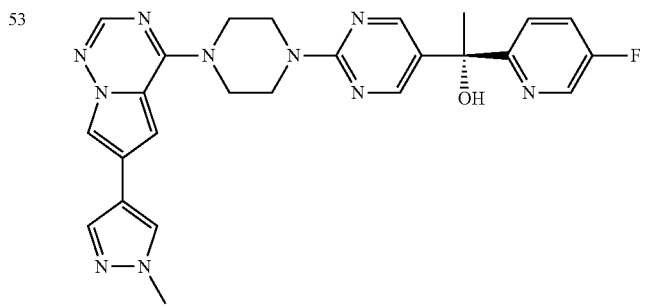 |
| 54 | 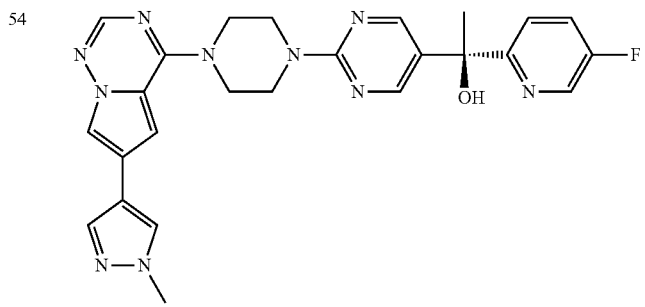 |
| 55 | 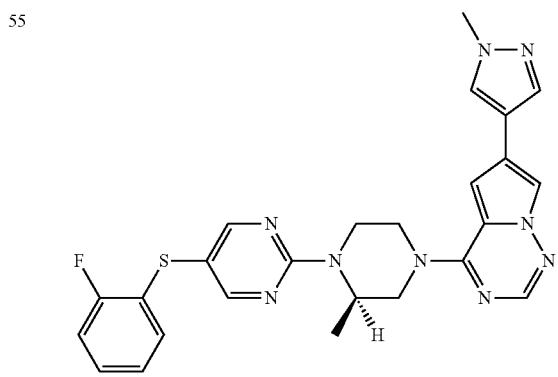 |

-continued
| Compound Number | Structure |
|---|---|
| 56 | 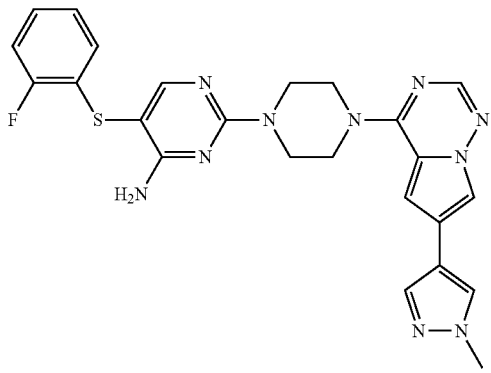 [SMILES: Cn1cc(-c2cc3c(N4CCN(c5ncc(Sc6ccccc6F)c(N)n5)CC4)ncnn3c2)cn1] |
| 57 | 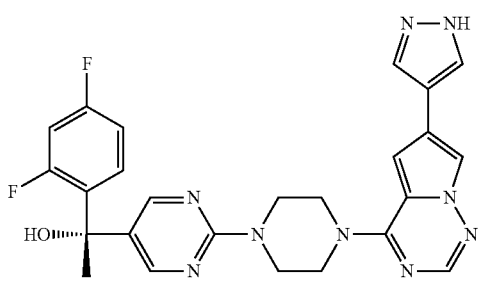 [SMILES: C[C@](O)(c1cnc(N2CCN(c3ncnn4cc(-c5cn[nH]c5)cc34)CC2)nc1)c1ccc(F)cc1F] |
| 58 | 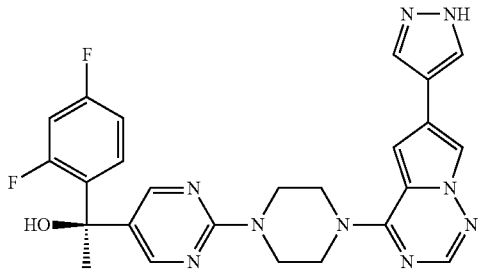 [SMILES: C[C@@](O)(c1cnc(N2CCN(c3ncnn4cc(-c5cn[nH]c5)cc34)CC2)nc1)c1ccc(F)cc1F] |
| 59 | 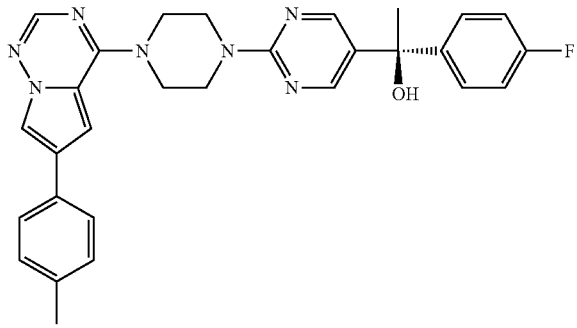 [SMILES: Cc1ccc(-c2cc3c(N4CCN(c5ncc([C@@](C)(O)c6ccc(F)cc6)cn5)CC4)ncnn3c2)cn1] |

| Compound Number | Structure |
|---|---|
| 60 | 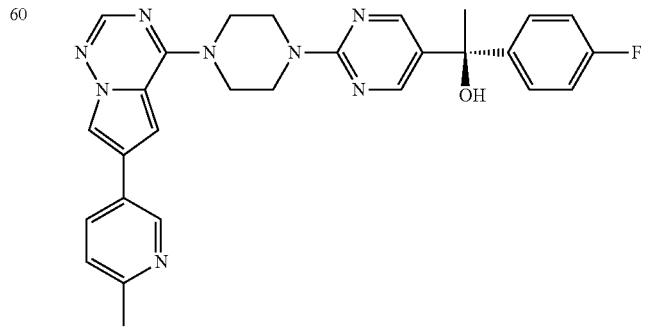 |
| 61 | 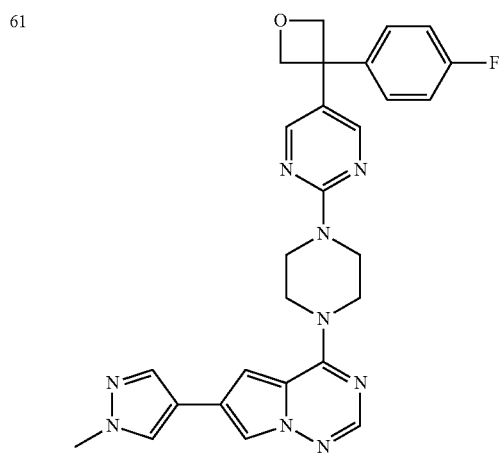 |
| 62 | 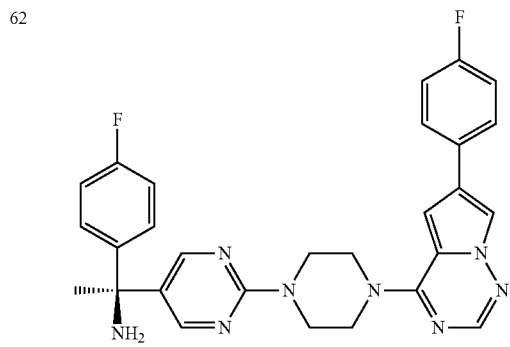 |
| 63 | 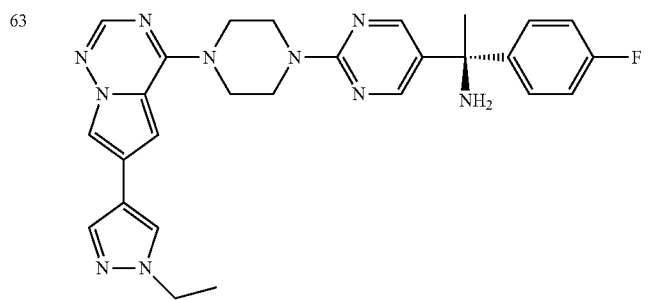 |

| Compound Number | Structure |
|---|---|
| 64 | 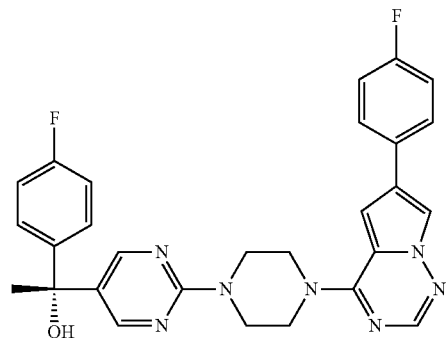 [SMILES: C[C@@](O)(c1ccc(F)cc1)c1cnc(N2CCN(c3ncnn4cc(-c5ccc(F)cc5)cc34)CC2)nc1] |
| 65 | 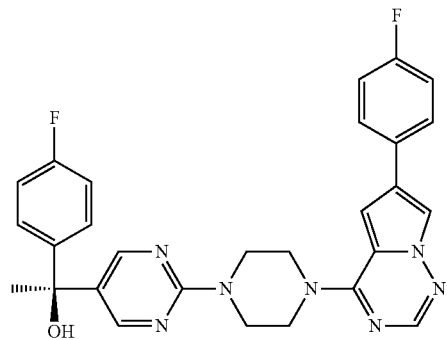 [SMILES: C[C@](O)(c1ccc(F)cc1)c1cnc(N2CCN(c3ncnn4cc(-c5ccc(F)cc5)cc34)CC2)nc1] |
| 66 | 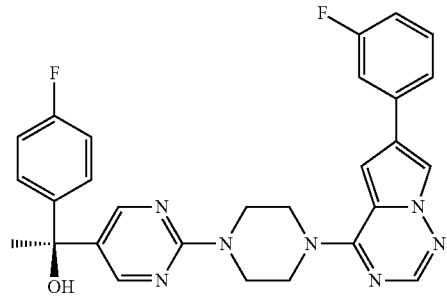 [SMILES: C[C@](O)(c1ccc(F)cc1)c1cnc(N2CCN(c3ncnn4cc(-c5cccc(F)c5)cc34)CC2)nc1] |
| 67 | 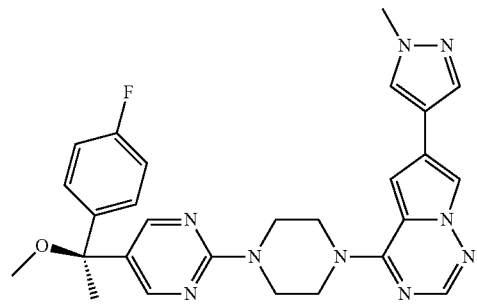 [SMILES: CO[C@@](C)(c1ccc(F)cc1)c1cnc(N2CCN(c3ncnn4cc(-c5cnn(C)c5)cc34)CC2)nc1] |

-continued
| Compound Number | Structure |
|---|---|
| 68 | 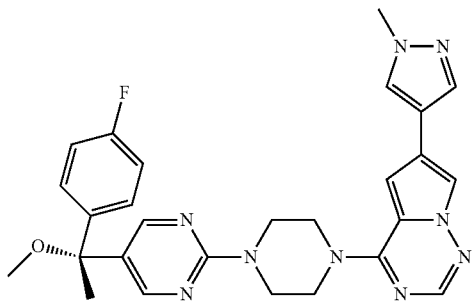 [SMILES: CO[C@](C)(c1ccc(F)cc1)c1cnc(N2CCN(c3ncnn4cc(-c5cnn(C)c5)cc34)CC2)nc1] |
| 69 | 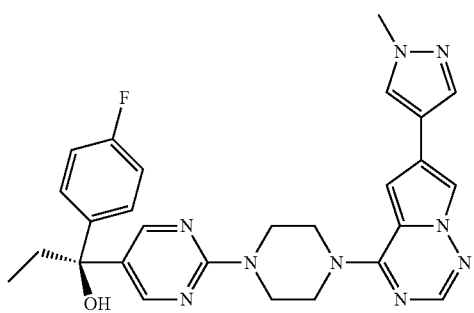 [SMILES: CC[C@](O)(c1ccc(F)cc1)c1cnc(N2CCN(c3ncnn4cc(-c5cnn(C)c5)cc34)CC2)nc1] |
| 70 | 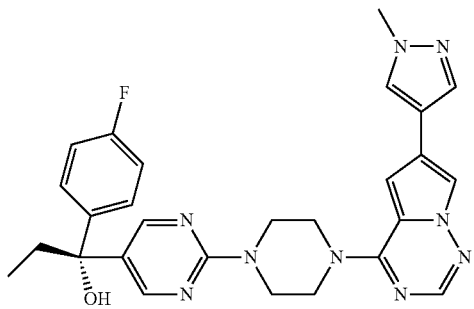 [SMILES: CC[C@@](O)(c1ccc(F)cc1)c1cnc(N2CCN(c3ncnn4cc(-c5cnn(C)c5)cc34)CC2)nc1] |
| 71 | 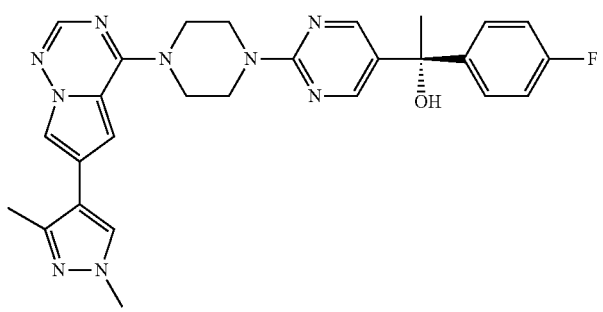 [SMILES: Cc1nn(C)cc1-c1cc2c(N3CCN(c4ncc([C@](C)(O)c5ccc(F)cc5)cn4)CC3)ncnn2c1] |
| 72 | 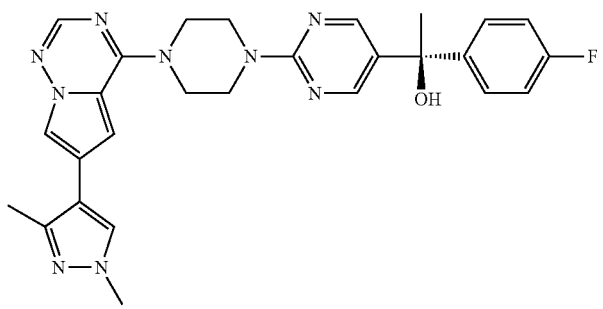 [SMILES: Cc1nn(C)cc1-c1cc2c(N3CCN(c4ncc([C@@](C)(O)c5ccc(F)cc5)cn4)CC3)ncnn2c1] |

-continued
| Compound Number | Structure |
|---|---|
| 73 | 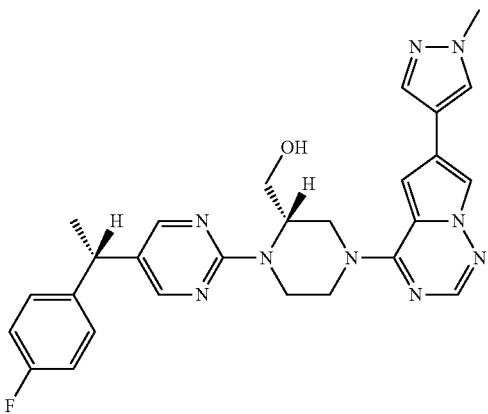 [SMILES: C[C@@H](c1ccc(F)cc1)c1cnc(N2CCN(c3ncnn4cc(-c5cnn(C)c5)cc34)C[C@H]2CO)nc1] |
| 74 | 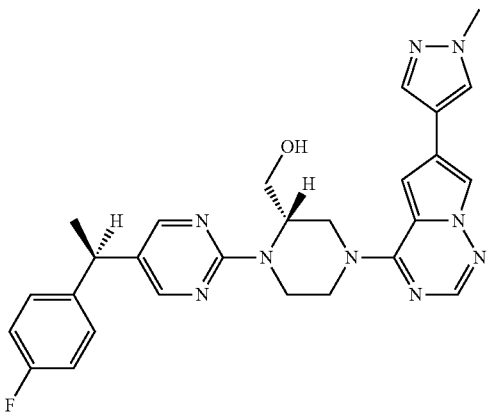 [SMILES: C[C@H](c1ccc(F)cc1)c1cnc(N2CCN(c3ncnn4cc(-c5cnn(C)c5)cc34)C[C@H]2CO)nc1] |
| 75 | 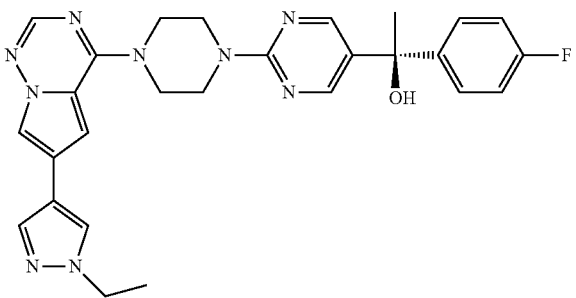 [SMILES: CCn1cc(-c2cc3c(N4CCN(c5ncc([C@@](C)(O)c6ccc(F)cc6)cn5)CC4)ncnn3c2)cn1] |
| 76 | 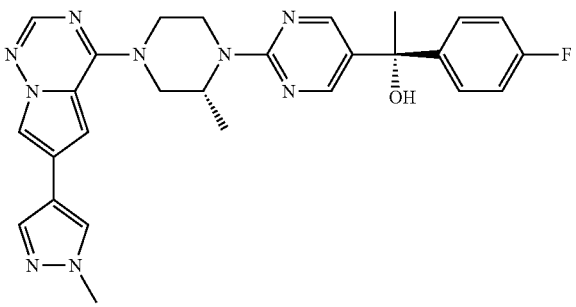 [SMILES: C[C@@H]1CN(c2ncnn3cc(-c4cnn(C)c4)cc23)CCN1c1ncc([C@](C)(O)c2ccc(F)cc2)cn1] |

-continued
| Compound Number | Structure |
|---|---|
| 77 | 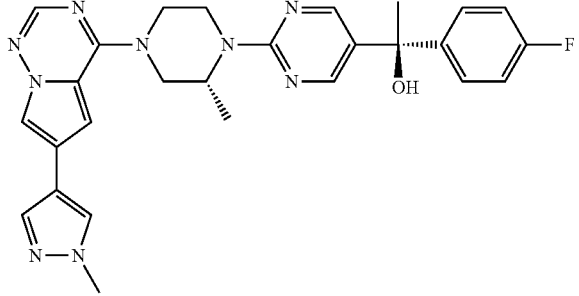 [SMILES: C[C@@H]1CN(c2ncnn3cc(-c4cnn(C)c4)cc23)CCN1c1ncc([C@@](C)(O)c2ccc(F)cc2)cn1] |
| 78 | 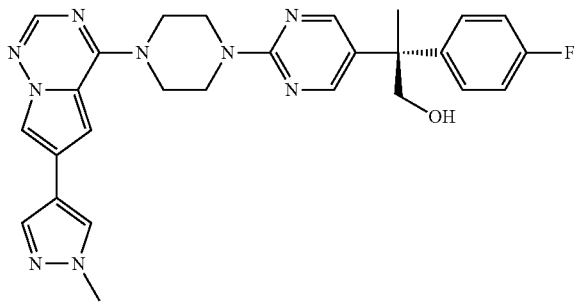 [SMILES: Cn1cc(-c2cc3c(N4CCN(c5ncc([C@@](C)(CO)c6ccc(F)cc6)cn5)CC4)ncnn3c2)cn1] |
| 79 | 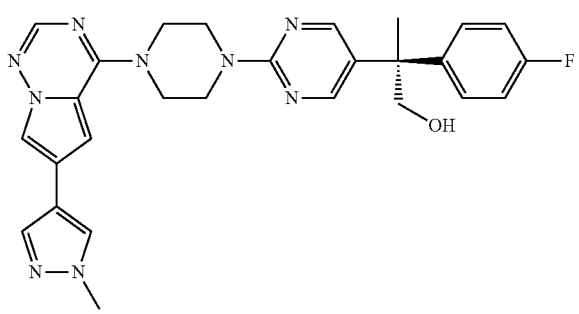 [SMILES: Cn1cc(-c2cc3c(N4CCN(c5ncc([C@](C)(CO)c6ccc(F)cc6)cn5)CC4)ncnn3c2)cn1] |
| 80 | 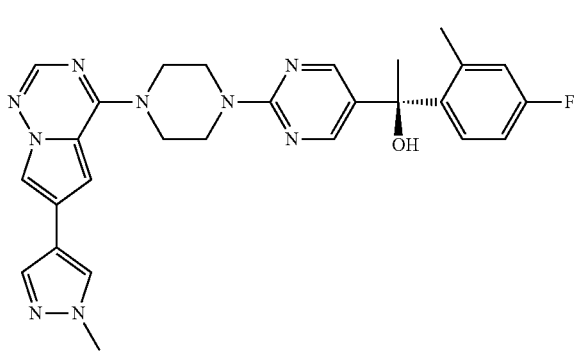 [SMILES: Cc1cc(F)ccc1[C@](C)(O)c1cnc(N2CCN(c3ncnn4cc(-c5cnn(C)c5)cc34)CC2)nc1] |
| 81 | 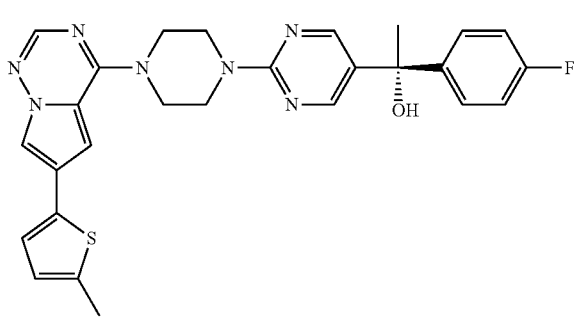 [SMILES: Cc1ccc(-c2cc3c(N4CCN(c5ncc([C@](C)(O)c6ccc(F)cc6)cn5)CC4)ncnn3c2)s1] |

-continued
| Compound Number | Structure |
|---|---|
| 82 | 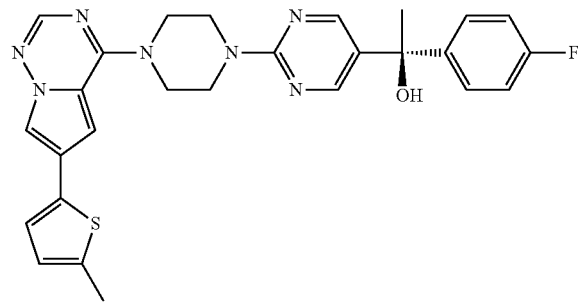 [SMILES: Cc1ccc(-c2cc3c(N4CCN(c5ncc([C@@](C)(O)c6ccc(F)cc6)cn5)CC4)ncnn3c2)s1] |
| 83 | 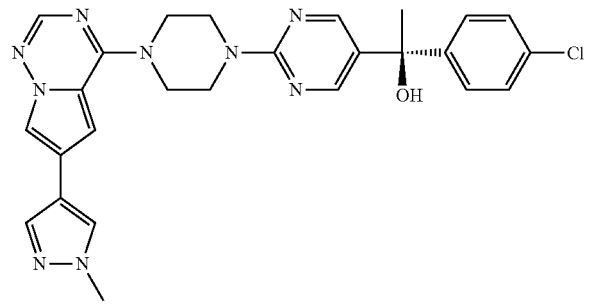 [SMILES: Cn1cc(-c2cc3c(N4CCN(c5ncc([C@@](C)(O)c6ccc(Cl)cc6)cn5)CC4)ncnn3c2)cn1] |
| 84 | 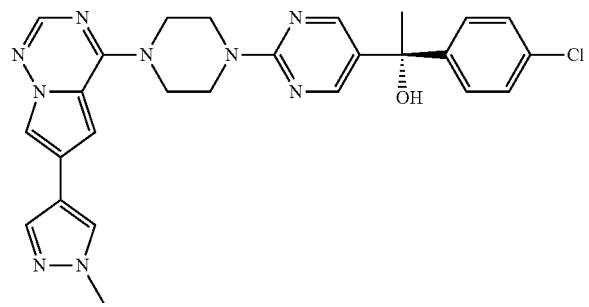 [SMILES: Cn1cc(-c2cc3c(N4CCN(c5ncc([C@](C)(O)c6ccc(Cl)cc6)cn5)CC4)ncnn3c2)cn1] |
| 85 | 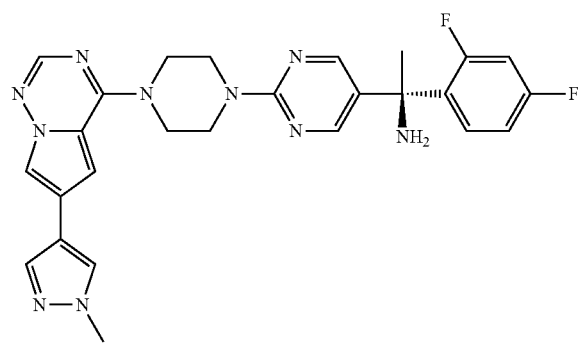 |

-continued
| Compound Number | Structure |
|---|---|
| 86 | 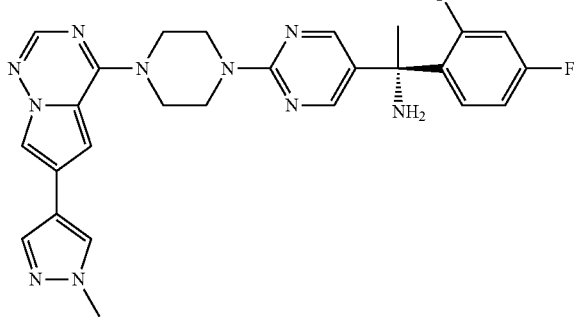 |
| 87 | 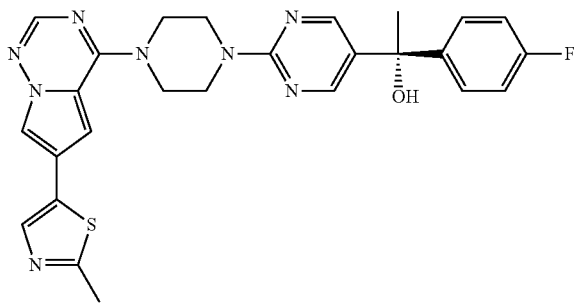 [SMILES: Cc1ncc(-c2cc3c(N4CCN(c5ncc([C@](C)(O)c6ccc(F)cc6)cn5)CC4)ncnn3c2)s1] |
| 88 | 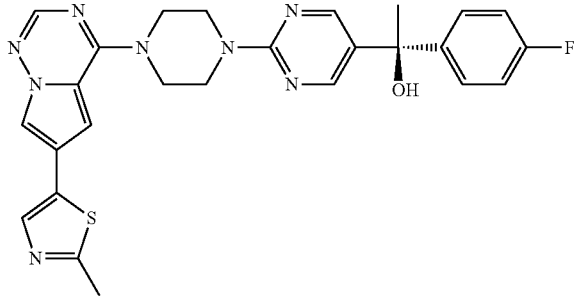 |
| 89 | 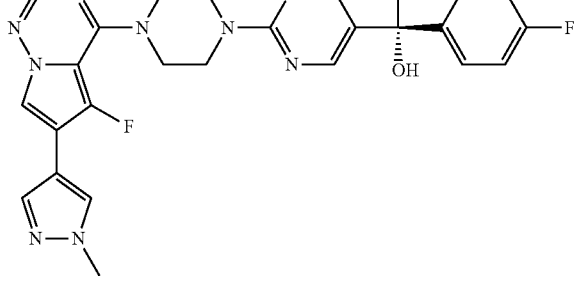 |
| 90 | 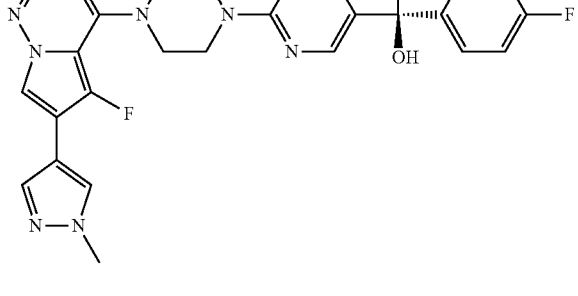 |

| Compound Number | Structure |
|---|---|
| 91 | 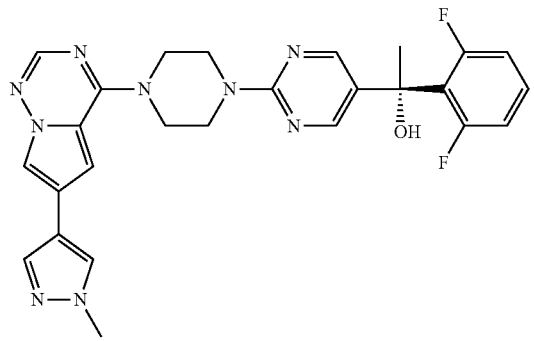 |
| 92 | 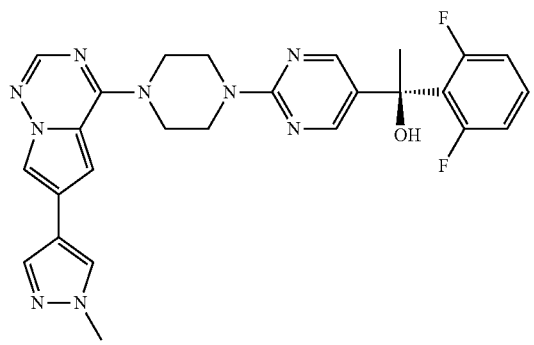 [SMILES: Cn1cc(-c2cc3c(N4CCN(c5ncc([C@@](C)(O)c6c(F)cccc6F)cn5)CC4)ncnn3c2)cn1] |
| 93 | 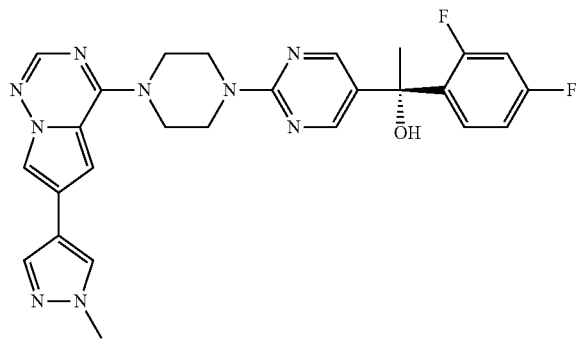 |
| 95 | 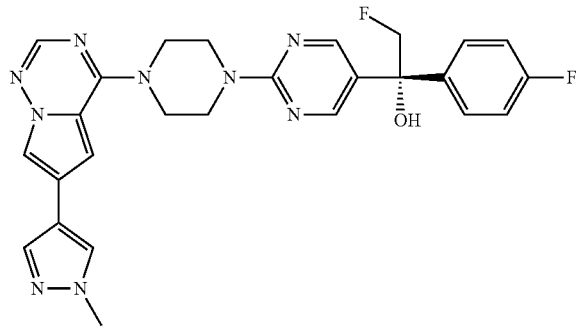 [SMILES: Cn1cc(-c2cc3c(N4CCN(c5ncc([C@@](O)(CF)c6ccc(F)cc6)cn5)CC4)ncnn3c2)cn1] |

-continued
| Compound Number | Structure |
|---|---|
| 96 | 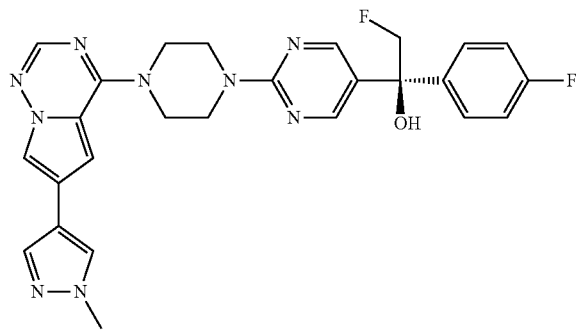 |
| 97 | 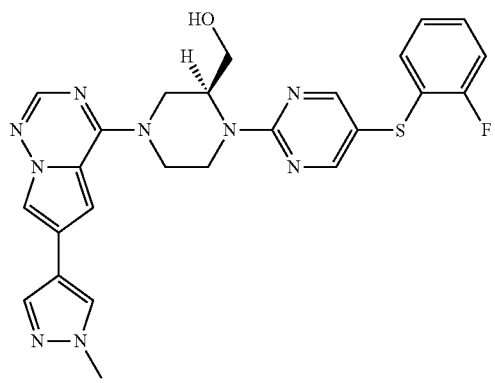 [SMILES: Cn1cc(-c2cc3c(N4CCN(c5ncc(Sc6ccccc6F)cn5)[C@H](CO)C4)ncnn3c2)cn1] |
| 94 | 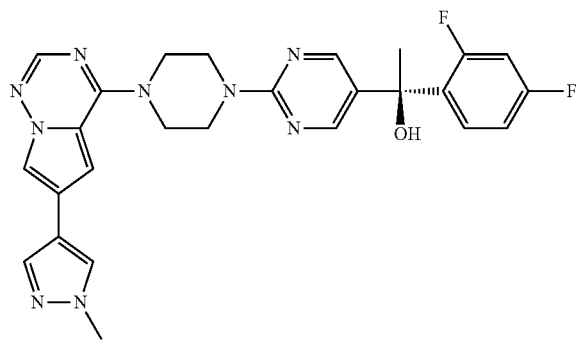 [SMILES: Cn1cc(-c2cc3c(N4CCN(c5ncc([C@@](C)(O)c6ccc(F)cc6F)cn5)CC4)ncnn3c2)cn1] |
| 98 | 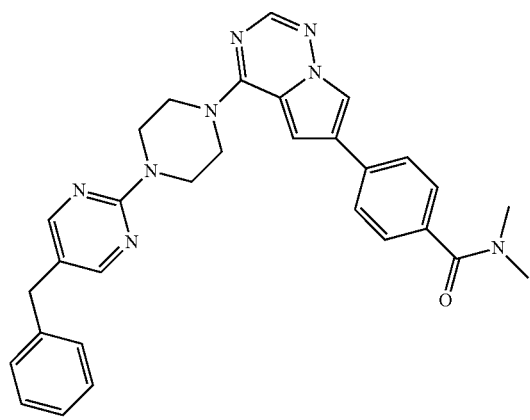 [SMILES: CN(C)C(=O)c1ccc(-c2cc3c(N4CCN(c5ncc(Cc6ccccc6)cn5)CC4)ncnn3c2)cc1] |

-continued
| Compound Number | Structure |
|---|---|
| 99 | 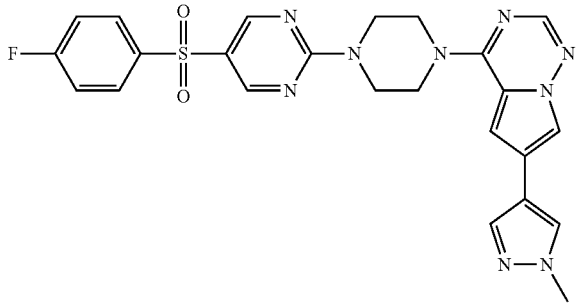 [SMILES: Cn1cc(-c2cc3c(N4CCN(c5ncc(S(=O)(=O)c6ccc(F)cc6)cn5)CC4)ncnn3c2)cn1] |
| 100 | 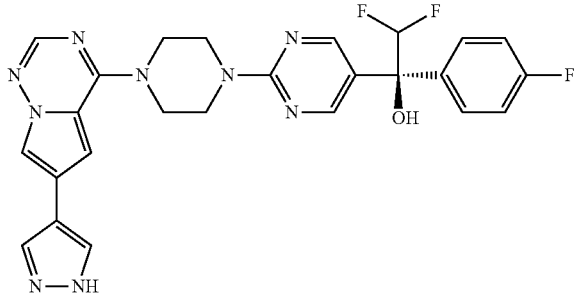 [SMILES: O[C@@](c1ccc(F)cc1)(c1cnc(N2CCN(c3ncnn4cc(-c5cn[nH]c5)cc34)CC2)nc1)C(F)F] |
| 101 | 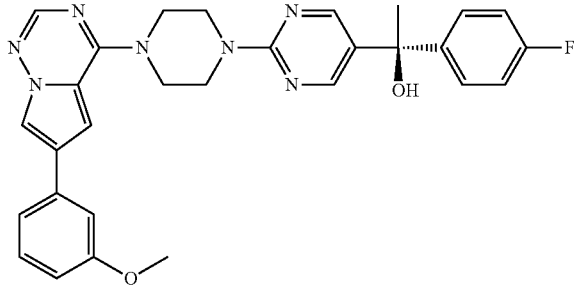 [SMILES: COc1cccc(-c2cc3c(N4CCN(c5ncc([C@@](C)(O)c6ccc(F)cc6)cn5)CC4)ncnn3c2)c1] |
| 102 | 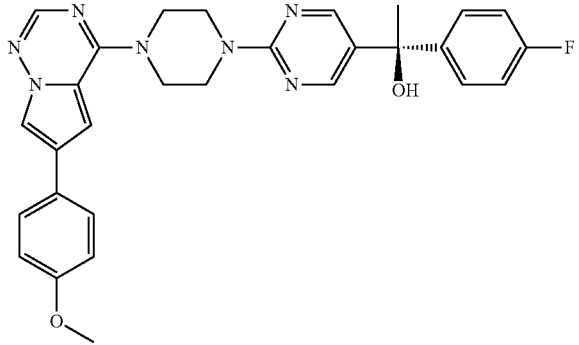 [SMILES: COc1ccc(-c2cc3c(N4CCN(c5ncc([C@@](C)(O)c6ccc(F)cc6)cn5)CC4)ncnn3c2)cc1] |

| Compound Number | Structure |
|---|---|
| 103 | 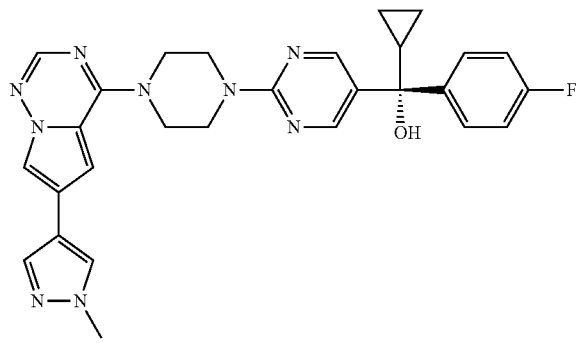 [SMILES: Cn1cc(-c2cc3c(N4CCN(c5ncc([C@](O)(c6ccc(F)cc6)C6CC6)cn5)CC4)ncnn3c2)cn1] |
| 104 | 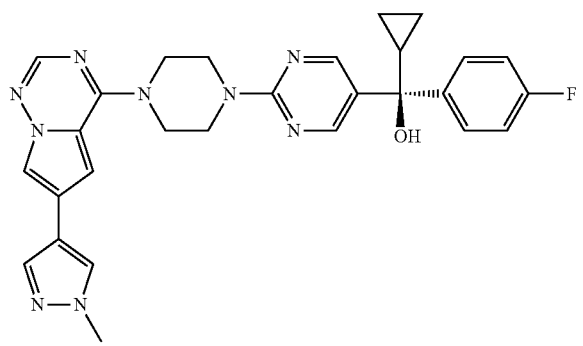 [SMILES: Cn1cc(-c2cc3c(N4CCN(c5ncc([C@@](O)(c6ccc(F)cc6)C6CC6)cn5)CC4)ncnn3c2)cn1] |
| 105 | 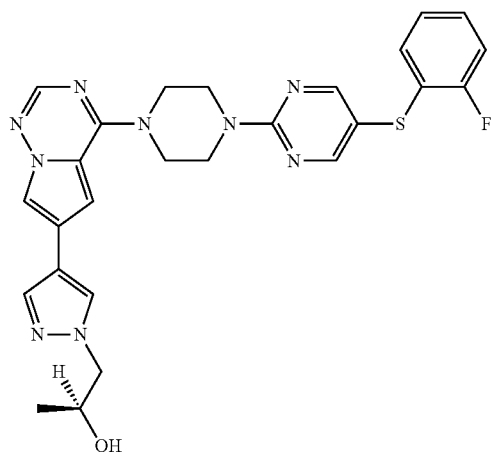 [SMILES: C[C@H](O)Cn1cc(-c2cc3c(N4CCN(c5ncc(Sc6ccccc6F)cn5)CC4)ncnn3c2)cn1] |
| 106 | 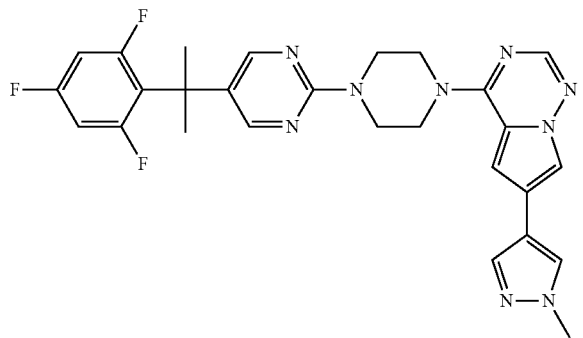 [SMILES: Cn1cc(-c2cc3c(N4CCN(c5ncc(C(C)(C)c6c(F)cc(F)cc6F)cn5)CC4)ncnn3c2)cn1] |

| Compound Number | Structure |
|---|---|
| 107 | *(structure)* |
| 108 | *(structure)* |
| 109 | *(structure)* |
| 110 | *(structure)* |

-continued
| Compound Number | Structure |
|---|---|
| 111 | 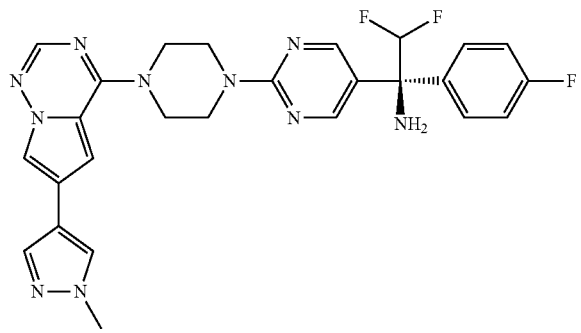 |
| 112 | 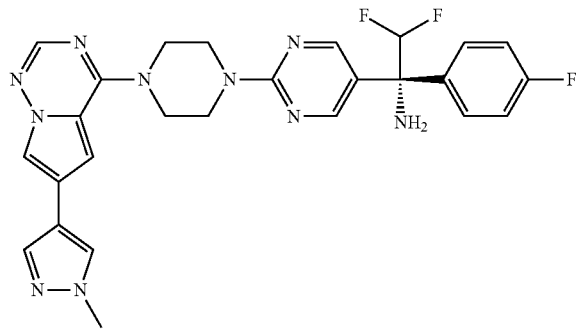 [SMILES: Cn1cc(-c2cc3c(N4CCN(c5ncc([C@](N)(c6ccc(F)cc6)C(F)F)cn5)CC4)ncnn3c2)cn1] |
| 113 | 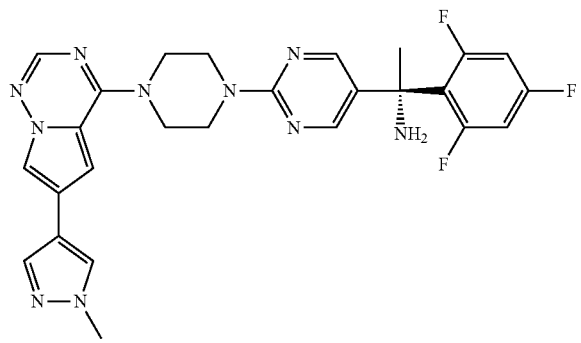 |
| 114 | 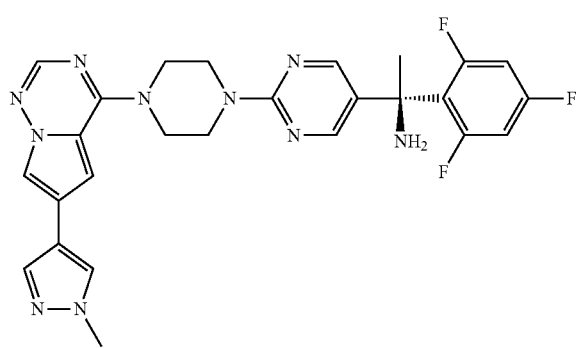 |

-continued
| Compound Number | Structure |
|---|---|
| 115 | 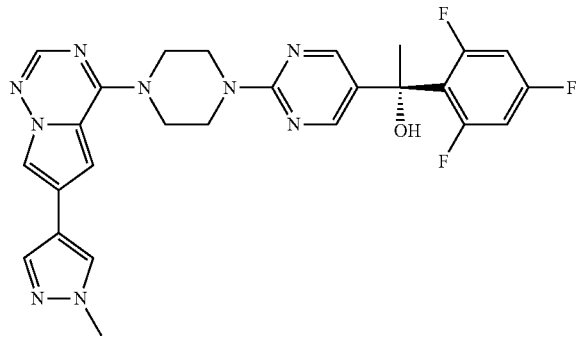 [SMILES: Cn1cc(-c2cc3c(N4CCN(c5ncc([C@](C)(N)c6c(F)cc(F)cc6F)cn5)CC4)ncnn3c2)cn1] |
| 116 | 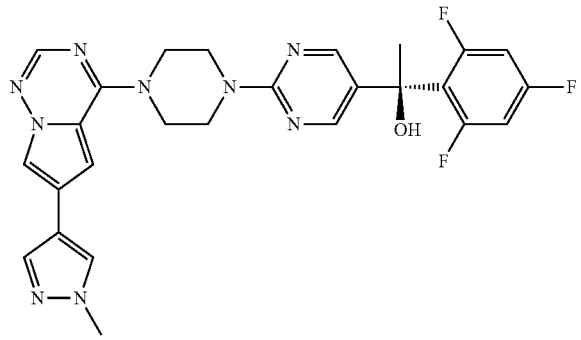 [SMILES: Cn1cc(-c2cc3c(N4CCN(c5ncc([C@@](C)(N)c6c(F)cc(F)cc6F)cn5)CC4)ncnn3c2)cn1] |
| 117 | 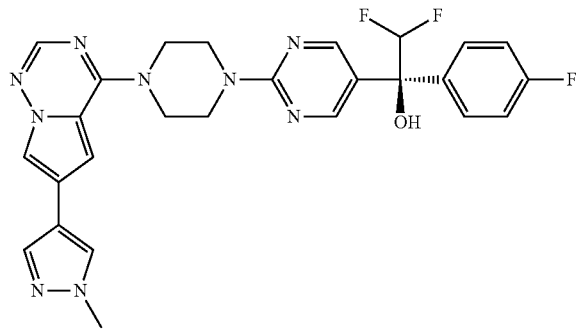 [SMILES: Cn1cc(-c2cc3c(N4CCN(c5ncc([C@@](O)(c6ccc(F)cc6)C(F)F)cn5)CC4)ncnn3c2)cn1] |
| 118 | 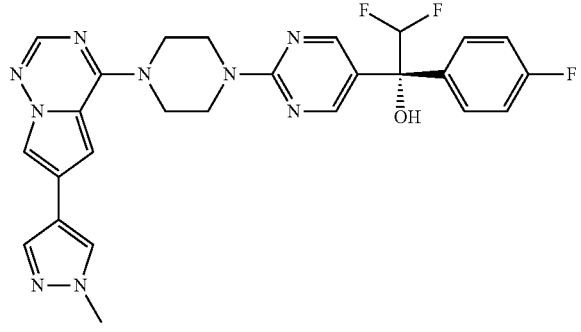 [SMILES: Cn1cc(-c2cc3c(N4CCN(c5ncc([C@](O)(c6ccc(F)cc6)C(F)F)cn5)CC4)ncnn3c2)cn1] |

US 9,994,575 B2
-continued
| Compound Number | Structure |
|---|---|
| 119 | 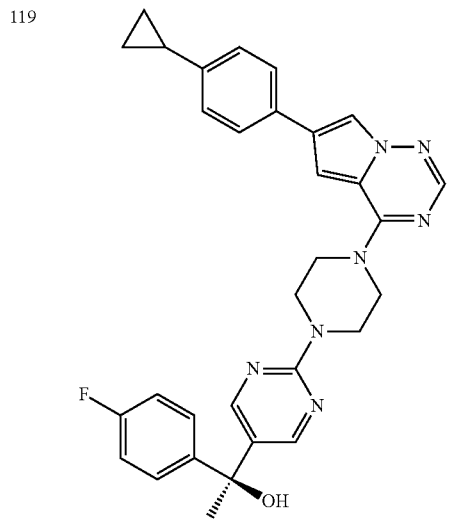 |
| 120 | 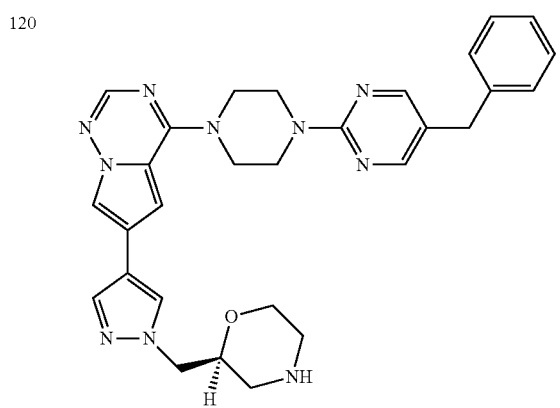 |
| 121 | 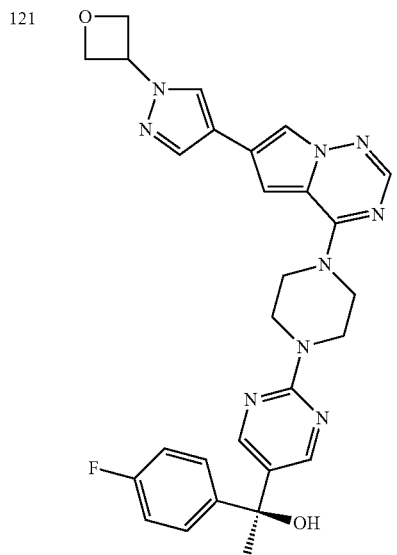 |

| Compound Number | Structure |
|---|---|
| 122 | 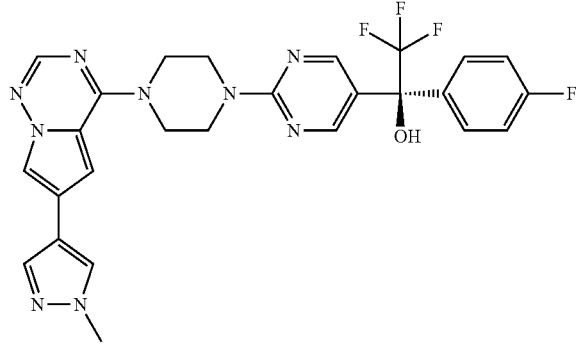 [SMILES: Cn1cc(-c2cc3c(N4CCN(c5ncc([C@@](O)(c6ccc(F)cc6)C(F)(F)F)cn5)CC4)ncnn3c2)cn1] |
| 123 | 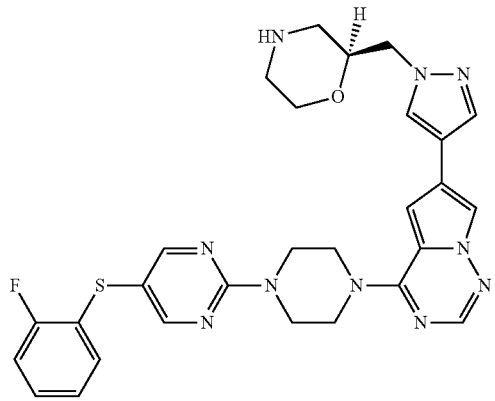 [SMILES: Fc1ccccc1Sc1cnc(N2CCN(c3ncnn4cc(-c5cnn(C[C@@H]6CNCCO6)c5)cc34)CC2)nc1] |
| 124 | 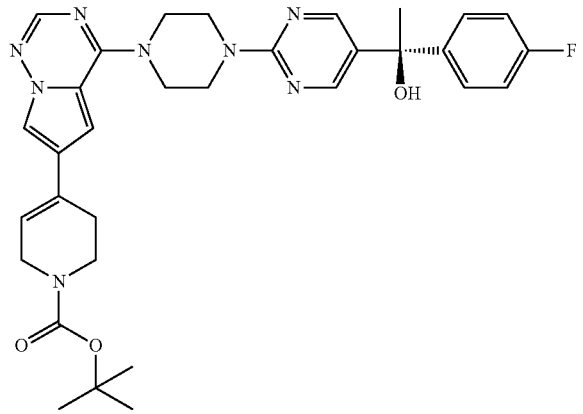 [SMILES: CC(C)(C)OC(=O)N1CC=C(c2cc3c(N4CCN(c5ncc([C@@](C)(O)c6ccc(F)cc6)cn5)CC4)ncnn3c2)CC1] |

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).

Indications

The compounds described herein can be useful for treating conditions associated with aberrant KIT activity, in humans or non-humans. Activating mutations in KIT are found in multiple indications, including systemic mastocytosis, GIST (gastrointestinal stromal tumors), AML (acute myeloid leukemia), melanoma, seminoma, intercranial germ cell tumors, and mediastinal B-cell lymphoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into five forms: indolent (ISM), smoldering (SSM), aggressive (ASM), SM with associated hemotologic non-mast cell lineage disease (SM-AHNMD), and mast cell leukemia (MCL).

Diagnosis of systemic mastocytosis is based in part on histological and cytological studies of bone marrow showing infiltration by mast cells of frequently atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT D816V mutation.

Activating mutations at the D816 position are found in the vast majority of mastocytosis cases (90-98%), with the most common mutations being D816V and D816H, and D816Y. The D816V mutation is found in the activation loop of the kinase domain, and leads to constitutive activation of KIT kinase.

The compounds described herein may also be useful to treat GIST. Complete surgical resection remains the principal treatment of choice for patients with a primary GIST. Surgery is effective in approximately 50% of patients with GIST; of the remaining patients, tumor recurrence is frequent. Primary treatment with a KIT inhibitor such as imatinib has also been shown to be sufficient for initial treatment. However, resistance to imatinib occurs within months through somatic mutation. These secondary imatinib resistant mutations are most frequently located on Exon 11, 13, 14, 17 or 18. Sunitinib is the standard of care second line treatment for most imatinib resistant tumors and is effective for those containing mutations in exons 11, 13 and 14. However, secondary KIT mutations in exons 17 and 18 are resistant to sunitinib treatment and furthermore, tumors containing tertiary resistance mutations in exon 17 and 18 emerge several months after sunitinib treatment. Regorafenib has shown promising results in a phase 3 clinical trial of imatinib, sunitinib resistant GISTs with activity against several but not all exon 17 and 18 mutations, of which D816 is one. Thus, there is a need for therapeutic agents to treat GIST patients with exon 17 mutations not addressed by regorafenib.

In addition to the use of the compounds described herein as single agents in the refractory GIST setting, the use of combinations of imatinib, sunitinib and/or regorafenib with the compounds disclosed herein may allow for the prevention of emergence of resistance to exon 17 mutations.

There is a subset of GIST patients with a D842V mutation in PDGFRα; this subgroup of GIST patients can be stratified by identifying this mutation. This subset of patients is refractory to all tyrosine kinase inhibitors currently available. The compounds described herein, due to their activity against PDGFRα D842V, can be useful in treating these patients.

The compounds described herein may also be useful in treating AML. AML patients harbor KIT mutations as well, with the majority of these mutations at the D816 position.

In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers.

The compounds disclosed herein may be used to treat conditions associated with the KIT mutations in Exon 9, Exon 11, Exon 13, Exon 14, Exon 17 and/or Exon 18. They may also be used to treat conditions associated with wild-type KIT. The compounds described herein may be used as single agents to treat the conditions described herein, or they may be used in combination with other therapeutic agents, including, without limitation, imatinib, sunitinib and regorafenib. Other agents include the compounds described in WO 2014/039714 and WO 2014/100620.

Compounds described herein can be active against one or more KIT mutations in Exon 17 (e.g., D816V, D816Y, D816F, D816K, D816H, D816A, D816G, D820A, D820E, D820G, N822K, N822H, Y823D, and A829P), and much less active against wild-type KIT. These compounds can be administered in combination with an agent that is (a) active against other activating mutations of KIT, such as Exon 9 and 11 mutations, but (b) not active against the Exon 17 mutations. Such agents include imatinib, sunitinib, and regorafenib. The combination of the compound and the agent will thus inhibit Exon 17 mutant KIT, as well as inhibiting Exon 9/11 mutant KIT. The compound and agent can be co-administered, or administered in an alternating regimen. That is, the Exon 17 mutant KIT inhibitor can be administered alone for a period of time; then the Exon 9/11 mutant KIT inhibitor can be administered alone for a period of time following. This cycle may then be repeated. It is believed that such a regimen could slow the development of resistance to the Exon 17 mutant KIT inhibitor and/or the Exon 9/11 mutant KIT inhibitor.

In addition, compounds described herein that can be selective for Exon 17 KIT mutations can be administered with agents that are active against Exon 9/11 mutations, in combination with a third agent that covers mutations that are missed with the two-way combo. The combination of the three agents could inhibit a spectrum of KIT mutations, as well as wild-type KIT in some instances. The agents could be administered simultaneously, or in an alternating regimen. They can be administered one at a time, or two agents can be administered together for a period of time; then the third agent can be administered alone for a following period of time. It is believed that such a regimen could slow the development of resistance to the mutant KIT inhibitors.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. In some embodiments, the dose for humans will be 100-400 mg, or 200-300 mg, administered twice daily; or 400-700 mg, or 500-600 mg, administered once daily.

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1

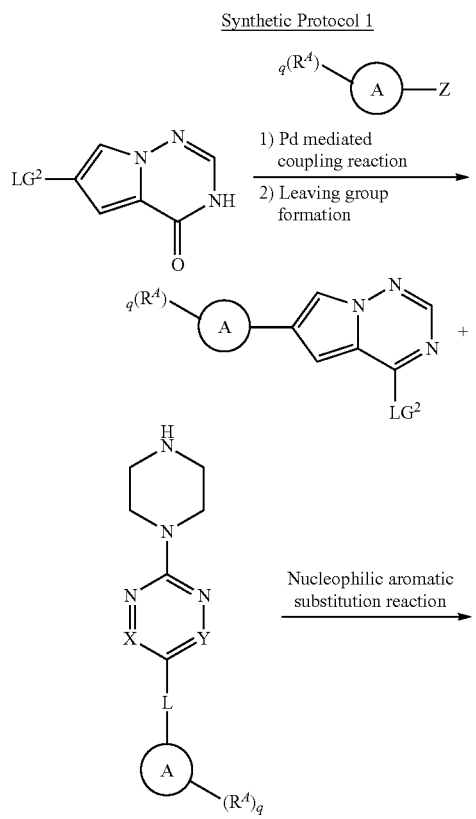

-continued

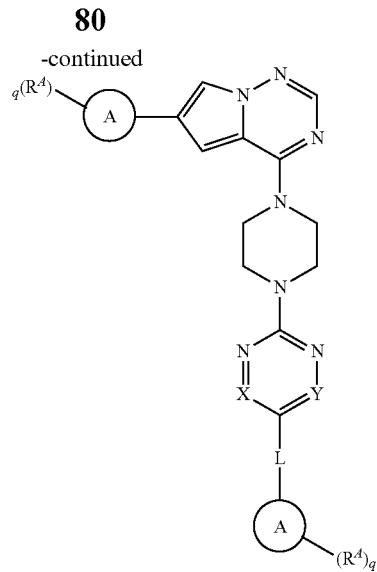

The pyrrolotriazinone can be coupled ($LG^2$ can be, e.g., Cl, Br, or I) to a boron, tin or zinc aryl, heteroaryl, alkenyl, alkyl reagent via a palladium-mediated coupling reaction, e.g., Suzuki, Stille, Negishi coupling, to provide an intermediate with a new carbon-carbon bond formed after subsequent leaving group formation (via $POCl_3$ or other similar reagents). The resulting pyrrolotriazine can be substituted with an amine under nucleophilic aromatic substitution reaction conditions using a base such as diisopropylethylamine (DIPEA) or triethylamine (TEA) in a polar solvent such as dioxane to provide the piperazine-substituted pyrrolotriazine. As shown below, Compounds 9, 10, and 107 were prepared using Synthetic Protocol 1.

Example 1

Synthesis of (R)-6-(1-methyl-1H-pyrazol-4-yl)-4-(4-(5-(1-phenylethyl)pyrimidin-2-yl)piperazin-1-yl)pyrrolo[1,2-f][1,2,4]triazine and (S)-6-(1-methyl-1H-pyrazol-4-yl)-4-(4-(5-(1-phenylethyl)pyrimidin-2-yl)piperazin-1-yl)pyrrolo[1,2-f][1,2,4]triazine (Compounds 9 and 10)

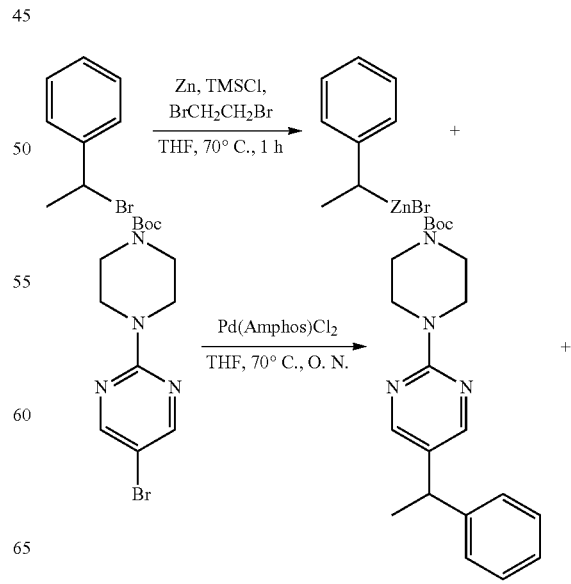

81
-continued

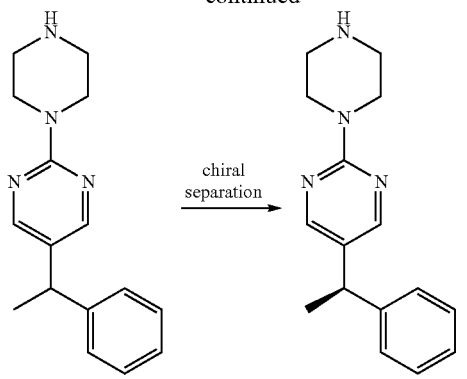

82
-continued

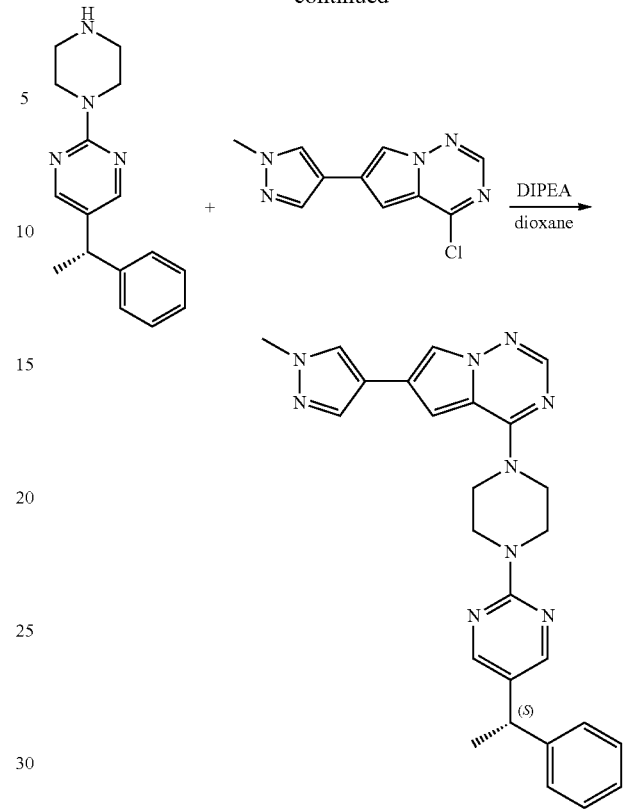

Step 1: Synthesis of (1-phenylethyl)zinc(II) bromide

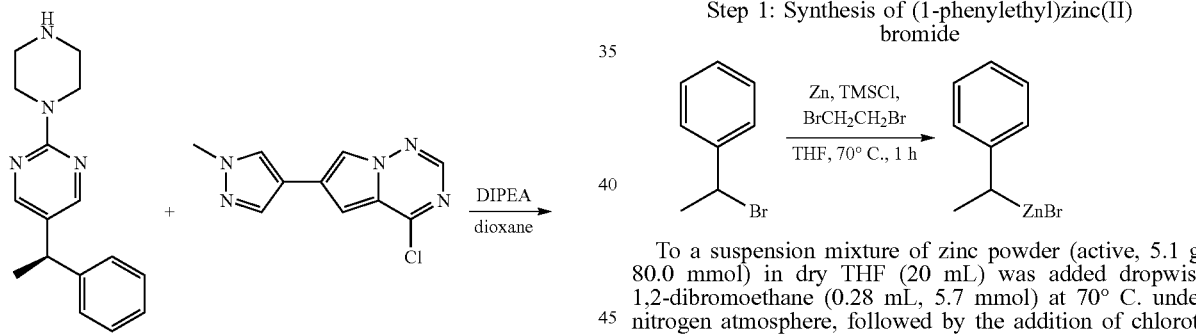

To a suspension mixture of zinc powder (active, 5.1 g, 80.0 mmol) in dry THF (20 mL) was added dropwise 1,2-dibromoethane (0.28 mL, 5.7 mmol) at 70° C. under nitrogen atmosphere, followed by the addition of chlorotrimethylsilane (1.2 mL, 10.6 mmol). Subsequently, (1-bromoethyl)benzene (3.7 g, 20 mmol) was added dropwise. The resultant suspension was stirred at 70° C. for another 1 h. The reaction mixture was cooled to RT and directly used for the next step.

Step 2: Synthesis of 5-(1-phenylethyl)-2-(piperazin-1-yl)pyrimidine

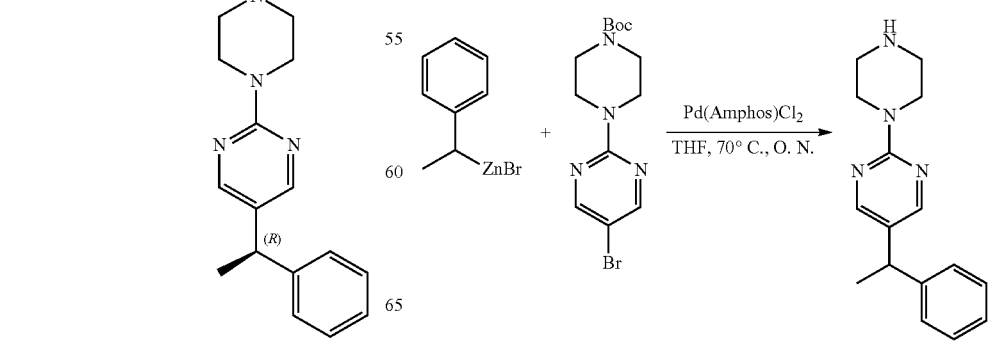

To a solution of tert-butyl 4-(5-bromopyrimidin-2-yl) piperazine-1-carboxylate (4.1 g, 12.0 mmol) and tetrakis (triphenylphosphine)palladium (708 mg, 1.0 mmol) in THF (80 mL, dry) was added dropwise a solution of (1-phenylethyl)zinc(II) bromide in THF (20 mL, 1 M, 20 mmol) under nitrogen atmosphere, and the mixture was stirred at 70° C. overnight. The reaction mixture was cooled to RT and filtered through a pad of Celite. The filtration was concentrated and purified by silica gel chromatography to give tert-butyl 4-(5-(1-phenylethyl)pyrimidin-2-yl)piperazine-1-carboxylate (1.0 g, yield 23%) as a white solid (ethyl acetate/petroleum ether=1/5 as elute) and 5-(1-phenylethyl)-2-(piperazin-1-yl)pyrimidine (2.4 g, 75%) as a yellow oil (methanol/dichloromethane=1/20 as elute). MS (ES+) $C_{16}H_{20}N_4$ requires: 268, found: 269 $[M+H]^+$.

Step 3: Chiral separation of (R)-5-(1-phenylethyl)-2-(piperazin-1-yl)pyrimidine and (S)-5-(1-phenylethyl)-2-(piperazin-1-yl)pyrimidine

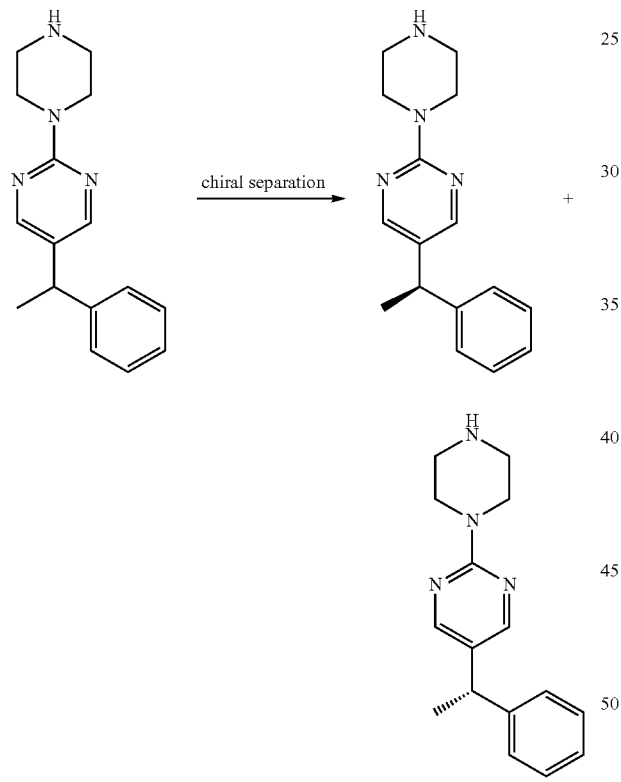

Racemate compound 5-(1-phenylethyl)-2-(piperazin-1-yl) pyrimidine (900 mg) was separated by Chiral-HPLC under the below conditions:
Chiral column: AD-3 (150*4.6 mm 3 um)
Mobile phase hexane (0.1% DEA)/EtOH (0.1% DEA)
(R)-5-(1-phenylethyl)-2-(piperazin-1-yl)pyrimidine (400 mg, 44%) as a yellow oil and (S)-5-(1-phenylethyl)-2-(piperazin-1-yl)pyrimidine (350 mg, 39%) as a yellow oil were obtained.
Absolute stereochemistry was assigned randomly. MS (ES+) $C_{16}H_{20}N_4$ requires: 268, found: 269 $[M+H]^+$.

Synthesis of 4-chloro-6-(1-methyl-1H-pyrazol-4-yl) pyrrolo[1,2-f][1,2,4]triazine

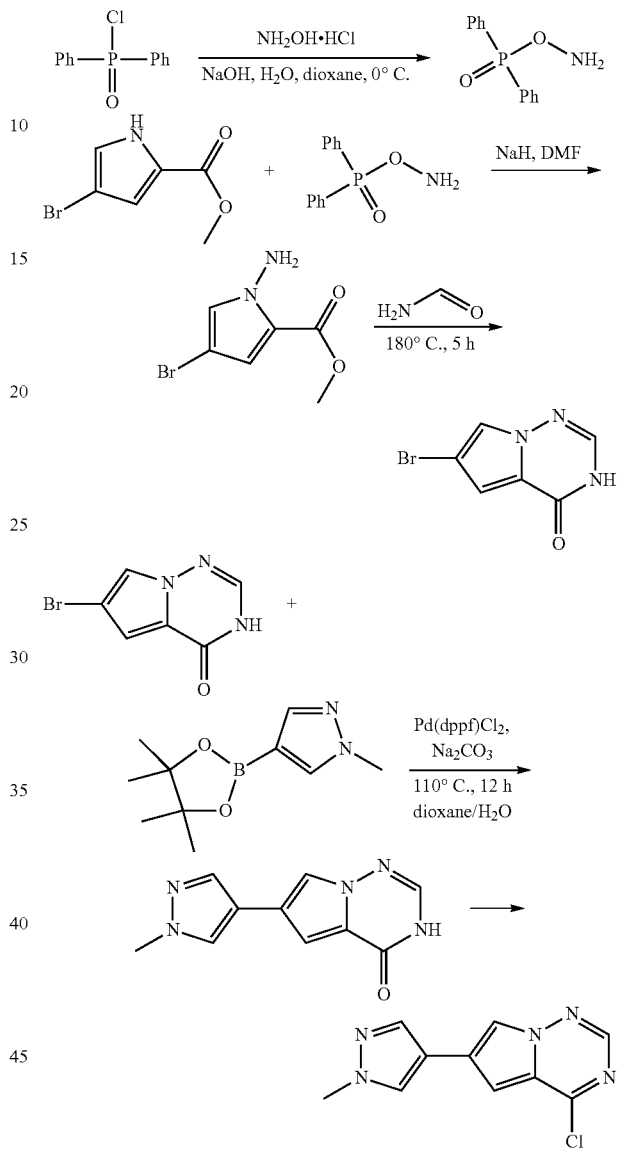

Step 4: Synthesis of O-(diphenylphosphoryl)hydroxylamine

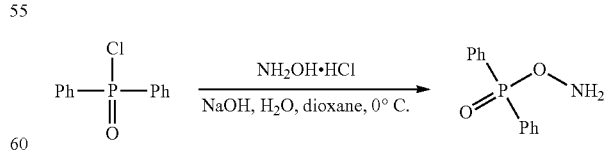

To a solution of hydroxylamine hydrochloride (7.3 g, 106 mmol, 2.5 eq) in water (12 mL) and dioxane (12 mL) was added a solution of NaOH (4.07 g, 102 mmol, 2.4 eq) in water (12 mL), and the mixture was cooled to −5° C. in an ice/salt bath. A solution of diphenylphosphinic chloride (10 g, 42 mmol, 1 eq) in dioxane (12 mL), precooled to below 10° C., was rapidly added to the above solution in an ice/salt bath under vigorous stirring. After completion of the addition, the mixture was stirred for additional 5 minutes in an ice/salt bath, then diluted with ice water (150 mL) and filtered. The filtration cake was washed with ice water, and lyophilized to give o-(diphenylphosphoryl)hydroxylamine (6.0 g, yield 61%) as a white solid. MS (ES+) requires: 233, found 234 [M+H]+; purity: 75%.

Step 5: Synthesis of 1-amino-4-bromo-1H-pyrrole-2-carboxylic acid methyl ester

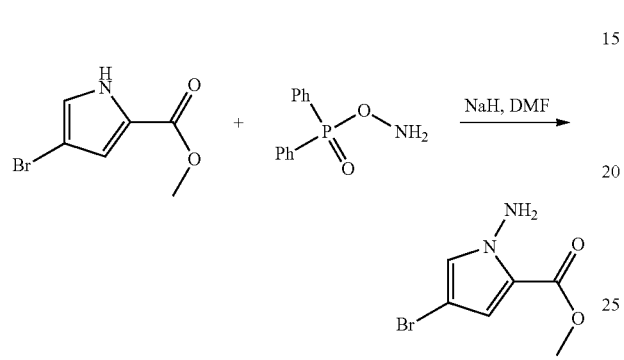

To a solution of 4-bromo-1H-pyrrole-2-carboxylic acid methyl ester (3.5 g, 17.2 mmol, 1 eq) in DMF (120 mL) was added NaH (0.82 g, 20.6 mmol, 1.2 eq) at 0° C., and the mixture was stirred at 0° C. for 1 h, followed by the addition of o-(diphenylphosphinyl)-hydroxylamine (6 g, 25.8 mmol). The reaction mixture was stirred for another 1 h, then neutralized with 20% NH4Cl solution, and extracted with EA. The combined organic layers were washed with water and brine, dried over sodium sulfate, filtered, and concentrated by evaporation. The residue was purified by column chromatography on silica gel (PE/EA=4:1) to give 1-amino-4-bromo-1H-pyrrole-2-carboxylic acid methyl ester (2.9 g, yield 77%) as a light yellow solid. MS (ES+) requires: 218, 220, found 219, 221 [M+H]+; purity: 97%.

Step 6: Synthesis of 6-bromo-3H-pyrrolo[2,1-f][1,2,4]triazin-4-one

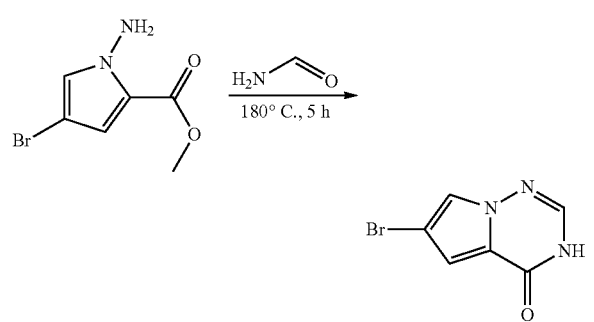

A solution of 1-amino-4-bromo-1H-pyrrole-2-carboxylic acid methyl ester (2.9 g, 13.2 mmol) in formamide (12 mL) was heated at 180° C. for 5 hrs. The mixture was diluted with ethyl acetate (300 mL), and then washed with water (100 mL*2), brine (100 mL*3). The organic layer was dried over sodium sulfate, filtered and concentrated under reduced pressure. The resulting solid was washed with PE/EA (4:1, 50 mL) to give 6-bromo-3H-pyrrolo[2,1-f][1,2,4]triazin-4-one (1.4 g, yield 50%) as yellow solid. MS (ES+) requires: 213, 215, found 214, 216 [M+H]+; purity: 92%.

Step 7: Synthesis of 6-(1-methyl-1H-pyrazol-4-yl)pyrrolo[1,2-f][1,2,4]triazin-4(3H)-one

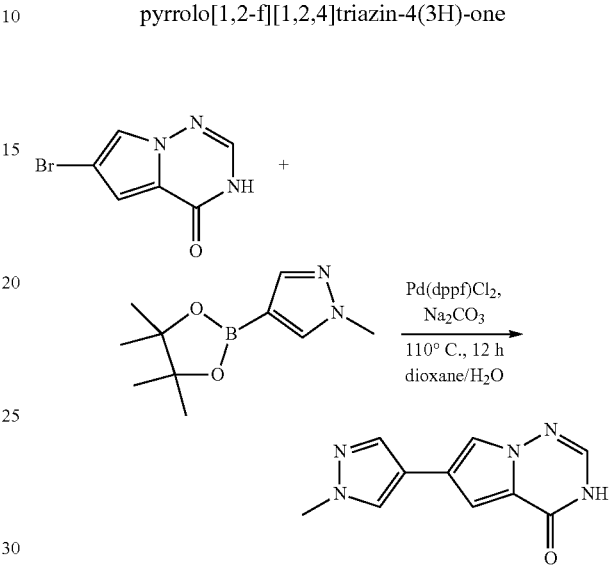

A mixture of 6-bromo-3H-pyrrolo[2,1-f][1,2,4]triazin-4-one (2.15 g, 10 mmol), 1-methyl-4-(4,4,5,5-tetramethyl-1,3,2-dioxaborolan-2-yl)-1H-pyrazole (4.2 g, 20 mmol), Cs2CO3 (9.8 g, 30 mmol), PdCl2dppf (814 mg, 1 mmol), water (15 mL), ethanol (15 mL) and dioxane (70 mL) in a 250 mL flask was degassed with N2 for 10 min, and then heated at 120° C. under N2 atmosphere overnight. The mixture was cooled to RT, followed by the addition of silica gel (~50 g). The residue was subjected to a silica gel column and eluted with DCM:MeOH (20:0-20:1) to afford 6-(1-methyl-1H-pyrazol-4-yl)pyrrolo[1,2-f][1,2,4]triazin-4(3H)-one (600 mg, 28% yield) as a yellow solid. MS (ES+) requires: 215, found 216.1 [M+H]+; purity: 90%.

Step 8: Synthesis of 4-chloro-6-(1-methyl-1H-pyrazol-4-yl)pyrrolo[1,2-f][1,2,4]triazine

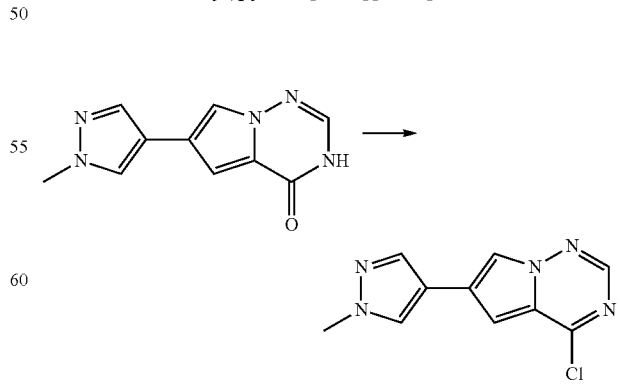

6-(1-methyl-1H-pyrazol-4-yl)pyrrolo[1,2-f][1,2,4]triazin-4(3)-one mg, 2.8 mmol) was treated with phosphorus oxychloride (20 mL) under reflux for 3 hours. The mixture was cooled to RT, concentrated under reduced pressure and the residue was diluted with ice water (100 mL).

The mixture was extracted with dichloromethane (50 mL*4), and the combined organic layers were dried by MgSO$_4$, filtered, concentrated to give 4-chloro-6-(1-methyl-1H-pyrazol-4-yl)pyrrolo[1,2-f][1,2,4]triazine (600 mg, 92% yield) as a brown solid. MS (ES+) requires: 233, 235, found 234, 236 [M+H]$^+$; purity:90%.

Step 9: Synthesis of (R)-6-(1-methyl-1H-pyrazol-4-yl)-4-(4-(5-(1-phenylethyl)pyrimidin-2-yl)piperazin-1-yl)pyrrolo[1,2-f][1,2,4]triazine

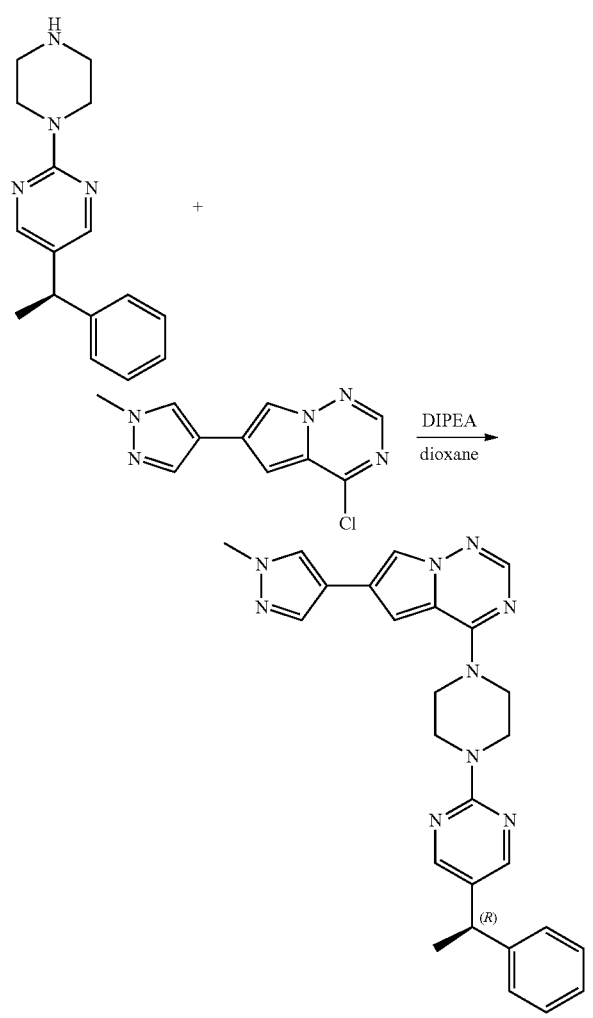

A mixture of 4-chloro-6-(1-methyl-1H-pyrazol-4-yl)pyrrolo[1,2-f][1,2,4]triazine (56 mg, 0.21 mmol), (R)-5-(1-phenylethyl)-2-(piperazin-1-yl)pyrimidine (49 mg, 0.21 mmol) and diisopropylethylamine (97 mg, 0.84 mmol) in dioxane (10 mL) was stirred at RT overnight. LCMS monitored the reaction was completed. The reaction mixture was concentrated to give a residue, which was purified by Prep-HPLC to afford the title compound (45 mg, 46%) as a white solid. MS (ES+) C$_{26}$H$_{27}$N$_9$ requires: 465 found: 466 [M+H]$^+$.

Step 10: Synthesis of (S)-6-(1-methyl-1H-pyrazol-4-yl)-4-(4-(5-(1-phenylethyl)pyrimidin-2-yl)piperazin-1-yl)pyrrolo[1,2-f][1,2,4]triazine

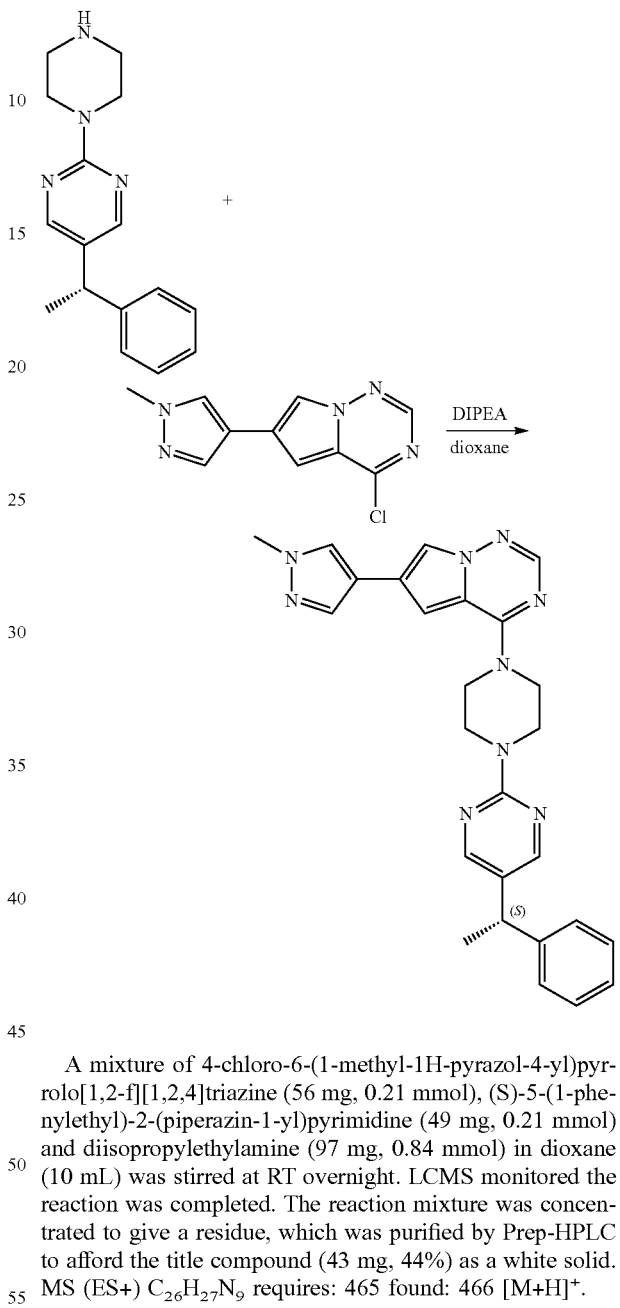

A mixture of 4-chloro-6-(1-methyl-1H-pyrazol-4-yl)pyrrolo[1,2-f][1,2,4]triazine (56 mg, 0.21 mmol), (S)-5-(1-phenylethyl)-2-(piperazin-1-yl)pyrimidine (49 mg, 0.21 mmol) and diisopropylethylamine (97 mg, 0.84 mmol) in dioxane (10 mL) was stirred at RT overnight. LCMS monitored the reaction was completed. The reaction mixture was concentrated to give a residue, which was purified by Prep-HPLC to afford the title compound (43 mg, 44%) as a white solid. MS (ES+) C$_{26}$H$_{27}$N$_9$ requires: 465 found: 466 [M+H]$^+$.

Example 2: Synthesis of (S)-1-(2-(4-(5-chloro-6-(1-methyl-1H-pyrazol-4-yl)pyrrolo[1,2-f][1,2,4]triazin-4-yl)piperazin-1-yl)pyrimidin-5-yl)-1-(4-fluorophenyl)ethanol (Compound 107)

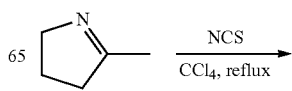

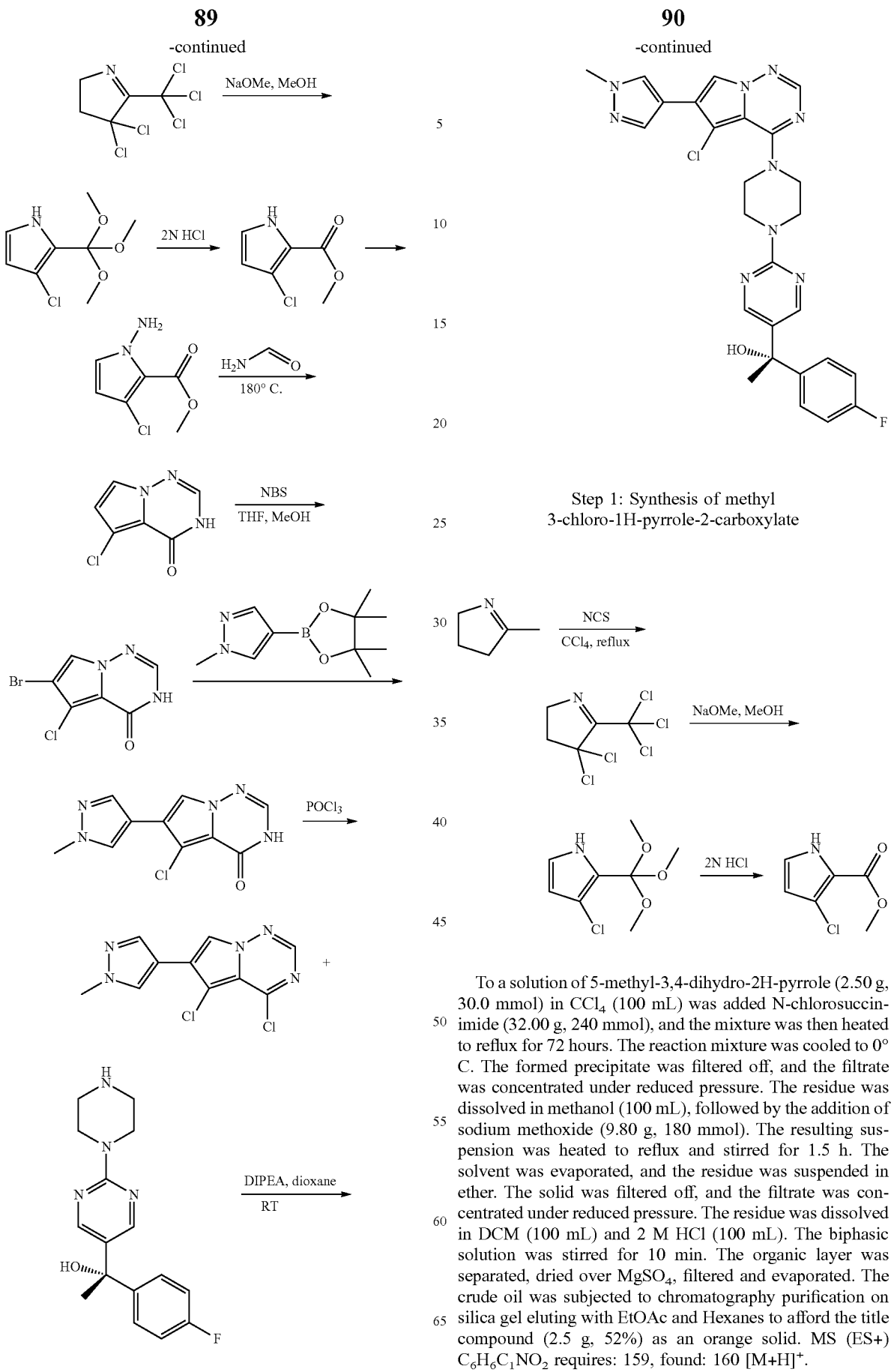

Step 1: Synthesis of methyl 3-chloro-1H-pyrrole-2-carboxylate

To a solution of 5-methyl-3,4-dihydro-2H-pyrrole (2.50 g, 30.0 mmol) in CCl₄ (100 mL) was added N-chlorosuccinimide (32.00 g, 240 mmol), and the mixture was then heated to reflux for 72 hours. The reaction mixture was cooled to 0° C. The formed precipitate was filtered off, and the filtrate was concentrated under reduced pressure. The residue was dissolved in methanol (100 mL), followed by the addition of sodium methoxide (9.80 g, 180 mmol). The resulting suspension was heated to reflux and stirred for 1.5 h. The solvent was evaporated, and the residue was suspended in ether. The solid was filtered off, and the filtrate was concentrated under reduced pressure. The residue was dissolved in DCM (100 mL) and 2 M HCl (100 mL). The biphasic solution was stirred for 10 min. The organic layer was separated, dried over MgSO₄, filtered and evaporated. The crude oil was subjected to chromatography purification on silica gel eluting with EtOAc and Hexanes to afford the title compound (2.5 g, 52%) as an orange solid. MS (ES+) $C_6H_6C_1NO_2$ requires: 159, found: 160 [M+H]⁺.

Step 2: Synthesis of methyl 1-amino-3-chloro-1H-pyrrole-2-carboxylate

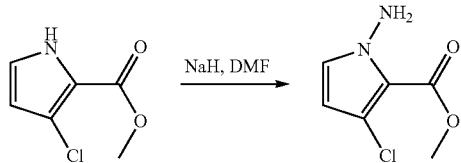

To a suspension of sodium hydride (60 percent, 1.5 g, 37.5 mmol) in DMF (250 mL) was added methyl 3-chloro-1H-pyrrole-2-carboxylate (5.0 g, 31.3 mmol) at 0° C., and the mixture was stirred for 25 min, followed by the addition of O-(diphenylphosphoryl)hydroxylamine (10.0 g, 43.75 mmol). The reaction mixture was stirred at RT for 4 h and quenched by aq. Na$_2$SO$_3$ solution. After stirred for another 5 min, the mixture was extracted with EtOAc (3×300 mL). The combined organic layers were washed with brine, dried over Na$_2$SO$_4$, filtered and concentrated to give crude product as a brown oil, which was purified by chromatography purification on silica gel (PE:EA=4:1) to obtain the title compound (5.00 g, 91%) as a white solid. MS (ES+) C$_6$H$_7$C$_1$N$_2$O$_2$ requires: 174, 176, found: 175, 177 [M+H]$^+$.

Step 3: Synthesis of 5-chloropyrrolo[1,2-f][1,2,4]triazin-4(3H)-one

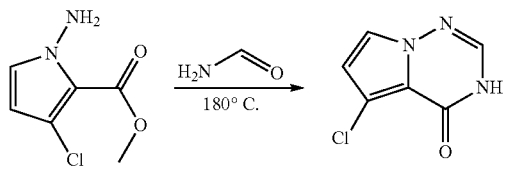

A mixture of methyl 1-amino-3-chloro-1H-pyrrole-2-carboxylate (4.00 g, 23 mmol) and formamide (15 mL) was heated to 180° C. for 3 h. After cooled to RT, the precipitated solid was collected via filtration and washed with CH$_2$CH$_2$ to obtain the title compound (2.50 g, 64%) as a yellow solid. MS (ES+) C$_6$H$_4$C$_1$N$_3$O requires: 169, found: 170 [M+H]+.

Step 4: Synthesis of 6-bromo-5-chloropyrrolo[1,2-f][1,2,4]triazin-4(3H)-one

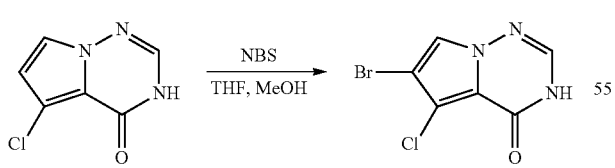

To a mixture of 5-chloropyrrolo[1,2-f][1,2,4]triazin-4(3H)-one (2.50 g, 14.7 mmol) in THF (100 mL) and MeOH (50 mL) was added N-bromosuccinimide (2.6 g, 14.7 mmol), and the mixture was stirred at RT for 2 h. The reaction was quenched by water and extracted with EA. The organic layer was dried (Na$_2$SO$_4$), filtered and concentrated. The residue was purified by chromatography purification on silica gel (EA:MeOH=10:1) to obtain the title compound (2.00 g, 55%) as a yellow solid. MS (ES+) C$_6$H$_3$BrClN$_3$O requires: 246.9, found: 247.9 [M+H]$^+$.

Step 5: Synthesis of 5-chloro-6-(1-methyl-1H-pyrazol-4-yl)pyrrolo[1,2-f][1,2,4]triazin-4(3H)-one

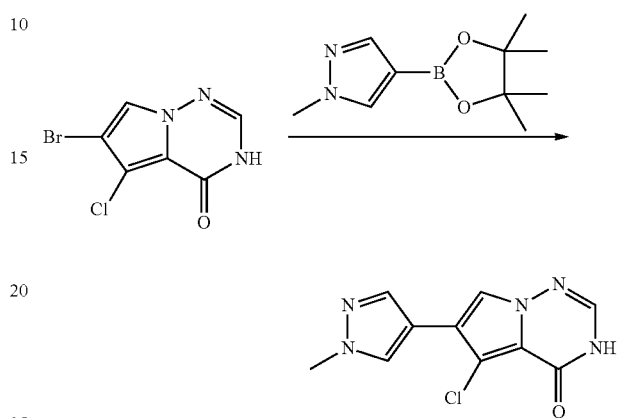

A mixture of 6-bromo-5-chloropyrrolo[1,2-f][1,2,4]triazin-4(3H)-one (2.00 g, 8.1 mmol), 1-methyl-4-(4,4,5,5-tetramethyl-1,3,2-dioxaborolan-2-yl)-1H-pyrazole (2.5 g, 12.1 mmol), K$_3$PO$_4$ (3.4 g, 16.1 mmol) and Pd(dppf)Cl$_2$ (589 mg, 0.81 mmol) in 1,4-dioxane (30 mL) and water (3 mL) was purged with N$_2$ and then heated to 90° C. for 15 h. The reaction mixture was cooled to RT and concentrated. The residue was passed a column (silica gel, EA:DCM:MeOH=10:10:1) to obtain the title compound (600 mg, 30%) as a yellow solid. MS (ES+) C$_{10}$H$_8$ClN$_5$O requires: 249, 251, found: 250, 252 [M+H]$^+$.

Step 6: Synthesis of 4,5-dichloro-6-(1-methyl-1H-pyrazol-4-yl)pyrrolo[1,2-f][1,2,4]triazine

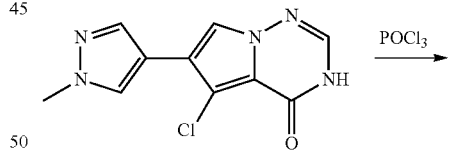

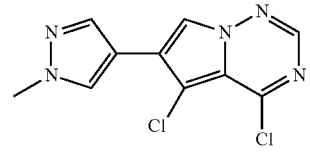

A mixture of 1-methyl-4-(4,4,5,5-tetramethyl-1,3,2-dioxaborolan-2-yl)-1H-pyrazole (600 mg, 2.4 mmol) in POCl$_3$ (4 mL) was heated to reflux for 12 h. The reaction mixture was cooled to RT and concentrated under reduced pressure. The residue was washed with a mixture of THF (20 mL) and 1,4-dioxane (10 mL) to give the title compound (450 mg, 69%) as a yellow solid. MS (ES+) C$_{10}$H$_8$ClN$_5$O requires: 267, 269, found: 268, 270 [M+H]$^+$.

Step 7: Synthesis of (S)-1-(2-(4-(5-chloro-6-(1-methyl-1H-pyrazol-4-yl)pyrrolo[1,2-f][1,2,4]triazin-4-yl)piperazin-1-yl)pyrimidin-5-yl)-1-(4-fluorophenyl)ethanol

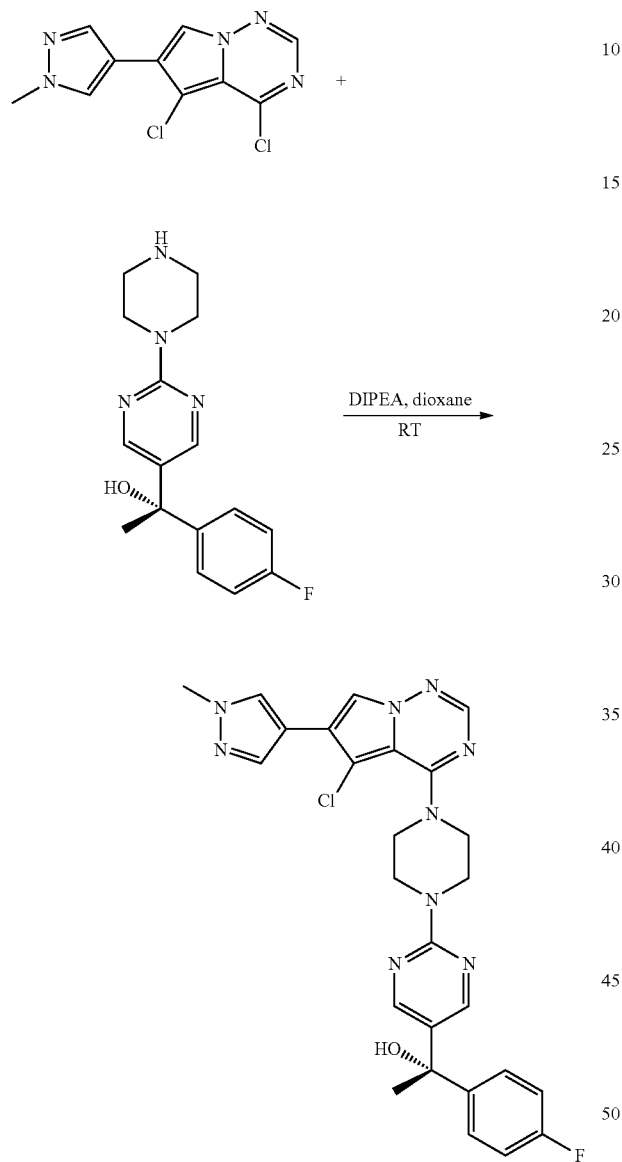

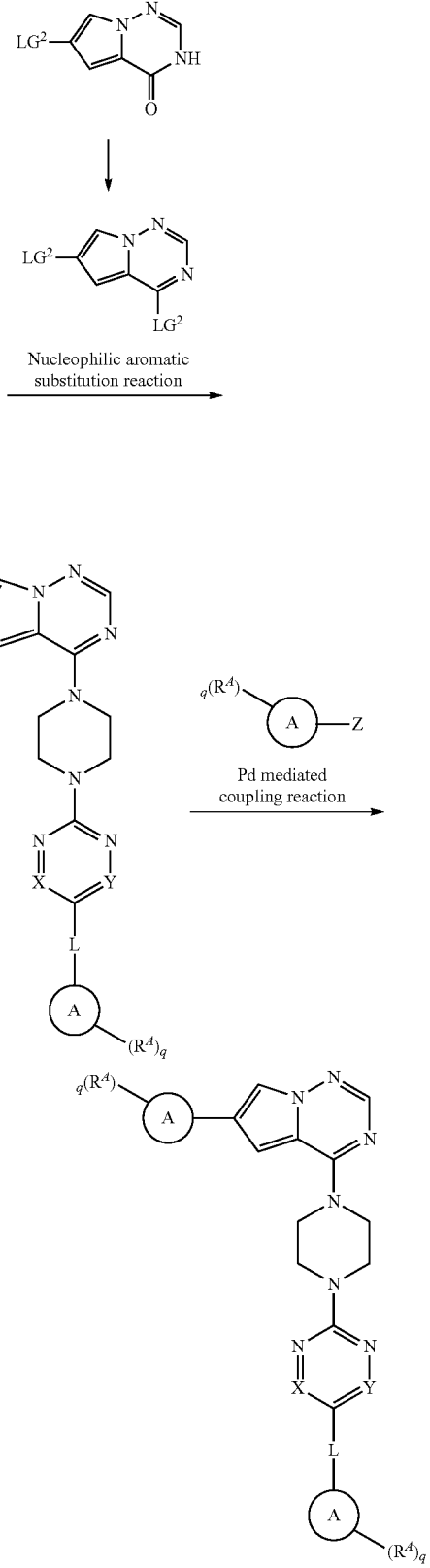

Synthetic Protocol 2

Nucleophilic aromatic substitution reaction

Pd mediated coupling reaction

LG² = halogen (e.g., chloro)
Z = B or Sn group

To a mixture of 4,5-dichloro-6-(1-methyl-1H-pyrazol-4-yl)pyrrolo[1,2-f][1,2,4]triazine (150 mg, 0.56 mmol) and (S)-1-(4-fluorophenyl)-1-(2-(piperazin-1-yl)pyrimidin-5-yl)ethanol (135 mg, 0.45 mmol) in 1,4-dioxane (10 mL) was added DIPEA (361 mg, 2.8 mmol). After stirred at RT for 15 h, the mixture was concentrated under reduced pressure and purified by Prep-HPLC to give the title compound (40.9 mg, 17%) as a white solid. MS (ES+) $C_{26}H_{25}ClFN_9O$ requires: 533, found: 534 [M+H]⁺. ¹H-NMR (400 MHz, DMSO-$d_6$) δ ppm 8.41 (s, 1H), 8.39 (s, 2H), 8.13 (s, 1H), 8.09 (s, 1H), 7.48-7.44 (m, 2H), 7.22 (s, 1H), 7.14-7.10 (m, 2H), 5.91 (s, 1H), 3.95-3.89 (m, 7H), 3.71-3.68 (m, 4H), 1.82 (s, 3H).

95

The pyrrolotriazinone can be transformed into a pyrrolotriazine via treatment with POCl₃ or other similar reagents. The pyrrolotriazine can be substituted with an amine under nucleophilic aromatic substitution reaction conditions using an amine base such as diisopropylethylamine (DIPEA) or triethylamine (TEA) in a polar solvent such as dioxane to provide the piperazine-substituted pyrrolotriazine. The pyrrolotriazinone can be coupled (LG² can be, e.g., Cl, Br, or I) to a boron, tin or zinc aryl, heteroaryl, alkenyl, or alkyl reagent via a palladium-mediated coupling reaction, e.g., Suzuki, Stille, Negishi coupling, to provide the product. As shown below, Compound 123 was prepared using Synthetic Protocol 2.

Example 3: Synthesis of (S)-2-((4-(4-(4-(5-(2-fluorophenylthio)pyrimidin-2-yl)piperazin-1-yl)pyrrolo[1,2-f][1,2,4]triazin-6-yl)-1H-pyrazol-1-yl)methyl)morpholine (Compound 123)

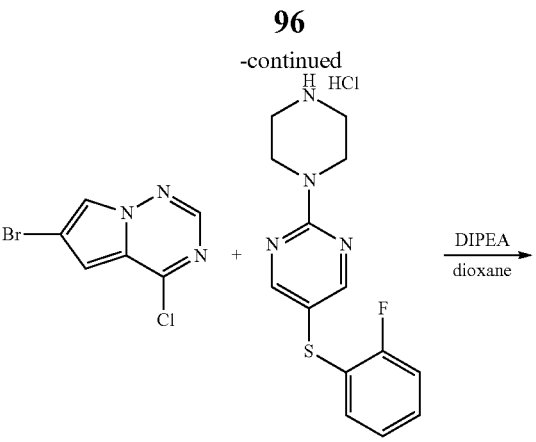

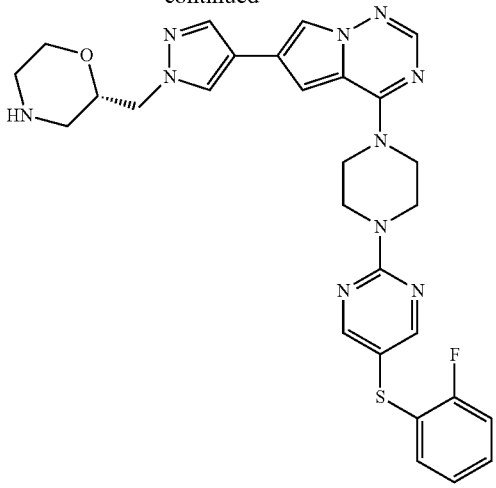

Step 1: Synthesis of (S)-tert-butyl 2-((methylsulfonyloxy)methyl)morpholine-4-carboxylate

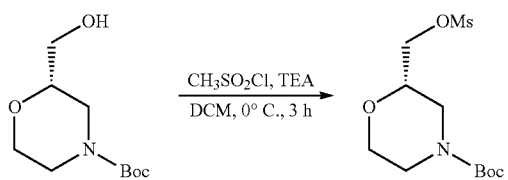 [SMILES: CC(C)(C)OC(=O)N1CCO[C@H](CO)C1 ; CC(C)(C)OC(=O)N1CCO[C@H](COS(C)(=O)=O)C1]

To a mixture of (S)-tert-butyl 2-(hydroxymethyl)morpholine-4-carboxylate (400 mg, 1.84 mmol) in 10 mL of dichloromethane was added triethylamine (372 mg, 3.68 mmol) and methanesulfonyl chloride (316 mg, 2.76 mmol) dropwise at 0° C. The reaction mixture was stirred at 0° C. for 3 h, and LCMS showed the reaction was completed. The reaction solution was diluted with 20 mL of dichloromethane, and washed with saturated aqueous NaHCO$_3$ (30 mL×3) and brine. The organic layer was separated, dried over sodium sulfate, filtered and concentrated. The crude product was purified by silica gel chromatography (petroleum ether:ethyl acetate=5:1) to afford the title product (430 mg, 79%) as a white solid. MS (ES+) $C_{11}H_{21}NO_6S$ requires: 295, found: 296 [M+H]$^+$.

Step 2: Synthesis of (S)-tert-butyl 2-((4-(4,4,5,5-tetramethyl-1,3,2-dioxaborolan-2-yl)-1H-pyrazol-1-yl)methyl)morpholine-4-carboxylate

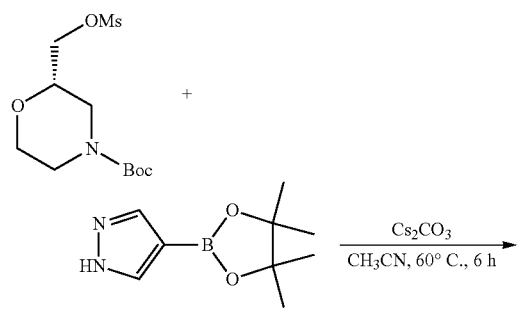

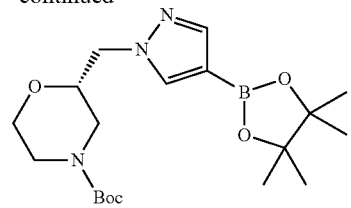

To a mixture of (S)-tert-butyl 2-((methylsulfonyloxy)methyl)morpholine-4-carboxylate (430 mg, 1.46 mmol) and 4-(4,4,5,5-tetramethyl-1,3,2-dioxaborolan-2-yl)-1H-pyrazole (283 mg, 1.46 mmol) in 50 mL of acetonitrile was added cerium carbonate (1.43 g, 4.37 mmol), and the mixture was stirred at 60° C. for 3 h. TLC and LCMS showed the reaction was completed. After the solvents were removed under reduced pressure, the residue was diluted with 50 mL of ethyl acetate, and washed with water (50 mL×3) and brine. The organic layer was separated, dried over sodium sulfate, filtered and concentrated. The crude product was purified by silica gel chromatography (petroleum ether:ethyl acetate=5:1) to get the title product (300 mg, 52%) as colorless oil. MS (ES+) $C_{19}H_{32}BN_3O_5$ requires: 393, found: 394 [M+H]$^+$.

Step 3: Synthesis of tert-butyl 4-(5-(2-fluorophenylthio)pyrimidin-2-yl)piperazine-1-carboxylate

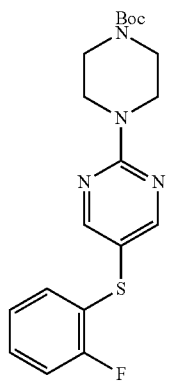

A mixture of tert-butyl 4-(5-bromopyrimidin-2-yl)piperazine-1-carboxylate (5.0 g, 14.6 mmol), 2-fluorobenzenethiol (9.3 g, 73 mmol), 1,10-Phenanthroline (7.9 g, 43.8 mmol), copper iodide (13.9 g, 73 mmol) and cerium carbonate (28.6 g, 87.6 mmol) in dioxane (100 mL) was refluxed for 3 days. The reaction mixture was cooled to RT and concentrated. The residue was directly purified by silica gel chromatography to give the title compound. MS (ES+) $C_{19}H_{23}FN_4O_2S$ requires: 390, found: 391 [M+H]$^+$.

Step 4: Synthesis of 5-(2-fluorophenylthio)-2-(piperazin-1-yl)pyrimidine HCl salt

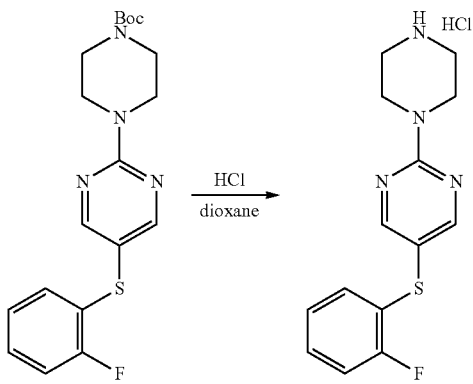 [SMILES: Cl ; CC(C)(C)OC(=O)N1CCN(c2ncc(Sc3ccccc3F)cn2)CC1 ; Cl ; Fc1ccccc1Sc1cnc(N2CCNCC2)nc1]

To a solution of tert-butyl 4-(5-(2-fluorophenylthio)pyrimidin-2-yl)piperazine-1-carboxylate (5 g, 12.8 mmol) in dioxane (150 mL) was added HCl in dioxane (4 M, ca. 30 mL), and the mixture was stirred at 40° C. overnight. LCMS showed the reaction was completed. The reaction mixture was concentrated to afford 5-(2-fluorophenylthio)-2-(piperazin-1-yl)pyrimidine HCl salt (3.6 g, 88%) as a solid. MS (ES+) $C_{14}H_{15}FN_4S$ requires: 290, found: 291 $[M+H]^+$.

Step 5: Synthesis of 6-bromo-4-(4-(5-(2-fluorophenylthio)pyrimidin-2-yl)piperazin-1-yl)pyrrolo[1,2-f][1,2,4]triazine

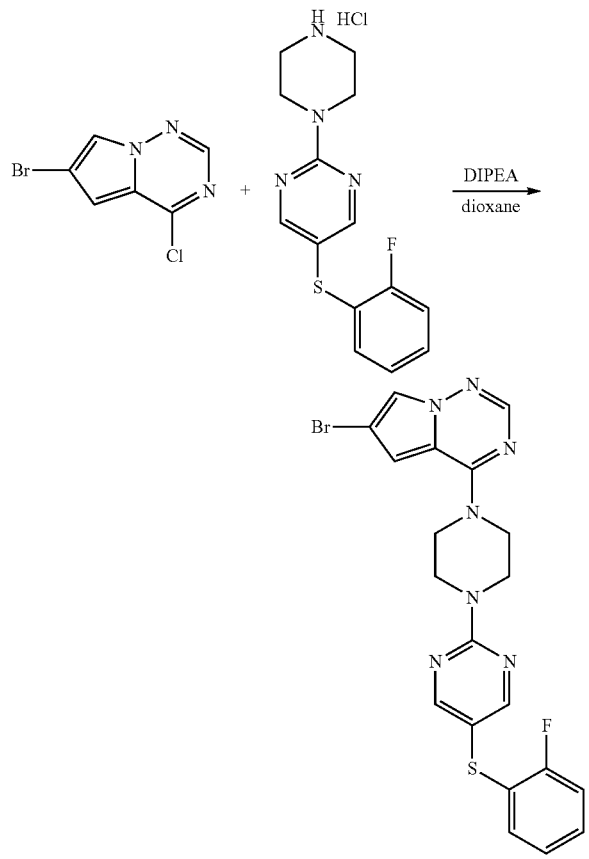

A mixture of 6-bromo-4-chloropyrrolo[1,2-f][1,2,4]triazine (100 mg, 0.43 mmol), 5-(2-fluorophenylthio)-2-(piperazin-1-yl)pyrimidine HCl salt (126 mg, 0.43 mmol) and diisopropylethylamine (280 mg, 2.15 mmol) in dioxane (5 mL) was stirred at RT overnight. The reaction mixture was concentrated and purified by silica gel chromatography (petroleum ether:ethyl acetate=2:1) to afford the title compound as (100 mg, 49%) a yellow solid. MS (ES+) $C_{20}H_{17}BrFN_7S$ requires: 485, 487, found: 486, 488 $[M+H]^+$.

Step 6: Synthesis of (S)-tert-butyl 2-((4-(4-(4-(5-(2-fluorophenylthio)pyrimidin-2-yl)piperazin-1-yl)pyrrolo[1,2-f][1,2,4]triazin-6-yl)-1H-pyrazol-1-yl)methyl)morpholine-4-carboxylate

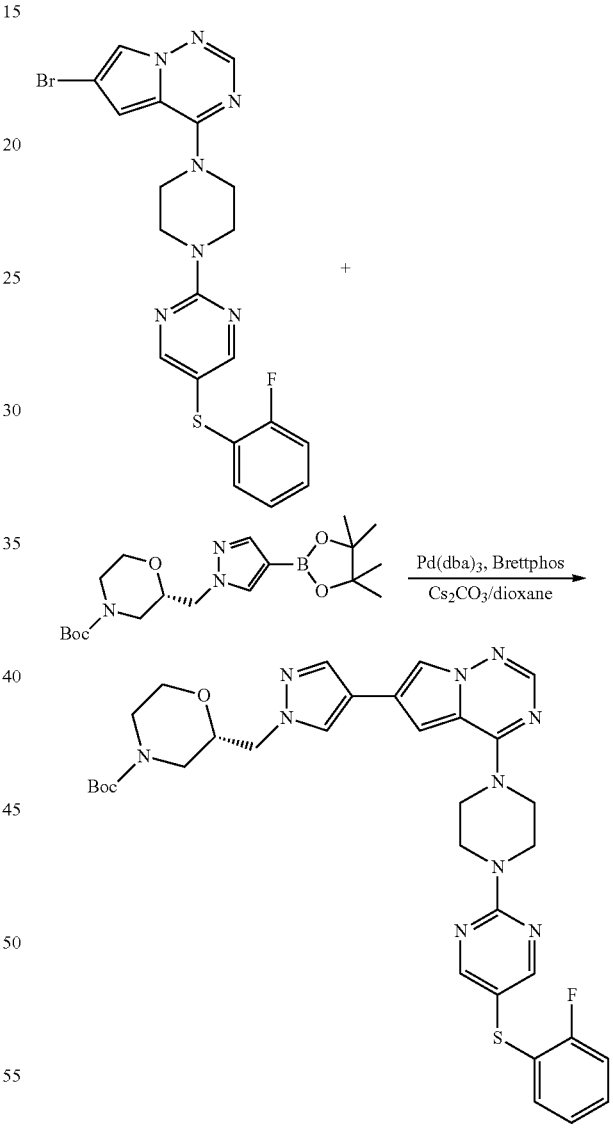

A mixture of 6-bromo-4-(4-(5-(2-fluorophenylthio)pyrimidin-2-yl)piperazin-1-yl)pyrrolo[1,2-f][1,2,4]triazine (100 mg, 0.2 mmol), (S)-tert-butyl 2-((4-(4,4,5,5-tetramethyl-1,3,2-dioxaborolan-2-yl)-H-pyrazol-1-yl)methyl)morpholine-4-carboxylate (80 mg, 0.2 mmol), $Pd_2(dba)_3$ (34 mg, 0.02 mmol), Brettphos (40 mg, 0.04 mmol) and cerium carbonate (260 mg, 0.4 mmol) in dioxane (5 mL) was degassed with nitrogen for three times, and then heated at 120° C. overnight. The reaction mixture was cooled to RT and concentrated to give a residue, which was purified by silica gel chromatography (dichloromethane:methanol=15:1) to afford the title compound (40 mg, 30%) as a white solid. MS (ES+) $C_{33}H_{37}FN_{10}O_3S$ requires: 672, found: 617 [M−56+H]$^+$.

Step 7: Synthesis of (S)-2-((4-(4-(4-(5-(2-fluorophenylthio)pyrimidin-2-yl)piperazin-1-yl)pyrrolo[1,2-f][1,2,4]triazin-6-yl)-1H-pyrazol-1-yl)methyl)morpholine

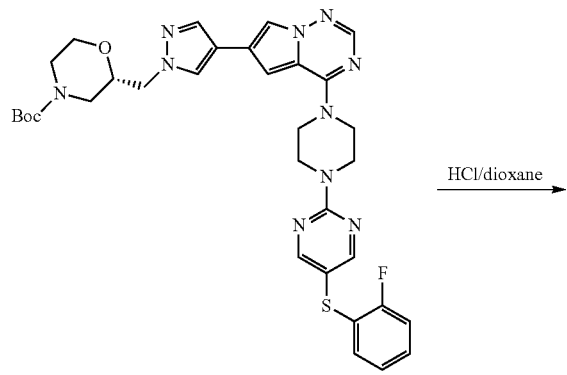

HCl/dioxane →

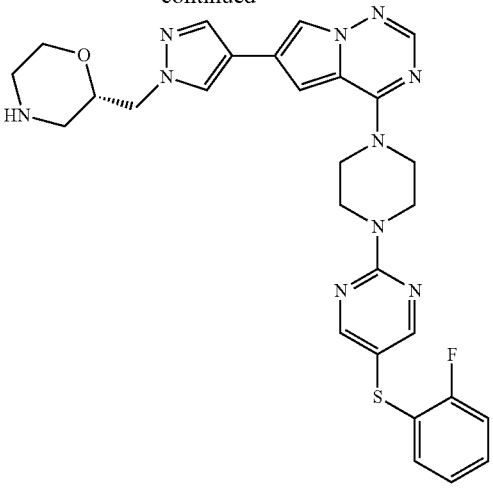

A mixture of (S)-tert-butyl 2-((4-(4-(4-(5-(2-fluorophenylthio)pyrimidin-2-yl)piperazin-1-yl)pyrrolo[1,2-f][1,2,4]triazin-6-yl)-1H-pyrazol-1-yl)methyl)morpholine-4-carboxylate (40 mg, 0.06 mmol) in HCl/dioxane (5 mL) was stirred at RT for 2 h. The reaction mixture was concentrated to give a residue, which was purified by Prep-HPLC to afford the title compound (8.9 mg, 26%) as a yellow solid. MS (ES+) $C_{28}H_{29}FN_{10}OS$ requires: 572, found: 573 [M+H]$^+$.

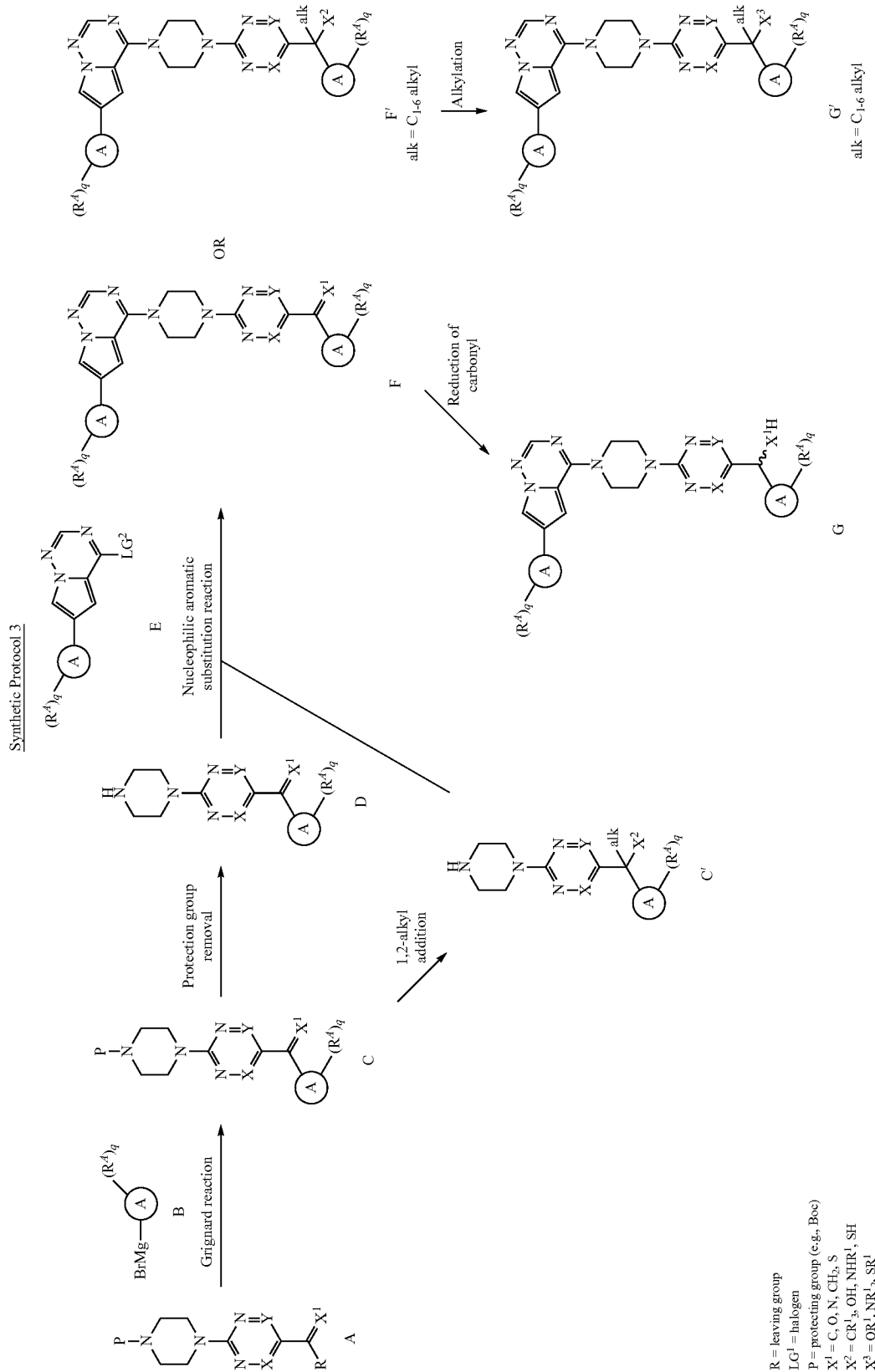

The piperazine carbonyl derivative, e.g., carbomoyl, (A, X and Y are each —CH—) can be coupled to the Grignard bromide (B, Ring A is aryl), to provide the protected di-substituted carbonyl (C', $X^1$ is $CH_2$, S, NH, or O). When $X^1$ is O, i.e., forming a carbonyl, the carbonyl can be further reacted with an organometallic reagent such as Grignard, lithium, zinc reagents and trialkylaluminum, e.g., trimethylaluminum, which can also deprotect the piperazine nitrogen to provide the further substituted compound (C'). Removal of the protecting group (P) from the piperazine ring of (C) can be carried out using strong acids such as 4M hydrochloric acid (HCl) in dioxane or trifluoroacetic acid (TFA) in a polar solvent such as methanol or dichloromethane (DCM) to afford amine (D). Pyrrolotriazine (E) can be substituted with amine (C') or (D) under nucleophilic aromatic substitution reaction conditions using an amine base such as diisopropylethylamine (DIPEA) or triethylamine (TEA) in a polar solvent such as dioxane to provide the piperazine-substituted pyrrolotriazine (F) or (F'). Reduction of —C(=$X^1$)—, wherein $X^1$ is $CH_2$, S, NH, or O, e.g., carbonyl, of (F) can be performed using a reducing agent such as sodium borohydride to provide —C—(XH)—, e.g., the alcohol (G). Alternatively, alkylation of $X^2$ can be performed using alkyl halides (alternative leaving groups) to provide $X^3$-containing analogs (G'). Enantiomeric enriched products can be obtained via catalytic asymmetric synthesis, chiral auxiliary based synthesis and resolution of a racemate. As shown below, Compounds 40 and 41 were prepared using Synthetic Protocol 3.

Example 4: Synthesis of 4-(4-(5-(1-(4-fluorophenyl)propyl)pyrimidin-2-yl)piperazin-1-yl)-6-(1-methyl-1H-pyrazol-4-yl)pyrrolo[1,2-f][1,2,4]triazine (Compounds 40 and 41)

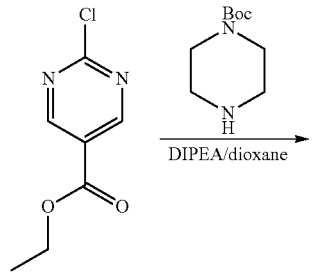

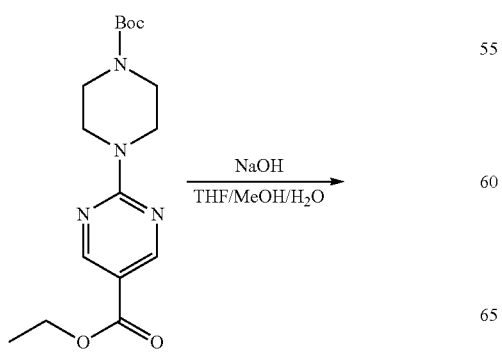

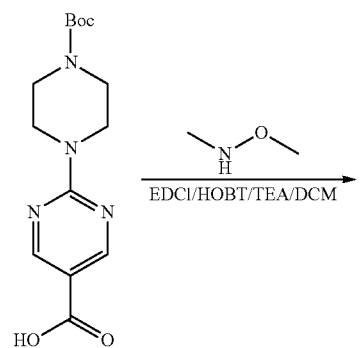

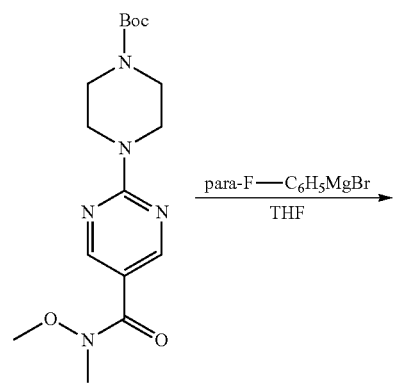

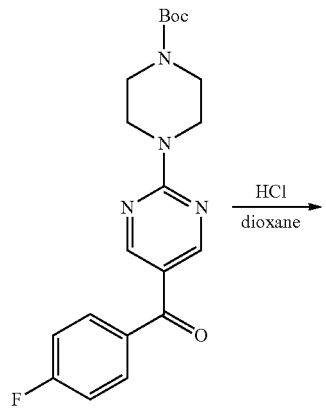

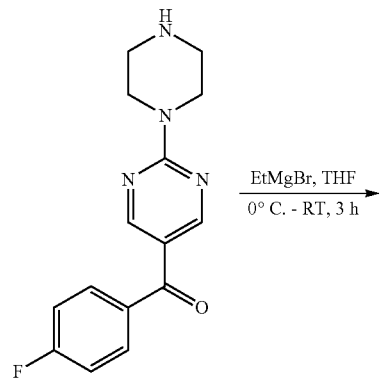

107
-continued
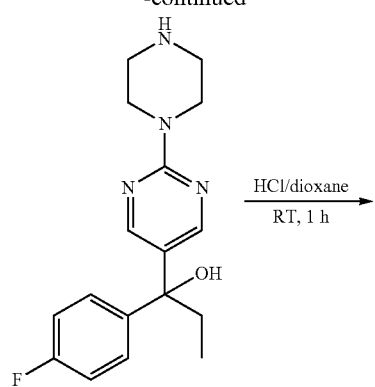
HCl/dioxane
RT, 1 h →
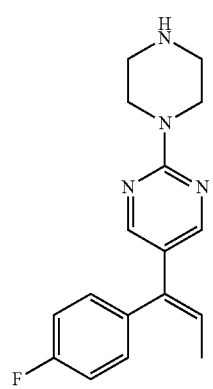
Pd/C, MeOH
RT, 1 h →
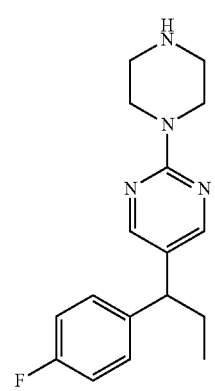
chiral HPLC →
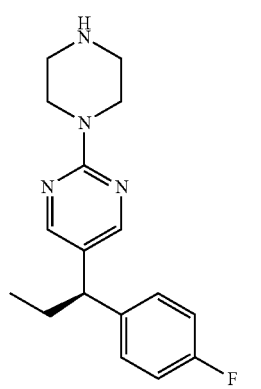 + 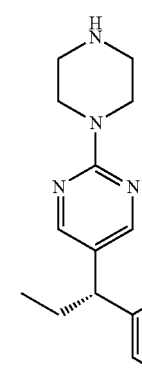
108
-continued
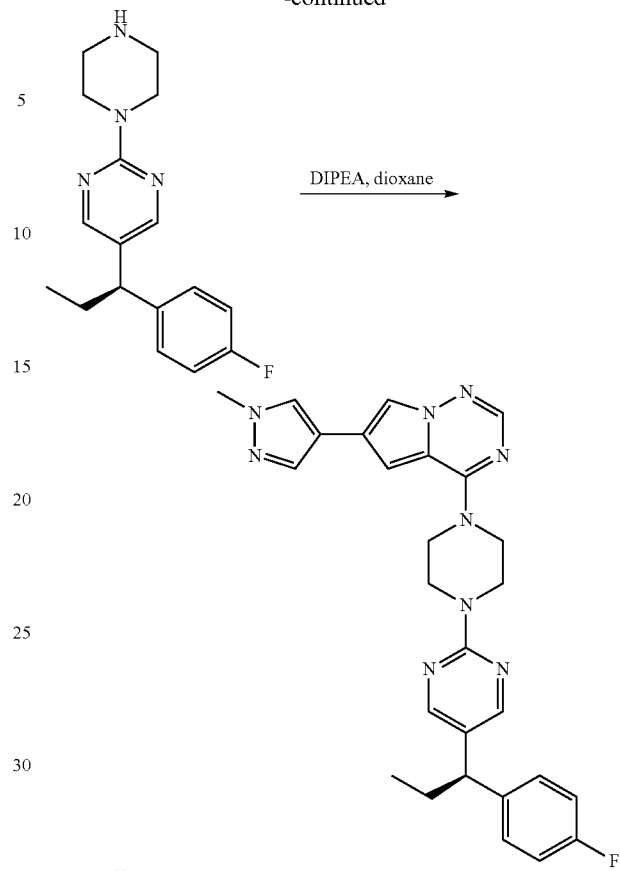
DIPEA, dioxane →
DIPEA, dioxane →
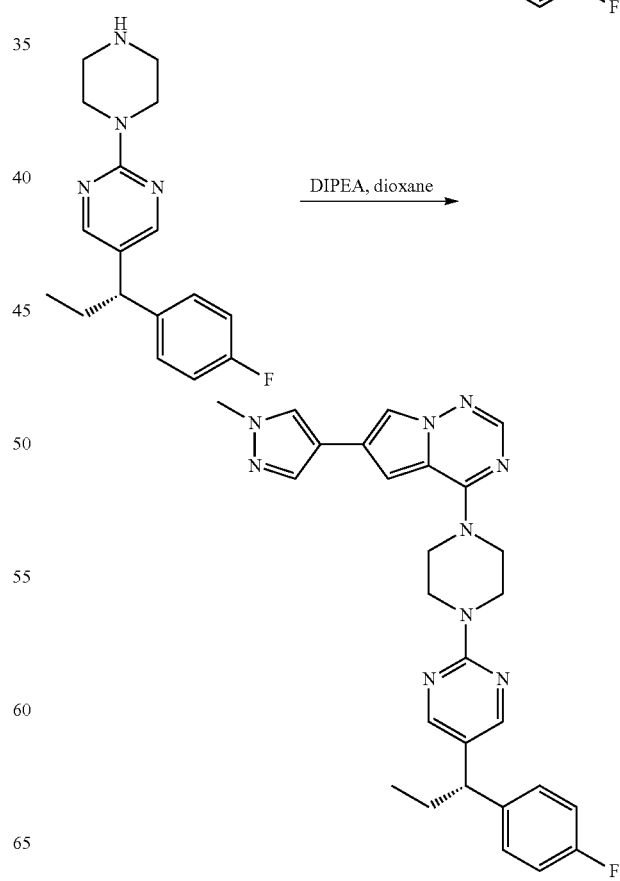

Step 1: Synthesis of ethyl 2-(4-(tert-butoxycarbonyl)piperazin-1-yl)pyrimidine-5-carboxylate

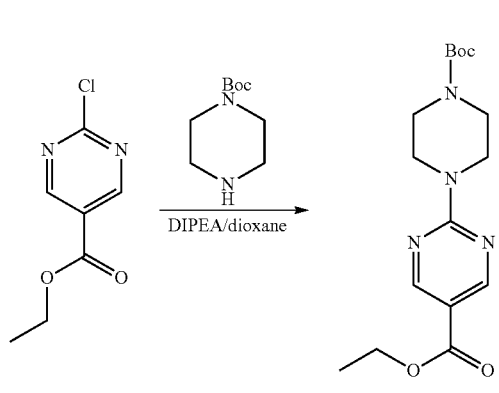 [SMILES: CCOC(=O)c1cnc(Cl)nc1 ; CC(C)(C)OC(=O)N1CCNCC1 ; CCOC(=O)c1cnc(N2CCN(C(=O)OC(C)(C)C)CC2)nc1]

To a solution of tert-butyl piperazine-1-carboxylate (10.0 g, 53.7 mmol) and diisopropylethylamine (23.4 mL, 134.25 mmol) in dioxane (80 mL) was added ethyl 2-chloropyrimidine-5-carboxylate (10 g, 53.7 mmoL), and the reaction mixture was stirred at RT for 3 h. LCMS showed the reaction was completed. The reaction was concentrated to afford the title compound (17 g, crude), which was directly used in the next step without the further purification. MS (ES+) $C_{16}H_{24}N_4O_4$ requires: 336, found: 237, 281 [M−56+H]$^+$.

Step 2: Synthesis of 2-(4-(tert-butoxycarbonyl)piperazin-1-yl)pyrimidine-5-carboxylic acid

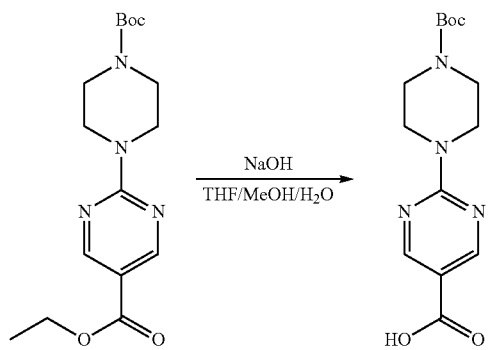 [SMILES: CCOC(=O)c1cnc(N2CCN(C(=O)OC(C)(C)C)CC2)nc1 ; "NaOH" ; CC(C)(C)OC(=O)N1CCN(c2ncc(C(=O)O)cn2)CC1]

To a solution of ethyl 2-(4-(tert-butoxycarbonyl)piperazin-1-yl)pyrimidine-5-carboxylate (17 g, crude) in THF/MeOH/water (300 mL) was added sodium hydroxide (4.3 g, 107.5 mmol), and the reaction was stirred at 70° C. for 2 h. LCMS showed the reaction was completed. The reaction mixture was cooled to RT, acidified to pH=5-6 with 1 M HCl and filtered. The solid was collected and dried to give the title compound (16 g, 96%) as a white solid, which was directly used in the next step without further purification. MS (ES+) $C_{14}H_{20}N_4O_4$ requires: 308, found: 253 [M−56+H]$^+$.

Step 3: Synthesis of tert-butyl 4-(5-(methoxy(methyl)carbamoyl)pyrimidin-2-yl)piperazine-1-carboxylate

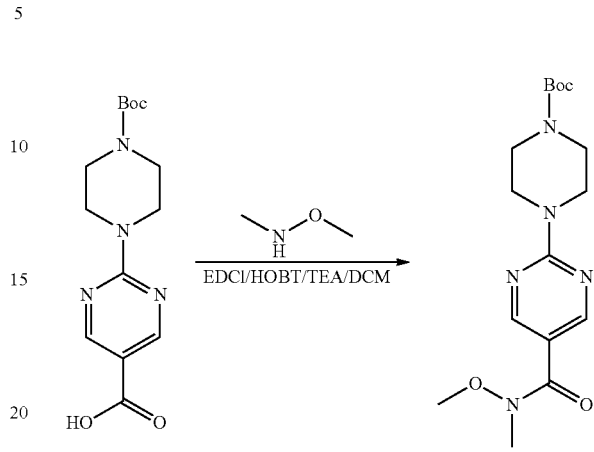

To a suspension of 2-(4-(tert-butoxycarbonyl)piperazin-1-yl)pyrimidine-5-carboxylic acid (13.8 g, 44.8 mmol), EDCI (12.8 g, 67.2 mmol) and HOBT (7.2 g, 53.7 mmol) in dichloromethane (200 mL) was added triethylamine (25 mL, 179.2 mmol), and the mixture was stirred at RT for 1 h, followed by the addition of N,O-dimethylhydroxylamine (5 g, 53.7 mmol). The reaction was stirred for another 3 h. LCMS showed the reaction was completed. The reaction mixture was washed with water (100 mL), and the organic layer was dried, filtered and concentrated. The residue was purified by silica gel chromatography (petroleum ether:ethyl acetate=1:1) to give the title compound (11.2 g, 67%) as a white solid. MS (ES+) $C_{16}H_{25}N_5O_4$ requires: 351, found: 296 [M−56+H]$^+$.

Step 4: Synthesis of tert-butyl 4-(5-(4-fluorobenzoyl)pyrimidin-2-yl)piperazine-1-carboxylate

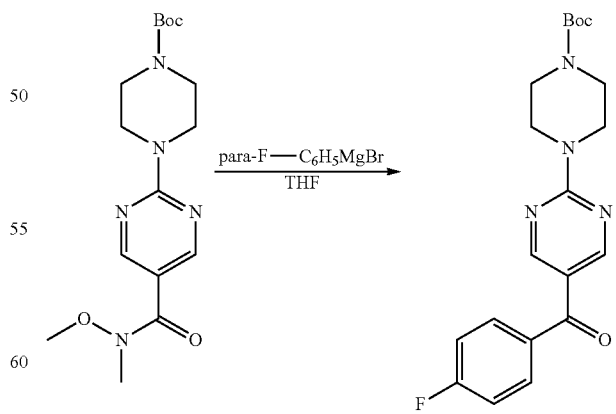

To a solution of tert-butyl 4-(5-(methoxy(methyl)carbamoyl)pyrimidin-2-yl)piperazine-1-carboxylate (7.8 g, 22.22 mmol) in dry THF (50 mL) was added $C_6H_5MgFBr$ (1 M in THF, 50 mL) at 0° C. under nitrogen, and the mixture was stirred at RT for 3 h. LCMS showed the reaction was completed. The reaction was quenched with 1 M HCl and extracted with ethyl acetate. The combined organic layers were washed with water and brine, dried over sodium sulfate, filtered and concentrated. The residue was purified by silica gel chromatography (petroleum ether:ethyl acetate=5:1) to give the title compound (7.2 g, 84%) as a yellow solid. MS (ES+) $C_{20}H_{23}FN_4O_3$ requires: 386, found: 331 [M−56+H]+.

Step 5: Synthesis of (4-fluorophenyl)(2-(piperazin-1-yl)pyrimidin-5-yl)methanone

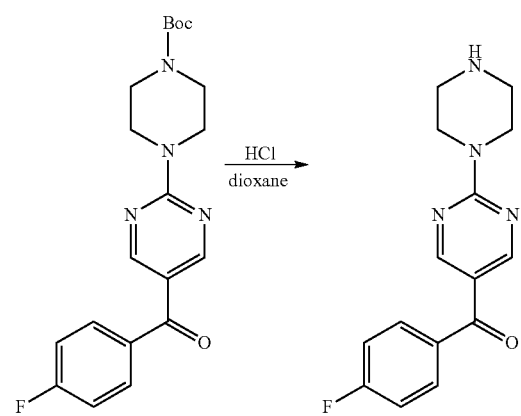 [SMILES: CC(C)(C)OC(=O)N1CCN(c2ncc(C(=O)c3ccc(F)cc3)cn2)CC1 ; Cl ; O=C(c1ccc(F)cc1)c1cnc(N2CCNCC2)nc1]

To a solution of tert-butyl 4-(5-(4-fluorobenzoyl)pyrimidin-2-yl)piperazine-1-carboxylate (8.2 g, 21.24 mmol) in dioxane (50 mL) was added HCl in dioxane (4 M, 20 mL). The reaction mixture was stirred at RT overnight. LCMS showed the reaction was completed. The mixture was concentrated to get the title compound as a light yellow solid (5.5 g, 90%). MS (ES+) $C_{15}H_{15}FN_4O$ requires: 286, found: 287 [M+H]+.

Step 6: Synthesis of 1-(4-fluorophenyl)-1-(2-(piperazin-1-yl)pyrimidin-5-yl)propan-1-ol

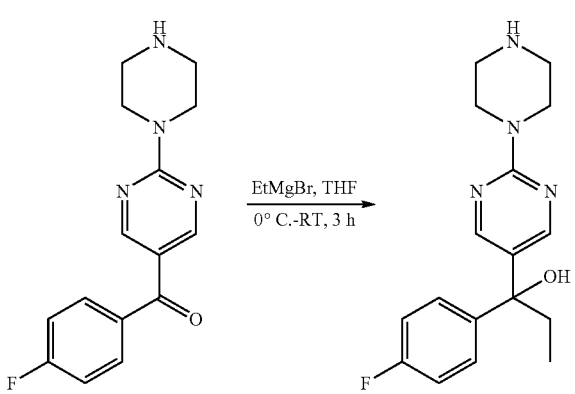 [SMILES: O=C(c1ccc(F)cc1)c1cnc(N2CCNCC2)nc1 ; CCC(O)(c1ccc(F)cc1)c1cnc(N2CCNCC2)nc1]

To a solution of (4-fluorophenyl)(2-(piperazin-1-yl)pyrimidin-5-yl)methanone (4.0 g, 21.84 mmol) in dry THF (150 mL) was added EtMgBr (1 M in THF, 150 mL) at 0° C. under nitrogen. The mixture was stirred at RT for 3 h, then quenched with NH$_4$Cl solution and extracted with ethyl acetate (200*3 mL). The combined organic layers were washed with water and brine, dried over sodium sulfate, filtered and concentrated. The residue was purified by combi-flash with dichloromethane:methanol=10:1 to give the title compound (440 mg, 10%) as a yellow solid. MS (ES+) $C_{17}H_{21}FN_4O$ requires: 316, found: 317 [M+H]+.

Step 7: Synthesis of (E)-5-(1-(4-fluorophenyl)prop-1-enyl)-2-(piperazin-1-yl)pyrimidine

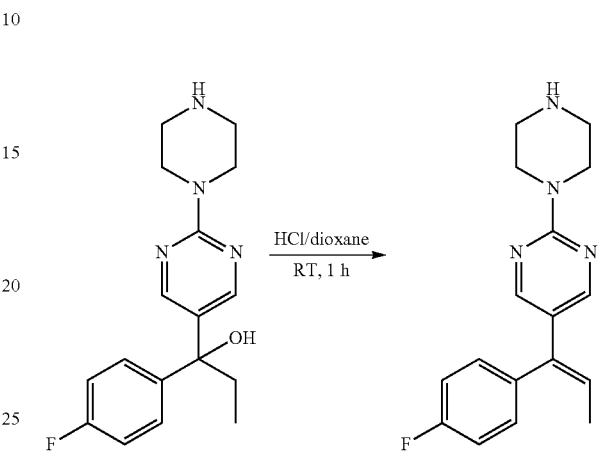

To a solution of 1-(4-fluorophenyl)-1-(2-(piperazin-1-yl)pyrimidin-5-yl)propan-1-ol (200 mg, 0.6 mmol) in dioxane (10 mL) was added HCl in dioxane (4 M, 10 mL), and the reaction was stirred at RT for 1 h. LCMS showed the reaction was completed. The mixture was concentrated to an oil, which was purified by Combiflash with dichloromethane:methanol=20:1 to give the title compound as a light yellow solid (185 mg, 98%). MS (ES+) $C_{17}H_{19}FN_4$ requires: 298, found: 299 [M+H]+.

Step 8: Synthesis of 5-(4-fluorophenyl)propy)-2-(piperazin-1-yl)pyrimidine

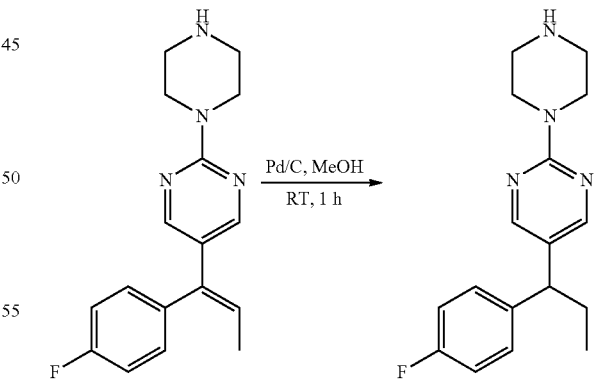

To a solution of (E)-5-(1-(4-fluorophenyl)prop-1-enyl)-2-(piperazin-1-yl)pyrimidine (170 mg, 0.57 mmol) in methanol (10 mL) was added Pd/C (30 mg). The mixture was exposed to 1 atm hydrogen (balloon) and stirred at RT for 1 h. The mixture was filtrated, and the filtrate was concentrated to an oil, which was purified by combiflash with dichloromethane:methanol=50:1 to give the title compound (racemate, 90 mg, 53%) as a yellow oil.

Step 9: Chiral separation of (R)-5-(1-(4-fluorophenyl)propyl)-2-(piperazin-1-yl)pyrimidine and (S)-5-(1-(4-fluorophenyl)propyl)-2-(piperazin-1-yl)pyrimidine

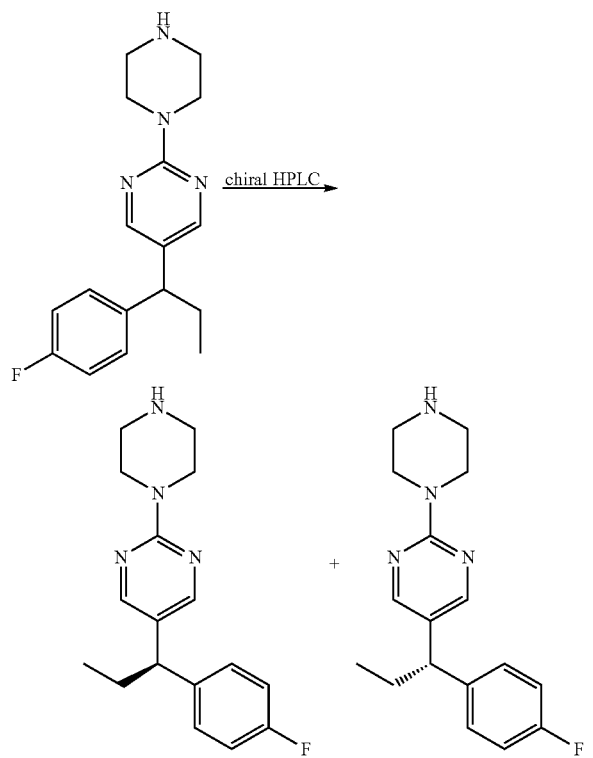 [SMILES: CCC(c1ccc(F)cc1)c1cnc(N2CCNCC2)nc1 ; CC[C@H](c1ccc(F)cc1)c1cnc(N2CCNCC2)nc1 ; CC[C@@H](c1ccc(F)cc1)c1cnc(N2CCNCC2)nc1]

The above racemate compound (90 mg) was separated by Chiral-HPLC to afford the enantiomers (35 mg). MS (ES+) $C_{17}H_{21}FN_4$ requires: 300, found: 301 [M+H]$^+$. The absolute stereochemistry was assigned randomly.
Chiral separation condition: Chiral column: OJ-H (250*4.6 mm 5 um)
Mobile phase: n-Hexane(0.1% DEA):EtOH (0.1% DEA)= 95:5

Step 10a: Synthesis of (R)-4-(4-(5-(1-(4-fluorophenyl)propyl)pyrimidin-2-yl)piperazin-1-yl)-6-(1-methyl-1H-pyrazol-4-yl)pyrrolo[1,2-f][1,2,4]triazine A solution of (R)-5-(1-(4-fluorophenyl)propyl)-2-(piperazin-1-yl)pyrimidine 36 mg, 0.12 mmol), 4-chloro-6-(1-methyl-1H-pyrazol-4-yl)pyrrolo[1,2-f][1,2,4]triazine (31 mg, 0.132 mmol) and diisopropylethylamine (47 mg, 0.36 mmol) in 1,4-dioxane (5 mL) was stirred at RT for 3 h. The reaction mixture was concentrated, and the residue was purified by Prep-HPLC to give the title compound (21.1 mg, 35%) as a white solid. MS (ES+) $C_{26}H_{26}FN_9O$ requires: 497, found: 498 [M+H]$^+$.

Step 10b: Synthesis of (S)-4-(4-(5-(1-(4-fluorophenyl)propyl)pyrimidin-2-yl)piperazin-1-yl)-6-(1-methyl-1H-pyrazol-4-yl)pyrrolo[1,2-f][1,2,4]triazine

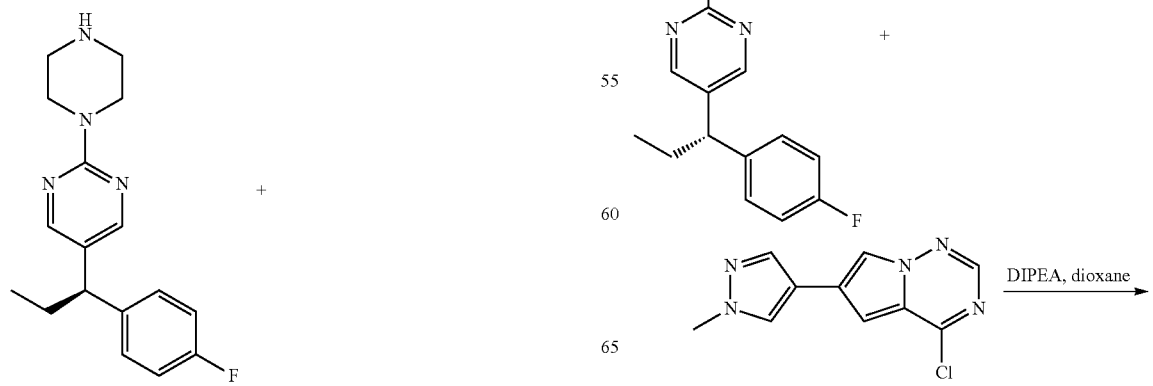

115

-continued

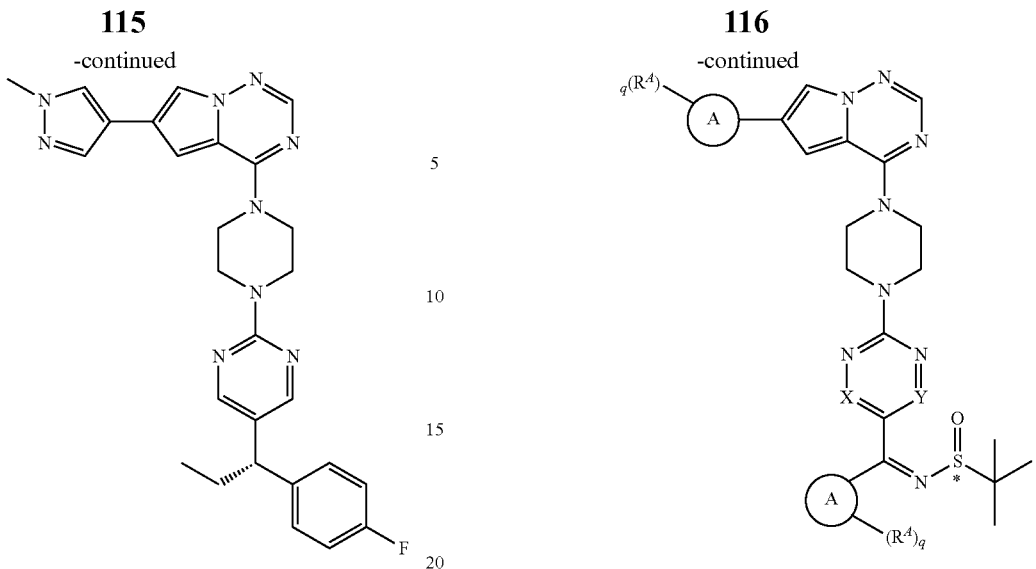

A mixture of (S)-5-(1-(4-fluorophenyl)propyl)-2-(piperazin-1-yl)pyrimidine 35 mg, 0.12 mmol), 4-chloro-6-(1-methyl-1H-pyrazol-4-yl)pyrrolo[1,2-f][1,2,4]triazine (30 mg, 0.132 mmol) and diisopropylethylamine (47 mg, 0.36 mmol) in 1,4-dioxane (5 mL) was stirred at RT for 3 h. The reaction mixture was concentrated, and the residue was purified by Prep-HPLC to give the title compound (24.4 mg, 35%) as a white solid. MS (ES+) $C_{26}H_{26}FN_9O$ requires: 497, found: 498 [M+H]$^+$.

Synthetic Protocol 4

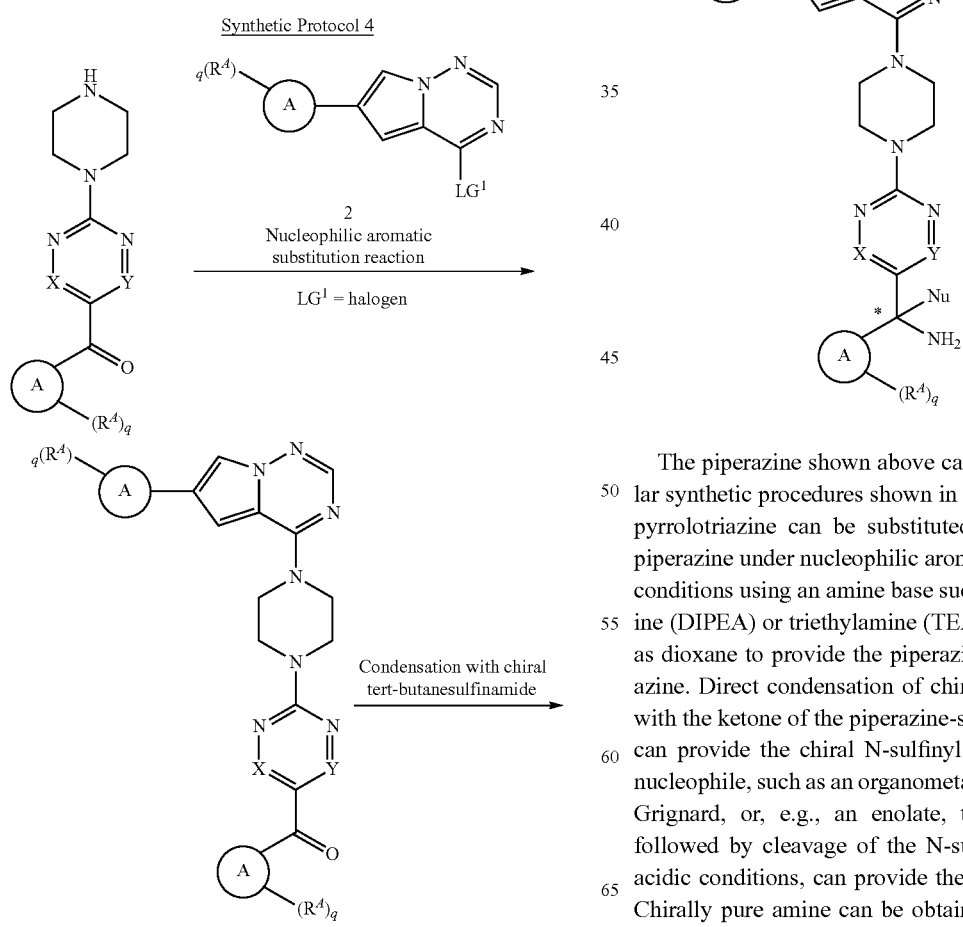

116

-continued

The piperazine shown above can be prepared using similar synthetic procedures shown in Synthetic Protocol 3. The pyrrolotriazine can be substituted with the amine of the piperazine under nucleophilic aromatic substitution reaction conditions using an amine base such as diisopropylethylamine (DIPEA) or triethylamine (TEA) in a polar solvent such as dioxane to provide the piperazine-substituted pyrrolotriazine. Direct condensation of chiral tert-butanesulfinamide with the ketone of the piperazine-substituted pyrrolotriazine can provide the chiral N-sulfinyl imine. 1,2-addition of a nucleophile, such as an organometallic reagent, e.g., an alkyl Grignard, or, e.g., an enolate, to the N-sulfinyl imine, followed by cleavage of the N-sulfinyl group under, e.g., acidic conditions, can provide the chirally enriched amine. Chirally pure amine can be obtained by chiral chromatography, e.g., SFC or HPLC. The compounds prepared by Synthetic Protocol 4 were separated by chiral SFC using the following separation conditions:

Column: ChiralPak AS-H 20×250 mm

Mobile Phase: 45% ethanol containing 0.25% DEA in $CO_2$

Flow rate: 70 ml/min

Sample: 93.7 mg racemic mixture was dissolved in 15 ml solvent consisting of methanol/ethanol=1/1 containing 150 uL diethylamine Injection: 2 mL per run Detection: 254 nm As shown below, Compounds 12, 13, 36, 43 and 44 were prepared using Synthetic Protocol 4.

Example 5: Synthesis of (S)-(2-(4-(6-(1-methyl-1H-pyrazol-4-yl)pyrrolo[2,1-f][1,2,4]triazin-4-yl)piperazin-1-yl)pyrimidin-5-yl)(phenyl)methanamine and (R)-(2-(4-(6-(1-methyl-1H-pyrazol-4-yl)pyrrolo[2,1-f][1,2,4]triazin-4-yl)piperazin-1-yl)pyrimidin-5-yl)(phenyl)methanamine (Compounds 12 and 13)

Step 1: Synthesis of (2-(4-(6-(1-methyl-1H-pyrazol-4-yl)pyrrolo[2,1-f][1,2,4]triazin-4-yl)piperazin-1-yl)pyrimidin-5-yl)(phenyl)methanimine

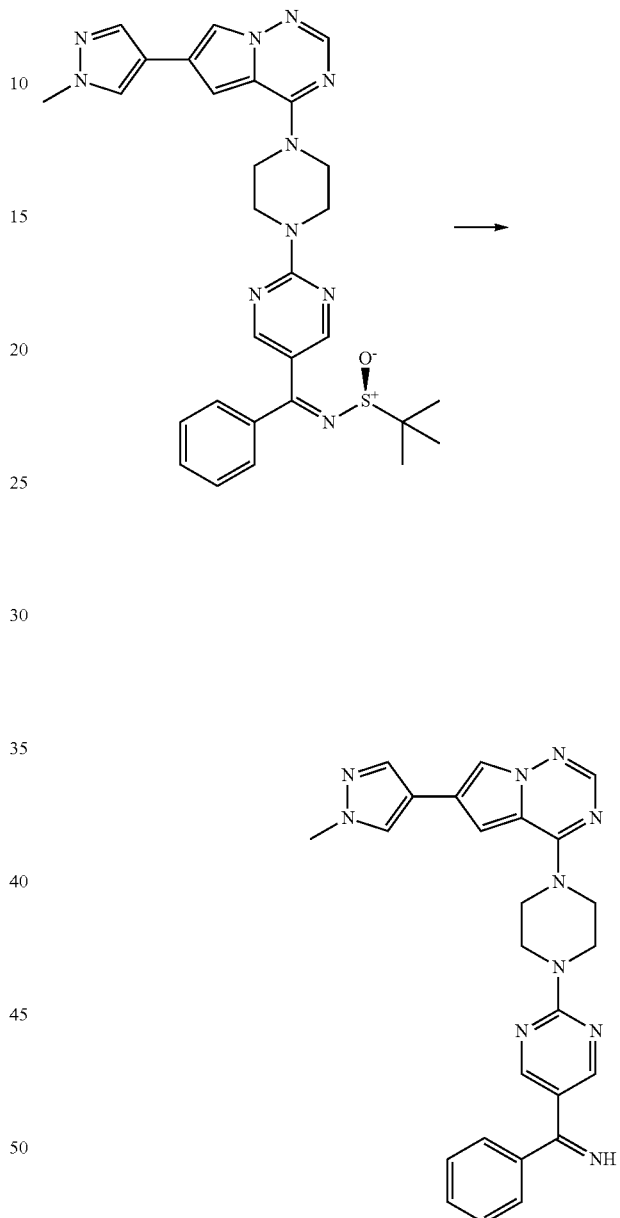

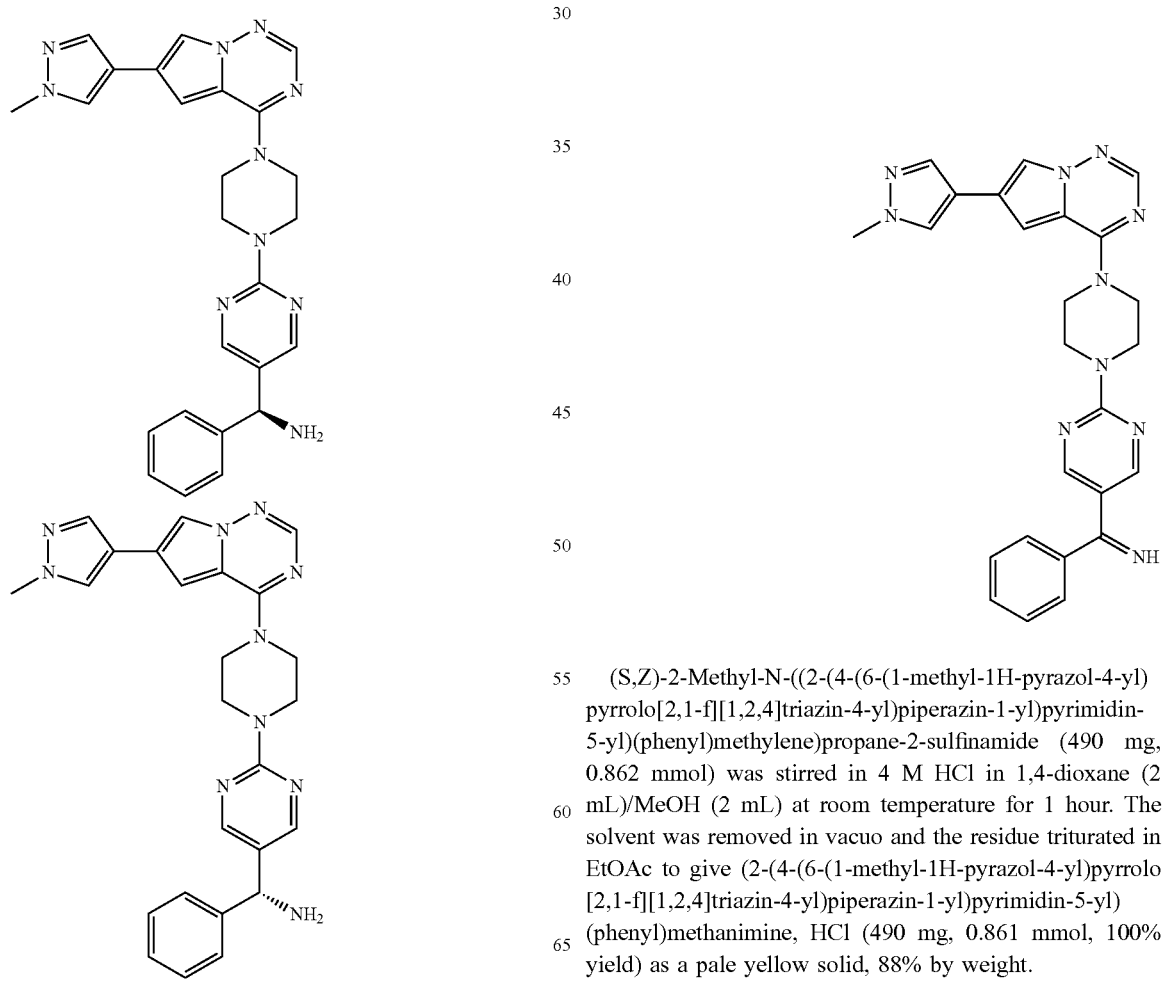

(S,Z)-2-Methyl-N-((2-(4-(6-(1-methyl-1H-pyrazol-4-yl)pyrrolo[2,1-f][1,2,4]triazin-4-yl)piperazin-1-yl)pyrimidin-5-yl)(phenyl)methylene)propane-2-sulfinamide (490 mg, 0.862 mmol) was stirred in 4 M HCl in 1,4-dioxane (2 mL)/MeOH (2 mL) at room temperature for 1 hour. The solvent was removed in vacuo and the residue triturated in EtOAc to give (2-(4-(6-(1-methyl-1H-pyrazol-4-yl)pyrrolo[2,1-f][1,2,4]triazin-4-yl)piperazin-1-yl)pyrimidin-5-yl)(phenyl)methanimine, HCl (490 mg, 0.861 mmol, 100% yield) as a pale yellow solid, 88% by weight.

MS (ES+) $C_{25}H_{24}N_{10}$ requires: 464, found: 465 [M+H]$^+$.

Step 2: Synthesis of rac-(2-(4-(6-(1-methyl-1H-pyrazol-4-yl)pyrrolo[2,1-f][1,2,4]triazin-4-yl)piperazin-1-yl)pyrimidin-5-yl)(phenyl)methanamine

Step 3: Separation of Enantiomers

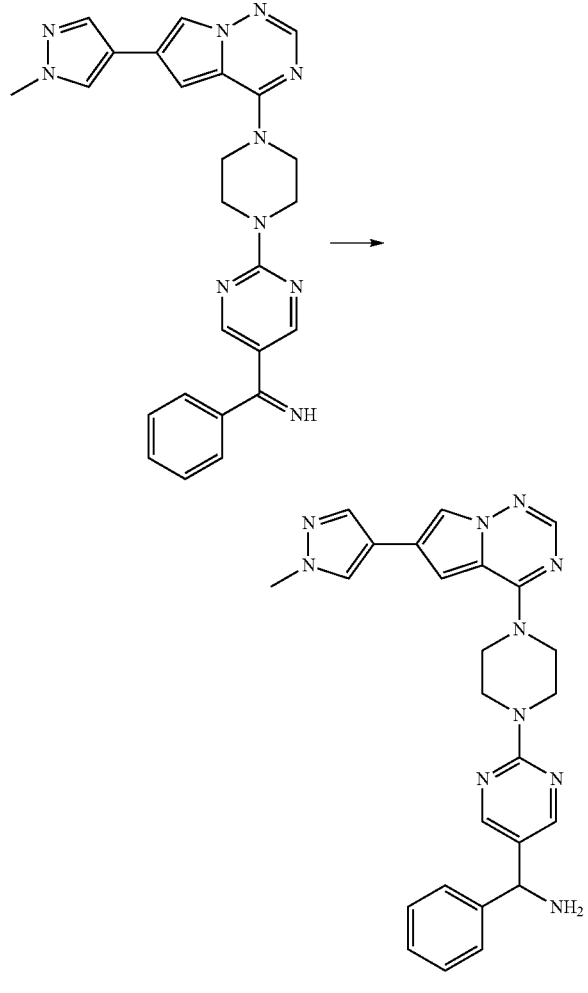

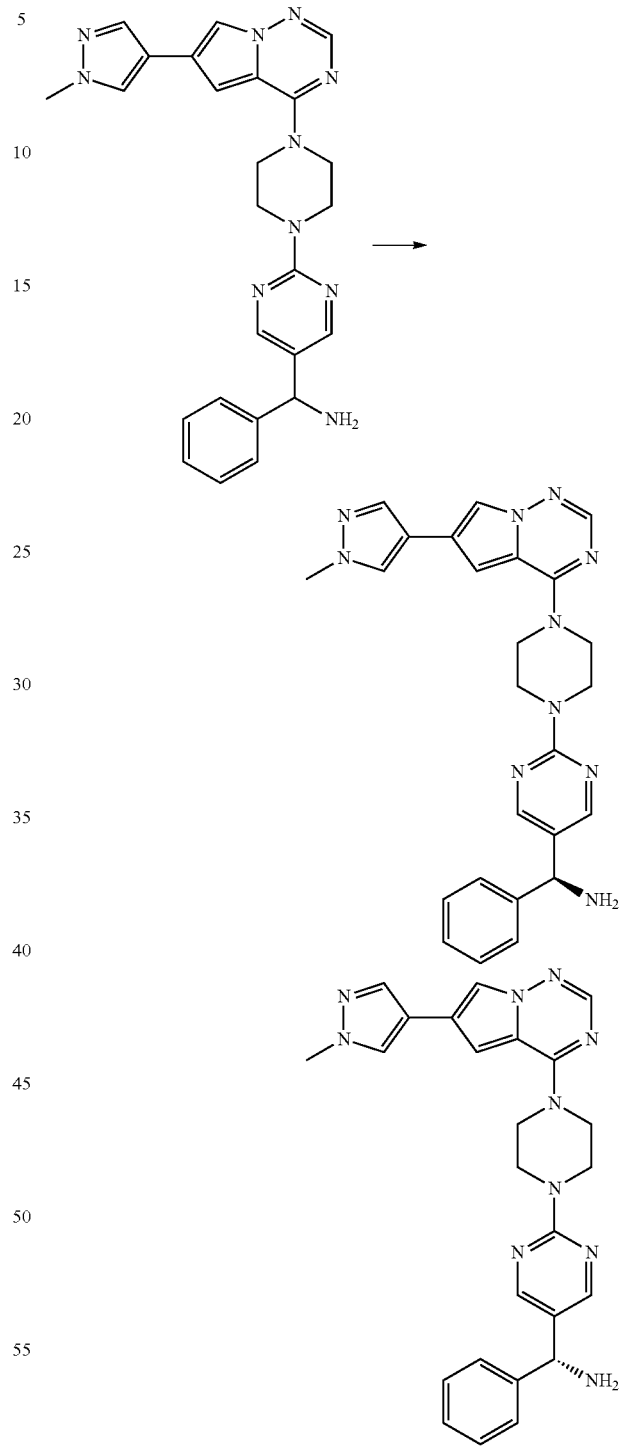

(2-(4-(6-(1-Methyl-1H-pyrazol-4-yl)pyrrolo[2,1-f][1,2,4]triazin-4-yl)piperazin-1-yl)pyrimidin-5-yl)(phenyl)methanimine, HCl (410 mg, 0.818 mmol) was suspended in MeOH (8 mL). Sodium borohydride (40 mg, 1.057 mmol) was added in one portion, producing an exotherm and forming a clear solution. Additional sodium borohydride (40 mg, 1.057 mmol) was added in one portion, producing an exotherm and forming a suspension. The MeOH was removed in vacuo and the residue partitioned between EtOAc—NaHCO$_3$. The aqueous phase was extracted a second time with EtOAc. The combined organic extracts were washed with brine, dried over Na$_2$SO$_4$, filtered, and concentrated in vacuo. The residue was recrystallized from EtOH to give (2-(4-(6-(1-methyl-1H-pyrazol-4-yl)pyrrolo[2,1-f][1,2,4]triazin-4-yl)piperazin-1-yl)pyrimidin-5-yl)(phenyl)methanamine (182 mg, 0.390 mmol, 47.7% yield) as an off-white solid.

MS (ES+) C$_{25}$H$_{26}$N$_{10}$ requires: 466, found: 467 [M+H]$^+$.

The enantiomers of racemic (2-(4-(6-(1-methyl-1H-pyrazol-4-yl)pyrrolo[2,1-f][1,2,4]triazin-4-yl)piperazin-1-yl)pyrimidin-5-yl)(phenyl)methanamine (185 mg, 0.397 mmol) were separated by chiral SFC to give (S)-(2-(4-(6-(1-methyl-1H-pyrazol-4-yl)pyrrolo[2,1-f][1,2,4]triazin-4-yl)piperazin-1-yl)pyrimidin-5-yl)(phenyl)methanamine (74 mg, 0.159 mmol, 80.0% yield) and (R)-(2-(4-(6-(1-methyl-1H-pyrazol-4-yl)pyrrolo[2,1-f][1,2,4]triazin-4-yl)piperazin-1-yl)pyrimidin-5-yl)(phenyl)methanamine (94 mg, 0.201 mmol, 100% yield). The absolute stereochemistry was assigned randomly.

MS (ES+) $C_{25}H_{26}N_{10}$ requires: 466, found: 467 [M+H]$^+$.

Example 6: Synthesis of (S)—N,N-dimethyl-1-(2-(4-(6-(1-methyl-1H-pyrazol-4-yl)pyrrolo[2,1-f][1,2,4]triazin-4-yl)piperazin-1-yl)pyrimidin-5-yl)-1-phenylmethanamine (Compound 36)

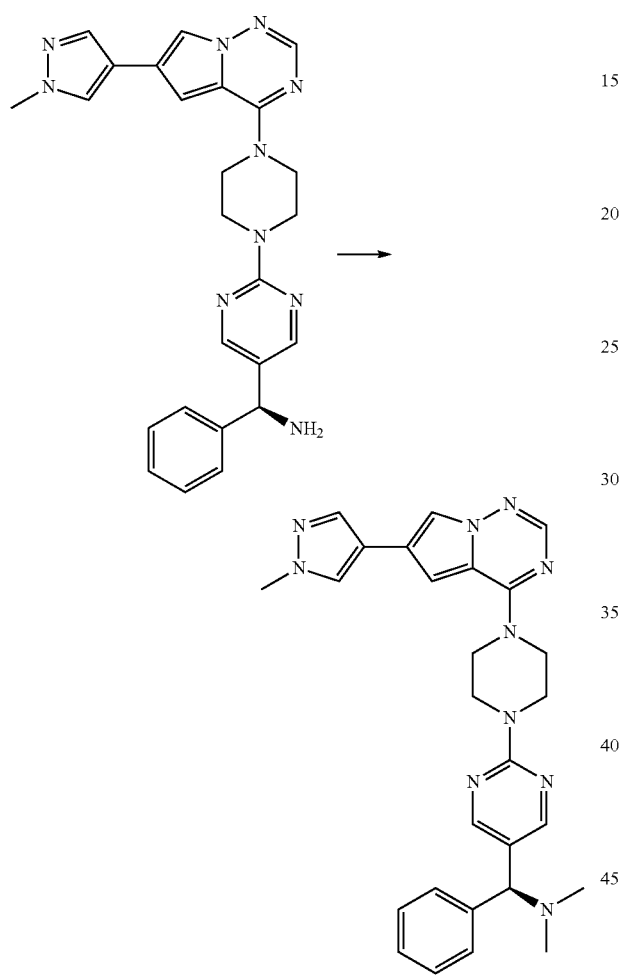

(S)-(2-(4-(6-(1-Methyl-1H-pyrazol-4-yl)pyrrolo[2,1-f][1,2,4]triazin-4-yl)piperazin-1-yl)pyrimidin-5-yl)(phenyl)methanamine (72 mg, 0.154 mmol) and formaldehyde (125 mg, 1.543 mmol) were taken up in MeCN (1.5 mL). Sodium cyanoborohydride (25 mg, 0.398 mmol) was added, followed by acetic acid (0.02 mL, 0.349 mmol) and the resulting mixture was stirred at room temperature for 3 hours. Saturated NaHCO$_3$ was added and the products extracted into DCM (×2). The combined organic extracts were washed with brine, dried over Na$_2$SO$_4$, filtered, and concentrated in vacuo. Purification of the residue by MPLC (0-10% MeOH-DCM), followed by MPLC (0-10% MeOH-EtOAc), followed by MPLC (0-8% MeOH-EtOAc) gave (S)—N,N-dimethyl-1-(2-(4-(6-(1-methyl-1H-pyrazol-4-yl)pyrrolo[2,1-f][1,2,4]triazin-4-yl)piperazin-1-yl)pyrimidin-5-yl)-1-phenylmethanamine (15 mg, 0.030 mmol, 19.65% yield). MS (ES+) $C_{27}H_{30}N_{10}$ requires: 494, found: 495 [M+H]$^+$.

Example 7: Synthesis of (R)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine and (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine (Compounds 43 and 44)

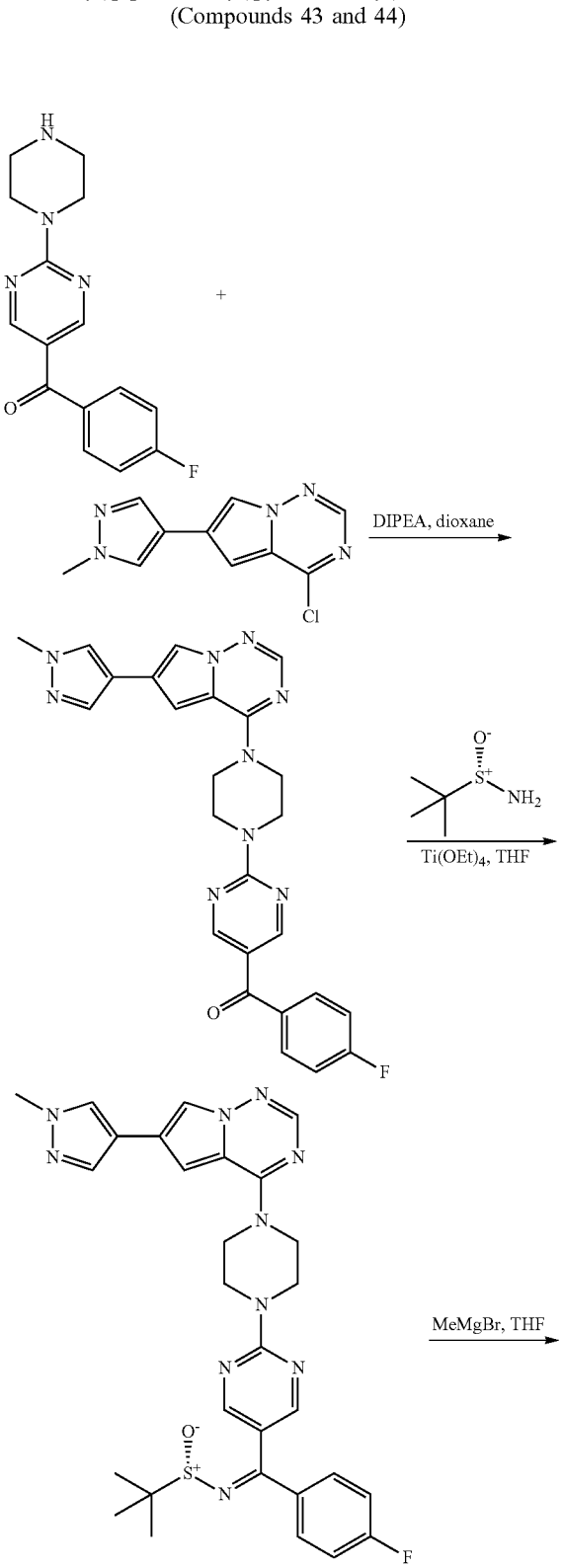

123

-continued

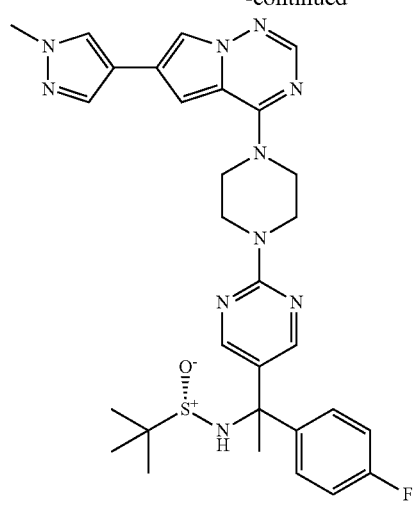

124

Step 1: Synthesis of (4-fluorophenyl)(2-(4-(6-(1-methyl-1H-pyrazol-4-yl)pyrrolo[2,1-f][1,2,4]triazin-4-yl)piperazin-1-yl)pyrimidin-5-yl)methanone

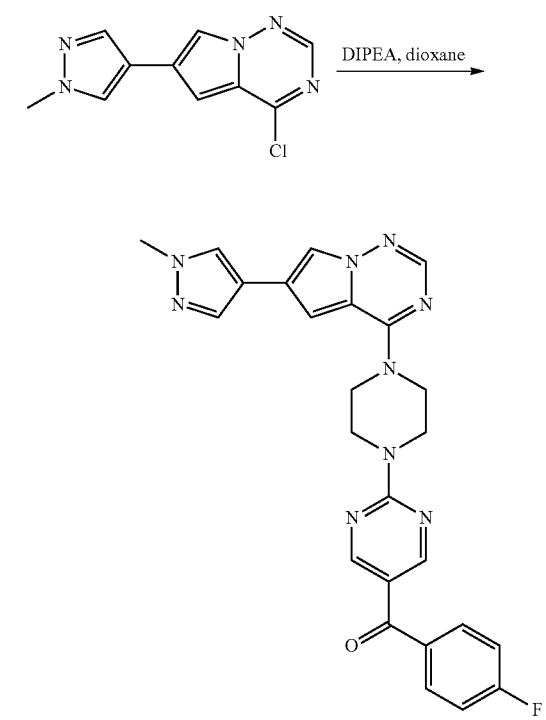

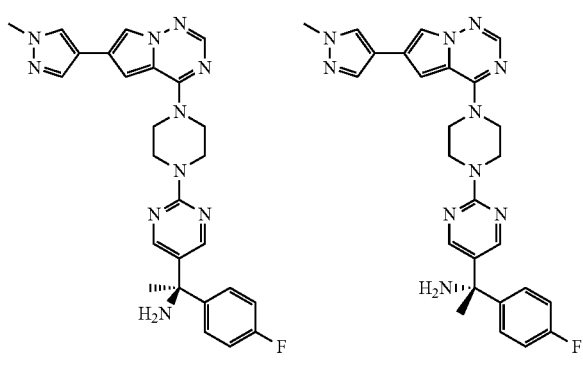

4-Chloro-6-(1-methyl-1H-pyrazol-4-yl)pyrrolo[2,1-f][1,2,4]triazine (180 mg, 0.770 mmol), (4-fluorophenyl)(2-(piperazin-1-yl)pyrimidin-5-yl)methanone, HCl (265 mg, 0.821 mmol) and DIPEA (0.40 mL, 2.290 mmol) were stirred in 1,4-dioxane (4 mL) at room temperature for 18 hours. Saturated ammonium chloride was added and the products extracted into DCM (×2). The combined organic extracts were dried over $Na_2SO_4$, filtered through Celite eluting with DCM, and the filtrate concentrated in vacuo. Purification of the residue by MPLC (25-100% EtOAc-DCM) gave (4-fluorophenyl)(2-(4-(6-(1-methyl-1H-pyrazol-4-yl)pyrrolo[2,1-f][1,2,4]triazin-4-yl)piperazin-1-yl)pyrimidin-5-yl)methanone (160 mg, 0.331 mmol, 43% yield) as an off-white solid. MS (ES+) $C_{25}H_{22}FN_9O$ requires: 483, found: 484 $[M+H]^+$.

Step 2: Synthesis of (S,Z)—N-((4-fluorophenyl)(2-(4-(6-(1-methyl-1H-pyrazol-4-yl)pyrrolo[2,1-f][1,2,4]triazin-4-yl)piperazin-1-yl)pyrimidin-5-yl)methylene)-2-methylpropane-2-sulfinamide

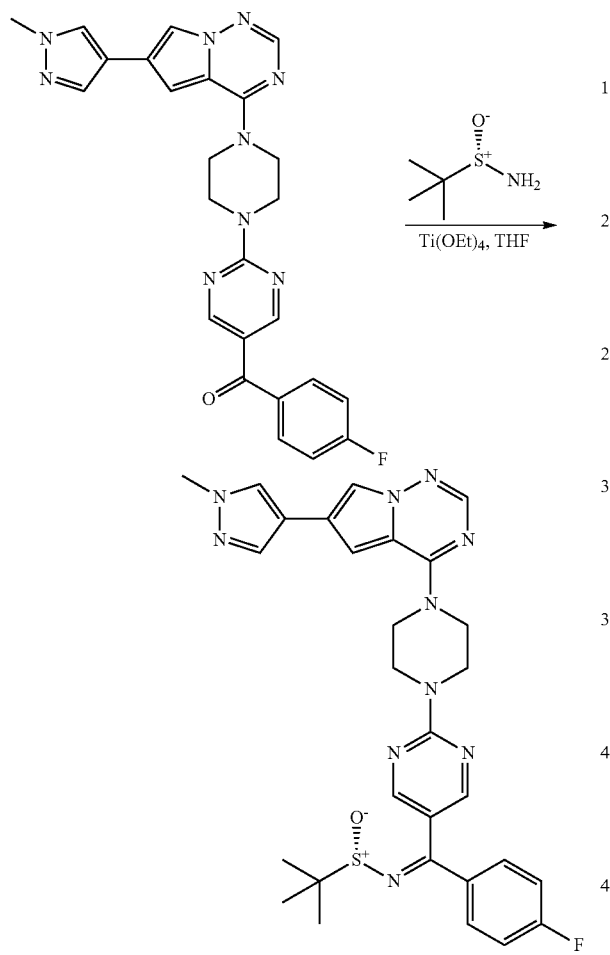

(S)-2-Methylpropane-2-sulfinamide (110 mg, 0.908 mmol), (4-fluorophenyl)(2-(4-(6-(1-methyl-1H-pyrazol-4-yl)pyrrolo[2,1-f][1,2,4]triazin-4-yl)piperazin-1-yl)pyrimidin-5-yl)methanone (158 mg, 0.327 mmol) and ethyl orthotitanate (0.15 mL, 0.715 mmol) were stirred in THF (3.2 mL) at 70° C. for 18 hours. Room temperature was attained, water was added, and the products extracted into EtOAc (×2). The combined organic extracts were washed with brine, dried over $Na_2SO_4$, filtered, and concentrated in vacuo while loading onto Celite. Purification of the residue by MPLC (0-10% MeOH-EtOAc) gave (S,Z)—N-((4-fluorophenyl)(2-(4-(6-(1-methyl-1H-pyrazol-4-yl)pyrrolo[2,1-f][1,2,4]triazin-4-yl)piperazin-1-yl)pyrimidin-5-yl)methylene)-2-methylpropane-2-sulfinamide (192 mg, 0.327 mmol, 100% yield) as an orange solid. MS (ES+) $C_{29}H_{31}FN_{10}OS$ requires: 586, found: 587 $[M+H]^+$.

Step 3: Synthesis of (S)—N-(1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethyl)-2-methylpropane-2-sulfinamide

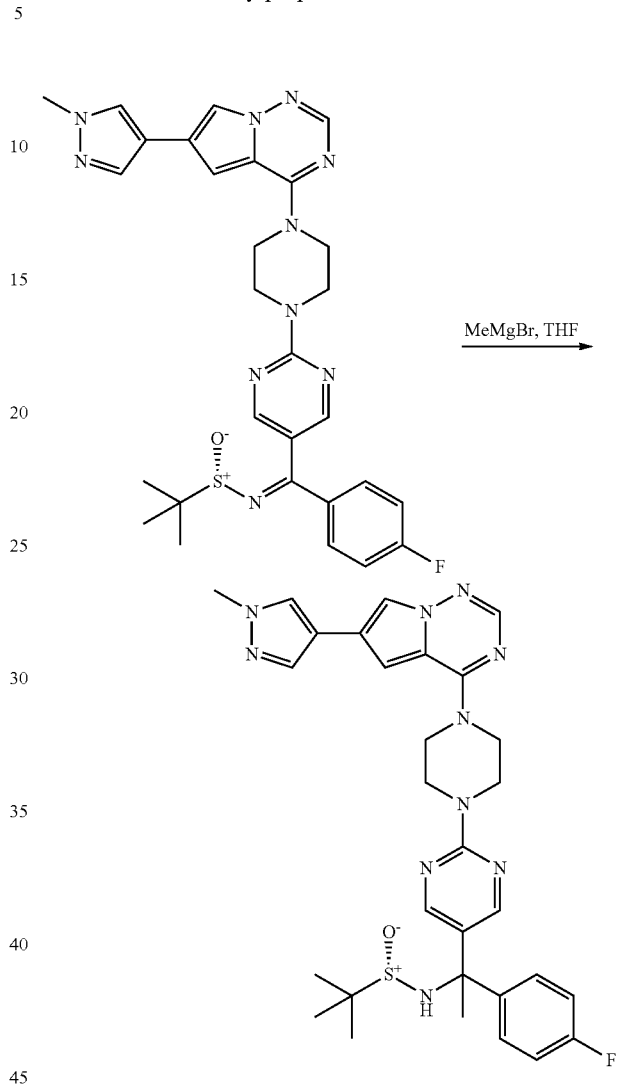

(S,Z)—N-((4-Fluorophenyl)(2-(4-(6-(1-methyl-1H-pyrazol-4-yl)pyrrolo[2,1-f][1,2,4]triazin-4-yl)piperazin-1-yl)pyrimidin-5-yl)methylene)-2-methylpropane-2-sulfinamide (190 mg, 0.324 mmol) was taken up in THF (3 mL) and cooled to 0° C. Methylmagnesium bromide (3 M solution in diethyl ether, 0.50 mL, 1.500 mmol) was added and the resulting mixture stirred at 0° C. for 45 minutes. Additional methylmagnesium bromide (3 M solution in diethyl ether, 0.10 mL, 0.300 mmol) was added and stirring at 0° C. continued for 20 minutes. Saturated ammonium chloride was added and the products extracted into EtOAc (×2). The combined organic extracts were washed with brine, dried over $Na_2SO_4$, filtered, and concentrated in vacuo while loading onto Celite. Purification of the residue by MPLC (0-10% MeOH-EtOAc) gave (S)—N-(1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethyl)-2-methylpropane-2-sulfinamide (120 mg, 0.199 mmol, 61.5% yield) as a yellow solid (mixture of diastereoisomers). MS (ES+) $C_{30}H_{35}FN_{10}OS$ requires: 602, found: 603 $[M+H]^+$.

127

Step 4: Synthesis of 1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine

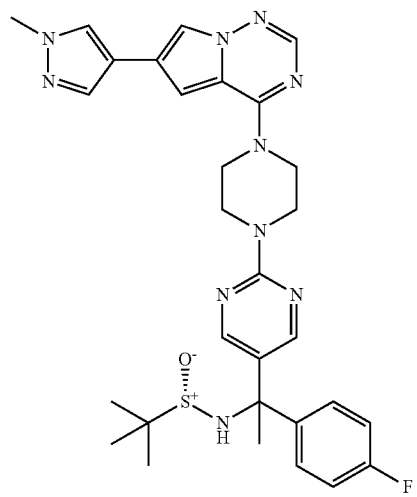

(S)—N-(1-(4-Fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethyl)-2-methylpropane-2-sulfinamide (120 mg, 0.199 mmol) was stirred in 4 M HCl in 1,4-dioxane (1.5 mL)/MeOH (1.5 mL) at room temperature for 1 hour. The solvent was removed in vacuo and the residue triturated in EtOAc to give 1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine, HCl (110 mg, 0.206 mmol, 103% yield) as a pale yellow solid. MS (ES+) $C_{26}H_{27}FN_{10}$ requires: 498, found: 482 [M−17+H]+, 499 [M+H]+.

128

Step 5: Chiral separation of (R)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine and (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine

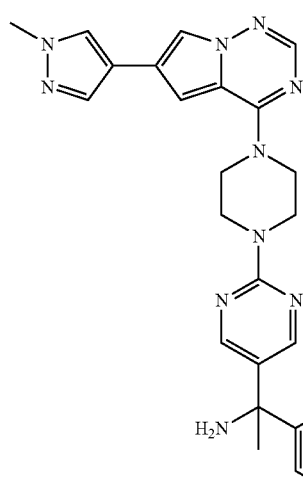

The enantiomers of racemic 1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine (94 mg, 0.189 mmol) were separated by chiral SFC to give (R)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine (34.4 mg, 0.069 mmol, 73.2% yield) and (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethanamine (32.1 mg, 0.064 mmol, 68.3% yield). The absolute stereochemistry was assigned randomly. MS (ES+) $C_{26}H_{27}FN_{10}$ requires: 498, found: 499 [M+H]+.

Preparation of Common Intermediates

Synthesis of 5-(2-phenylpropan-2-yl)-2-(piperazin-1-yl)pyrimidine

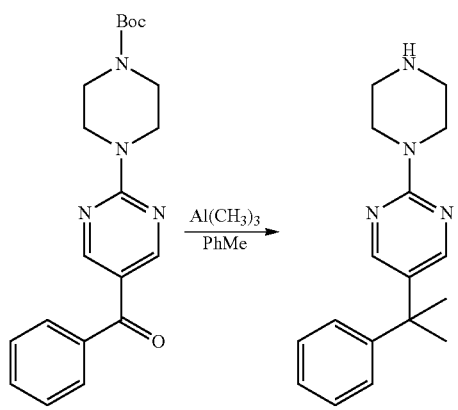

In a sealed tube, the mixture of tert-butyl 4-(5-benzoylpyrimidin-2-yl)piperazine-1-carboxylate (500 mg, 1.36 mmol) and trimethylaluminum (2 M in toluene, 2.7 mL) in dry toluene (10 mL) was stirred at 100 0° C. overnight. LCMS showed the reaction was completed. The reaction mixture was cooled to RT, quenched with ice-water and extracted with ethyl acetate. The organic layer was washed with water and brine, dried over sodium sulfate, filtered and concentrated. The residue was purified by Prep-HPLC to get 5-(2-phenylpropan-2-yl)-2-(piperazin-1-yl)pyrimidine (40 mg, 7%) as a yellowish solid. MS (ES+) $C_{17}H_{22}N_4$ requires: 282, found: 283 $[M+H]^+$.

Synthesis of tert-butyl 4-(5-bromopyrimidin-2-yl)piperazine-1-carboxylate

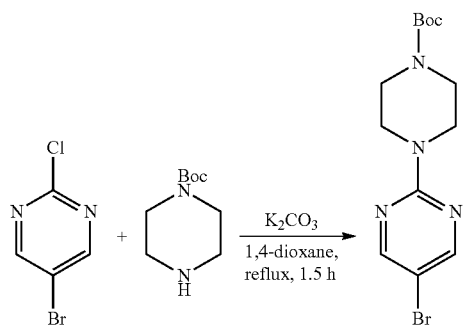

To a solution of 5-bromo-2-chloropyrimidine (50.0 g, 258 mmol) and 1-tert-butoxycarbonylpiperazine (72.2 g, 387 mmol) in 1,4-dioxane (500 mL) was added potassium carbonate (67.8 g, 491 mmol), and the mixture was stirred under reflux for 1.5 h. The reaction was cooled to RT, quenched by water (500 mL) and extracted with diethyl ether (1000 mL*2). The combined organic layers were dried over sodium sulfate, filtered and concentrated. The residue was purified with silica gel chromatography (petroleum ether:ethyl acetate=8:1-4:1) to give the title compound (70.5 g, 80%) as a white solid. MS (ES+) $C_{13}H_{19}BrN_4O_2$ requires: 342, found: 243 $[M+H-100]^+$.

Synthesis of tert-butyl 4-(5-acetylpyrimidin-2-yl)piperazine-1-carboxylate

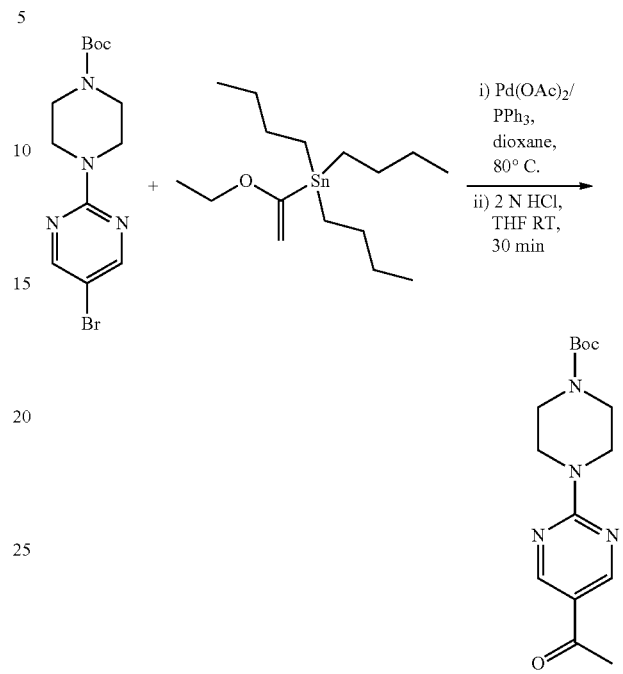

A mixture of tert-butyl 4-(5-bromopyrimidin-2-yl)piperazine-1-carboxylate (5.0 g, 14.6 mmol), palladium diacetate (240 mg, 1.46 mmol), triphenylphosphine (376 mg, 2.92 mmol) and tributyl(1-ethoxyvinyl)stannane (5.3 mL, 16.1 mmol) in dioxane (100 mL) was degassed with nitrogen for three times, and the reaction mixture was stirred at 80° C. overnight. The reaction was cooled to RT and diluted with THF (100 mL), followed by the addition of 2 N HCl (100 mL). The mixture was stirred at RT for 30 mins, and LCMS showed the reaction was completed. The reaction mixture was diluted with ethyl acetate (200 mL). The organic phase was separated, washed with water (3×100 mL), dried over sodium sulfate, filtered and concentrated. The residue was purified by silica gel chromatography to afford the title compound (3.0 g, 67%). MS (ES+) $C_{15}H_{22}N_4O_3$ requires: 306, found: 251 $[M-56+H]^+$.

Synthesis of 1-(2-(piperazin-1-yl)pyrimidin-5-yl)ethanone

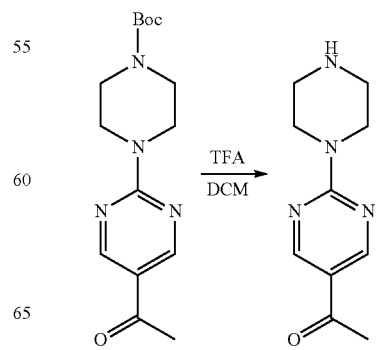

To a solution of tert-butyl 4-(5-acetylpyrimidin-2-yl)piperazine-1-carboxylate (3 g, 9.8 mmol) in dichloromethane (30 mL) was added trifluoroethyl acetate (15 mL), and the mixture was stirred at RT for 30 min. LCMS showed the reaction was completed. The reaction mixture was neutralized with sodium carbonate solution and extracted with dichloromethane. The organic layer was dried over sodium sulfate, filtered and concentrated to afford the title compound as a light yellow solid (2 g, 100%), which was directly used in the next step without further purification. MS (ES+) $C_{10}H_{14}N_4O$ requires: 206, found: 207 $[M+H]^+$.

Synthesis of 1-(4-fluorophenyl)-1-(2-(piperazin-1-yl)pyrimidin-5-yl)ethanol

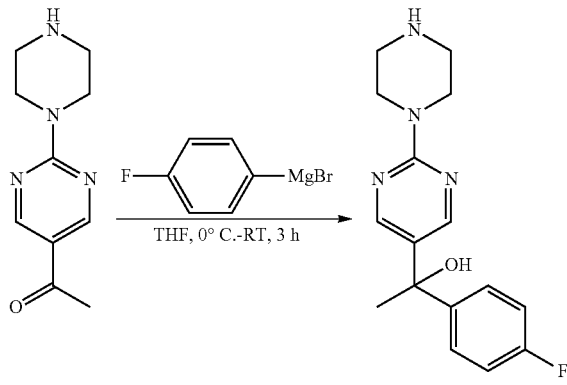

To a solution of 1-(2-(piperazin-1-yl)pyrimidin-5-yl)ethanone (1.8 g, 8.73 mmol) in dry THF (100 mL) was added (4-fluorophenyl)magnesium bromide (1 M in THF, 87.3 mL) at 0° C. under $N_2$. The mixture was stirred at RT for 3 h, then quenched with ammonium chloride solution and extracted with dichloromethane (300 mL). The organic layer was dried over sodium sulfate, filtered and concentrated. The residue was purified by Combi-flash (dicholomethane:methanol=10:1) to give the title compound (1.02 g, 38%) as a yellow solid.

Chiral separation of 1-(4-fluorophenyl)-1-(2-(piperazin-1-yl)pyrimidin-5-yl)ethanol

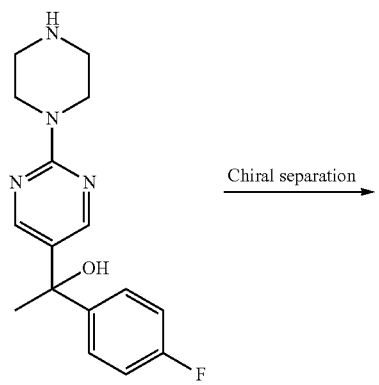

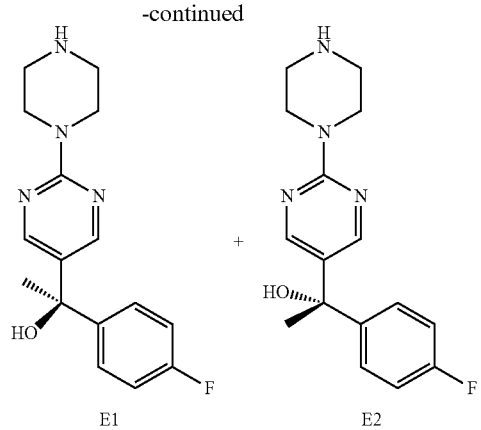

The racemate compound (1.02 g) was separated by chiral HPLC to afford enantiomer 1 (E1, 320 mg) and enantiomer 2 (E2, 220 mg). MS (ES+) $C_{16}H_{19}FN_4O$ requires: 302, found: 303 $[M+H]^+$. The absolute configuration was assigned randomly.

Chiral separation conditions: Chiral column: OZ—H (4.6*250 mm, 5 um); Mobile phase: co-solvent EtOH (0.1% DEA)

Synthesis of (S)-2-(4-fluorophenyl)-2-(2-(piperazin-1-yl)pyrimidin-5-yl)ethanol and (R)-2-(4-fluorophenyl)-2-(2-(piperazin-1-yl)pyrimidin-5-yl)ethanol

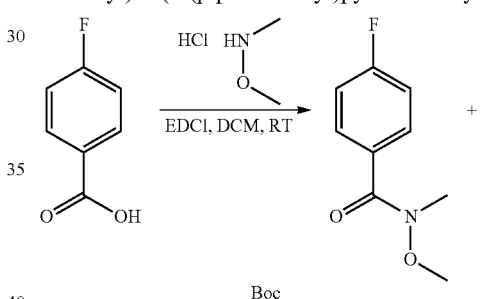

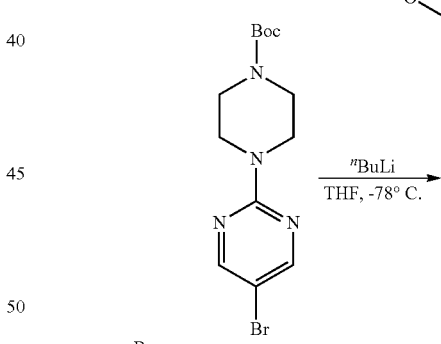

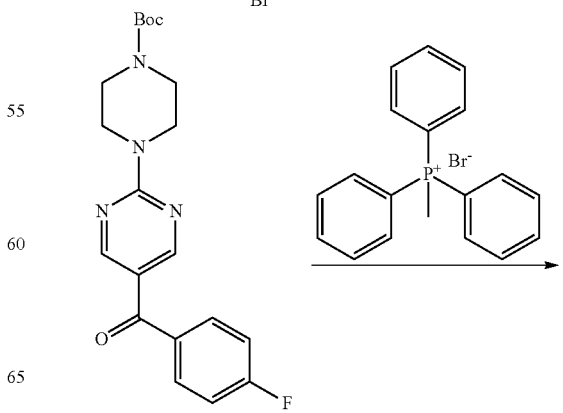

-continued

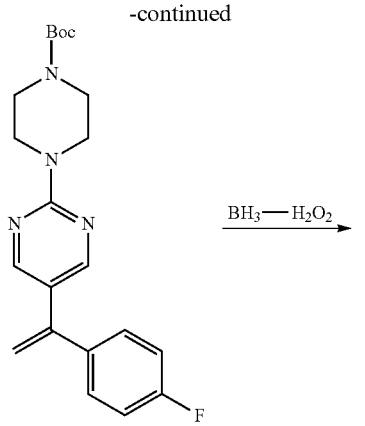

BH₃—H₂O₂ →

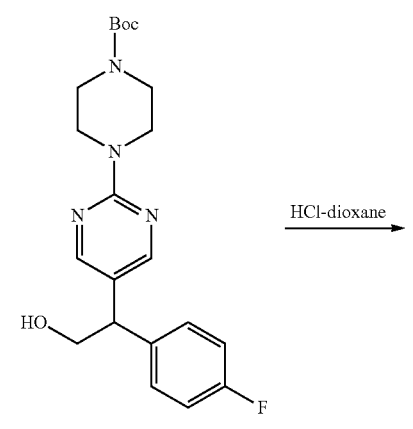

HCl-dioxane →

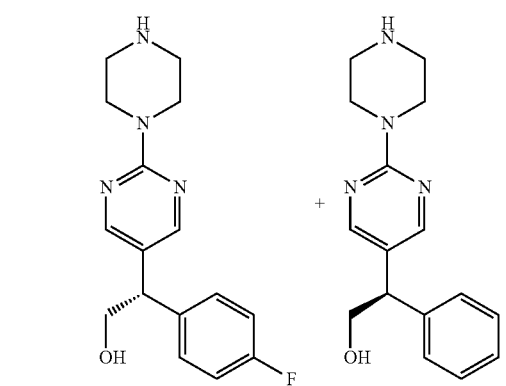

chiral separation →

Step 1: Synthesis of 4-fluoro-N-methoxy-N-methylbenzamide

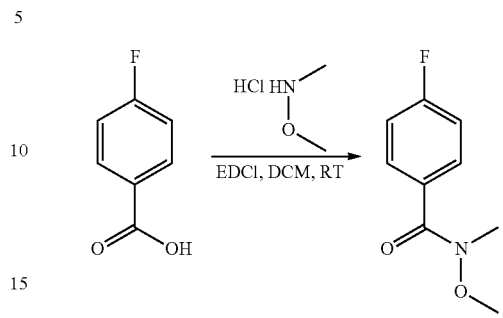

To a solution of 4-fluorobenzoic acid (200 g, 1.43 mol), N,O-dimethylhydroxylamine hydrochloride (207 g, 2.14 mol) and EDCI (407 g, 2.14 mol) in dichloromethane (2 L) was added diisopropylethylamine (553 g, 4.28 mol) at 0° C. and the mixture was stirred at RT overnight. The reaction mixture was then washed with aqueous HCl (1 N, 1 L*4), water (1 L) and brine (1 L) sequentially. The organic layer was dried over MgSO₄, filtered and concentrated in vacuo to give the title compound (150 g, yield 57%). MS (ES+) $C_9H_{10}FNO_2$ requires: 183, found 184 $[M+H]^+$; purity: 90% (UV254).

Step 2: Synthesis of tert-butyl 4-(5-(4-fluorobenzoyl)pyrimidin-2-yl)piperazine-1-carboxylate

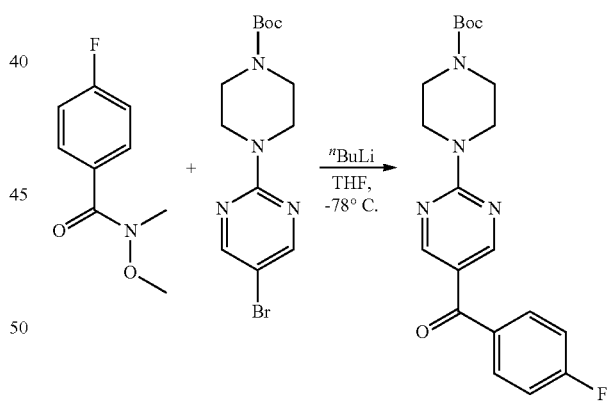

To a solution of tert-butyl 4-(5-bromopyrimidin-2-yl)piperazine-1-carboxylate (50 g, 146.2 mmol) in anhydrous THF (700 mL) was dropwise added n-BuLi (2.5 M in hexane, 70 mL, 175 mmol) at −78° C. under nitrogen. The mixture was stirred at −78° C. for 1 h, followed by the addition of a solution of 4-fluoro-N-methoxy-N-methylbenzamide (30 g, 163.9 mmol) in anhydrous THF (100 mL). After stirred at −78° C. for another 2 h, the reaction mixture was quenched with saturated aqueous NH₄Cl (250 mL) and extracted with ethyl acetate (200 mL*3). The combined organic layers were dried over sodium sulfate, filtered and concentrated in vacuo. The residue was diluted with propan-2-ol (150 mL) and stirred at RT for 30 mins. The solid was collected via filtration, washed with propan-2-ol (100 mL) and petroleum ether (300 mL), and dried under vacuum to give the title compound (26 g, yield 46%) as a yellow solid. MS (ES+) $C_{20}H_{23}FN_4O_3$ requires: 386, found 331 [M−56+H]$^+$; purity: 100% (UV214).

Step 3: Synthesis of tert-butyl 4-(5-(1-(4-fluorophenyl)vinyl)pyrimidin-2-yl)piperazine-1-carboxylate

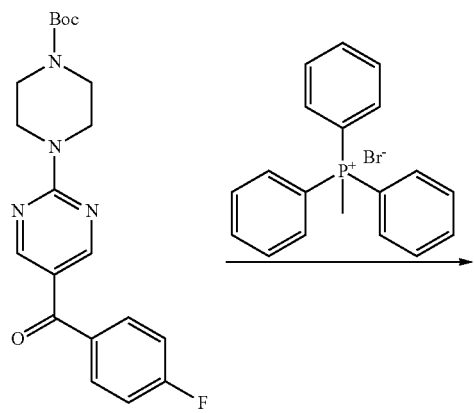

Step 4: Synthesis of tert-butyl 4-(5-(1-(4-fluorophenyl)-2-hydroxyethyl)pyrimidin-2-yl)piperazine-1-carboxylate

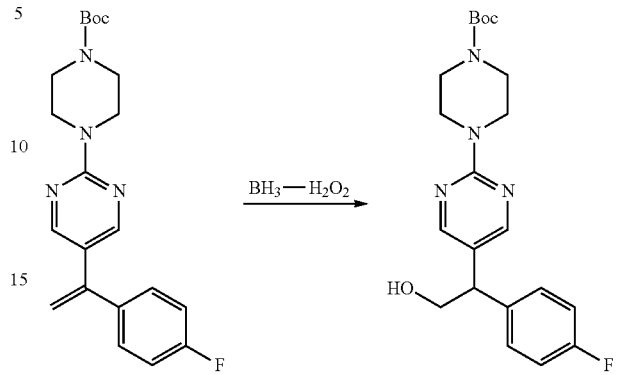

Tert-butyl 4-(5-(1-(4-fluorophenyl)vinyl)pyrimidin-2-yl)piperazine-1-carboxylate (1.2 g, 3.12 mmol) was dissolved in THF (30 mL) and then cooled to 0° C., followed by the addition of BH$_3$.THF (6.24 mL, 6.24 mmol) dropwise. The mixture was stirred at RT for 3 h. To the mixture was added H$_2$O in THF (10%, 8 mL), a solution of NaOH (1.25 g) in 30 mL H$_2$O and H$_2$O$_2$ (35%, 18 g) sequentially at 0° C. The mixture was stirred at RT overnight. The mixture was acidified with 1 N HCl and extracted with EA (3×50 mL). The organic phases were washed with aqueous NaHCO$_3$ (50 mL), brine (50 mL), dried over sodium sulfate, filtered, concentrated and purified by silica gel chromatography (DCM:CH$_3$OH=30:1) to get the title compound as a white solid (0.3 g, 24%). MS (ES+) $C_{21}H_{27}FN_4O_3$ requires: 402, found: 403 [M+H]$^+$.

Step 5: Synthesis of 2-(4-fluorophenyl)-2-(2-(piperazin-1-yl)pyrimidin-5-yl)ethanol

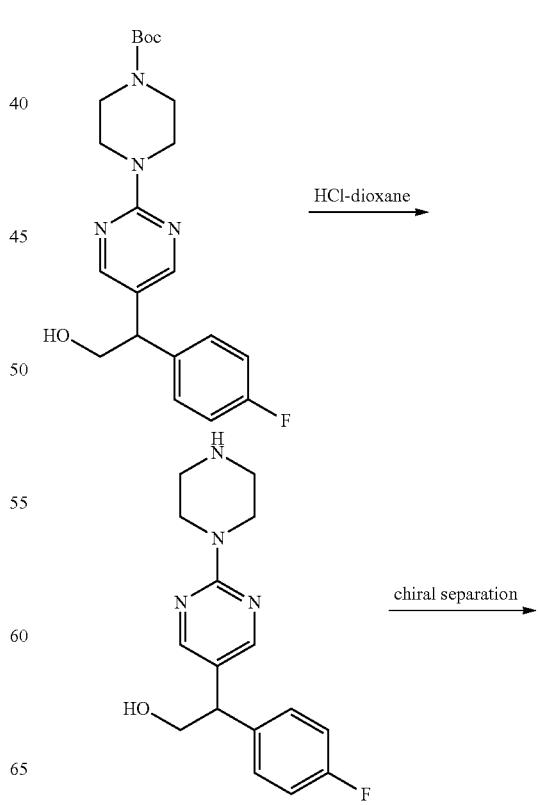

To a solution of methyltriphenylphosphonium bromide (6.0 g, 16.84 mmol) in THF (40 mL) at −78° C. was dropwise added n-BuLi (2.4 M, 7.2 mL, 17.19 mmol). After stirred at −78° C. for 1 h, tert-butyl 4-(5-(4-fluorobenzoyl)pyrimidin-2-yl)piperazine-1-carboxylate (1.3 g, 3.37 mmol) was added. The reaction mixture was stirred at RT overnight. LCMS showed the reaction was completed. The reaction was quenched with aqueous NH$_4$Cl solution and extracted with EA (2×50 mL). The organic phases were washed with H$_2$O (3×30 mL) and brine (50 mL), dried over sodium sulfate, filtered, concentrated and purified by silica gel chromatography (PE:EA=10:1) to get the title compound as a white solid (1.2 g, 93%). MS (ES+) $C_{21}H_{25}FN_4O_2$ requires: 384, found: 329 [M−56+1]$^+$.

-continued

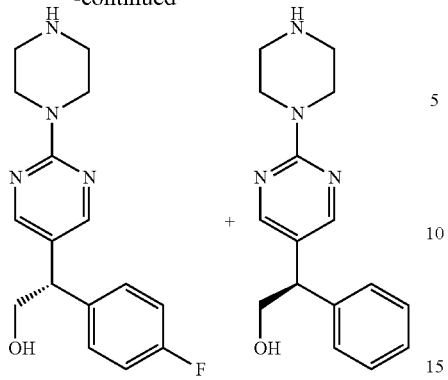

To a solution of tert-butyl 4-(5-(1-(4-fluorophenyl)-2-hydroxyethyl)pyrimidin-2-yl)piperazine-1-carboxylat (450 mg, 1.08 mmol) in dioxane (5 mL) was added HCl/dioxane (5 mL). The mixture was stirred at RT overnight. LCMS showed the reaction was completed. The solution was concentrated and purified by silica gel chromatography (DCM:CH$_3$OH=10:1) to get the title compound as a yellow solid (0.2 g, 53%). MS (ES+) C$_{16}$H$_{19}$FN$_4$O requires: 302, found: 303 [M+H]$^+$.

The above sample (200 mg, 0.66 mmol) was separated by Chiral-HPLC to get (S)-2-(4-fluorophenyl)-2-(2-(piperazin-1-yl)pyrimidin-5-yl)ethanol assumed (1$^{st}$ peak, 50 mg, 25%) and (R)-2-phenyl-2-(2-(piperazin-1-yl)pyrimidin-5-yl)ethanol assumed (2$^{nd}$ peak, 50 mg, 25%).

Synthesis of tert-butyl 4-(5-(4-fluorophenoxy)pyrimidin-2-yl)piperazine-1-carboxylate

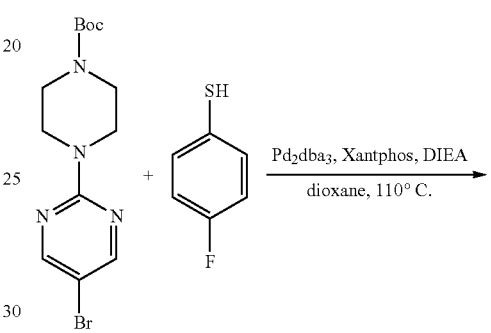

A mixture of tert-butyl 4-(5-bromopyrimidin-2-yl)piperazine-1-carboxylate (684 mg, 2.0 mmol), 4-fluorophenol (1.1 g, 5.0 mmol), copper (650 mg, 10.0 mmol) and Cs$_2$CO$_3$ (6.5 g, 20.0 mmol) in pyridine (15 mL) was heated at 120° C. for 12 h. The mixture was cooled to RT, diluted with ethyl acetate (200 mL) and filtered. The filtrate was concentrated under reduced pressure, and the residue was purified by silica gel column chromatography (petroleum ether/ethyl acetate=20/1) to afford the title compound (200 mg, 27%) as a brown solid. MS (ES+) C$_{19}$H$_{23}$FN$_4$O$_3$ requires: 374, found: 319 [M−56+1]$^+$.

Synthesis of 5-(4-fluorophenylsulfonyl)-2-(piperazin-1-yl)pyrimidine HCl salt

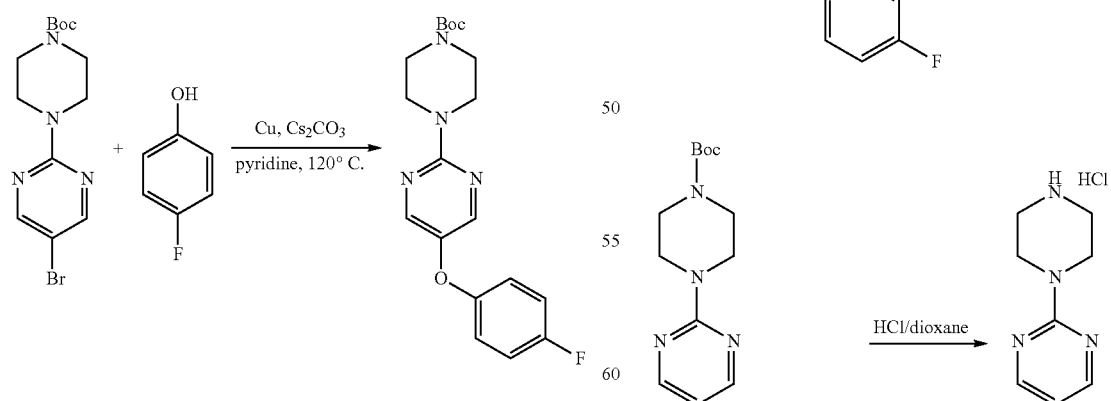

Step 1: Synthesis of tert-butyl 4-(5-(4-fluorophenyl-thio)pyrimidin-2-yl)piperazine-1-carboxylate

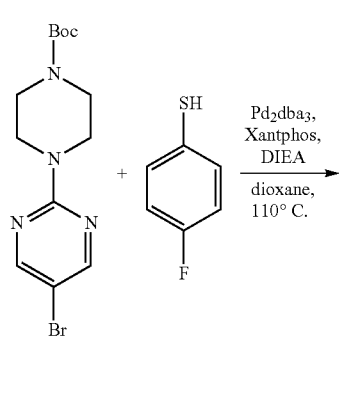

A stirred solution of tert-butyl 4-(5-bromopyrimidin-2-yl)piperazine-1-carboxylate (1 g, 2.924 mmol), 4-fluorobenzenethiol (561 mg, 4.386 mmol), Pd$_2$(dba)$_3$ (267 mg, 0.292 mmol), Xantphos (169 mg, 0.292 mmol) and DIPEA (754 mg, 5.848 mmol) in dioxane (50 mL) was degassed with nitrogen for three times, and then heated at 110° C. for 16 hrs. The reaction mixture was cooled to RT and concentrated under reduced pressure to give a residue, which was purified by flash chromatography (silica gel, 0-20% EtOAc/PE) to afford the title compound as a white solid. (500 mg, yield 44%, purity: 99%). MS (ES+) C$_{19}$H$_{23}$FN$_4$O$_2$S requires: 390, found 391 [M+H]$^+$.

Step 2: Synthesis of tert-butyl 4-(5-(4-fluorophenyl-sulfonyl)pyrimidin-2-yl)piperazine-1-carboxylate

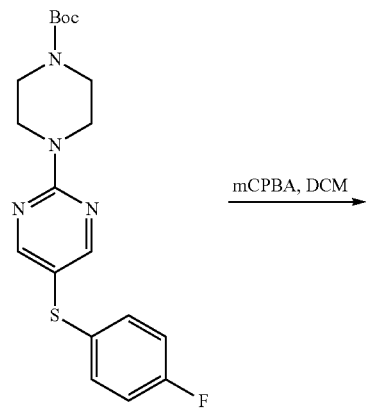

A solution of tert-butyl 4-(5-(4-fluorophenylthio)pyrimidin-2-yl)piperazine-1-carboxylate (700 mg, 1.799 mmol) and mCPBA (619 mg, 3.599 mmol) in DCM (20 mL) was stirred at RT for 16 hrs. The reaction mixture was washed sequentially with saturated potassium carbonate solution, water and brine. The organic layer was dried over anhydrous sodium sulfate, filtered and concentrated under vacuum. The residue was purified by flash chromatography (silica gel, 0-20% EtOAc/PE) to afford the title compound as a white solid. (600 mg, yield 83%, purity: 100%). MS (ES+) C$_{19}$H$_{23}$FN$_4$O$_4$S requires: 422, found 423 [M+H]$^+$.

Step 3: Synthesis of 5-(4-fluorophenylsulfonyl)-2-(piperazin-1-yl)pyrimidine HCl salt

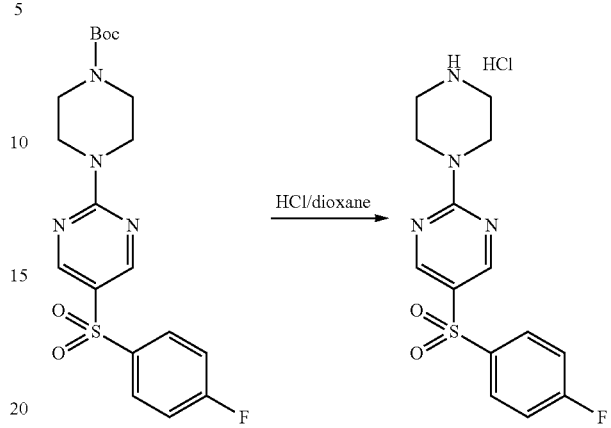

To a solution of tert-butyl 4-(5-(4-fluorophenylsulfonyl)pyrimidin-2-yl)piperazine-1-carboxylate (100 mg, 0.237 mmol) in dioxane was added 4 M HCl/dioxane (6 mL). The mixture was stirred at RT for 3 hrs and concentrated to afford the title compound as a yellow oil, which was used into the next step without further purification. MS (ES+) C$_{14}$H$_{15}$FN$_4$O$_2$S requires: 322, found 323 [M+H]$^+$.

Synthesis of (R)-2-(4-fluorophenyl)-2-(2-(piperazin-1-yl)pyrimidin-5-yl)propan-1-ol and (S)-2-(4-fluorophenyl)-2-(2-(piperazin-1-yl)pyrimidin-5-yl)propan-1-ol

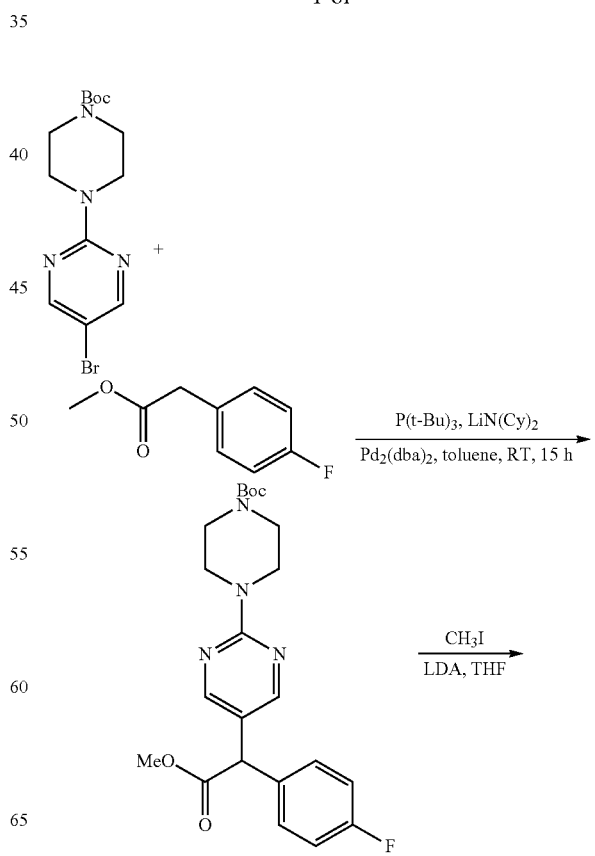

142

Step 1: Synthesis of tert-butyl 4-(5-(1-(4-fluorophenyl)-2-methoxy-2-oxoethyl)pyrimidin-2-yl)piperazine-1-carboxylate

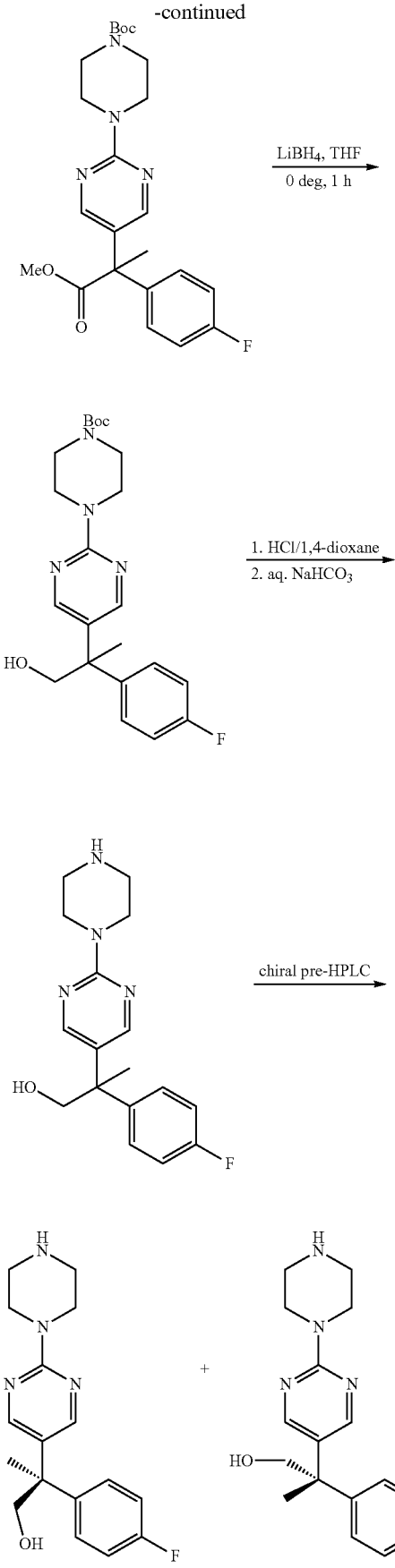

To a solution of dicyclohexylamine (3.43 g, 18.94 mmol) in THF (60 mL) at −78° C. was added n-BuLi (2.5 M, 7.9 mL, 18.94 mmol) dropwise. The mixture was stirred at RT for 10 min, followed by the addition of methyl 2-(4-fluorophenyl)acetate (2.69 g, 16.02 mmol) in toluene (60 mL). After stirred at RT for another 10 min, tert-butyl 4-(5-bromopyrimidin-2-yl)piperazine-1-carboxylate (5.0 g, 14.57 mmol), $Pd_2(dba)_3$ (667 mg, 0.728 mmol) and $P(t-Bu)_3$ (10%, 1.47 g, 0.728 mmol) were added sequentially. The reaction mixture was stirred at RT for 15 h, quenched by water (150 mL) and extracted with EA. The combined organic layers were washed with water and brine, dried over $Na_2SO_4$, filtered and concentrated. The residue was passed a column (silica gel, PE:EA=6:1) to afford the title compound (0.5 g, 8%) as an orange solid. MS (ES+) $C_{22}H_{27}FN_4O_4$ requires: 430, found: 431 [M+H]$^+$.

Step 2: Synthesis of tert-butyl 4-(5-(2-(4-fluorophenyl)-1-methoxy-1-oxopropan-2-yl)pyrimidin-2-yl)piperazine-1-carboxylate

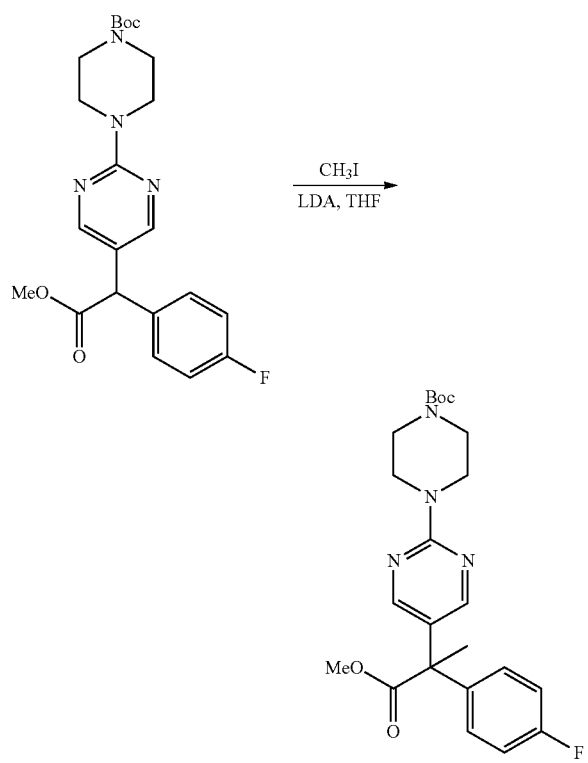

To a mixture of tert-butyl 4-(5-(1-(4-fluorophenyl)-2-methoxy-2-oxoethyl)pyrimidin-2-yl)piperazine-1-carboxylate (1.0 g, 2.33 mmol) in THF (20 mL) at −78° C. was added LDA (2 M, 2.33 mL, 4.65 mmol) dropwise, After stirred at −78° C. for 30 min, CH$_3$I (0.66 g, 4.65 mmol) was added. After stirred at RT for another 1 h, the reaction was quenched by water and extracted with EA. The combined organic layers were washed with water and brine, dried over Na$_2$SO$_4$, filtered and concentrated. The residue was passed a column (silica gel, PE:EA=6:1) to afford the title compound (0.8 g, 77%) as a yellow solid. MS (ES+) C$_{23}$H$_{29}$FN$_4$O$_4$ requires: 444, found: 445 [M+H]$^+$.

Step 3: Synthesis of tert-butyl 4-(5-(2-(4-fluorophenyl)-1-hydroxypropan-2-yl)pyrimidin-2-yl)piperazine-1-carboxylate

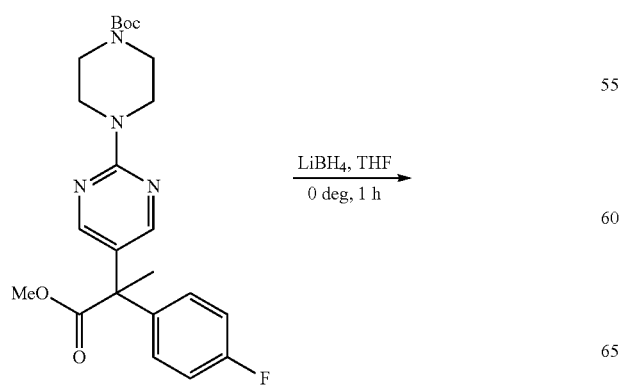

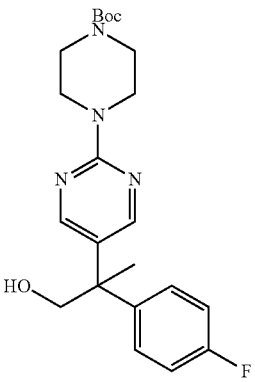

To a mixture of tert-butyl 4-(5-(2-(4-fluorophenyl)-1-methoxy-1-oxopropan-2-yl)pyrimidin-2-yl)piperazine-1-carboxylate (0.4 g, 0.9 mmol) in THF (10 mL) was added LiBH$_4$ (40 mg, 1.8 mmol). After stirred at RT for 2 h, the reaction was quenched by aq. NH$_4$Cl and extracted with EA. The combined organic layers were washed with water and brine, dried over Na$_2$SO$_4$, filtered and concentrated. The residue was passed a column (silica gel, PE:EA=1:1) to afford the title compound (225 mg, 60%) as a yellow solid. MS (ES+) C$_{22}$H$_{29}$FN$_4$O$_3$ requires: 416, found: 417 [M+H]$^+$.

Step 4: Synthesis of (R)-2-(4-fluorophenyl)-2-(2-(piperazin-1-yl)pyrimidin-5-yl)propan-1-ol

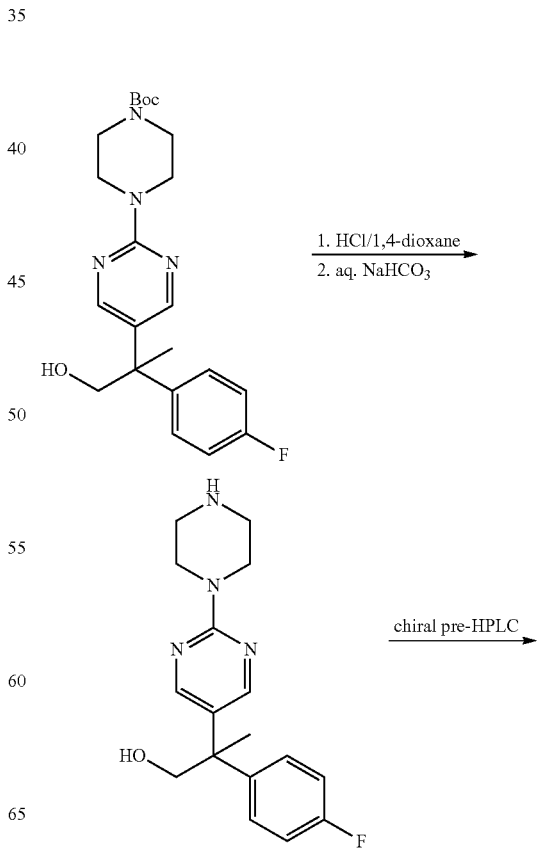

-continued

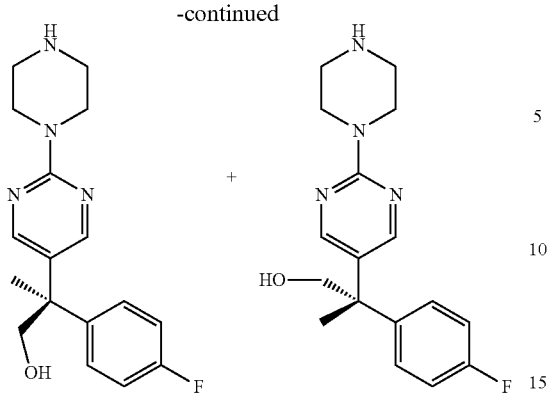

To a mixture of tert-butyl 4-(5-(2-(4-fluorophenyl)-1-hydroxypropan-2-yl)pyrimidin-2-yl)piperazine-1-carboxylate (450 mg, 1.08 mmol) in DCM (20 mL) was added 4 M HCl/1,4-dioxane (3 mL). After stirred at RT for 15 h, the reaction mixture was concentrated, the residue was diluted by aq. NaHCO$_3$ (20 mL) and extracted with DCM. The combined organic layers were washed with water and brine, dried (Na$_2$SO$_4$), filtered and concentrated. The residue was separated by chiral Prep-HPLC to give (R)-2-(4-fluorophenyl)-2-(2-(piperazin-1-yl)pyrimidin-5-yl)propan-1-ol (100 mg, 29%) as a white solid. MS (ES+) C$_{17}$H$_{21}$FN$_4$O requires: 316, found: 317 [M+H]$^+$. Chiral HPLC, Column: IC 4.6*150 mm 5 um, Co-Solvent: EtOH:Hexane=1:1 (0.1% DEA), RT=4.22 min.

(S)-2-(4-fluorophenyl)-2-(2-(piperazin-1-yl)pyrimidin-5-yl)propan-1-ol (100 mg, 29%) as a white solid. MS (ES+) C$_{17}$H$_{21}$FN$_4$O requires: 316, found: 317 [M+H]$^+$. Chiral HPLC, Column: IC 4.6*150 mm 5 um, Co-Solvent: EtOH:Hexane=1:1(0.1% DEA), RT=5.43 min.

Synthesis of 5-(3-(4-fluorophenyl)oxetan-3-yl)-2-(piperazin-1-yl)pyrimidine

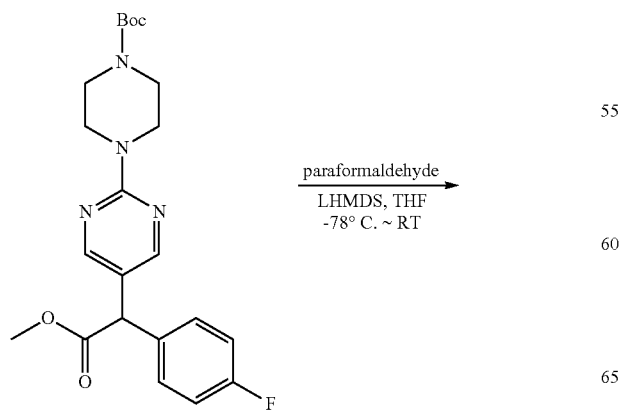

-continued

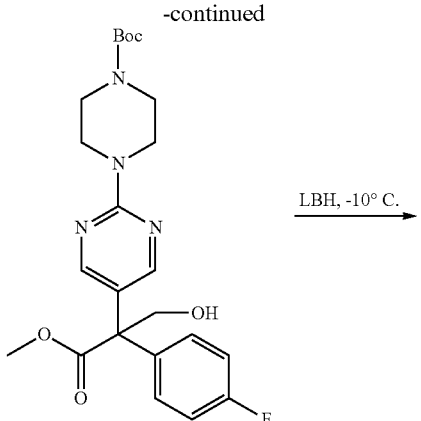

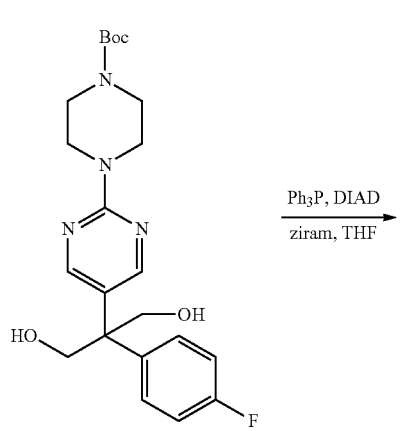

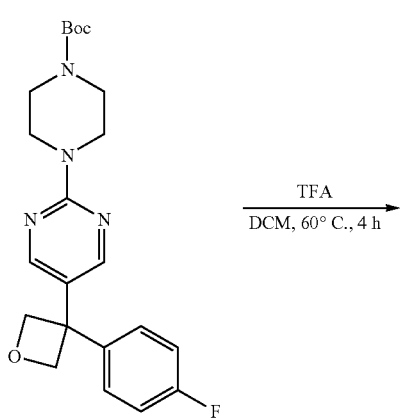

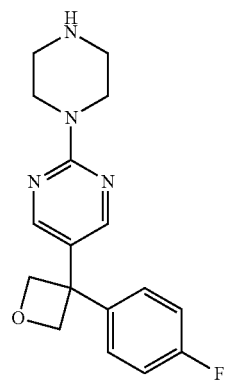

Step 1: Synthesis of tert-butyl 4-(5-(2-(4-fluorophenyl)-3-hydroxy-1-methoxy-1-oxopropan-2-yl)pyrimidin-2-yl)piperazine-1-carboxylate

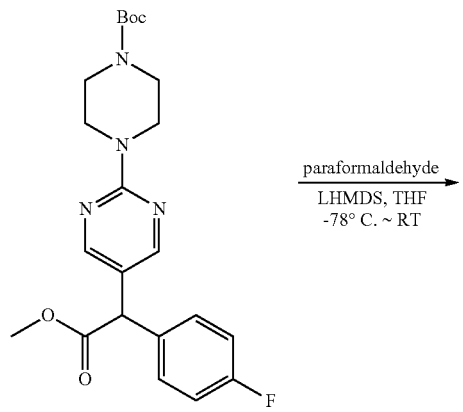

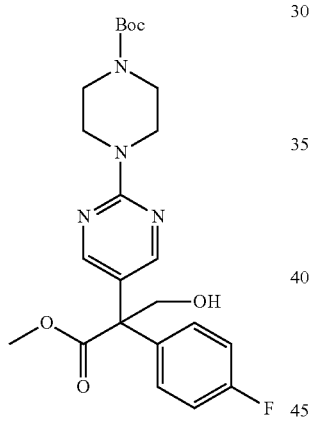

A solution of tert-butyl 4-(5-(1-(4-fluorophenyl)-2-methoxy-2-oxoethyl)pyrimidin-2-yl)piperazine-1-carboxylate (650 mg, 1.5 mmol) in THF (20 mL, dry) was cooled to −78° C. and protected with $N_2$. Another solution of n-BuLi (1.5 M, 3 mL, ~4.5 mmol) in THF was added to the above cooled solution during 5 min. The reaction mixture was stirred at −78° C. for 1 h, followed by the addition of paraformaldehyde (405 mg, 15.0 mmol) in one portion under −78° C. This solution was stirred at RT overnight. The reaction was quenched by saturated aqueous $NH_4Cl$ (50 mL) and water (50 mL), and extracted with EtOAc (50 mL*4). The combined organic layer were washed with brine, dried over $Na_2SO_4$, filtered and concentrated under reduced pressure. The residue was purified by silica gel column eluting with PE:EA (4:1) to obtain the title compound as a yellow thicky oil (300 mg, 44% yield). MS (ES+) $C_{23}H_{29}FN_4O_5$ requires: 460, found 461 [M+H]$^+$; purity: 93% (UV214).

Step 2: Synthesis of tert-butyl 4-(5-(2-(4-fluorophenyl)-1,3-dihydroxypropan-2-yl)pyrimidin-2-yl)piperazine-1-carboxylate

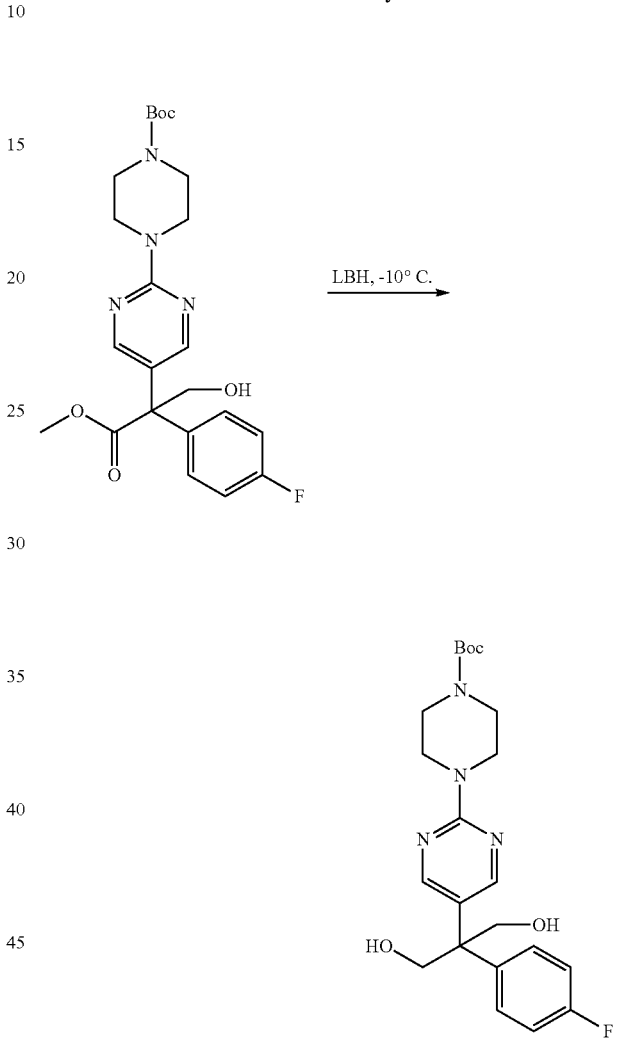

A solution of 4-(5-(2-(4-fluorophenyl)-3-hydroxy-1-methoxy-1-oxopropan-2-yl)pyrimidin-2-yl)piperazine-1-carboxylate (700 mg, 1.5 mmol) in 20 mL of THF was cooled to −10° C., followed by the addition of $LiBH_4$ (180 mg, 7.5 mmol) slowly. This mixture was allowed to warm to RT and stirred overnight. The reaction was quenched by MeOH (3 mL) and then concentrated in vacuo. The residue was purified by silica gel column (DCM:MeOH, 10:1) to obtain the desired product (300 mg, yield 47%) as a yellow foam. MS (ES+) $C_{22}H_{29}FN_4O_4$ requires: 432, found 433 [M+H]$^+$; purity: 67% (UV254).

Step 3: Synthesis of tert-butyl 4-(5-(3-(4-fluorophenyl)oxetan-3-yl)pyrimidin-2-yl)piperazine-1-carboxylate

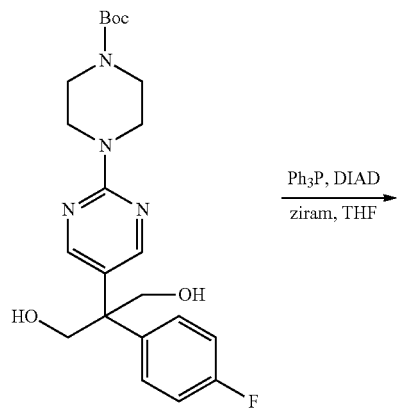

A mixture of tert-butyl 4-(5-(2-(4-fluorophenyl)-1,3-dihydroxypropan-2-yl)pyrimidin-2-yl)piperazine-1-carboxylate (650 mg, 1.5 mmol), triphenylphosphine (470 mg, 1.8 mmol), diisopropyl azodicarboxylate (360 mg, 1.8 mmol) and ziram (500 mg, 1.8 mmol) in THF (50 mL) was heated at 40° C. overnight under $N_2$ and concentrated. The residue was diluted with EtOAc (40 mL), washed with water (50 mL*2) and brine, dried over $Na_2SO_4$ and concentrated. The residue was purified by Prep-HPLC to give the desired product (35 mg, yield 6%) as a white solid. MS (ES+) $C_{22}H_{27}FN_4O_3$ requires: 414, found 359 [M+H−56]$^+$; purity: 93% (UV214).

Step 4: Synthesis of 5-(3-(4-fluorophenyl)oxetan-3-yl)-2-(piperazin-1-yl)pyrimidine

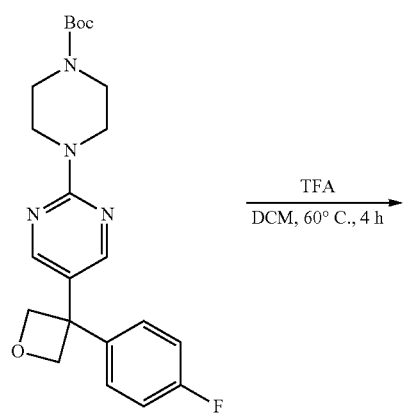

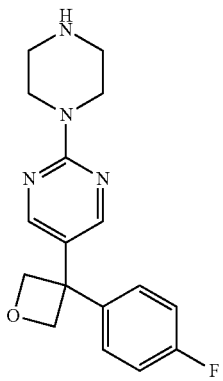 [SMILES: Fc1ccc(C2(c3cnc(N4CCNCC4)nc3)COC2)cc1]

A solution of tert-butyl 4-(5-(3-(4-fluorophenyl)oxetan-3-yl)pyrimidin-2-yl)piperazine-1-carboxylate (22 mg, 0.05 mmol) in DCM (1 mL) was treated with TFA (0.5 mL) at 60° C. for 3 h and then concentrated under reduced pressure. The residue (30 mg, crude, yellow solid, 100% yield) was directly used into the next step without further purification. MS (ES+) $C_{17}H_{19}FN_4O$ requires: 314, found 315 [M+H]$^+$; purity: 87% (UV254).

Synthesis of (S)-1-(5-fluoropyridin-2-yl)-1-(2-(piperazin-1-yl)pyrimidin-5-yl)ethanol and (R)-1-(5-fluoropyridin-2-yl)-1-(2-(piperazin-1-yl)pyrimidin-5-yl)ethanol

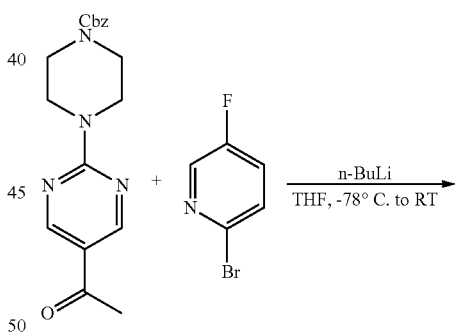

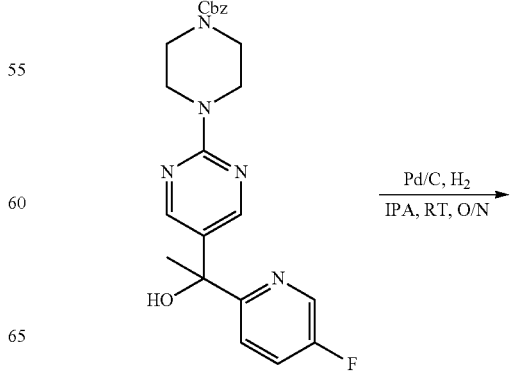

-continued

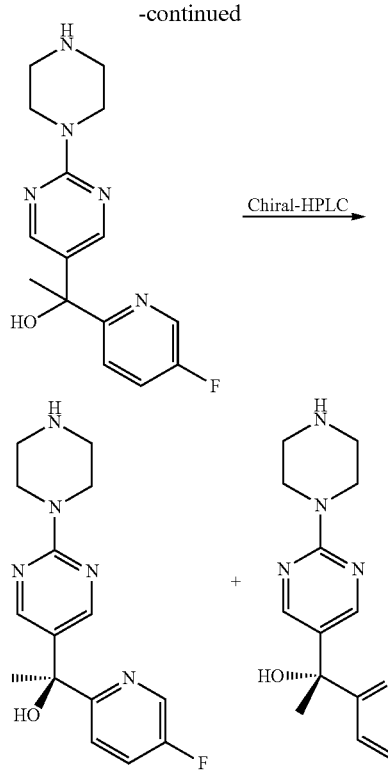

Step 1: Synthesis of benzyl 4-(5-(1-(5-fluoropyridin-2-yl)-1-hydroxyethyl)pyrimidin-2-yl)piperazine-1-carboxylate

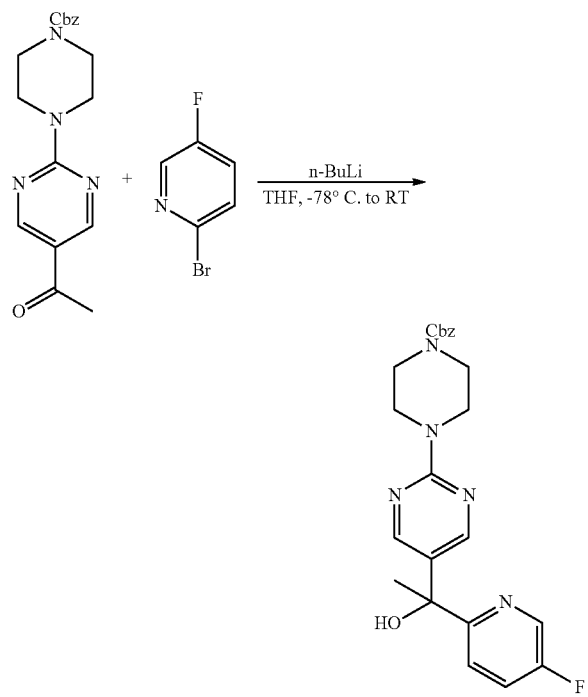

To a solution of 2-bromo-5-fluoropyridine (1.3 g, 7.50 mmol) in anhydrous THF (30 mL) was added n-BuLi (2.76 mL, 6.62 mmol) at −78° C. dropwise, and the mixture was stirred at −78° C. for 2 h, followed by the addition of benzyl 4-(5-acetylpyrimidin-2-yl)piperazine-1-carboxylate (1.5 g, 4.41 mmol). The reaction mixture was allowed to warm to RT and stirred overnight. LCMS showed the reaction was completed. The solution was quenched with aqueous $NH_4Cl$ (50 mL) and extracted with EtOAc (3×100 mL). The combined organic layers were washed with water (2×50 mL) and brine (50 mL), dried over sodium sulfate, filtered and concentrated. The residue was purified by Prep-HPLC to afford the title compound (0.4 g, 20%) as a white solid. MS (ES+) $C_{23}H_{24}FN_5O_3$ requires: 437, found: 438 [M+H]+.

Step 2: Synthesis of (S)-1-(5-fluoropyridin-2-yl)-1-(2-(piperazin-1-yl)pyrimidin-5-yl)ethanol and (R)-1-(5-fluoropyridin-2-yl)-1-(2-(piperazin-1-yl)pyrimidin-5-yl)ethanol

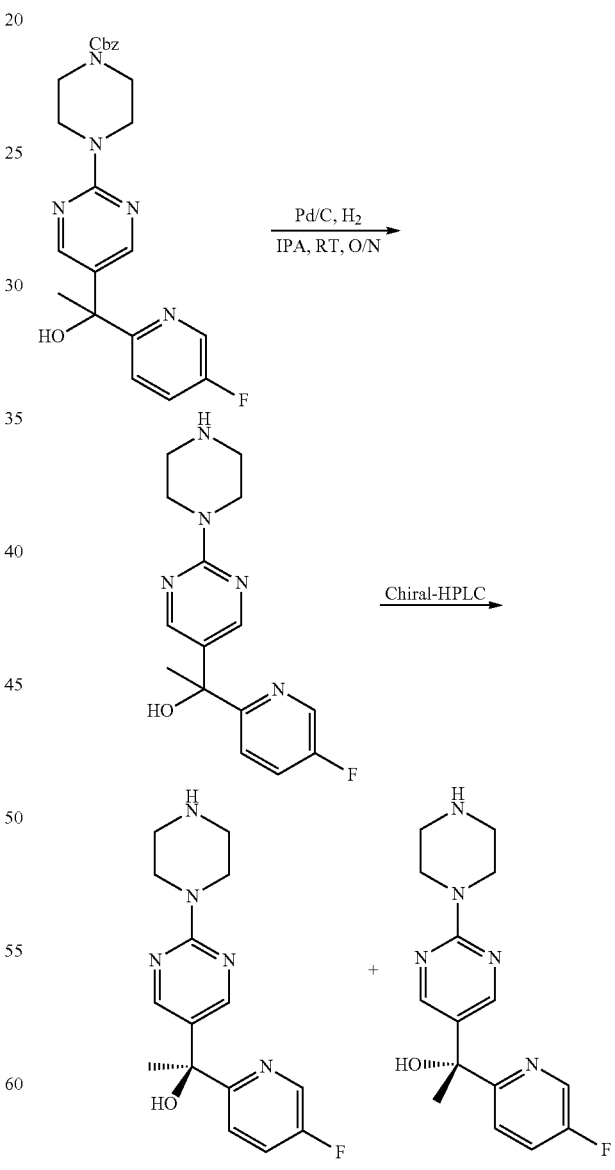

A suspension of benzyl 4-(5-(1-(5-fluoropyridin-2-yl)-1-hydroxyethyl)pyrimidin-2-yl)piperazine-1-carboxylate (420.0 mg, 0.96 mmol) and Pd/C (200.0 mg) in i-PrOH was exposed to 1 atm H₂ atmosphere (H₂ balloon) and stirred at RT overnight. LCMS showed the reaction was completed. The reaction mixture was filtered through a pad of Celite. The filtrate was concentrated and purified by silica gel chromatography (DCM:CH₃OH=10:1) to get the title compound as a white solid (153 mg, 53%). MS (ES+) $C_{15}H_{18}FN_5O$ requires: 303, found: 304 [M+H]⁺.

The racemate compound (290 mg, 0.96 mmol) was separated by Chiral-HPLC to get (S)-1-(5-fluoropyridin-2-yl)-1-(2-(piperazin-1-yl)pyrimidin-5-yl)ethanol (peak 1, 80 mg, 28%) and (R)-1-(5-fluoropyridin-2-yl)-1-(2-(piperazin-I-yl)pyrimidin-5-yl)ethanol (peak 2, 80 mg, 28%).

Synthesis of (S)-tert-butyl 4-(5-(1-(4-fluorophenyl)vinyl)pyrimidin-2-yl)-3-(hydroxymethyl)piperazine-1-carboxylate

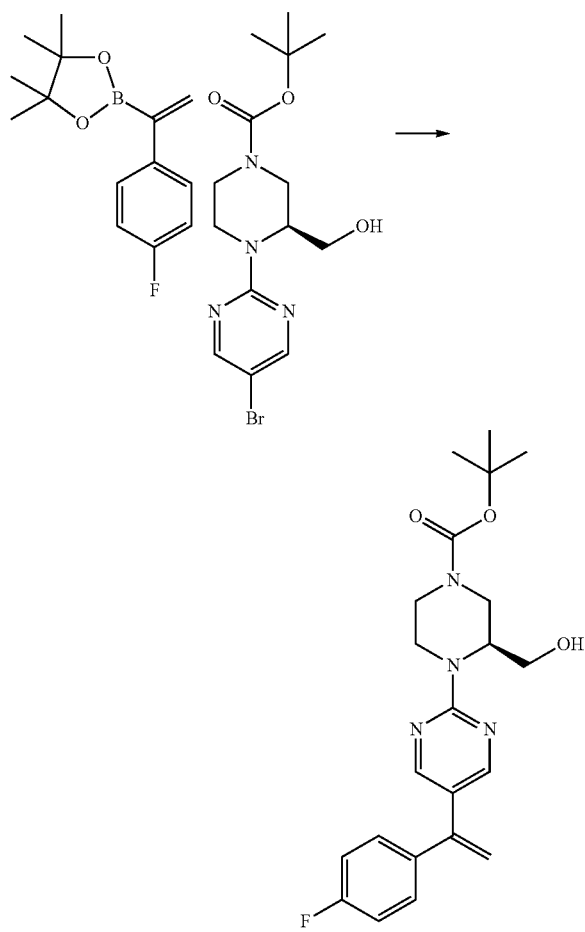

2-(1-(4-Fluorophenyl)vinyl)-4,4,5,5-tetramethyl-1,3,2-dioxaborolane (138 mg, 0.556 mmol), (S)-tert-butyl 4-(5-bromopyrimidin-2-yl)-3-(hydroxymethyl)piperazine-1-carboxylate (103 mg, 0.276 mmol), 2 M sodium carbonate (0.35 mL, 0.700 mmol), and PdCl2(dppf)-DCM adduct (17.3 mg, 0.021 mmol) were taken up in 1,4-dioxane (2 mL) in a 2-5 mL microwave vial. The reaction was stirred at 100° C. for 18 hours. Room temperature was attained, the reaction mixture was filtered through a plug of Celite eluting with MeOH, and the filtrate was concentrated in vacuo while loading onto Celite. The residue was purified by MPLC (0-100% EtOAc-hexanes) to give (S)-tert-butyl 4-(5-(1-(4-fluorophenyl)vinyl)pyrimidin-2-yl)-3-(hydroxymethyl)piperazine-1-carboxylate (107 mg, 0.258 mmol, 94% yield) as an orange gum. MS (ES+) $C_{22}H_{27}FN_4O_3$ requires: 414, found: 415 [M+H]⁺.

Synthesis of (S)-2,2,2-trifluoro-1-(4-fluorophenyl)-1-(2-(piperazin-1-yl)pyrimidin-5-yl)ethanamine

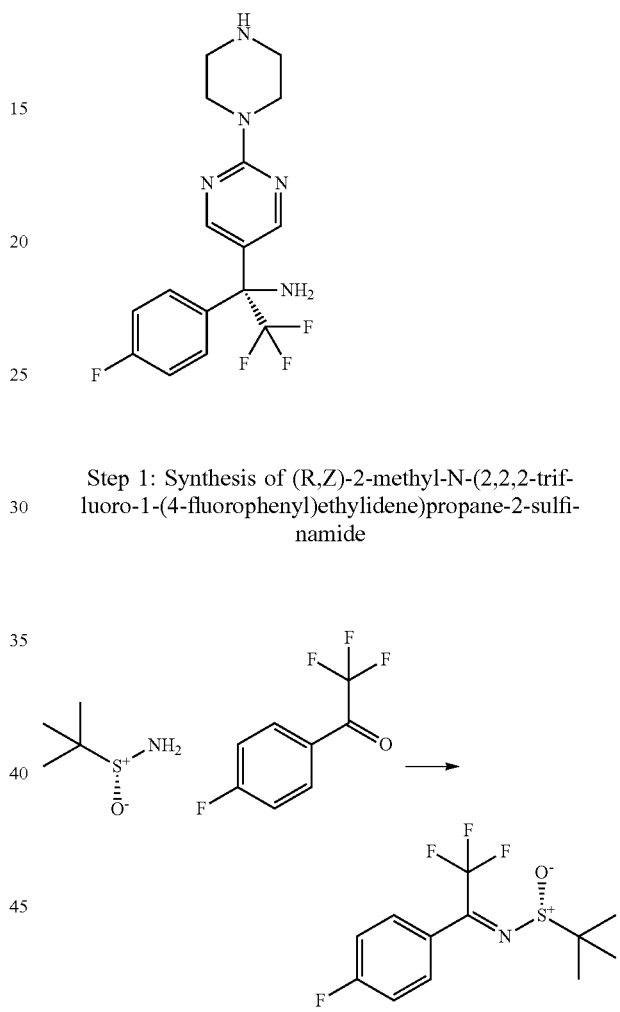

Step 1: Synthesis of (R,Z)-2-methyl-N-(2,2,2-trifluoro-1-(4-fluorophenyl)ethylidene)propane-2-sulfinamide (R)-2-Methylpropane-2-sulfinamide (0.64 g, 5.28 mmol), 2,2,2-trifluoro-1-(4-fluorophenyl)ethanone (0.53 g, 2.76 mmol) and titanium(IV) isopropoxide (1.5 mL, 5.12 mmol) were stirred in THF (13 mL) at 70° C. for 18 hours. Room temperature was attained, saturated NaCl and EtOAc were added, and the resulting biphasic suspension was stirred for 5 minutes. The suspension was filtered through Celite to remove the titanium residues, and the organic phase was separated. The aqueous phase was extracted a second time with EtOAc. The combined organic extracts were washed with brine, dried over Na₂SO₄, filtered, and concentrated in vacuo while loading onto silica. Purification of the residue by MPLC (0-20% EtOAc-hexanes) gave (R,Z)-2-methyl-N-(2,2,2-trifluoro-1-(4-fluorophenyl)ethylidene)propane-2-sulfinamide (0.23 g, 0.779 mmol, 28.2% yield) as a yellow oil.

Step 2: Synthesis of tert-butyl 4-(5-((S)-1-(((R)-tert-butylsulfinyl)amino)-2,2,2-trifluoro-1-(4-fluorophenyl)ethyl)pyrimidin-2-yl)piperazine-1-carboxylate

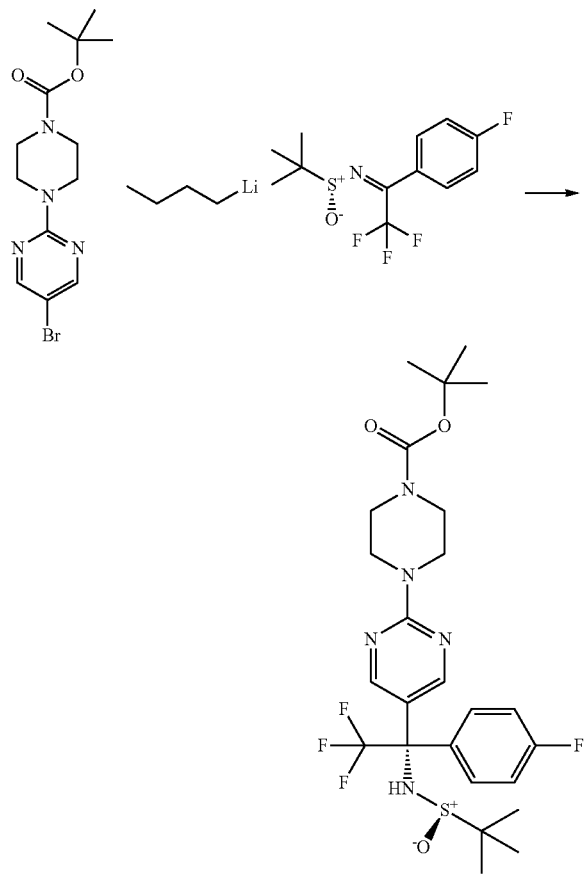

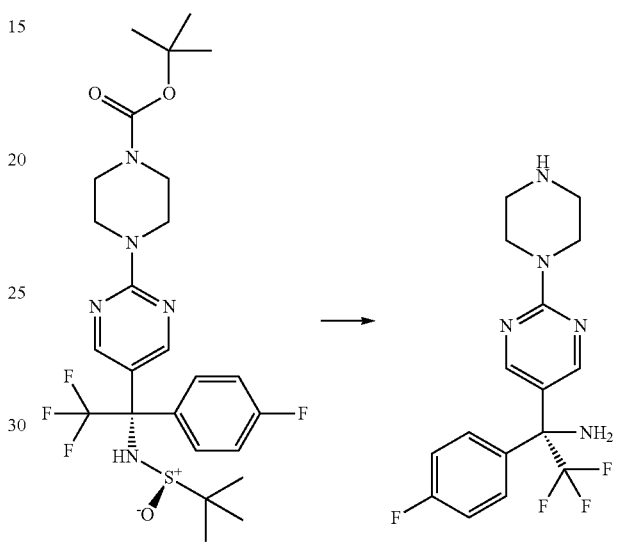

tert-Butyl 4-(5-bromopyrimidin-2-yl)piperazine-1-carboxylate (0.242 g, 0.705 mmol) was taken up in THF (3.5 mL) and cooled to −78° C. A solution of ″BuLi, 2.5 M in hexanes (0.31 mL, 0.775 mmol) was added at a fast dropwise rate from a syringe. The resulting mixture was stirred at −78° C. for 15 minutes. A solution of (R,Z)-2-methyl-N-(2,2,2-trifluoro-1-(4-fluorophenyl)ethylidene)propane-2-sulfinamide (0.225 g, 0.762 mmol) in THF (0.5 mL) was added at a fast dropwise rate from a syringe. The reaction mixture was stirred at −78° C. for 5 minutes before warming to room temperature. After 45 minutes, saturated NH$_4$Cl was added and the products extracted into EtOAc (×2). The combined organic extracts were washed with brine, dried over Na$_2$SO$_4$, filtered, and concentrated in vacuo. Purification of the residue by MPLC (0-80% EtOAc-hexanes) gave tert-butyl 4-(5-((S)-1-(((R)-tert-butylsulfinyl)amino)-2,2,2-trifluoro-1-(4-fluorophenyl)ethyl)pyrimidin-2-yl)piperazine-1-carboxylate (304 mg, 0.543 mmol, 77% yield) as a pale yellow gum. The absolute stereochemistry was assigned randomly.

MS (ES+) C$_{25}$H$_{33}$F$_4$N$_5$O$_3$S requires: 559, found: 560 [M+H]$^+$.

Step 3: Synthesis of (S)-2,2,2-trifluoro-1-(4-fluorophenyl)-1-(2-(piperazin-1-yl)pyrimidin-5-yl)ethanamine tert-Butyl 4-(5-((S)-1-(((R)-tert-butylsulfinyl)amino)-2,2,2-trifluoro-1-(4-fluorophenyl)ethyl)pyrimidin-2-yl)piperazine-1-carboxylate (302 mg, 0.540 mmol) was stirred in 4 M HCl in 1,4-dioxane (3 mL)/MeOH (3 mL) at room temperature for 1 hour. The solvent was removed in vacuo and the residue was partitioned between saturated NaHCO$_3$ and EtOAc. The organic phase was extracted a second time with EtOAc. The combined organic extracts were washed with brine, dried over Na$_2$SO$_4$, filtered, and concentrated in vacuo to give (S)-2,2,2-trifluoro-1-(4-fluorophenyl)-1-(2-(piperazin-1-yl)pyrimidin-5-yl)ethanamine (190 mg, 0.535 mmol, 99% yield) with ~88% e.e. Further purification by chiral SFC gave (S)-2,2,2-trifluoro-1-(4-fluorophenyl)-1-(2-(piperazin-1-yl)pyrimidin-5-yl)ethanamine (123.7 mg, 0.348 mmol, 71.2% yield) with ~99% e.e. MS (ES+) C$_{16}$H$_{17}$F$_4$N$_5$ requires: 355, found: 356 [M+H]$^+$.

The synthetic protocols that can be used to prepare the compounds disclosed herein are indicated below. The NMR and LC MS data obtained for compounds disclosed herein are also shown below.

| Compound Number | Synthetic Protocol | $^1$H NMR | LC/MS (M + 1) |
|---|---|---|---|
| 1 | 1 | | 360 |
| 2 | 1 | | 386 |
| 3 | 1 | $^1$H NMR (400 MHz, DMSO-d6) δ 8.32 (s, 2H), 8.15 (d, J = 5.2 Hz, 1H), 7.34-7.13 (m, 5H), 6.32 (d, J = 5.2 Hz, 1H), 5.95 (s, 1H), 3.93 (s, 3H), 3.89 (dd, J = 6.7, 3.6 Hz, 4H), 3.79 (s, 2H), 3.76 (dd, J = 6.4, 3.8 Hz, 4H). | 402 |

-continued

| Compound Number | Synthetic Protocol | ¹H NMR | LC/MS (M + 1) |
|---|---|---|---|
| 4 | 1 | | 416 |
| 5 | 1 | | 416 |
| 6 | 1 | | 427 |
| 7 | 1 | ¹H-NMR (400 MHz, DMSO-$d_6$ + 1d $D_2O$) δ ppm 8.33 (s, 2H), 7.99 (s, 1H), 7.94 (d, 1H, J = 1.6 Hz), 7.86 (s, 1H), 7.81 (s, 1H), 7.30-7.18 (m, 6H), 4.09-4.01 (m, 4H), 3.89-3.83 (m, 4H), 3.84 (s, 3H), 3.80 (s, 2H). | 452 |
| 8 | 1 | ¹H-NMR (500 MHz, $CDCl_3$) δ ppm 8.24 (s, 2H), 7.91 (s, 1H), 7.71, 7.70 (s, s, 2H), 7.58 (s, 1H), 7.32-7.29 (m, 2H), 7.24-7.17 (m, 5H), 6.82 (br. s., 1H), 4.94 (br. s., 1H), 4.61 (br. s., 1H), 4.52-4.49 (m, 2H), 3.96 (s, 3H), 3.87-3.85 (br., 1H), 3.82 (s, 2H), 3.71-3.64 (br, 2H), 1.29 (d, 3H, J = 7.0 Hz). | 466 |
| 9 | 1 | ¹H-NMR (400 MHz, DMSO-$d_6$) δ ppm 8.35 (s, 2H), 8.03 (s, 1H), 7.98 (d, 1H, J = 1.2 Hz), 7.87 (s, 1H), 7.82 (s, 1H), 7.31-7.29 (m, 4H), 7.22-7.18 (m, 2H), 4.09-4.06 (m, 5H), 3.96-3.88 (m, 4H), 3.85 (s, 3H), 1.58 (d, 3H, J = 7.6 Hz). | 466 |
| 10 | 1 | ¹H-NMR (400 MHz, DMSO-$d_6$) δ ppm 8.35 (s, 2H), 8.03 (s, 1H), 7.98 (s, 1H), 7.87 (s, 1H), 7.82 (s, 1H), 7.32-7.29 (m, 4H), 7.22-7.17 (m, 2H), 4.09-4.04 (m, 5H), 3.91-3.86 (m, 7H), 1.58 (d, 3H, J = 7.2 Hz). | 466 |
| 11 | 1 | ¹H NMR (400 MHz, DMSO-d6) δ 8.13 (d, J = 2.3 Hz, 1H), 8.02 (s, 1H), 7.96 (d, J = 1.6 Hz, 1H), 7.85 (s, 1H), 7.80 (d, J = 0.8 Hz, 1H), 7.47 (dd, J = 8.8, 2.4 Hz, 1H), 7.39-7.25 (m, 4H), 7.24-7.15 (m, 2H), 6.77 (d, J = 8.8 Hz, 1H), 5.79 (d, J = 4.1 Hz, 1H), 5.63 (d, J = 4.0 Hz, 1H), 4.13-4.05 (m, 4H), 3.84 (s, 4H), 3.71-3.64 (m, 4H). | 467 |
| 12 | 4 | 1H-NMR (400 MHz, DMSO-d6) δ ppm 12.83 (br. s., 1H), 8.40 (s, 2H), 8.10-7.86 (m, 4H), 7.44 (d, 2H, J = 7.6 Hz), 7.36-7.15 (m, 4H), 4.10-4.07 (m, 4H), 3.91-3.88 (m, 4H), 1.74 (s, 3H). | 467 |
| 13 | 4 | 1H-NMR (400 MHz, DMSO-d6) δ ppm 8.37 (s, 2H), 8.01 (s, 1H), 7.96 (s, 1H), 7.85 (s, 1H), 7.80 (s, 1H), 7.43-7.37 (m, 2H), 7.30 (t, 2H, J = 8.0 Hz), 7.23-7.16 (m, 2H), 5.01 (s, 1H), 4.11-4.03 (m, 4H), 3.92-3.85 (m, 4H), 3.84 (s, 3H), 2.32 (s, 2H). | 467 |
| 14 | 1 | 1H NMR (300 MHz, DMSO-d6) δ 8.34 (s, 2H), 8.03 (d, J = 0.8 Hz, 1H), 7.98 (d, J = 1.5 Hz, 1H), 7.87 (s, 1H), 7.82 (d, J = 0.8 Hz, 1H), 7.34-7.19 (m, 3H), 7.19-7.06 (m, 2H), 4.14-4.05 (m, 4H), 3.90 (dd, J = 6.7, 4.0 Hz, 4H), 3.85 (s, 3H), 3.80 (s, 2H). | 470 |
| 15 | 1 | 1H-NMR (500 MHz, DMSO-d6) δ ppm 8.38 (s, 2H), 8.04 (s, 1H), 8.00 (d, 1H, J = 1.0 Hz), 7.89 (s, 1H), 7.83 (s, 1H), 7.24 (d, 1H, J = 1.0 Hz), 7.21-7.18 (m, 2H), 7.06-7.03 (m, 2H), 4.14-4.12 (m, 4H), 3.94-3.92 (m, 4H), 3.86 (s, 3H). | 472 |
| 16 | 1 | ¹H-NMR (400 MHz, DMSO-$d_6$) δ ppm 8.45 (d, 1H, J = 1.6 Hz), 8.34 (s, 2H), 8.06 (d, 2H, J = 8.4 Hz), 7.93 (s, 1H), 7.86 (d, 2H, J = 8.4 Hz), 7.62 (d, 1H, J = 1.6 Hz), 7.32-7.18 (m, 5H), 4.14 (t, 4H, J = 5.2 Hz), 3.92 (t, 4H, J = 5.2 Hz), 3.81 (s, 2H). | 473 |
| 17 | 1 | 1H NMR (400 MHz, DMSO-d6) δ 12.84 (s, 1H), 8.57 (s, 2H), 8.10 (s, 1H), 8.02 (d, J = 1.5 Hz, 1H), 7.88 (s, 2H), 7.33-7.21 (m, 3H), 7.19-7.12 (m, 1H), 7.05 (td, J = 7.9, 1.6 Hz, 1H), 4.24-4.08 (m, 4H), 4.08-3.93 (m, 4H). | 480 |
| 18 | 1 | ¹H NMR (400 MHz, DMSO-$d_6$) δ 8.33 (s, 2H), 8.16 (d, J = 1.7 Hz, 1H), 7.88 (s, 1H), 7.79-7.70 (m, 2H), 7.36 (d, J = 1.8 Hz, 1H), 7.32-7.26 (m, 2H), 7.26-7.15 (m, 3H), 7.00-6.92 (m, 2H), 4.11 (dd, J = 6.6, 4.1 Hz, 4H), 3.93-3.85 (m, 4H), 3.80 (s, 2H), 3.77 (s, 3H). | 478 |
| 19 | 1 | ¹H-NMR (500 MHz, $CDCl_3$) δ ppm 8.24 (s, 2H), 7.96 (br. s., 1H), 7.70 (s, 1H), 7.60 (s, 1H), 7.32-7.17 (m, 5H), 6.84 (br. s., 1H), 4.97 (br. s., 1H), 4.65 (br. s., 1H), 4.54 (br. s., 2H), 3.87 (s, 3H), 3.86-3.82 (m, 5H), 2.41 (s, 3H), 1.32 (d, 3H, J = 3.5 Hz). | 480 |
| 20 | 3 | ¹H-NMR (400 MHz, DMSO-$d_6$) δ ppm 8.28 (s, 2H), 8.03 (s, 1H), 7.98 (d, 1H, J = 1.6 Hz), 7.87 (s, 1H), 7.82 (s, 1H), 7.35-7.25 (m, 4H), 7.24-7.16 (m, 2H), 4.11-4.09 (m, 4H), 3.92-3.89 (m, 4H), 3.85 (s, 3H), 1.64 (s, 6H). | 480 |
| 21 | 4 | ¹H-NMR (400 MHz, DMSO-$d_6$) δ ppm 8.39 (s, 2H), 8.01 (s, 1H), 7.96 (s, 1H), 7.85 (s, 1H), 7.80 (s, 1H), 7.44 (s, 1H), 7.42 (s, 1H), 7.28 (t, 2H, J = 8.0 Hz), 7.22-7.15 (m, 2H), 4.11-4.05 (m, 4H), 3.92-3.86 (m, 4H), 3.84 (s, 3H), 2.38 (s, 2H), 1.73 (s, 3H). | 481 |

| Compound Number | Synthetic Protocol | ¹H NMR | LC/MS (M + 1) |
|---|---|---|---|
| 22 | 4 | ¹H-NMR (400 MHz, DMSO-$d_6$) δ ppm 8.40 (s, 2H), 8.01 (s, 1H), 7.96 (s, 1H), 7.85 (s, 1H), 7.80 (s, 1H), 7.44 (s, 1H), 7.42 (s, 1H), 7.28 (t, 2H, J = 8.0 Hz), 7.22-7.15 (m, 2H), 4.11-4.05 (m, 4H), 3.92-3.86 (m, 4H), 3.84 (s, 3H), 2.39 (s, 2H), 1.73 (s, 3H). | 481 |
| 23 | 3 | 1H-NMR (400 MHz, DMSO-d6) δ ppm 8.36 (s, 2H), 8.04 (s, 1H), 8.00 (d, 1H, J = 1.6 Hz), 7.89 (s, 1H), 7.83 (s, 1H), 7.42-7.39 (m, 2H), 7.25-7.20 (m, 3H), 5.50 (s, 1H), 5.41 (s, 1H), 4.15-4.12 (m, 4H), 4.00-3.97 (m, 4H), 3.86 (s, 3H). | 482 |
| 24 | 3 | ¹H-NMR (400 MHz, DMSO-$d_6$) δ ppm 8.40 (s, 2H), 8.03 (s, 1H), 7.97 (d, 1H, J = 1.6 Hz), 7.87 (s, 1H), 7.81 (s, 1H), 7.46-7.44 (m, 2H), 7.33-7.29 (m, 2H), 7.22-7.19 (m, 2H), 5.81 (s, 1H), 4.10-4.07 (m, 4H), 3.92-3.87 (m, 4H), 3.85 (s, 3H), 1.83 (s, 3H). | 482 |
| 25 | 3 | ¹H-NMR (400 MHz, DMSO-$d_6$) δ ppm 8.40 (s, 2H), 8.03 (s, 1H), 7.97 (d, 1H, J = 2.0 Hz), 7.87 (s, 1H), 7.81 (s, 1H), 7.46-7.43 (m, 2H), 7.33-7.29 (m, 2H), 7.22-7.21 (m, 2H), 5.81 (s, 1H), 4.10-4.07 (m, 4H), 3.92-3.89 (m, 4H), 3.85 (s, 3H), 1.82 (s, 3H). | 482 |
| 26 | 3 | ¹H-NMR (400 MHz, DMSO-$d_6$) δ ppm 12.85 (s, 1H), 8.41 (s, 2H), 8.11 (s, 1H), 8.01 (d, 1H, J = 1.6 Hz), 7.89-7.87 (m, 2H), 7.48-7.45 (m, 2H), 7.25 (d, 1H, J = 1.6 Hz), 7.13-7.09 (m, 2H), 4.11-4.08 (m, 4H), 3.92-3.89 (m, 4H), 2.45 (br. s., 2H), 1.73 (s, 3H). | 485 |
| 27 | 4 | 1H-NMR (400 MHz, CDCl3) δ ppm 8.35 (s, 2H), 7.90 (s, 1H), 7.70-7.69 (m, 2H), 7.56 (s, 1H), 7.38-7.35 (m, 2H), 7.05-7.00 (m, 2H), 6.77 (d, 1H, J = 2.0 Hz), 5.13 (s, 1H), 4.15-4.12 (m, 4H), 4.02-3.99 (m, 4H), 3.99 (s, 3H). | 485 |
| 28 | 4 | 1H-NMR (400 MHz, CDCl3) δ ppm 8.35 (s, 2H), 7.90 (s, 1H), 7.70-7.69 (m, 2H), 7.57 (s, 1H), 7.38-7.35 (m, 2H), 7.05-7.00 (m, 2H), 6.77 (d, 1H, J = 2.0 Hz), 5.13 (s, 1H), 4.15-4.12 (m, 4H), 4.02-3.99 (m, 4H), 3.95 (s, 3H). | 485 |
| 29 | 3 | 1H-NMR (400 MHz, DMSO-d6) δ ppm 12.81 (br. s., 1H), 8.39 (s, 2H), 8.10-8.00 (br, 1H), 8.00 (d, 1H, J = 1.2 Hz), 7.95-7.85 (br, 1H), 7.86 (s, 1H), 7.47-7.44 (dd, 2H, J = 8.8, 5.6 Hz), 7.24 (d, 1H, J = 1.2 Hz), 7.12 (t, 2H, J = 8.8 Hz), 5.90 (s, 1H), 4.09-4.07 (m, 4H), 3.91-3.88 (m, 4H), 1.81 (s, 3H). | 486 |
| 30 | 3 | ¹H-NMR (400 MHz, DMSO-$d_6$) δ ppm 12.81 (br. s., 1H), 8.39 (s, 2H), 8.09 (br. s., 1H), 8.00 (d, 1H, J = 1.2 Hz), 7.87-7.86 (m, 2H), 7.47-7.44 (m, 2H), 7.24 (d, 1H, J = 1.2 Hz), 7.12 (t, 2H, J = 8.8 Hz), 5.90 (s, 1H), 4.09-4.07 (m, 4H), 3.91-3.88 (m, 4H), 1.81 (s, 3H). | 486 |
| 31 | 3 | 1H-NMR (500 MHz, DMSO-d6) δ ppm 8.34 (s, 2H), 8.03 (s, 1H), 7.98 (s, 1H), 7.87 (s, 1H), 7.82 (s, 1H), 7.44-7.41 (m, 2H), 7.22 (s, 1H), 7.18-7.14 (m, 2H), 6.01 (d, 1H, J = 3.5 Hz), 5.68 (d, 1H, J = 3.0 Hz), 4.09 (br. s., 4H), 3.91 (br. s., 4H), 3.85 (s, 3H). | 486 |
| 32 | 3 | 1H-NMR (500 MHz, DMSO-d6) δ ppm 8.34 (s, 2H), 8.03 (s, 1H), 7.98 (s, 1H), 7.87 (s, 1H), 7.82 (s, 1H), 7.44-7.41 (m, 2H), 7.22 (s, 1H), 7.18-7.14 (m, 2H), 6.01 (s, 1H), 5.68 (s, 1H), 4.09 (br. s., 4H), 3.91 (br. s., 4H), 3.85 (s, 3H). | 486 |
| 33 | 1 | ¹H-NMR (400 MHz, DMSO-$d_6$) δ ppm 8.37 (d, 1H, J = 1.2 Hz), 8.34 (s, 2H), 7.98 (s, 1H), 7.96-7.89 (m, 5H), 7.56 (s, 1H), 7.30-7.20 (m, 6H), 4.14 (t, 4H, J = 6.0 Hz), 3.87 (t, 4H, J = 5.2 Hz), 3.81 (s, 2H). | 491 |
| 34 | 4 | 1H-NMR (400 MHz, DMSO-d6) δ ppm 8.40 (s, 2H), 8.26 (d, 1H, J = 2.0 Hz), 7.90-7.86 (m, 3H), 7.46-7.41 (m, 3H), 7.31-7.18 (m, 5H), 4.13-4.10 (m, 4H), 3.91-3.89 (m, 4H), 3.31-3.29 (br, 2H), 1.73 (s, 3H). | 495 |
| 35 | 4 | 1H-NMR (400 MHz, DMSO-d6) δ ppm 8.40 (s, 2H), 8.08 (s, 1H), 7.97 (s, 1H), 7.86 (s, 1H), 7.81 (s, 1H), 7.42 (d, 2H, J = 8.0 Hz), 7.31-7.27 (m, 2H), 7.22-7.18 (m, 2H), 4.12 (q, 2H, J = 7.2 Hz), 4.09-4.07 (m, 4H), 3.92-3.88 (m, 4H), 2.70-2.60 (m, 2H), 1.74 (s, 3H), 1.39 (t, 3H, J = 7.6 Hz). | 495 |
| 36 | 4 | 1H-NMR (400 MHz, DMSO-d6) δ ppm 8.41 (s, 2H), 8.01 (s, 1H), 7.96 (s, 1H), 7.85 (s, 1H), 7.80 (s, 1H), 7.45-7.39 (m, 2H), 7.31 (t, 2H, J = 8.0 Hz), 7.23-7.17 (m, 2H), 4.11 (s, 1H), 4.10-4.04 (m, 4H), 3.92-3.86 (m, 4H), 3.84 (s, 3H), 2.11 (s, 6H). | 495 |

| Compound Number | Synthetic Protocol | ¹H NMR | LC/MS (M + 1) |
|---|---|---|---|
| 37 | 4 | 1H-NMR (400 MHz, DMSO-d6) δ ppm 8.41 (s, 2H), 8.02 (s, 1H), 7.97-7.96 (m, 1H), 7.85 (s, 1H), 7.80 (s, 1H), 7.45-7.39 (m, 2H), 7.31 (t, 2H, J = 8.0 Hz), 7.23-7.17 (m, 2H), 4.11 (s, 1H), 4.10-4.04 (m, 4H), 3.92-3.86 (m, 4H), 3.84 (s, 3H), 2.12 (s, 6H). | 495 |
| 38 | 3 | 1H-NMR (400 MHz, DMSO-d6) δ ppm 8.40 (s, 2H), 8.27 (d, 1H, J = 1.6 Hz), 7.90 (s, 1H), 7.84-7.82 (m, 2H), 7.48-7.44 (m, 3H), 7.41-7.37 (m, 2H), 7.27-7.23 (m, 1H), 7.14-7.10 (m, 2H), 5.89 (s, 1H), 4.14-4.11 (m, 4H), 3.92-3.90 (m, 4H), 1.81 (s, 3H). | 496 |
| 39 | 3 | ¹H-NMR (400 MHz, CDCl₃) δ ppm 8.23 (s, 2H), 7.90 (s, 1H), 7.70 (s, 2H), 7.57 (s, 1H), 7.21 (dd, 2H, J = 8.0, 4.0 Hz), 7.01-6.96 (m, 2H), 6.78 (s, 1H), 4.17-4.14 (m, 4H), 4.02-3.99 (m, 4H), 3.95 (s, 3H), 1.67 (s, 6H). | 498 |
| 40 | 3 | ¹H-NMR (400 MHz, CDCl₃) δ ppm 8.22 (s, 2H), 7.89 (s, 1H), 7.69, 7.68 (s, s, 2H), 7.56 (s, 1H), 7.18-7.15 (m, 2H), 7.01-6.97 (m, 2H), 6.77 (d, 1H, J = 1.6 Hz), 4.15-4.13 (m, 4H), 4.01-3.98 (m, 4H), 3.95 (s, 3H), 3.64 (t, 1H, J = 8.0 Hz), 2.05-1.98 (m, 2H), 0.92 (t, 3H, J = 8.0 Hz). | 498 |
| 41 | 3 | ¹H-NMR (400 MHz, CDCl₃-d₆) δ ppm 8.22 (s, 2H), 7.89 (s, 1H), 7.69, 7.68 (s, s, 2H), 7.56 (s, 1H), 7.18-7.15 (m, 2H), 7.01-6.97 (m, 2H), 6.77 (d, 1H, J = 1.6 Hz), 4.15-4.13 (m, 4H), 4.01-3.98 (m, 4H), 3.95 (s, 3H), 3.64 (t, 1H, J = 7.6 Hz), 2.04-1.99 (m, 2H), 0.92 (t, 3H, J = 7.6 Hz). | 498 |
| 43 | 4 | ¹H-NMR (400 MHz, DMSO-d6) δ ppm 8.39 (s, 2H), 8.02 (s, 1H), 7.96 (s, 1H), 7.86 (s, 1H), 7.80 (s, 1H), 7.47-7.43 (m, 2H), 7.21 (s, 1H), 7.12-7.07 (m, 2H), 4.11-4.05 (m, 4H), 3.92-3.86 (m, 4H), 3.84 (s, 3H), 1.72 (s, 3H). | 499 |
| 44 | 4 | ¹H-NMR (400 MHz, DMSO-d6) δ ppm 8.39 (s, 2H), 8.02 (s, 1H), 7.96 (s, 1H), 7.86 (s, 1H), 7.80 (s, 1H), 7.47-7.43 (m, 2H), 7.21 (s, 1H), 7.12-7.07 (m, 2H), 4.11-4.05 (m, 4H), 3.92-3.86 (m, 4H), 3.84 (s, 3H), 1.72 (s, 3H). | 499 |
| 42 | 3 | ¹H-NMR (400 MHz, CDCl₃) δ ppm 8.23 (s, 2H), 8.12 (s, 1H), 7.92 (s, 1H), 7.83 (s, 1H), 7.24-7.20 (m, 2H), 7.01-7.96 (m, 2H), 6.48 (s, 1H), 4.50 (br. s., 4H), 4.02-4.00 (m, 4H), 3.99 (s, 3H), 1.67 (s, 6H). | 499 |
| 45 | 3 | ¹H-NMR (400 MHz, CDCl₃) δ ppm 8.38 (s, 2H), 7.91 (s, 1H), 7.70 (s, 2H), 7.57 (s, 1H), 7.41 (dd, 2H, J = 8.0, 4.0 Hz), 7.05-7.01 (m, 2H), 6.79 (s, 1H), 4.17-4.15 (m, 4H), 4.05-4.02 (m, 4H), 3.95 (s, 3H), 1.94 (s, 3H). | 500 |
| 46 | 3 | ¹H-NMR (400 MHz, CDCl₃) δ ppm 8.38 (s, 2H), 7.89 (s, 1H), 7.69 (s, 2H), 7.57 (s, 1H), 7.41 (dd, 2H, J = 8.0, 4.0 Hz), 7.05-7.01 (m, 2H), 6.77 (d, 1H, J = 1.2 Hz), 4.17-4.15 (m, 4H), 4.05-4.02 (m, 4H), 3.95 (s, 3H), 1.94 (s, 3H). | 500 |
| 47 | 3 | 1H-NMR (400 MHz, CDCl3) δ ppm 8.37 (s, 2H), 7.88 (s, 1H), 7.67 (s, 2H), 7.65-7.63 (m, 1H), 7.55 (s, 1H), 7.32-7.29 (m, 1H), 7.21-7.17 (m, 1H), 7.03-6.98 (m, 1H), 6.76 (s, 1H), 4.14-4.11 (m, 4H), 4.01-3.99 (m, 4H), 3.93 (s, 3H), 2.90 (d, 1H, J = 4.0 Hz), 1.96 (s, 3H). | 500 |
| 48 | 3 | 1H-NMR (400 MHz, CDCl3) δ ppm 8.37 (s, 2H), 7.88 (s, 1H), 7.69 (s, 2H), 7.64 (t, 1H, J = 7.2 Hz), 7.56 (s, 1H), 7.31-7.28 (m, 1H), 7.19 (d, 1H, J = 7.6 Hz), 7.01 (dd, 1H, J = 11.6, 8.4 Hz), 6.77 (s, 1H), 4.15-4.13 (m, 4H), 4.03-4.00 (m, 4H), 3.94 (s, 3H), 2.74 (d, 1H, J = 4.4 Hz), 1.97 (s, 3H). | 500 |
| 49 | 3 | 1H-NMR (400 MHz, DMSO-d6) δ ppm 8.34 (s, 2H), 8.03 (s, 1H), 7.98 (d, 1H, J = 1.6 Hz), 7.87 (s, 1H), 7.82 (s, 1H), 7.35-7.32 (m, 2H), 7.23 (d, 1H, J = 1.6 Hz), 7.15-7.10 (m, 2H), 4.93 (t, 1H, J = 4.8 Hz), 4.12-4.06 (m, 4H), 4.02-3.97 (m, 1H), 3.94-3.86 (m, 6H), 3.85 (s, 3H). | 500 |
| 50 | 3 | 1H-NMR (400 MHz, DMSO-d6) δ ppm 8.34 (s, 2H), 8.03 (s, 1H), 7.98 (d, 1H, J = 1.6 Hz), 7.87 (s, 1H), 7.82 (s, 1H), 7.35-7.32 (m, 2H), 7.23 (d, 1H, J = 1.6 Hz), 7.15-7.10 (m, 2H), 4.93 (t, 1H, J = 4.8 Hz), 4.12-4.06 (m, 4H), 4.02-3.97 (m, 1H), 3.94-3.86 (m, 6H), 3.85 (s, 3H). | 500 |
| 51 | 3 | 1H-NMR (400 MHz, CDCl3) δ ppm 8.37 (br. s., 2H), 7.90 (br. s., 2H), 7.39 (br. s., 2H), 7.03 (br. s., 3H), 6.23 (s, 1H), 4.18-4.14 (m, 4H), 4.04-4.01 (m, 4H), 2.49 (s, 1H), 2.33 (s, 3H), 1.92 (s, 3H). | 501 |
| 52 | 3 | 1H-NMR (400 MHz, CDCl3) δ ppm 8.37 (s, 2H), 7.92, 7.91 (s, s, 2H), 8.42-7.38 (m, 2H), 7.05-7.00 (m, 3H), 6.23 (s, 1H), 4.18-4.14 (m, 4H), 4.04-4.01 (m, 4H), 2.36 (s, 1H), 2.34 (s, 3H), 1.93 (s, 3H). | 501 |

-continued

| Compound Number | Synthetic Protocol | ¹H NMR | LC/MS (M + 1) |
|---|---|---|---|
| 53 | 3 | 1H-NMR (400 MHz, DMSO-d6) δ ppm 8.48 (d, 1H, J = 4.8 Hz), 8.41 (d, 1H, J = 3.2 Hz), 8.38 (s, 2H), 8.03 (s, 1H), 7.99 (d, 1H, J = 1.6 Hz), 7.87 (s, 1H), 7.82 (s, 1H), 7.79-7.76 (m, 1H), 7.23 (d, 1H, J = 1.6 Hz), 6.25 (s, 1H), 4.11-4.08 (m, 4H), 3.94-3.91 (m, 4H), 3.85 (s, 3H), 1.88 (s, 3H). | 501 |
| 54 | 3 | 1H-NMR (400 MHz, DMSO-d6) δ ppm 8.48 (d, 1H, J = 4.8 Hz), 8.41 (d, 1H, J = 3.2 Hz), 8.38 (s, 2H), 8.03 (s, 1H), 7.99 (d, 1H, J = 1.6 Hz), 7.87 (s, 1H), 7.82 (d, 1H, J = 0.8 Hz), 7.79-7.76 (m, 1H), 7.23 (d, 1H, J = 2.0 Hz), 6.25 (s, 1H), 4.11-4.08 (m, 4H), 3.93-3.91 (m, 4H), 3.85 (s, 3H), 1.87 (s, 3H). | 501 |
| 55 | 1 | ¹H-NMR (500 MHz, CDCl₃) δ ppm 8.47 (s, 2H), 7.92 (s, 1H), 7.72, 7.70 (s, s, 2H), 7.57 (s, 1H), 7.20-7.17 (m, 1H), 7.11-7.02 (m, 3H), 6.83 (br. s., 1H), 4.97-4.95 (m, 1H), 4.62-4.47 (m, 3H), 3.97-3.95 (m, 4H), 3.76-3.72 (m, 2H), 1.33 (d, 3H, J = 6.5 Hz). | 502 |
| 56 | 1 | 1H NMR (400 MHz, DMSO-d6) δ 8.10 (s, 1H), 8.03 (s, 1H), 7.98 (d, J = 1.5 Hz, 1H), 7.87 (s, 1H), 7.82 (d, J = 0.8 Hz, 1H), 7.22 (d, J = 1.7 Hz, 1H), 7.20-7.10 (m, 4H), 4.15-4.04 (m, 4H), 3.98-3.88 (m, 4H), 3.86 (s, 3H). | 503 |
| 57 | 3 | 1H-NMR (400 MHz, DMSO-d6) δ ppm 12.84 (s, 1H), 8.38 (s, 2H), 8.05-8.01 (m, 3H), 7.88 (s, 1H), 7.83-7.77 (m, 1H), 7.26 (s, 1H), 7.14-7.09 (m, 2H), 6.05 (s, 1H), 4.12-4.09 (m, 4H), 3.93-3.91 (m, 4H), 1.84 (s, 3H). | 504 |
| 58 | 3 | 1H-NMR (400 MHz, DMSO-d6) δ ppm 12.80 (br s, 1H), 8.34 (s, 2H), 8.02 (s, 1H), 8.02 (s, 1H), 8.00 (s, 1H), 7.88 (s, 1H), 7.83-7.77 (m, 1H), 7.26 (d, 1H, J = 1.2 Hz), 7.14-7.08 (m, 2H), 6.05 (br s, 1H), 4.12-4.09 (m, 4H), 3.94-3.91 (m, 4H), 1.84 (s, 3H). | 504 |
| 59 | 3 | 1H-NMR (400 MHz, DMSO-d6) δ ppm 8.39 (s, 2H), 8.21 (s, 1H), 7.88 (s, 1H), 7.71 (d, 2H, J = 7.6 Hz), 7.47-7.42 (m, 3H), 7.19 (d, 2H, J = 7.6 Hz), 7.13-7.09 (m, 2H), 5.89 (br. s., 1H), 4.11 (br. s., 4H), 3.90 (s, 4H), 2.30 (s, 3H), 1.81 (s, 3H). | 510 |
| 60 | 3 | 1H-NMR (400 MHz, DMSO-d6) δ ppm 8.94 (d, 1H, J = 2.4 Hz), 8.41 (s, 2H), 8.34 (d, 1H, J = 1.6 Hz), 8.12-8.10 (m, 1H), 7.91 (s, 1H), 7.54 (d, 1H, J = 1.2 Hz), 7.48-7.45 (m, 2H), 7.30-7.27 (m, 1H), 7.15-7.11 (m, 2H), 5.90 (s, 1H), 4.13-4.11 (m, 4H), 3.93-3.90 (m, 4H), 2.47 (s, 3H), 1.82 (s, 3H). | 511 |
| 61 | 1 | 1H-NMR (400 MHz, CDCl3) δ ppm 8.26 (s, 2H), 7.90 (s, 1H), 7.70 (s, 1H), 7.57 (s, 1H), 7.18-7.05 (m, 4H), 6.77 (d, 1H, J = 1.6 Hz), 5.25 (d, 2H, J = 6.0 Hz), 5.10 (d, 2H, J = 6.0 Hz), 4.17-4.14 (m, 4H), 4.05-4.01 (m, 4H), 3.95 (s, 3H). | 512 |
| 62 | 4 | 1H-NMR (400 MHz, DMSO-d6) δ ppm 8.40 (s, 2H), 8.26 (s, 1H), 7.90-7.86 (m, 3H), 7.47-7.44 (m, 3H), 7.26-7.21 (m, 2H), 7.12-7.08 (m, 2H), 4.13-4.09 (m, 4H), 3.92-3.89 (m, 4H), 2.56-2.54 (br, 2H), 1.72 (s, 3H). | 513 |
| 63 | 4 | 1H-NMR (400 MHz, DMSO-d6) δ ppm 8.40 (s, 2H), 8.08 (s, 1H), 7.97 (s, 1H), 7.86 (s, 1H), 7.82 (s, 1H), 7.45 (dd, 2H, J = 6.0, 8.8 Hz), 7.22 (s, 1H), 7.12-7.08 (m, 2H), 4.12 (q, 2H, J = 7.2 Hz), 4.10-4.07 (m, 4H), 3.91-3.88 (m, 4H), 2.54-2.50 (br, 2H), 1.72 (s, 3H), 1.40 (t, 3H, J = 7.2 Hz). | 513 |
| 64 | 3 | ¹H-NMR (400 MHz, CDCl₃) δ ppm 8.38 (s, 2H), 7.92 (s, 1H), 7.83 (d, 1H, J = 1.6 Hz), 7.59-7.55 (m, 2H), 7.43-7.39 (m, 2H), 7.13-7.09 (m, 2H), 7.05-7.01 (m, 2H), 6.91 (d, 1H, J = 1.6 Hz), 4.18-4.16 (m, 4H), 4.04-4.02 (m, 4H), 2.21 (s, 1H), 1.94 (s, 3H). | 514 |
| 65 | 3 | ¹H-NMR (400 MHz, CDCl₃-d₆) δ ppm 8.38 (s, 2H), 7.92 (s, 1H), 7.83 (d, 1H, J = 1.6 Hz), 7.59-7.55 (m, 2H), 7.43-7.39 (m, 2H), 7.13-7.09 (m, 2H), 7.05-7.01 (m, 2H), 6.91 (d, 1H, J = 1.6 Hz), 4.18-4.16 (m, 4H), 4.04-4.02 (m, 4H), 2.21 (s, 1H), 1.94 (s, 3H). | 514 |
| 66 | 3 | 1H-NMR (400 MHz, DMSO-d6) δ ppm 8.41 (s, 2H), 8.35 (d, 1H, J = 1.6 Hz), 7.92 (s, 1H), 7.76-7.69 (m, 2H), 7.54 (d, 1H, J = 1.2 Hz), 7.49-7.42 (m, 3H), 7.15-7.06 (m, 3H), 5.89 (s, 1H), 4.14 (t, 4H, J = 6.0 Hz), 3.92 (t, 4H, J = 5.2 Hz), 1.82 (s, 3H). | 514 |
| 67 | 3 | ¹H-NMR (400 MHz, CDCl₃) δ ppm 8.29 (s, 2H), 7.90 (s, 1H), 7.69 (d, 2H, J = 1.6 Hz), 7.56 (s, 1H), 7.35-7.31 (m, 2H), 7.04-6.99 (m, 2H), 6.77 (d, 1H, J = 1.6 Hz), 4.16-4.14 (m, 4H), 4.03-4.01 (m, 4H), 3.95 (s, 3H), 3.16 (s, 3H), 1.82 (s, 3H). | 514 |

-continued

| Compound Number | Synthetic Protocol | ¹H NMR | LC/MS (M + 1) |
|---|---|---|---|
| 68 | 3 | ¹H-NMR (400 MHz, DMSO-d₆) δ ppm 8.31 (s, 2H), 8.03 (s, 1H), 7.97 (d, 1H, J = 1.6 Hz), 7.87 (s, 1H), 7.81 (s, 1H), 7.41-7.38 (m, 2H), 7.22 (d, 1H, J = 1.6 Hz), 7.18-7.13 (m, 2H), 4.11-4.09 (m, 4H), 3.94-3.91 (m, 4H), 3.85 (s, 3H), 3.09 (s, 3H), 1.81 (s, 3H). | 514 |
| 69 | 3 | ¹H-NMR (400 MHz, CDCl₃) δ ppm 8.36 (s, 2H), 7.89 (s, 1H), 7.69 (s, 2H), 7.56 (s, 1H), 7.40-7.37 (m, 2H), 7.05-6.99 (m, 2H), 6.77 (d, 1H, J = 1.2 Hz), 4.16-4.13 (m, 4H), 4.03-4.00 (m, 4H), 3.95 (s, 3H), 2.26 (q, 2H, J = 8.0 Hz), 2.07 (br. s., 1H), 0.91 (t, 3H, J = 8.0 Hz). | 514 |
| 70 | 3 | ¹H-NMR (400 MHz, CDCl₃) δ ppm 8.36 (s, s, 2H), 7.89 (s, 1H), 7.69 (s, 2H), 7.56 (s, 1H), 7.40-7.37 (m, 2H), 7.05-7.00 (m, 2H), 6.77 (d, 1H, J = 1.6 Hz), 4.16-4.13 (m, 4H), 4.03-4.00 (m, 4H), 3.95 (s, 3H), 2.26 (q, 2H, J = 8.0 Hz), 2.07 (br. s., 1H), 0.91 (t, 3H, J = 8.0 Hz). | 514 |
| 71 | 3 | 1H-NMR (400 MHz, DMSO-d6) δ ppm 8.40 (s, 2H), 7.94 (s, 1H), 7.89 (s, 1H), 7.84 (d, 1H, J = 1.2 Hz), 7.46 (dd, 2H, J = 5.6, 8.8 Hz), 7.15-7.09 (m, 2H), 5.93-5.87 (br, 1H), 4.11-4.08 (m, 4H), 3.92-3.89 (m, 4H), 3.78 (s, 3H), 2.32 (s, 3H), 1.82 (s, 3H). | 514 |
| 72 | 3 | 1H-NMR (400 MHz, DMSO-d6) δ ppm 8.40 (s, 2H), 7.94 (s, 1H), 7.89 (s, 1H), 7.84 (d, 1H, J = 1.6 Hz), 7.48-7.45 (m, 2H), 7.15-7.09 (m, 3H), 5.89 (s, 1H), 4.11-4.08 (m, 4H), 3.92-3.89 (m, 4H), 3.78 (s, 3H), 2.32 (s, 3H), 1.82 (s, 3H). | 514 |
| 73 | 1 | 1H-NMR (400 MHz, DMSO-d6) δ ppm 8.32 (s, 2H), 8.00 (s, 1H), 7.95 (s, 1H), 7.85 (s, 1H), 7.77 (s, 1H), 7.35-7.29 (m, 2H), 7.20 (s, 1H), 7.11 (t, 2H, J = 8.0 Hz), 4.92 (t, 1H, J = 4.0 Hz), 4.69-4.56 (m, 2H), 4.39-4.26 (m, 2H), 4.07 (q, 1H, J = 8.0 Hz), 3.84 (s, 3H), 3.83-3.78 (m, 1H), 3.76-3.58 (m, 2H), 3.55-3.40 (m, 2H), 1.55 (d, 3H, J = 8.0 Hz). | 514 |
| 74 | 1 | 1H-NMR (400 MHz, DMSO-d6) δ ppm 8.32 (s, 2H), 8.00 (s, 1H), 7.96-7.95 (m, 1H), 7.85 (s, 1H), 7.78-7.77 (m, 1H), 7.34-7.29 (m, 2H), 7.21-7.20 (m, 1H), 7.14-7.08 (m, 2H), 4.92 (t, 1H, J = 4.0 Hz), 4.67-4.55 (m, 2H), 4.38-4.26 (m, 2H), 4.07 (q, 1H, J = 8.0 Hz), 3.84 (s, 3H), 3.83-3.78 (m, 1H), 3.77-3.58 (m, 2H), 3.55-3.42 (m, 2H), 1.55 (d, 3H, J = 8.0 Hz). | 514 |
| 75 | 3 | 1H NMR (400 MHz, DMSO-d6) δ ppm 8.40 (s, 2H), 8.09 (s, 1H), 7.98 (d, 1H, J = 1.6 Hz), 7.87 (s, 1H), 7.82 (s, 1H), 7.48-7.45 (m, 2H), 7.23 (d, 1H, J = 2.0 Hz), 7.15-7.12 (m, 2H), 5.89 (s, 1 H), 4.15-4.08 (m, 6H), 3.92 (t, 4H, J = 6.4 Hz), 1.82 (s, 3H), 1.42 (t, 3H, J = 7.2 Hz). | 514 |
| 76 | 1 | 1H-NMR (400 MHz, DMSO-d6) δ ppm 8.39 (s, 2H), 8.03 (s, 1H), 7.98-7.96 (m, 1H), 7.85 (s, 1H), 7.81 (s, 1H), 7.49-7.44 (m, 2H), 7.22-7.19 (m, 1H), 7.15-7.09 (m, 2H), 5.85 (s, 1H), 4.85-4.77 (m, 1H), 4.64-4.56 (m, 1H), 4.56-4.48 (m, 1H), 4.44-4.37 (m, 1H), 3.85 (s, 3H), 3.78-3.71 (m, 1H), 3.64-3.49 (m, 2H), 1.81 (s, 3H), 1.15 (d, 3H, J = 8.0 Hz). | 514 |
| 77 | 1 | 1H-NMR (400 MHz, DMSO-d6) δ ppm 8.39 (s, 2H), 8.03 (s, 1H), 7.98-7.96 (m, 1H), 7.85 (s, 1H), 7.81 (s, 1H), 7.49-7.44 (m, 2H), 7.22-7.19 (m, 1H), 7.15-7.09 (m, 2H), 5.85 (s, 1H), 4.85-4.77 (m, 1H), 4.64-4.56 (m, 1H), 4.56-4.48 (m, 1H), 4.44-4.37 (m, 1H), 3.85 (s, 3H), 3.78-3.71 (m, 1H), 3.64-3.49 (m, 2H), 1.81 (s, 3H), 1.15 (d, 3H, J = 8.0 Hz). | 514 |
| 78 | 3 | 1H-NMR (400 MHz, DMSO-d6) δ ppm 8.24 (s, 2H), 8.04 (s, 1H), 7.98 (d, 1H, J = 1.2 Hz), 7.87 (s, 1H), 7.82 (s, 1H), 7.30-7.23 (m, 3H), 7.11-7.09 (m, 2H), 5.08-5.05 (m, 1H), 4.11-4.08 (m, 4H), 3.92-3.87 (m, 4H), 3.85 (s, 3H), 3.78-3.74 (m, 2H), 1.58 (s, 3H). | 514 |
| 79 | 3 | 1H-NMR (400 MHz, DMSO-d6) δ ppm 8.24 (s, 2H), 8.04 (s, 1H), 7.99 (s, 1H), 7.87 (s, 1H), 7.82 (s, 1H), 7.30-7.23 (m, 3H), 7.13-7.09 (m, 2H), 5.08-5.05 (br. s., 1H), 4.10 (br. s., 4H), 3.90 (br. s., 4H), 3.85 (s, 3H), 3.78-3.74 (m, 2H), 1.58 (s, 3H). | 514 |
| 80 | 3 | 1H-NMR (400 MHz, DMSO-d6) δ ppm 8.22 (s, 2H), 8.04 (s, 1H), 7.99 (d, 1H, J = 1.2 Hz), 7.87 (s, 1H), 7.82 (s, 1H), 7.65 (dd, 1H, J = 8.4, 6.0 Hz), 7.23 (d, 1H, J = 1.2 Hz), 7.03 (td, 1H, J = 8.4, 2.8 Hz), 6.96 (dd, 1H, J = 10.0, 2.8 Hz), 5.81 (s, 1H), 4.11-4.08 (m, 4H), 3.92-3.89 (m, 4H), 3.85 (s, 3H), 2.07 (s, 3H), 1.81 (s, 3H). | 514 |

| Compound Number | Synthetic Protocol | ¹H NMR | LC/MS (M + 1) |
|---|---|---|---|
| 81 | 3 | 1H-NMR (400 MHz, DMSO-d6) δ ppm 8.40 (s, 2H), 8.01 (s, 1H), 7.90 (s, 1H), 7.52-7.40 (m, 2H), 7.23-7.19 (m, 2H), 7.15-7.10 (m, 2H), 6.78 (s, 1H), 5.89 (s, 1H), 4.10 (br. s., 4H), 3.91 (br. s., 4H), 2.45 (s, 3H), 1.82 (s, 3H). | 516 |
| 82 | 3 | 1H-NMR (400 MHz, DMSO-d6) δ ppm 8.40 (s, 2H), 8.02 (s, 1H, J = 1.6 Hz), 7.90 (s, 1H), 7.49-7.45 (m, 2H), 7.23-7.19 (m, 2H), 7.15-7.10 (m, 2H), 6.80-6.76 (m, 1H), 5.89 (s, 1H), 4.11-4.05 (m, 4H), 3.95-3.86 (m, 4H), 2.45 (s, 3H), 1.82 (s, 3H). | 516 |
| 83 | 3 | ¹H-NMR (400 MHz, DMSO-$d_6$) δ ppm 8.41 (s, 2H), 8.03 (s, 1H), 7.98 (d, 1H, J = 1.6 Hz), 7.87 (s, 1H), 7.82 (s, 1H), 7.46 (d, 1H, J = 8.8 Hz), 7.36 (d, 1H, J = 8.4 Hz), 7.22 (d, 1H, J = 1.6 Hz), 5.93 (s, 1H), 4.10-4.08 (m, 4H), 3.92-3.90 (m, 4H), 3.85 (s, 3H), 1.82 (s, 3H). | 516 |
| 84 | 3 | ¹H-NMR (400 MHz, DMSO-$d_6$) δ ppm 8.41 (s, 2H), 8.03 (s, 1H), 7.98 (d, 1H, J = 1.2 Hz), 7.87 (s, 1H), 7.82 (s, 1H), 7.46 (d, 1H, J = 8.8 Hz), 7.36 (d, 1H, J = 8.4 Hz), 7.22 (d, 1H, J = 1.6 Hz), 5.93 (s, 1H), 4.10-4.08 (m, 4H), 3.92-3.90 (m, 4H), 3.85 (s, 3H), 1.82 (s, 3H). | 516 |
| 85 | 3 | ¹H-NMR (400 MHz, DMSO-$d_6$) δ ppm 8.32 (s, 2H), 8.04 (s, 1H), 7.99 (d, 1H, J = 1.2 Hz), 7.87 (s, 1H), 7.82-7.77 (m, 2H), 7.23 (d, 1H, J = 1.2 Hz), 7.14-7.08 (m, 2H), 4.10-4.07 (m, 4H), 3.92-3.88 (m, 4H), 3.85 (s, 3H), 1.73 (s, 3H). | 517 |
| 86 | 3 | ¹H-NMR (400 MHz, DMSO-$d_6$) δ ppm 8.32 (s, 2H), 8.04 (s, 1H), 7.99 (s, 1H), 7.87 (s, 1H), 7.82-7.77 (m, 2H), 7.23 (s, 1H), 7.14-7.08 (m, 2H), 4.10-4.07 (m, 4H), 3.92-3.88 (m, 4H), 3.85 (s, 3H), 1.73 (s, 3H). | 517 |
| 87 | 3 | 1H-NMR (400 MHz, DMSO-d6) δ ppm 8.39 (s, 2H), 8.10 (d, 1H, J = 1.2 Hz), 7.96 (s, 1H), 7.91 (s, 1H), 7.47-7.44 (m, 2H), 7.29 (d, 1H, J = 1.2 Hz), 7.12 (t, 2H, J = 8.8 Hz), 5.89 (s, 1H), 4.10-4.08 (m, 4H), 3.91-3.89 (m, 4H), 2.65 (s, 3H), 1.81 (s, 3H). | 517 |
| 88 | 3 | 1H-NMR (400 MHz, DMSO-d6) δ ppm 8.38 (s, 1H), 8.37 (s, 1H), 8.10 (d, 1H, J = 1.2 Hz), 7.96 (d, 1H, J = 1.6 Hz), 7.91 (d, 1H, J = 2.0 Hz), 7.46-7.43 (m, 2H), 7.28 (s, 1H), 7.12 (t, 2H, J = 8.8 Hz), 5.92 (br. s., 1H), 4.09 (br. s., 4H), 3.89 (br. s., 4H), 2.65 (s, 3H), 1.80 (s, 3H). | 517 |
| 89 | 3 | 1H-NMR (400 MHz, DMSO-d6) δ ppm 8.40 (s, 1H), 8.39 (s, 2H), 8.07 (s, 1H), 7.98 (s, 1H), 7.48-7.44 (m, 2H), 7.15-7.10 (m, 2H), 7.00 (s, 1H), 5.90 (s, 1H), 3.91 (s, 3H), 3.87 (s, 8H), 1.82 (s, 3H). | 518 |
| 90 | 3 | 1H-NMR (400 MHz, DMSO-d6) δ ppm 8.40 (s, 1H), 8.39 (s, 2H), 8.07 (s, 1H), 7.98 (s, 1H), 7.48-7.45 (m, 2H), 7.15-7.10 (m, 2H), 7.00 (s, 1H), 5.90 (s, 1H), 3.91 (s, 3H), 3.87 (s, 8H), 1.82 (s, 3H). | 518 |
| 91 | 3 | 1H-NMR (400 MHz, DMSO-d6) δ ppm 8.37 (s, 2H), 8.04 (s, 1H), 7.99 (d, 1H, J = 1.6 Hz), 7.87 (s, 1H), 7.82 (d, 1H, J = 1.2 Hz), 7.41-7.33 (m, 1H), 7.23 (d, 1H, J = 1.6 Hz), 7.05-6.98 (m, 2H), 6.10 (s, 1H), 4.12-4.09 (m, 4H), 3.93-3.91 (m, 4H), 3.85 (s, 3H), 1.90 (s, 3H). | 518 |
| 92 | 3 | 1H-NMR (400 MHz, DMSO-d6) δ ppm 8.37 (s, 2H), 8.04 (s, 1H), 7.99 (d, 1H, J = 1.6 Hz), 7.87 (s, 1H), 7.82 (s, 1H), 7.41-7.34 (m, 1H), 7.23 (d, 1H, J = 1.6 Hz), 7.05-6.98 (m, 2H), 6.10 (s, 1H), 4.12-4.09 (m, 4H), 3.93-3.90 (m, 4H), 3.85 (s, 3H), 1.90 (s, 3H). | 518 |
| 93 | 3 | ¹H-NMR (400 MHz, DMSO-$d_6$) δ ppm 8.34 (s, 2H), 8.03 (s, 1H), 7.98 (d, 1H, J = 1.6 Hz), 7.87 (s, 1H), 7.83-7.77 (m, 2H), 7.23 (d, 1H, J = 1.2 Hz), 7.14-7.08 (m, 2H), 6.04 (s, 1H), 4.11-4.08 (m, 4H), 3.93-3.90 (m, 4H), 3.85 (s, 3H), 1.84 (s, 3H). | 518 |
| 95 | 3 | ¹H-NMR (400 MHz, DMSO-$d_6$) δ ppm 8.37 (s, 2H), 8.02 (s, 1H), 7.97 (s, 1H), 7.86 (s, 1H), 7.81 (s, 1H), 7.47 (dd, 2H, J = 8.4, 5.6 Hz), 7.22-7.16 (m, 3H), 6.40 (s, 1H), 4.86 (td, 2H, J = 45.2, 10.0 Hz), 4.09 (br. s., 4H), 3.92 (br. s., 4H), 3.84 (s, 3H). | 518 |
| 96 | 3 | ¹H-NMR (400 MHz, DMSO-$d_6$) δ ppm 8.38 (s, 2H), 8.02 (s, 1H), 7.97 (s, 1H), 7.86 (s, 1H), 7.81 (s, 1H), 7.48 (br. s., 2H), 7.22-7.16 (m, 3H), 6.39 (s, 1H), 4.86 (td, 2H, J = 45.6, 10.0 Hz), 4.09 (br. s., 4H), 3.92 (br. s., 4H), 3.84 (s, 3H). | 518 |

| Compound Number | Synthetic Protocol | ¹H NMR | LC/MS (M + 1) |
|---|---|---|---|
| 97 | 1 | ¹H NMR (400 MHz, DMSO-$d_6$) δ 8.57 (s, 2H), 8.02 (s, 1H), 7.98 (d, J = 1.5 Hz, 1H), 7.88 (s, 1H), 7.79 (d, J = 0.8 Hz, 1H), 7.33-7.20 (m, 3H), 7.20-7.11 (m, 1H), 7.10-7.01 (m, 1H), 5.02 (t, J = 5.2 Hz, 1H), 4.67 (d, J = 11.0 Hz, 2H), 4.40 (d, J = 10.2 Hz, 2H), 3.95-3.71 (m, 6H), 3.65-3.48 (m, 3H). | 518 |
| 94 | 4 | ¹H-NMR (400 MHz, DMSO-$d_6$) δ ppm δ 8.34 (s, 2H), 8.03 (s, 1H), 7.98 (d, 1H, J = 1.2 Hz), 7.87 (s, 1H), 7.83-7.77 (m, 2H), 7.23 (d, 1H, J = 1.2 Hz), 7.14-7.09 (m, 2H), 6.04 (s, 1H), 4.11-4.08 (m, 4H), 3.93-3.90 (m, 4H), 3.85 (s, 3H), 1.84 (s, 3H). | 518 |
| 98 | 1 |  | 519 |
| 103 | 3 | ¹H-NMR (400 MHz, CDCl$_3$) δ ppm 8.39 (s, 2H), 7.90 (s, 1H), 7.70 (s, 2H), 7.56 (s, 1H), 7.46-7.43 (m, 2H), 7.05-7.00 (m, 2H), 6.78 (d, 1H, J = 1.2 Hz), 4.17-4.14 (m, 4H), 4.05-4.02 (m, 4H), 3.95 (s, 3H), 1.93 (br. s., 1H), 0.66-0.62 (m, 2H), 0.49-0.45 (m, 2H). | 526 |
| 104 | 3 | ¹H-NMR (400 MHz, CDCl$_3$) δ ppm 8.39 (s, 2H), 7.91 (s, 1H), 7.70 (s, 2H), 7.57 (s, 1H), 7.46-7.43 (m, 2H), 7.05-7.01 (m, 2H), 6.79 (s, 1H), 4.18-4.15 (m, 4H), 4.05-4.02 (m, 4H), 3.95 (s, 3H), 1.90 (br. s., 1H), 0.67-0.63 (m, 2H), 0.48-0.44 (m, 2H). | 526 |
| 105 | 2 | ¹H-NMR (400 MHz, DMSO-$d_6$) δ ppm 8.56 (s, 2H), 8.04 (s, 1H), 8.00 (s, 1H), 7.87 (s, 1H), 7.83 (s, 1H), 7.27-7.24 (m, 3H), 7.17-7.14 (m, 1H), 7.06-7.02 (m, 1H), 4.97 (d, 1H, J = 4.4 Hz), 4.15-4.13 (m, 4H), 4.00 (br. s., 7H), 1.05 (d, 3H, J = 5.6 Hz). | 532 |
| 111 | 3 | ¹H-NMR (400 MHz, DMSO-$d_6$) δ ppm 8.40 (s, 2H), 8.02 (s, 1H), 7.97 (d, 1H, J = 1.6 Hz), 7.86 (s, 1H), 7.81 (s, 1H), 7.54-7.50 (m, 2H), 7.22-7.17 (m, 3H), 6.75 (t, 1H, J = 55.2 Hz), 4.10-4.05 (m, 4H), 3.93-3.90 (m, 4H), 3.84 (s, 3H), 2.70 (s, 2H). | 535 |
| 112 | 3 | ¹H-NMR (400 MHz, DMSO-$d_6$) δ ppm 8.39 (s, 2H), 8.02 (s, 1H), 7.99 (d, 1H, J = 1.2 Hz), 7.86 (s, 1H), 7.81 (s, 1H), 7.52 (dd, 2H, J = 5.6, 8.8 Hz), 7.22-7.17 (m, 3H), 6.74 (t, 1H, J = 55.2 Hz), 4.10-4.07 (m, 4H), 3.90-3.90 (m, 4H), 3.84 (s, 3H), 2.69 (s, 2H). | 535 |
| 117 | 3 | ¹H-NMR (400 MHz, DMSO-$d_6$) δ ppm 8.35 (s, 2H), 8.02 (s, 1H), 7.97 (d, 1H, J = 1.6 Hz), 7.86 (s, 1H), 7.81 (s, 1H), 7.50 (dd, 2H, J = 5.2, 8.8 Hz), 7.25-7.20 (m, 3H), 6.78 (s, 1H), 6.70 (t, 1H, J = 54.4 Hz), 4.10-4.08 (m, 4H), 3.94-3.93 (m, 4H), 3.84 (s, 3H). | 536 |
| 118 | 3 | ¹H-NMR (400 MHz, DMSO-$d_6$) δ ppm 8.35 (s, 2H), 8.02 (s, 1H), 7.97 (d, 1H, J = 1.2 Hz), 7.86 (s, 1H), 7.81 (s, 1H), 7.49 (dd, 2H, J = 5.6, 8.8 Hz), 7.25-7.20 (m, 3H), 6.78 (s, 1H), 6.70 (t, 1H, J = 54.8 Hz), 4.21-4.05 (m, 4H), 4.00-3.91 (m, 4H), 3.84 (s, 3H). | 536 |
| 120 | 2 | ¹H-NMR (400 MHz, DMSO-$d_6$) δ 8.34 (s, 2H), 8.04 (s, 1H), 8.00 (d, 1H, J = 1.2 Hz), 7.87-7.86 (m, 2H), 7.34-7.15 (m, 6H), 4.22-4.04 (m, 6H), 3.91-3.80 (m, 8H), 3.512-3.46 (m, 1H), 2.99-2.52 (m, 3H), 2.55-2.33 (m, 1H). | 537 |
| 123 | 2 | ¹H-NMR (400 MHz, DMSO-$d_6$) δ ppm 8.57 (s, 2H), 8.04 (s, 1H), 8.01 (s, 1H), 7.88 (s, 1H), 7.84 (s, 1H), 7.29-7.14 (m, 4H), 7.07-7.03 (m, 1H), 4.17-4.14 (m, 4H), 4.11-4.10 (m, 2H), 4.02-4.00 (m, 4H), 3.73-3.71 (m, 2H), 3.42-3.37 (m, 1H), 2.77-2.59 (m, 3H), 2.40-2.33 (m, 2H). | 573 |
| 124 | 2 | 1H NMR (400 MHz, DMSO-d6) δ 8.38 (s, 2H), 7.85 (d, J = 2.1 Hz, 2H), 7.52-7.37 (m, 2H), 7.19-7.03 (m, 3H), 6.22 (s, 1H), 5.87 (s, 1H), 4.12-4.02 (m, 4H), 3.98 (br.s, 2H), 3.94-3.81 (m, 4H), 3.52 (t, J = 5.8 Hz, 2H), 2.44 (br.s, 2H), 1.80 (s, 3H). | 601 |

Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

KIT D816V assay at Km: In each well of a 384-well plate, 0.04 ng/ul (0.5 nM) of D816V KIT (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSFPAKKK-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35 s). Data was normalized to 0% and 100% inhibition controls and the $IC_{50}$ or $EC_{50}$ calculated using a 4-parameter fit using GraphPad Prism.

PDGFRA D842V assay at Km: In each well of a 384-well plate, 0.7 ng/ul (8 nM) of PDGFRA D842V (ProQinase 0761-0000-1) was incubated in a total of 12.5 ul of buffer (100 mM HEPES pH 7.5, 0.015% Brij 35, 10 mM MgCl2, 1 mM DTT) with 1 uM CSKtide (5-FAM-KKKKEEIYFFF-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −500, downstream voltage −3000, post sample sip 38 s). Data was normalized to 0% and 100% inhibition controls and the $IC_{50}$ or $EC_{50}$ calculated using a 4-parameter fit using GraphPad Prism.

Cellular Activity

HMC1.2 Autophosphorylation Assay:

10,000 HMC1.2 cells were incubated in 22 ul culture media (phenol-red free IMDM, no serum) in each well of a 384-well plate and serum starved overnight in a tissue culture incubator (5% $CO_2$, 37° C.). A 10-point dose concentration series of compound (25 uM-95.4 pM) were then added to the cells in a volume of 3.1 ul to each well (0.25% DMSO final concentration). After 90 minutes, 6 ul of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 ul of phospho-Y719 c-KIT and total c-KIT antibodies (15 nM final concentration, Cell Signaling Technologies) and 50 ug/ml AlphaLISA rabbit acceptor beads (Perkin Elmer) were added to each well and shaken at 300 rpm at room temperature for 2 hours. 10 ul of 100 ug/ml streptavidin donor beads (Perkin Elmer) were added to each well, blocked from light with aluminum adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the IC50 was calculated using Four Parameter Logistic IC50 curve fitting.

The Table below shows the activity of compounds in a Mast cell leukemia cell line, HMC 1.2. This cell line contains KIT mutated at positions V560G and D816V resulting in constitutive activation of the kinase. The following compounds were tested in an assay to measure direct inhibition of KIT D816V kinase activity by assaying KIT autophosphorylation at tyrosine 719 on the KIT protein.

In the Table below, for biochemical D816V and D842V activity, the following designations are used: <1.00 nM=A; 1.01-10.0 nM=B; 10.01-100.0 nM=C; >100 nM=D; and ND=not determined. For cellular activity in the HMC1.2 cell line, the following designations are used: A means <50 nM; B means ≥50 and <100 nM; C means ≥100 and <1000 nM; D means ≥1000 and less than 10000 nM; E means ≥10000 nM; and ND=not determined.

| Compound Number | INH KIT D816V | INH PDFGRA D842V | INH-KIT-PHOS-HMC1.2 |
| --- | --- | --- | --- |
| 1 | D | | |
| 2 | D | | E |
| 3 | C | | D |
| 4 | D | | E |
| 5 | C | | D |
| 6 | D | | E |
| 7 | A | A | B |
| 8 | B | | C |
| 9 | B | B | A |
| 10 | A | A | A |
| 11 | B | | C |
| 12 | A | | A |
| 13 | B | | C |
| 14 | A | B | A |
| 15 | C | | C |
| 16 | B | | C |
| 17 | B | | C |
| 18 | C | C | E |
| 19 | B | | C |
| 20 | B | B | A |
| 21 | B | A | B |
| 22 | A | A | A |
| 23 | C | | C |
| 24 | B | | C |
| 25 | A | | A |
| 26 | A | A | A |
| 27 | B | | A |
| 28 | B | | A |
| 29 | B | B | B |
| 30 | A | A | A |
| 31 | B | | A |
| 32 | B | | A |
| 33 | B | | C |
| 34 | A | A | B |
| 35 | A | A | A |
| 36 | B | | C |
| 37 | C | | D |
| 38 | B | B | B |
| 39 | B | A | A |
| 40 | B | | C |
| 41 | B | B | B |
| 42 | C | | D |
| 43 | B | | A |
| 44 | A | A | A |
| 45 | A | A | A |
| 46 | A | A | A |
| 47 | A | | A |
| 48 | B | | A |
| 49 | A | | A |
| 50 | B | | A |
| 51 | C | | |
| 52 | B | | C |
| 53 | C | | D |
| 54 | B | | C |
| 55 | C | | C |
| 56 | A | | A |
| 57 | A | B | A |
| 58 | A | A | |
| 59 | C | | C |
| 60 | B | | A |
| 61 | B | | C |
| 62 | B | B | B |
| 63 | A | | A |
| 64 | C | | C |
| 65 | B | B | C |
| 66 | B | | C |
| 67 | C | | C |
| 68 | B | B | A |
| 69 | B | | C |
| 70 | B | | A |
| 71 | B | | B |
| 72 | A | | A |
| 73 | B | | A |

-continued

| Compound Number | INH KIT D816V | INH PDFGRA D842V | INH-KIT-PHOS-HMC1.2 |
|---|---|---|---|
| 74 | B | | B |
| 75 | A | | A |
| 76 | B | B | B |
| 77 | B | A | A |
| 78 | A | A | A |
| 79 | B | A | A |
| 80 | C | | |
| 81 | C | | D |
| 82 | C | | C |
| 83 | A | | A |
| 84 | B | B | A |
| 85 | A | | A |
| 86 | A | A | A |
| 87 | B | B | C |
| 88 | A | | A |
| 89 | D | | D |
| 90 | D | | D |
| 91 | A | | B |
| 92 | B | | A |
| 93 | B | A | A |
| 94 | A | A | A |
| 95 | A | | B |
| 96 | A | A | A |
| 97 | B | B | A |
| 98 | A | A | C |
| 99 | C | | D |
| 100 | A | A | A |
| 101 | C | | B |
| 102 | B | B | B |
| 103 | B | | C |
| 104 | B | | C |
| 105 | B | | A |
| 106 | B | | A |
| 107 | D | | D |
| 108 | D | | D |
| 109 | C | | C |
| 110 | B | | A |
| 111 | A | A | A |
| 112 | B | | C |
| 113 | A | | A |
| 114 | A | | A |
| 115 | B | A | A |
| 116 | A | A | A |
| 117 | A | B | A |
| 118 | B | | C |
| 119 | C | | C |
| 120 | A | | B |
| 121 | A | A | A |
| 122 | B | B | A |
| 123 | B | B | B |
| 124 | B | | A |

Efficacy in an In Vivo Model

Compound 46 and Dasatinib were evaluated in a P815 mastocytoma xenograft model. P815 tumor cells (ATCC, Manassas, Va., cat # ATCC® TIB-64) were maintained in vitro as a suspension and monolayer culture in RPMI1640 medium supplemented with 10% fetal calf serum at 37° C. in an atmosphere of 5% $CO_2$ in air. The tumor cells were sub-cultured twice weekly by trypsin-EDTA treatment. The cells growing in an exponential growth phase were harvested and counted for tumor inoculation.

Female BALB/c nude mice were used for the study. Each mouse was inoculated subcutaneously in the right flank with the P815 tumor cells ($1\times10^6$) in 0.1 ml of PBS for tumor development. The treatments were started on day 6 after tumor inoculation when the average tumor size reached approximately 89 $mm^3$. The testing article and vehicle were administrated to the mice according to the regimen shown below.

| Group | n | Treatment | Dose (mg/kg) | Dosing Volume (ml/kg) | Dosing Route | Schedule* |
|---|---|---|---|---|---|---|
| 1 | 13 | Vehicle | 0 | 10 | p.o. | QD × 10 |
| 2 | 10 | Dasatinib | 25 | 10 | p.o. | BID × 10 |
| 3 | 16 | Compound 46 | 3 | 10 | p.o. | QD × 10 |
| 4 | 16 | Compound 46 | 10 | 10 | p.o. | QD × 10 |
| 5 | 16 | Compound 46 | 30 | 10 | p.o. | QD × 10 |
| 6 | 16 | Compound 46 | 100 | 10 | p.o. | QD × 10 |

Note:
*QD = once per day, BID = twice per day.

Tumor sizes were measured every other day in two dimensions using a caliper, and the volume was expressed in $mm^3$ using the formula: $V=0.5\ a \times b^2$ where a and b were the long and short diameters of the tumor, respectively. The tumor size was then used for calculations of both T-C and T/C values. T-C was calculated with T as the median time (in days) required for the treatment group tumors to reach a predetermined size (e.g., 1000 $mm^3$), and C as the median time (in days) for the control group tumors to reach the same size. The T/C value (in percent) is an indication of antitumor effectiveness; T and C are the mean volumes of the treated and control groups, respectively, on a given day.

TGI was calculated for each group using the formula: TGI (%)=$[1-(Ti-T0)/(Vi-V0)]\times100$; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start. Tumor weight was measured at the endpoint.

A statistical analysis of difference in tumor volume and tumor weight among the groups was conducted on the data obtained at the best therapeutic time point after the final dose (the $8^{th}$ day after the start of treatment). A one-way ANOVA was performed to compare tumor volume and tumor weight among groups. All data were analyzed using Prism 5.0. $p<0.05$ was considered to be statistically significant.

Results. The tumor growth curves of different treatment groups are shown in FIG. 1. Data points represent group mean tumor volume, error bars represent standard error of the mean (SEM). As shown in FIG. 1, Compound 46 was effective in inhibiting tumor growth. Increasing the dose of Compound 46 enhanced the tumor inhibition efficiency.

Figure 2:
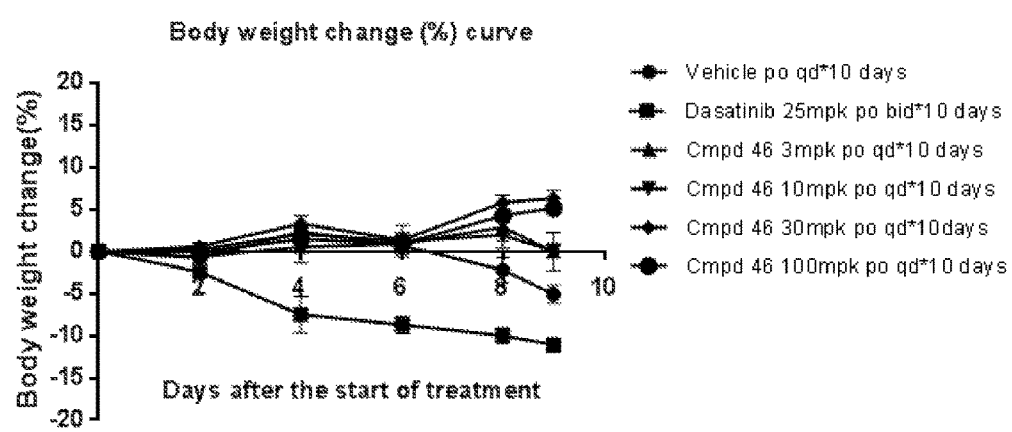
FIG. 2 is a line graph depicting the results from the body weight changes in the tumor bearing mice of different treatment groups: vehicle (●), Dasatinib at 25 mpk po bid*10 days (■), Compound 46 at 3 mpk po qd*10 days (▲), Compound 46 at 10 mpk po qd*10 days (▼), Compound 46 at 30 mpk po qd*10 days (♦), and Compound 46 at 100 mpk po qd*10 days (●).

The results of the body weight changes in the tumor bearing mice are shown in FIG. 2. Data points represent group mean body weight change. Error bars represent standard error of the mean (SEM). As shown in FIG. 2, body weight change was limited to less than 5%, even at the higher doses of Compound 46. In contrast, animals treated with vehicle or Dasatinib lost more than 5% body weight.

Thus, Compound 46, as a single agent, produced an observable antitumor activity against the P815 mouse mastocytoma cancer xenograft model in this study. In addition, the compound was well tolerated by the tumor-bearing animals, as demonstrated by lack of weight loss.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound of Formula II:

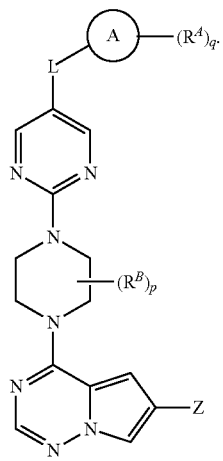

or a pharmaceutically acceptable salt thereof, wherein:
Ring A is selected from monocyclic or bicyclic aryl, monocyclic or bicyclic heteroaryl, cycloalkyl, and heterocyclyl;
Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl, wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl is independently substituted with 0-5 occurrences of $R^C$;
L is selected from a bond, —(C($R^2$)($R^2$))$_m$—, —($C_2$-$C_6$ alkynylene)-, —($C_2$-$C_6$ alkenylene)-, —($C_1$-$C_6$ haloalkylene)-, —($C_1$-$C_6$ heteroalkylene)-, —($C_1$-$C_6$ hydroxyalkylene)-, —C(O)—, —O—, —S—, —S(O), —S(O)$_2$—, —N($R^2$)—, —O—($C_1$-$C_6$ alkylene)-, —($C_1$-$C_6$ alkylene)-O—, —N($R^2$)—C(O)—, —C(O)—N($R^2$)—, —($C_1$-$C_6$ alkylene)-N($R^2$)—, —N($R^2$)—($C_1$-$C_6$ alkylene)-, —N($R^2$)—C(O)—($C_1$-$C_6$ alkylene)-, —C(O)—N($R^2$)—($C_1$-$C_6$ alkylene)-, —N($R^2$)—S(O)$_2$—, —S(O)$_2$—N($R^2$)—, —N($R^2$)—S(O)$_2$—($C_1$-$C_6$ alkylene)-, and —S(O)$_2$—N($R^2$)—($C_1$-$C_6$ alkylene)-;
each $R^A$ and $R^B$ is independently selected from $C_1$-$C_6$ alkyl, $C_3$-$C_6$ cycloalkyl, $C_3$-$C_6$ heterocyclyl, halo, $C_1$-$C_6$ haloalkyl, $C_1$-$C_6$ hydroxyalkyl, $C_1$-$C_6$ heteroalkyl, monocyclic or bicyclic aralkyl, —N($R^2$)($R^2$), cyano, and —OR$^2$;
each $R^C$ is independently selected from $C_1$-$C_6$ alkyl, $C_2$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)R$^2$, —OC(O)R$^2$, —C(O)OR$^2$, —SR$^2$, —S(O)$_2$R$^2$, —S(O)$_2$—N(R$^2$)(R$^2$), —($C_1$-$C_6$ alkylene)-S(O)$_2$—N(R$^2$)(R$^2$), —N(R$^2$)(R$^2$), —C(O)—N(R$^2$)(R$^2$), —N(R$^2$)(R$^2$)—C(O)R$^2$, —($C_1$-$C_6$ alkylene)-N(R$^2$)—C(O)R$^2$, —NR$^2$S(O)$_2$R$^2$, —P(O)(R$^2$)(R$^2$), and —OR$^2$, wherein each of $C_1$-$C_6$ heteroalkyl, $C_1$-$C_6$ haloalkyl, $C_1$-$C_6$ haloalkoxy, $C_1$-$C_6$ alkyl, $C_2$-$C_6$ alkynyl, cycloalkyl, monocyclic or bicyclic aryl, monocyclic or bicyclic aryloxy, monocyclic or bicyclic aralkyl, monocyclic or bicyclic heterocyclyl, and monocyclic or bicyclic heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;
each $R^2$ is independently selected from hydrogen, hydroxyl, halo, thiol, $C_1$-$C_6$ thioalkyl, —NR"R", $C_1$-$C_6$ alkyl, $C_1$-$C_6$ alkoxy, $C_1$-$C_6$ haloalkyl, $C_1$-$C_6$ hydroxyalkyl, cycloalkyl, cycloalkylalkyl, heterocyclyl, and heterocyclylalkyl, wherein each of $C_1$-$C_6$ alkyl, cycloalkyl, and heterocyclyl is independently substituted with 0-5 occurrences of $R^b$, or 2 $R^2$ together with the atoms to which they are attached form a cycloalkyl or heterocyclyl ring;
each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';
each R' is hydrogen, hydroxyl, or $C_1$-$C_6$ alkyl;
each R" is hydrogen, $C_1$-$C_6$ alkyl, —C(O)—$C_1$-$C_6$ alkyl, —C(O)—NR'R'; or —C(S)—NR'R'; and
m, p, and q are each independently 0, 1, 2, 3, or 4.
2. The compound of claim 1 or a pharmaceutically acceptable salt thereof, wherein the compound is a compound of Formula III:

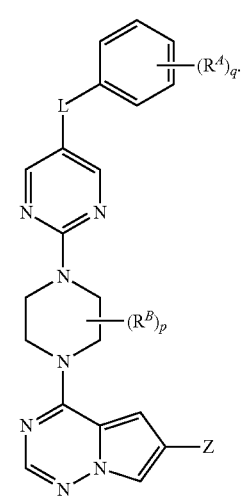

3. The compound of claim 1 or a pharmaceutically acceptable salt thereof, wherein L is —(C($R^2$)($R^2$))$_m$—.
4. The compound of claim 1 or a pharmaceutically acceptable salt thereof, wherein A is monocyclic or bicyclic aryl.

5. The compound of claim 1 or a pharmaceutically acceptable salt thereof, wherein Z is monocyclic or bicyclic aryl.

6. The compound of claim 1 or a pharmaceutically acceptable salt thereof, wherein Z is monocyclic or bicyclic heteroaryl.

7. The compound of claim 1 or a pharmaceutically acceptable salt thereof, wherein Z is monocyclic heteroaryl.

8. The compound of claim 1 or a pharmaceutically acceptable salt thereof, wherein Z is selected from pyrazolyl, isoxazolyl, thiophenyl, thiazolyl, and pyridyl.

9. The compound of claim 1 or a pharmaceutically acceptable salt thereof, wherein Z is phenyl.

10. The compound of claim 1 or a pharmaceutically acceptable salt thereof, wherein Z is monocyclic or bicyclic heterocyclyl.

11. The compound of claim 1 or a pharmaceutically acceptable salt thereof, wherein $R^4$ is fluoro and q is 1.

12. A pharmaceutical composition comprising a pharmaceutically acceptable carrier and a compound of claim 1 or a pharmaceutically acceptable salt thereof.

13. A method of treating mastocytosis, the method comprising administering to a patient in need thereof a therapeutically effective amount of a compound of claim 1 or a pharmaceutically acceptable salt thereof.

14. A method of treating gastrointestinal stromal tumor, the method comprising administering to a patient in need thereof a therapeutically effective amount of a compound of claim 1 or a pharmaceutically acceptable salt thereof.

15. A method of treating acute myeloid leukemia, the method comprising administering to a patient in need thereof a therapeutically effective amount of a compound of claim 1 or a pharmaceutically acceptable salt thereof.

16. The method of claim 13, wherein the mastocytosis is selected from cutaneous mastocytosis (CM) and systemic mastocytosis (SM).

17. The method of claim 16, wherein the systemic mastocytosis is selected from indolent systemic mastocytosis (ISM), smoldering systemic mastocytosis (SSM), aggressive systemic mastocytosis (ASM), SM with associated hematologic non-mast cell lineage disease (SM-AHNMD), and mast cell leukemia (MCL).

18. The compound of claim 2 or a pharmaceutically acceptable salt thereof, wherein L is $—(C(R^2)(R^2))_m—$.

19. The compound of claim 2 or a pharmaceutically acceptable salt thereof, wherein Z is monocyclic or bicyclic heteroaryl.

20. The compound of claim 2 or a pharmaceutically acceptable salt thereof, wherein $R^4$ is fluoro and q is 1.

* * * * *